US011566248B2

(12) United States Patent
Dudek et al.

(10) Patent No.: US 11,566,248 B2
(45) Date of Patent: Jan. 31, 2023

(54) PCSK9 TARGETING OLIGONUCLEOTIDES FOR TREATING HYPERCHOLESTEROLEMIA AND RELATED CONDITIONS

(71) Applicant: Dicerna Pharmaceuticals, Inc., Lexington, MA (US)

(72) Inventors: Henryk T. Dudek, Wellesley, MA (US); Jihye Park, Lexington, MA (US)

(73) Assignee: Dicerna Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 17/048,846

(22) PCT Filed: Apr. 1, 2019

(86) PCT No.: PCT/US2019/025253
§ 371 (c)(1),
(2) Date: Oct. 19, 2020

(87) PCT Pub. No.: WO2019/204021
PCT Pub. Date: Oct. 24, 2019

(65) Prior Publication Data
US 2021/0238606 A1    Aug. 5, 2021

Related U.S. Application Data

(60) Provisional application No. 62/659,693, filed on Apr. 18, 2018, provisional application No. 62/820,558, filed on Mar. 19, 2019.

(51) Int. Cl.
*C12N 15/11*   (2006.01)
*C12N 15/113*  (2010.01)

(52) U.S. Cl.
CPC ...... *C12N 15/1137* (2013.01); *C12N 2310/11* (2013.01); *C12N 2310/315* (2013.01); *C12N 2310/321* (2013.01); *C12N 2310/322* (2013.01); *C12N 2310/346* (2013.01); *C12N 2310/351* (2013.01)

(58) Field of Classification Search
CPC .................................................. C12N 2310/14
See application file for complete search history.

(56) References Cited

U.S. PATENT DOCUMENTS

| 2010/0144834 A1 | 6/2010 | Freier et al. |
| 2017/0137823 A1 | 5/2017 | Kamens et al. |

FOREIGN PATENT DOCUMENTS

| WO | 2008109472 A2 | 9/2008 |
| WO | 2009114475 A2 | 9/2009 |
| WO | 2010148013 A2 | 12/2010 |
| WO | 2012058693 A2 | 5/2012 |
| WO | 2019204021 A1 | 10/2019 |

OTHER PUBLICATIONS

GenBank Accession No. AY829011, "*Homo sapiens* proprotein convertase subtilisin/kexin type 9 (PCSK9) gene, complete cds" (2004).
GenBank Accession No. GS418540, "MG_Ba0047J05.F MG_Ba Erythranthe guttata genomic 5', genomic survey sequence" (2009).
International Search Report and Written Opinion issued by the United States Patent Office as International Searching Authority for International Application No. PCT/US2019/025253, dated Sep. 4, 2019 (13 pages).

*Primary Examiner* — Ekaterina Poliakova-Georgantas
(74) *Attorney, Agent, or Firm* — Dechert LLP; Andrea L. C. Reid; Gang Wang

(57) ABSTRACT

This disclosure relates to oligonucleotides, compositions and methods useful for reducing PCSK9 expression, particularly in hepatocytes. Disclosed oligonucleotides for the reduction of PCSK9 expression may be double-stranded or single-stranded, and may be modified for improved characteristics such as stronger resistance to nucleases and lower immunogenicity. Disclosed oligonucleotides for the reduction of PCSK9 expression may also include targeting ligands to target a particular cell or organ, such as the hepatocytes of the liver, and may be used to treat hypercholesterolemia, atherosclerosis, and/or one or more symptoms or complications thereof.

20 Claims, 21 Drawing Sheets
Specification includes a Sequence Listing.

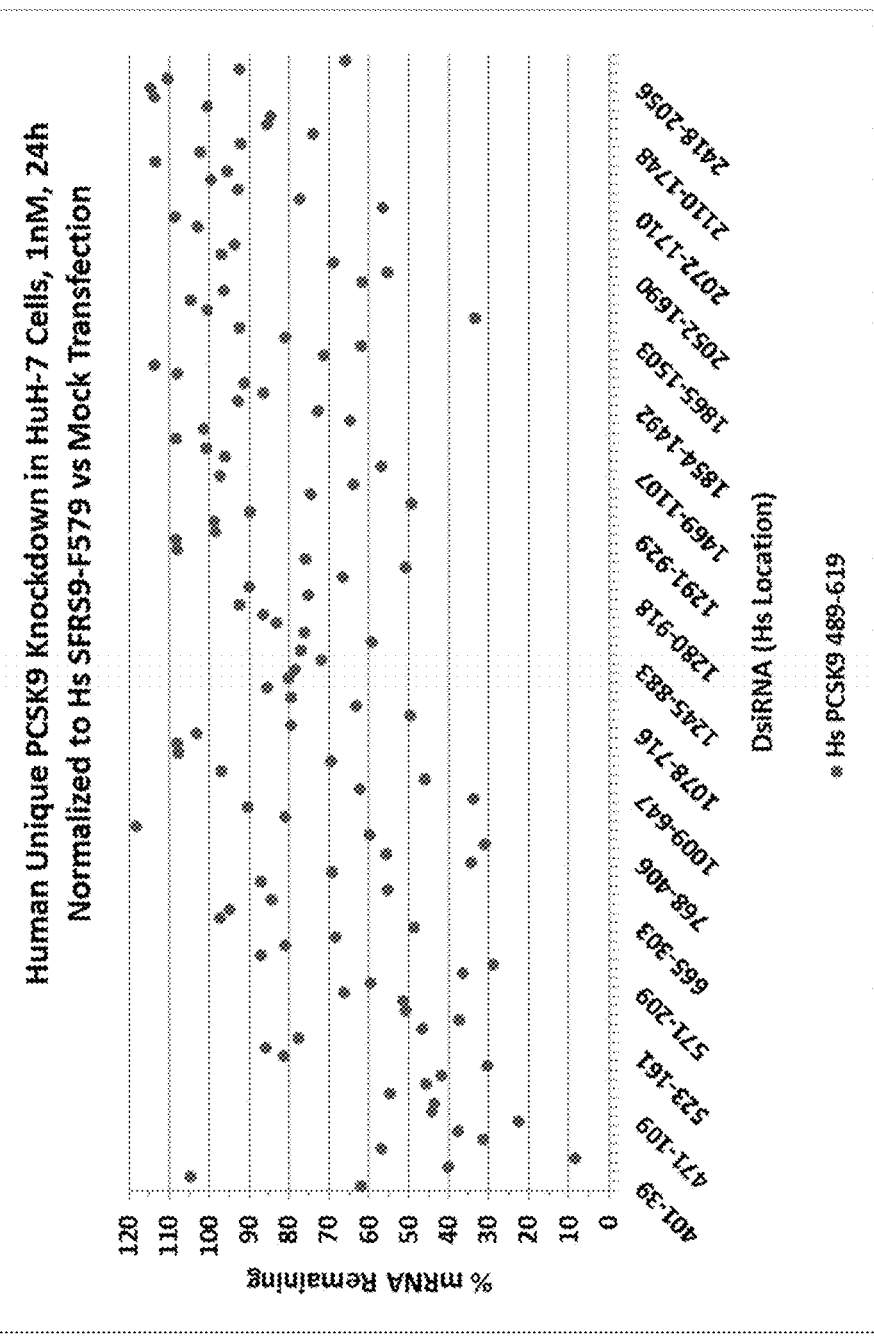

PCSK9 TARGETING OLIGONUCLEOTIDES FOR TREATING HYPERCHOLESTEROLEMIA AND RELATED CONDITIONS

CROSS-REFERENCE TO RELATED APPLICATIONS

This application is a National Stage application, filed under 35 U.S.C. § 371, of International Application No. PCT/US2019/025253, filed Apr. 1, 2019, which claims the benefit under 35 U.S.C. § 119(e) to U.S. Provisional Application No. 62/659,693, filed Apr. 18, 2018, and entitled "PCSK9 TARGETING OLIGONUCLEOTIDES FOR TREATING HYPERCHOLESTEREMIA AND RELATED CONDITIONS," and U.S. Provisional Application No. 62/820,558, filed Mar. 19, 2019, and entitled "PCSK9 TARGETING OLIGONUCLEOTIDES FOR TREATING HYPERCHOLESTEREMIA AND RELATED CONDITIONS," the entire contents of each of which are incorporated herein by reference.

FIELD OF THE INVENTION

The present application relates to oligonucleotides and uses thereof, particularly uses relating to the treatment of hypercholesterolemia, atherosclerosis, and/or one or more symptoms or complications thereof.

REFERENCE TO THE SEQUENCE LISTING

The present application is being filed along with a Sequence Listing in electronic format. The Sequence Listing is provided as a file entitled D080070015WO00-SEQ-ZJG.txt created on Apr. 1, 2019 which is 257 kilobytes in size. The information in electronic format of the sequence listing is incorporated herein by reference in its entirety.

BACKGROUND OF THE INVENTION

Cholesterol is one of three major classes of lipids manufactured by animal cells and used to construct cell membranes. Cholesterol is water insoluble and transported in the blood plasma within protein particles (lipoproteins). Any lipoprotein (e.g., very low density lipoprotein (VLDL), low density lipoprotein (LDL), intermediate density lipoprotein (IDL) and high density lipoprotein (HDL)) may carry cholesterol, but elevated levels of non-HDL cholesterol (most particularly LDL-cholesterol) are associated with an increased risk of atherosclerosis and coronary heart disease (e.g., coronary artery disease). This type of elevated cholesterol is known as hypercholesterolemia. Hypercholesterolemia can lead to the deposition of plaques on artery walls, known as atherosclerosis. Proprotein convertase subtilisin/kexin-9 (also known as PCSK9) is a serine protease that indirectly regulates plasma LDL cholesterol levels by controlling both hepatic and extrahepatic LDL receptor (LDLR) expression at the plasma membrane. Decreased expression of the PCSK9 protein increases expression of the LDLR receptor, thereby decreasing plasma LDL cholesterol and the resultant hypercholesterolemia and/or atherosclerosis as well as complications arising from the same.

BRIEF SUMMARY OF THE INVENTION

Aspects of the disclosure relate to oligonucleotides and related methods for treating hypercholesterolemia, atherosclerosis, and/or one or more symptoms or complications thereof in a subject. In some embodiments, potent RNAi oligonucleotides have been developed for selectively inhibiting PCSK9 expression in a subject. In some embodiments, the RNAi oligonucleotides are useful for reducing PCSK9 activity, and thereby decreasing or preventing hypercholesterolemia (high levels of low density lipoprotein (LDL)-cholesterol), atherosclerosis, and/or one or more symptoms or complications thereof. In some embodiments, key regions of PCSK9 mRNA (referred to as hotspots) have been identified herein that are particularly amenable to targeting using such oligonucleotide-based approaches (See Example 1).

One aspect of the present disclosure provides oligonucleotides for reducing expression of PCSK9. In some embodiments, the oligonucleotides comprise an antisense strand comprising a sequence as set forth in any one of SEQ ID NOs: 454-906, 1030-1152, 1193-1232, 1257-1265, or 1269-1271. In some embodiments, the oligonucleotides further comprise a sense strand that comprises a sequence as set forth in any one of SEQ ID NOs: 1-453, 907-1029, 1153-1192, 1248-1256, or 1266-1268. In some embodiments, the antisense strand consists of a sequence as set forth in any one of SEQ ID NOs: 454-906, 1030-1152, 1193-1232, 1257-1265, or 1269-1271. In some embodiments, the sense strand consists of a sequence as set forth in any one of SEQ ID NOs: 1-453, 907-1029, 1153-1192, 1248-1256, or 1266-1268. One aspect of the present disclosure provides oligonucleotides for reducing expression of PCSK9, in which the oligonucleotides comprise an antisense strand of 15 to 30 nucleotides in length. In some embodiments, the antisense strand has a region of complementarity to a target sequence of PCSK9 as set forth in any one of SEQ ID NOs: 1233-1244. In some embodiments, the region of complementarity is at least 15, at least 16, at least 17, at least 18, at least 19, at least 20, or at least 21 contiguous nucleotides in length. In some embodiments, the region of complementarity is fully complementary to the target sequence of PCSK9. In some embodiments, the region of complementarity is at least 19 contiguous nucleotides in length.

In some embodiments, the sense strand comprises a sequence as set forth in any one of SEQ ID NOs: 1-453, 907-1029, or 1153-1192. In some embodiments, the sense strand consists of a sequence as set forth in any one of SEQ ID NOs: 1-453, 907-1029, or 1153-1192. In some embodiments, the antisense strand comprises a sequence as set forth in any one of SEQ ID NOs: 454-906, 1030-1152, or 1193-1232. In some embodiments, the antisense strand consists of a sequence as set forth in any one of SEQ ID NOs: 454-906, 1030-1152, or 1193-1232.

In some embodiments, the antisense strand is 19 to 27 nucleotides in length. In some embodiments, the antisense strand is 21 to 27 nucleotides in length. In some embodiments, the oligonucleotide further comprises a sense strand of 15 to 40 nucleotides in length, in which the sense strand forms a duplex region with the antisense strand. In some embodiments, the sense strand is 19 to 40 nucleotides in length. In some embodiments, the duplex region is at least 15, at least 16, at least 17, at least 18, at least 19, at least 20, at least 21, or at least 22 nucleotides in length. In some embodiments, the antisense strand is 27 nucleotides in length and the sense strand is 25 nucleotides in length. In some embodiments, the antisense strand and sense strand form a duplex region of 25 nucleotides in length.

In some embodiments, an oligonucleotide comprises an antisense strand and a sense strand that are each in a range of 21 to 23 nucleotides in length. In some embodiments, an oligonucleotide comprises a duplex structure in a range of 19 to 21 nucleotides in length. In some embodiments, an oligonucleotide comprises a 3'-overhang sequence of one or more nucleotides in length, in which the 3'-overhang sequence is present on the antisense strand, the sense strand, or the antisense strand and sense strand. In some embodiments, an oligonucleotide further comprises a 3'-overhang sequence on the antisense strand of two nucleotides in length. In some embodiments, an oligonucleotide comprises a 3'-overhang sequence of two nucleotides in length, in which the 3'-overhang sequence is present on the antisense strand, and in which the sense strand is 21 nucleotides in length and the antisense strand is 23 nucleotides in length, such that the sense strand and antisense strand form a duplex of 21 nucleotides in length.

Another aspect of the present disclosure provides an oligonucleotide for reducing expression of PCSK9, the oligonucleotide comprising an antisense strand and a sense strand, in which the antisense strand is 21 to 27 nucleotides in length and has a region of complementarity to PCSK9, in which the sense strand comprises at its 3'-end a stem-loop set forth as: $S_1$-L-$S_2$, in which $S_1$ is complementary to $S_2$, and in which L forms a loop between $S_1$ and $S_2$ of 3 to 5 nucleotides in length, and in which the antisense strand and the sense strand form a duplex structure of at least 19 nucleotides in length but are not covalently linked. In some embodiments, the sense strand comprises at its 3'-end a stem-loop set forth as: $S_1$-L-$S_2$, in which $S_1$ is complementary to $S_2$, and in which L forms a loop between $S_1$ and $S_2$ of 3 to 5 nucleotides in length. In some embodiments, the region of complementarity is fully complementary to at least 15, at least 16, at least 17, at least 18, at least 19, at least 20, or at least 21 contiguous nucleotides of PCSK9 mRNA. In some embodiments, L is a tetraloop. In some embodiments, L is 4 nucleotides in length. In some embodiments, L comprises a sequence set forth as GAAA.

In some embodiments, an oligonucleotide comprises at least one modified nucleotide. In some embodiments, the modified nucleotide comprises a 2'-modification. In some embodiments, the 2'-modification is a modification selected from: 2'-aminoethyl, 2'-fluoro, 2'-O-methyl, 2'-O-methoxyethyl, and 2'-deoxy-2'-fluoro-β-d-arabinonucleic acid. In some embodiments, all of the nucleotides of an oligonucleotide are modified.

In some embodiments, an oligonucleotide comprises at least one modified internucleotide linkage. In some embodiments, the at least one modified internucleotide linkage is a phosphorothioate linkage. In some embodiments, the 4'-carbon of the sugar of the 5'-nucleotide of the antisense strand comprises a phosphate analog. In some embodiments, the phosphate analog is oxymethylphosphonate, vinylphosphonate, or malonylphosphonate.

In some embodiments, at least one nucleotide of an oligonucleotide is conjugated to one or more targeting ligands. In some embodiments, each targeting ligand comprises a carbohydrate, amino sugar, cholesterol, polypeptide, or lipid. In some embodiments, each targeting ligand comprises a N-acetylgalactosamine (GalNAc) moiety. In some embodiments, the GalNac moiety is a monovalent GalNAc moiety, a bivalent GalNAc moiety, a trivalent GalNAc moiety, or a tetravalent GalNAc moiety. In some embodiments, up to 4 nucleotides of L of the stem-loop are each conjugated to a monovalent GalNAc moiety. In other embodiments, a bi-valent, tri-valent, or tetravalent GalNac moiety is conjugated to a single nucleotide, e.g., of the nucleotides of L of a stem loop. In some embodiments, the targeting ligand comprises an aptamer.

Another aspect of the present disclosure provides a composition comprising an oligonucleotide of the present disclosure and an excipient. Another aspect of the present disclosure provides a method comprising administering a composition of the present disclosure to a subject. In some embodiments, the method results in a decrease in level or severity of, or results in prevention of, hypercholesterolemia (high levels of low density lipoprotein (LDL)-cholesterol), atherosclerosis, coronary heart disease (e.g., coronary artery disease), angina, shortness of breath, sweating, nausea, dizziness, shortness of breath, arrhythmias, heart palpitations, stroke (i.e., death of brain cells resulting from insufficient blood and oxygen flow to the brain), feelings of weakness, confusion, difficulty speaking, dizziness, difficulty in walking or standing up straight, blurred vision, numbness of the face, arms, and legs, severe headaches, loss of consciousness, peripheral artery disease, and/or kidney problems (e.g., chronic kidney disease). Another aspect of the present disclosure provides a method for treating hypercholesterolemia, atherosclerosis, and/or one or more symptoms or complications thereof.

Another aspect of the present disclosure provides an oligonucleotide for reducing expression of PCSK9, the oligonucleotide comprising a sense strand of 15 to 40 nucleotides in length and an antisense strand of 15 to 30 nucleotides in length, in which the sense strand forms a duplex region with the antisense strand, in which the sense strand comprises a sequence as set forth in any one of SEQ ID NOs: 1-453, 907-1029, 1153-1192, 1248-1256, or 1266-1268 and the antisense strand comprises a complementary sequence selected from SEQ ID NOs: 454-906, 1030-1152, 1193-1232, 1257-1265, or 1269-1271.

In some embodiments, the oligonucleotide comprises a pair of sense and antisense strands selected from a row of the table set forth in Table 4.

BRIEF DESCRIPTION OF THE DRAWINGS

The accompanying drawings, which are incorporated in and constitute a part of this specification, illustrate certain embodiments, and together with the written description, serve to provide non-limiting examples of certain aspects of the compositions and methods disclosed herein.

FIGS. 1A and 1B are graphs showing the percentage of PCSK9 mRNA remaining after a screen of 576 PCSK9 oligonucleotides in Huh-7 cells. The nucleotide position in NM_174936.3 that corresponds to the 3' end of the sense strand of each siRNA is indicated on the x axis.

FIG. 5A is a graph showing the percentage of PCSK9 mRNA remaining after screening of 40 nicked-tetraloop structures. The same modification pattern was used, and the oligonucleotides were tested at two different concentrations (0.03 nM and 0.1 nM; labeled as "Phase T2" in FIG. 5A). FIG. 5B shows a human-specific PCSK9 tetraloop conjugate screen in the mouse HDI model at a 2 mg/kg subcutaneous dose using three different modification patterns. FIG. 5C shows the same test as described in FIG. 5B, except at a 1 mg/kg subcutaneous dose (except for the control, which was dosed at both 1 and 2 mg/kg). Two different modification patterns were used. PBS was used as a control and is shown to the left.

FIG. 7A shows the analysis of PCSK9 remaining and LDL-C lowering using a candidate PCSK9 tetraloop conjugate with two different modification patterns. The ability of the oligonucleotide to lower plasma PCSK9 through Day 30 (FIG. 7B) and through Day 90 (FIG. 7C) was measured using a PCSK9 ELISA. Serum levels of LDL were also measured, as shown in FIG. 7D.

DETAILED DESCRIPTION OF THE INVENTION

Figure 1B:
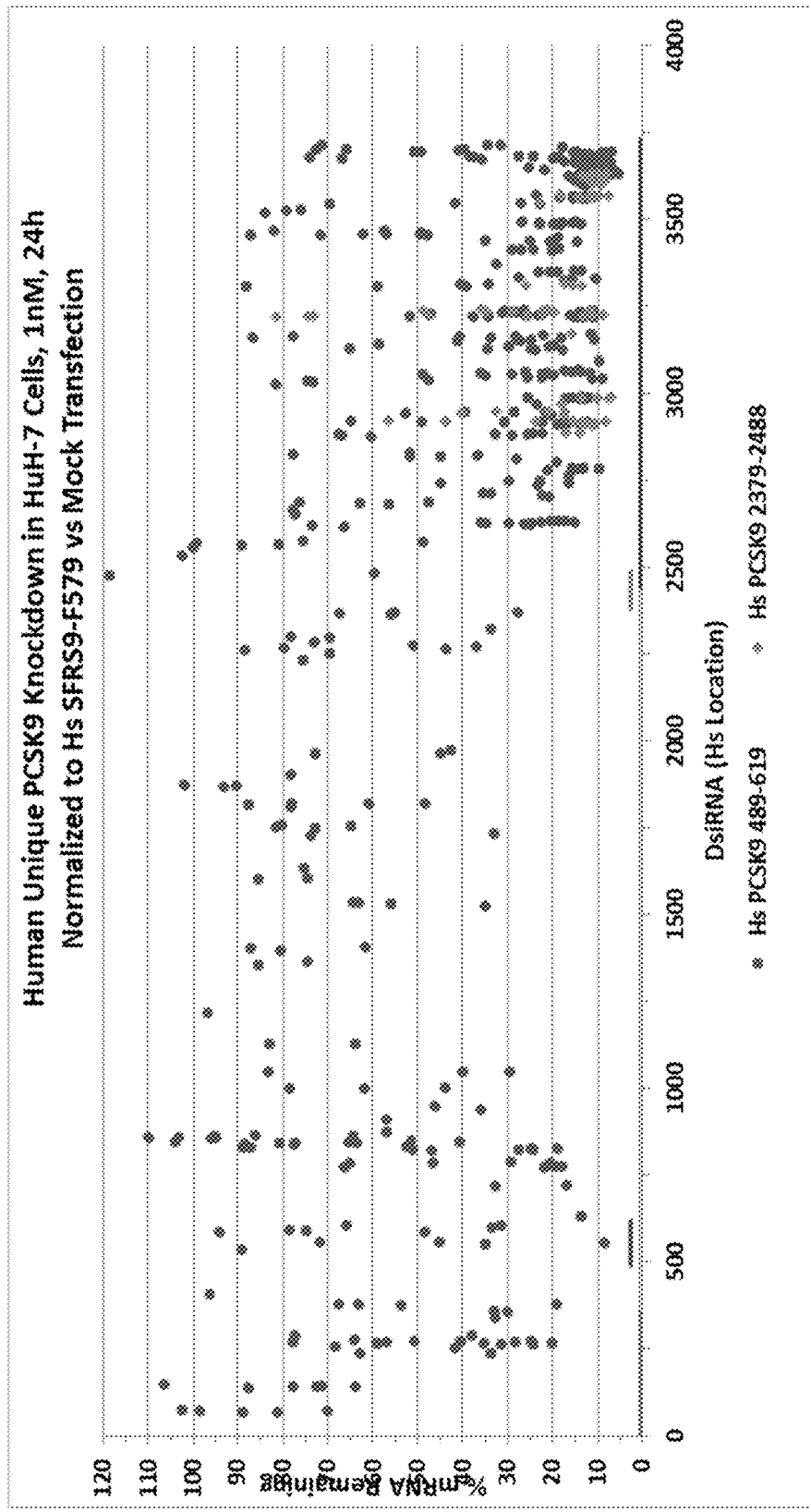

According to some aspects, the disclosure provides oligonucleotides targeting PCSK9 mRNA that are effective for reducing PCSK9 expression in cells, particularly liver cells (e.g., hepatocytes) for the treatment of hypercholesterolemia, atherosclerosis, and/or one or more symptoms or complications thereof. Accordingly, in related aspects, the disclosure provides methods of treating hypercholesterolemia, atherosclerosis, and/or one or more symptoms or complications thereof that involve selectively reducing PCSK9 gene expression in liver. In certain embodiments, PCSK9 targeting oligonucleotides provided herein are designed for delivery to selected cells of target tissues (e.g., liver hepatocytes) to treat hypercholesterolemia, atherosclerosis, and/or one or more symptoms or complications thereof in a subject.

Further aspects of the disclosure, including a description of defined terms, are provided below.

I. Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Administering: As used herein, the terms "administering" or "administration" means to provide a substance (e.g., an oligonucleotide) to a subject in a manner that is pharmacologically useful (e.g., to treat a condition in the subject).

Asialoglycoprotein receptor (ASGPR): As used herein, the term "Asialoglycoprotein receptor" or "ASGPR" refers to a bipartite C-type lectin formed by a major 48 kDa (ASGPR-1) and minor 40 kDa subunit (ASGPR-2). ASGPR is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins).

Atherosclerosis: As used herein, the term "atherosclerosis" refers to a disease involving a narrowing of arteries (e.g., coronary, carotid, peripheral, and/or renal arteries) typically due to the buildup of plaques (made from fat, cholesterol, calcium, and other substances). In some embodiments, narrowing of the coronary arteries may produce symptoms such as angina, shortness of breath, sweating, nausea, dizziness, shortness of breath, arrhythmias, and/or palpitations. In some embodiments, narrowing of the carotid arteries may result in a stroke (i.e., death of brain cells resulting from insufficient blood and oxygen flow to the brain) and/or may produce symptoms such as feelings of weakness, confusion, difficulty speaking, dizziness, difficulty in walking or standing up straight, blurred vision, numbness of the face, arms, and legs, severe headaches, and/or loss of consciousness. In some embodiments, narrowing of the peripheral arteries may result in numbness or pain within the arms or legs. In some embodiments, narrowing of the renal arteries (resulting in decreased kidney blood flow) may result in chronic kidney disease. Complications of atherosclerosis may include coronary artery disease, stroke, peripheral artery disease, and kidney problems (e.g., chronic kidney disease).

Complementary: As used herein, the term "complementary" refers to a structural relationship between nucleotides (e.g., on two nucleotides on opposing nucleic acids or on opposing regions of a single nucleic acid strand) that permits the nucleotides to form base pairs with one another. For example, a purine nucleotide of one nucleic acid that is complementary to a pyrimidine nucleotide of an opposing nucleic acid may base pair together by forming hydrogen bonds with one another. In some embodiments, complementary nucleotides can base pair in the Watson-Crick manner or in any other manner that allows for the formation of stable duplexes. In some embodiments, two nucleic acids may have nucleotide sequences that are complementary to each other so as to form regions of complementarity, as described herein.

Deoxyribonucleotide: As used herein, the term "deoxyribonucleotide" refers to a nucleotide having a hydrogen at the 2' position of its pentose sugar as compared with a ribonucleotide. A modified deoxyribonucleotide is a deoxyribonucleotide having one or more modifications or substitutions of atoms other than at the 2' position, including modifications or substitutions in or of the sugar, phosphate group or base.

Double-stranded oligonucleotide: As used herein, the term "double-stranded oligonucleotide" refers to an oligonucleotide that is substantially in a duplex form. In some embodiments, complementary base-pairing of duplex region(s) of a double-stranded oligonucleotide is formed between antiparallel sequences of nucleotides of covalently separate nucleic acid strands. In some embodiments, complementary base-pairing of duplex region(s) of a double-stranded oligonucleotide is formed between antiparallel sequences of nucleotides of nucleic acid strands that are covalently linked. In some embodiments, complementary base-pairing of duplex region(s) of a double-stranded oligonucleotide is formed from a single nucleic acid strand that is folded (e.g., via a hairpin) to provide complementary antiparallel sequences of nucleotides that base pair together. In some embodiments, a double-stranded oligonucleotide comprises two covalently separate nucleic acid strands that are fully duplexed with one another. However, in some embodiments, a double-stranded oligonucleotide comprises two covalently separate nucleic acid strands that are partially duplexed, e.g., having overhangs at one or both ends. In some embodiments, a double-stranded oligonucleotide comprises antiparallel sequences of nucleotides that are partially complementary, and thus, may have one or more mismatches, which may include internal mismatches or end mismatches.

Duplex: As used herein, the term "duplex," in reference to nucleic acids (e.g., oligonucleotides), refers to a structure formed through complementary base-pairing of two antiparallel sequences of nucleotides.

Excipient: As used herein, the term "excipient" refers to a non-therapeutic agent that may be included in a composition, for example, to provide or contribute to a desired consistency or stabilizing effect.

Hepatocyte: As used herein, the term "hepatocyte" or "hepatocytes" refers to cells of the parenchymal tissues of the liver. These cells make up approximately 70-85% of the liver's mass and manufacture serum albumin, fibrinogen, and the prothrombin group of clotting factors (except for Factors 3 and 4). Markers for hepatocyte lineage cells may include, but are not limited to: transthyretin (Ttr), glutamine synthetase (Glul), hepatocyte nuclear factor 1a (Hnf1a), and hepatocyte nuclear factor 4a (Hnf4a). Markers for mature hepatocytes may include, but are not limited to: cytochrome P450 (Cyp3a11), fumarylacetoacetate hydrolase (Fah), glucose 6-phosphate (G6p), albumin (Alb), and OC2-2F8. See, e.g., Huch et al., (2013), Nature, 494(7436): 247-250, the contents of which relating to hepatocyte markers is incorporated herein by reference.

Hypercholesterolemia: As used herein, the term "hypercholesterolemia" refers to the presence of high levels of cholesterol (e.g., low density lipoprotein (LDL)-cholesterol) in the blood. Cholesterol is one of three major classes of lipids manufactured by animal cells and used to construct cell membranes. Cholesterol is water insoluble and transported in the blood plasma within protein particles (lipoproteins). Any lipoprotein (e.g., very low density lipoprotein (VLDL), low density lipoprotein (LDL), intermediate density lipoprotein (IDL) and high density lipoprotein (HDL)) may carry cholesterol, but elevated levels of non-HDL cholesterol (most particularly LDL-cholesterol) are associated with an increased risk of atherosclerosis and coronary heart disease (e.g., coronary artery disease).

Loop: As used herein, the term "loop" refers to an unpaired region of a nucleic acid (e.g., oligonucleotide) that is flanked by two antiparallel regions of the nucleic acid that are sufficiently complementary to one another, such that under appropriate hybridization conditions (e.g., in a phosphate buffer, in a cells), the two antiparallel regions, which flank the unpaired region, hybridize to form a duplex (referred to as a "stem").

Modified Internucleotide Linkage: As used herein, the term "modified internucleotide linkage" refers to an internucleotide linkage having one or more chemical modifications compared with a reference internucleotide linkage comprising a phosphodiester bond. In some embodiments, a modified nucleotide is a non-naturally occurring linkage. Typically, a modified internucleotide linkage confers one or more desirable properties to a nucleic acid in which the modified internucleotide linkage is present. For example, a modified nucleotide may improve thermal stability, resistance to degradation, nuclease resistance, solubility, bioavailability, bioactivity, reduced immunogenicity, etc.

Modified Nucleotide: As used herein, the term "modified nucleotide" refers to a nucleotide having one or more chemical modifications compared with a corresponding reference nucleotide selected from: adenine ribonucleotide, guanine ribonucleotide, cytosine ribonucleotide, uracil ribonucleotide, adenine deoxyribonucleotide, guanine deoxyribonucleotide, cytosine deoxyribonucleotide, and thymidine deoxyribonucleotide. In some embodiments, a modified nucleotide is a non-naturally occurring nucleotide. In some embodiments, a modified nucleotide has one or more chemical modifications in its sugar, nucleobase and/or phosphate group. In some embodiments, a modified nucleotide has one or more chemical moieties conjugated to a corresponding reference nucleotide. Typically, a modified nucleotide confers one or more desirable properties to a nucleic acid in which the modified nucleotide is present. For example, a modified nucleotide may improve thermal stability, resistance to degradation, nuclease resistance, solubility, bioavailability, bioactivity, reduced immunogenicity, etc. In certain embodiments, a modified nucleotide comprises a 2'-O-methyl or a 2'-F substitution at the 2' position of the ribose ring.

Nicked Tetraloop Structure: A "nicked tetraloop structure" is a structure of a RNAi oligonucleotide characterized by the presence of separate sense (passenger) and antisense (guide) strands, in which the sense strand has a region of complementarity to the antisense strand such that the two strands form a duplex, and in which at least one of the strands, generally the sense strand, extends from the duplex in which the extension contains a tetraloop and two self-complementary sequences forming a stem region adjacent to the tetraloop, in which the tetraloop is configured to stabilize the adjacent stem region formed by the self-complementary sequences of the at least one strand.

Oligonucleotide: As used herein, the term "oligonucleotide" refers to a short nucleic acid, e.g., of less than 100 nucleotides in length. An oligonucleotide can comprise ribonucleotides, deoxyribonucleotides, and/or modified nucleotides including, for example, modified ribonucleotides. An oligonucleotide may be single-stranded or double-stranded. An oligonucleotide may or may not have duplex regions. As a set of non-limiting examples, an oligonucleotide may be, but is not limited to, a small interfering RNA (siRNA), microRNA (miRNA), short hairpin RNA (shRNA), dicer substrate interfering RNA (dsiRNA), antisense oligonucleotide, short siRNA, or single-stranded siRNA. In some embodiments, a double-stranded oligonucleotide is an RNAi oligonucleotide.

Overhang: As used herein, the term "overhang" refers to terminal non-base-pairing nucleotide(s) resulting from one strand or region extending beyond the terminus of a complementary strand with which the one strand or region forms a duplex. In some embodiments, an overhang comprises one or more unpaired nucleotides extending from a duplex region at the 5' terminus or 3' terminus of a double-stranded oligonucleotide. In certain embodiments, the overhang is a 3' or 5' overhang on the antisense strand or sense strand of a double-stranded oligonucleotide.

Phosphate analog: As used herein, the term "phosphate analog" refers to a chemical moiety that mimics the electrostatic and/or steric properties of a phosphate group. In some embodiments, a phosphate analog is positioned at the 5' terminal nucleotide of an oligonucleotide in place of a 5'-phosphate, which is often susceptible to enzymatic removal. In some embodiments, a 5' phosphate analog contains a phosphatase-resistant linkage. Examples of phosphate analogs include 5' phosphonates, such as 5' methylenephosphonate (5'-MP) and 5'-(E)-vinylphosphonate (5'-VP). In some embodiments, an oligonucleotide has a phosphate analog at a 4'-carbon position of the sugar (referred to as a "4'-phosphate analog") at a 5'-terminal nucleotide. An example of a 4'-phosphate analog is oxymethylphosphonate, in which the oxygen atom of the oxymethyl group is bound to the sugar moiety (e.g., at its 4'-carbon) or analog thereof. See, for example, International Patent Application PCT/US2017/049909, filed on Sep. 1, 2017, U.S. Provisional Application No. 62/383,207, filed on Sep. 2, 2016, and 62/393,401, filed on Sep. 12, 2016, the contents of each of which relating to phosphate analogs are incorporated herein by reference. Other modifications have been developed for the 5' end of oligonucleotides (see, e.g., WO 2011/133871; U.S. Pat. No. 8,927,513; and Prakash et al. (2015), Nucleic Acids Res., 43(6):2993-3011, the contents of each of which relating to phosphate analogs are incorporated herein by reference).

Proprotein convertase subtilisin/kexin-9 (PCSK9): As used herein, the term "proprotein convertase subtilisin/kexin-9" (also known as PCSK9, NARC-1, neural apoptosis regulated convertase 1, HCHOLA3, and hypercholesterolemia, autosomal dominant 3) refers to the gene encoding PCSK9 protein.

Reduced expression: As used herein, the term "reduced expression" of a gene refers to a decrease in the amount of RNA transcript or protein encoded by the gene and/or a decrease in the amount of activity of the gene in a cell or subject, as compared to an appropriate reference cell or subject. For example, the act of treating a cell with a double-stranded oligonucleotide (e.g., one having an antisense strand that is complementary to PCSK9 mRNA sequence) may result in a decrease in the amount of RNA transcript, protein and/or enzymatic activity (e.g., encoded by the PCSK9 gene) compared to a cell that is not treated with the double-stranded oligonucleotide. Similarly, "reducing expression" as used herein refers to an act that results in reduced expression of a gene (e.g., PCSK9).

Region of Complementarity: As used herein, the term "region of complementarity" refers to a sequence of nucleotides of a nucleic acid (e.g., a double-stranded oligonucleotide) that is sufficiently complementary to an antiparallel sequence of nucleotides (e.g., a target nucleotide sequence within an mRNA) to permit hybridization between the two sequences of nucleotides under appropriate hybridization conditions, e.g., in a phosphate buffer, in a cell, etc. A region of complementarity may be fully complementary to a nucleotide sequence (e.g., a target nucleotide sequence present within an mRNA or portion thereof). For example, a region of complementarity that is fully complementary to a nucleotide sequence present in an mRNA has a contiguous sequence of nucleotides that is complementary, without any mismatches or gaps, to a corresponding sequence in the mRNA. Alternatively, a region of complementarity may be partially complementary to a nucleotide sequence (e.g., a nucleotide sequence present in an mRNA or portion thereof). For example, a region of complementary that is partially complementary to a nucleotide sequence present in an mRNA has a contiguous sequence of nucleotides that is complementary to a corresponding sequence in the mRNA but that contains one or more mismatches or gaps (e.g., 1, 2, 3, or more mismatches or gaps) compared with the corresponding sequence in the mRNA, provided that the region of complementarity remains capable of hybridizing with the mRNA under appropriate hybridization conditions.

Ribonucleotide: As used herein, the term "ribonucleotide" refers to a nucleotide having a ribose as its pentose sugar, which contains a hydroxyl group at its 2' position. A modified ribonucleotide is a ribonucleotide having one or more modifications or substitutions of atoms other than at the 2' position, including modifications or substitutions in or of the ribose, phosphate group or base.

RNAi Oligonucleotide: As used herein, the term "RNAi oligonucleotide" refers to either (a) a double stranded oligonucleotide having a sense strand (passenger) and antisense strand (guide), in which the antisense strand or part of the antisense strand is used by the Argonaute 2 (Ago2) endonuclease in the cleavage of a target mRNA or (b) a single stranded oligonucleotide having a single antisense strand, where that antisense strand (or part of that antisense strand) is used by the Ago2 endonuclease in the cleavage of a target mRNA.

Strand: As used herein, the term "strand" refers to a single contiguous sequence of nucleotides linked together through internucleotide linkages (e.g., phosphodiester linkages, phosphorothioate linkages). In some embodiments, a strand has two free ends, e.g., a 5'-end and a 3'-end.

Subject: As used herein, the term "subject" means any mammal, including mice, rabbits, and humans. In one embodiment, the subject is a human or non-human primate. The terms "individual" or "patient" may be used interchangeably with "subject."

Synthetic: As used herein, the term "synthetic" refers to a nucleic acid or other molecule that is artificially synthesized (e.g., using a machine (e.g., a solid state nucleic acid synthesizer)) or that is otherwise not derived from a natural source (e.g., a cell or organism) that normally produces the molecule.

Targeting ligand: As used herein, the term "targeting ligand" refers to a molecule (e.g., a carbohydrate, amino sugar, cholesterol, polypeptide, or lipid) that selectively binds to a cognate molecule (e.g., a receptor) of a tissue or cell of interest and that is conjugatable to another substance for purposes of targeting the other substance to the tissue or cell of interest. For example, in some embodiments, a targeting ligand may be conjugated to an oligonucleotide for purposes of targeting the oligonucleotide to a specific tissue or cell of interest. In some embodiments, a targeting ligand selectively binds to a cell surface receptor. Accordingly, in some embodiments, a targeting ligand when conjugated to an oligonucleotide facilitates delivery of the oligonucleotide into a particular cell through selective binding to a receptor expressed on the surface of the cell and endosomal internalization by the cell of the complex comprising the oligonucleotide, targeting ligand, and receptor. In some embodiments, a targeting ligand is conjugated to an oligonucleotide via a linker that is cleaved following or during cellular internalization such that the oligonucleotide is released from the targeting ligand in the cell.

Tetraloop: As used herein, the term "tetraloop" refers to a loop that increases stability of an adjacent duplex formed by hybridization of flanking sequences of nucleotides. The increase in stability is detectable as an increase in melting temperature ($T_m$) of an adjacent stem duplex that is higher than the $T_m$ of the adjacent stem duplex expected, on average, from a set of loops of comparable length consisting of randomly selected sequences of nucleotides. For example, a tetraloop can confer a melting temperature of at least 50°

C., at least 55° C., at least 56° C., at least 58° C., at least 60° C., at least 65° C., or at least 75° C. in 10 mM NaHPO₄ to a hairpin comprising a duplex of at least 2 base pairs in length. In some embodiments, a tetraloop may stabilize a base pair in an adjacent stem duplex by stacking interactions. In addition, interactions among the nucleotides in a tetraloop include, but are not limited to non-Watson-Crick base-pairing, stacking interactions, hydrogen bonding, and contact interactions (Cheong et al., Nature 1990 Aug. 16; 346(6285):680-2; Heus and Pardi, Science 1991 Jul. 12; 253(5016):191-4). In some embodiments, a tetraloop comprises or consists of 3 to 6 nucleotides, and is typically 4 to 5 nucleotides. In certain embodiments, a tetraloop comprises or consists of three, four, five, or six nucleotides, which may or may not be modified (e.g., which may or may not be conjugated to a targeting moiety). In one embodiment, a tetraloop consists of four nucleotides. Any nucleotide may be used in the tetraloop and standard IUPAC-IUB symbols for such nucleotides may be used as described in Cornish-Bowden (1985) Nucl. Acids Res. 13: 3021-3030. For example, the letter "N" may be used to mean that any base may be in that position, the letter "R" may be used to show that A (adenine) or G (guanine) may be in that position, and "B" may be used to show that C (cytosine), G (guanine), or T (thymine) may be in that position. Examples of tetraloops include the UNCG family of tetraloops (e.g., UUCG), the GNRA family of tetraloops (e.g., GAAA), and the CUUG tetraloop (Woese et al., Proc Natl Acad Sci USA. 1990 November; 87(21):8467-71; Antao et al., Nucleic Acids Res. 1991 Nov. 11; 19(21):5901-5). Examples of DNA tetraloops include the d(GNNA) family of tetraloops (e.g., d(GTTA)), the d(GNRA) family of tetraloops, the d(GNAB) family of tetraloops, the d(CNNG) family of tetraloops, and the d(TNCG) family of tetraloops (e.g., d(TTCG)). See, for example: Nakano et al. Biochemistry, 41 (48), 14281-14292, 2002. SHINJI et al. Nippon Kagakkai Koen Yokoshu VOL. 78th; NO. 2; PAGE. 731 (2000), which are incorporated by reference herein for their relevant disclosures. In some embodiments, the tetraloop is contained within a nicked tetraloop structure.

Treat: As used herein, the term "treat" refers to the act of providing care to a subject in need thereof, e.g., through the administration a therapeutic agent (e.g., an oligonucleotide) to the subject, for purposes of improving the health and/or well-being of the subject with respect to an existing condition (e.g., a disease, disorder) or to prevent or decrease the likelihood of the occurrence of a condition. In some embodiments, treatment involves reducing the frequency or severity of at least one sign, symptom or contributing factor of a condition (e.g., disease, disorder) experienced by a subject.

II. Oligonucleotide-Based Inhibitors i. PCSK9 Targeting Oligonucleotides

Potent oligonucleotides have been identified herein through examination of the PCSK9 mRNA, including mRNAs of different species (human and Rhesus macaque, (see, e.g., Example 1)) and in vitro and in vivo testing. Such oligonucleotides can be used to achieve therapeutic benefit for subjects with a hypercholesterolemia, atherosclerosis, and/or one or more symptoms or complications thereof by reducing PCSK9 activity, and consequently, by decreasing or preventing hypercholesterolemia (high levels of low density lipoprotein (LDL)-cholesterol), atherosclerosis, coronary heart disease (e.g., coronary artery disease), angina, shortness of breath, sweating, nausea, dizziness, shortness of breath, arrhythmias, heart palpitations, stroke (i.e., death of brain cells resulting from insufficient blood and oxygen flow to the brain), feelings of weakness, confusion, difficulty speaking, dizziness, difficulty in walking or standing up straight, blurred vision, numbness of the face, arms, and legs, severe headaches, loss of consciousness, peripheral artery disease, and/or kidney problems (e.g., chronic kidney disease). For example, potent RNAi oligonucleotides are provided herein that have a sense strand comprising, or consisting of, a sequence as set forth in any one of SEQ ID NO: 1-453, 907-1029, 1153-1192, 1248-1256, and 1266-1268 and an antisense strand comprising, or consisting of, a complementary sequence selected from SEQ ID NO: 454-906, 1030-1152, 1193-1232, 1257-1265, and 1269-1271, as is also arranged the table provided in Table 4 (e.g., a sense strand comprising a sequence as set forth in SEQ ID NO: 1 and an antisense strand comprising a sequence as set forth in SEQ ID NO: 454). The sequences can be put into multiple different structures (or formats), as described herein.

In some embodiments, it has been discovered that certain regions of PCSK9 mRNA are hotspots for targeting because they are more amenable than other regions to oligonucleotide-based inhibition. In some embodiments, a hotspot region of PCSK9 consists of a sequence as forth in any one of SEQ ID NOs: 1233-1244. These regions of PCSK9 mRNA may be targeted using oligonucleotides as discussed herein for purposes of inhibiting PCSK9 mRNA expression.

Accordingly, in some embodiments, oligonucleotides provided herein are designed so as to have regions of complementarity to PCSK9 mRNA (e.g., within a hotspot of PCSK9 mRNA) for purposes of targeting the mRNA in cells and inhibiting its expression. The region of complementarity is generally of a suitable length and base content to enable annealing of the oligonucleotide (or a strand thereof) to PCSK9 mRNA for purposes of inhibiting its expression.

In some embodiments, an oligonucleotide disclosed herein comprises a region of complementarity (e.g., on an antisense strand of a double-stranded oligonucleotide) that is at least partially complementary to a sequence as set forth in any of SEQ ID NOs: 1-453 or 907-1029, which include certain sequences mapping to within hotspot regions of PCSK9 mRNA. In some embodiments, an oligonucleotide disclosed herein comprises a region of complementarity (e.g., on an antisense strand of a double-stranded oligonucleotide) that is fully complementary to a sequence as set forth in any of SEQ ID NOs: 1-453 or 907-1029. In some embodiments, a region of complementarity of an oligonucleotide that is complementary to contiguous nucleotides of a sequence as set forth in any of SEQ ID NOs: 1-453 or 907-1029 spans the entire length of an antisense strand. In some embodiments, a region of complementarity of an oligonucleotide that is complementary to contiguous nucleotides of a sequence as set forth in any one of any of SEQ ID NOs: 1-453 or 907-1029 spans a portion of the entire length of an antisense strand (e.g., all but two nucleotides at the 3' end of the antisense strand). In some embodiments, an oligonucleotide disclosed herein comprises a region of complementarity (e.g., on an antisense strand of a double-stranded oligonucleotide) that is at least partially (e.g., fully) complementary to a contiguous stretch of nucleotides spanning nucleotides 1-19 of a sequence as set forth in SEQ ID NOs: 1153-1192.

In some embodiments, the region of complementarity is at least 12, at least 13, at least 14, at least 15, at least 16, at least 17, at least 18, at least 19, at least 20, at least 21, at least 22, at least 23, at least 24, or at least 25 nucleotides in length. In some embodiments, an oligonucleotide provided herein has a region of complementarity to PCSK9 mRNA that is in the range of 12 to 30 (e.g., 12 to 30, 12 to 22, 15 to 25, 17 to 21, 18 to 27, 19 to 27, or 15 to 30) nucleotides in length. In some embodiments, an oligonucleotide provided herein has a region of complementarity to PCSK9 mRNA that is 12, 13, 14, 15, 16, 17, 18, 19, 20, 21, 22, 23, 24, 25, 26, 27, 28, 29, or 30 nucleotides in length.

In some embodiments, a region of complementarity to PCSK9 mRNA may have one or more mismatches compared with a corresponding sequence of PCSK9 mRNA. A region of complementarity on an oligonucleotide may have up to 1, up to 2, up to 3, up to 4, etc. mismatches provided that it maintains the ability to form complementary base pairs with PCSK9 mRNA under appropriate hybridization conditions. Alternatively, a region of complementarity on an oligonucleotide may have no more than 1, no more than 2, no more than 3, or no more than 4 mismatches provided that it maintains the ability to form complementary base pairs with PCSK9 mRNA under appropriate hybridization conditions. In some embodiments, if there are more than one mismatches in a region of complementarity, they may be positioned consecutively (e.g., 2, 3, 4, or more in a row), or interspersed throughout the region of complementarity provided that the oligonucleotide maintains the ability to form complementary base pairs with PCSK9 mRNA under appropriate hybridization conditions.

Still, in some embodiments, double-stranded oligonucleotides provided herein comprise, of consist of, a sense strand having a sequence as set forth in any one of SEQ ID NOs: 1-453, 907-1029, 1153-1192, 1248-1256, and 1266-1268 and an antisense strand comprising a complementary sequence selected from SEQ ID NOs: 454-906, 1030-1152, 1193-1232, 1257-1265, and 1269-1271, as is arranged in the table provided in Table 4 (e.g., a sense strand comprising a sequence as set forth in SEQ ID NO: 1 and an antisense strand comprising a sequence as set forth in SEQ ID NO: 454).

ii. Oligonucleotide Structures

There are a variety of structures of oligonucleotides that are useful for targeting PCSK9 mRNA in the methods of the present disclosure, including RNAi, miRNA, etc. Any of the structures described herein or elsewhere may be used as a framework to incorporate or target a sequence described herein (e.g., a hotpot sequence of PCSK9 such as those illustrated in SEQ ID NOs: 1233-1244 or a sense or antisense strand that comprises or consists of a sequence as set forth as any of SEQ ID NOs: 1 to 453, 907-1029, and 1153-1192 or as set forth as any of SEQ ID NOs: 454-906, 1030-1152, and 1193-1232). Double-stranded oligonucleotides for targeting PCSK9 expression (e.g., via the RNAi pathway) generally have a sense strand and an antisense strand that form a duplex with one another. In some embodiments, the sense and antisense strands are not covalently linked. However, in some embodiments, the sense and antisense strands are covalently linked.

In some embodiments, double-stranded oligonucleotides for reducing PCSK9 expression engage RNA interference (RNAi). For example, RNAi oligonucleotides have been developed with each strand having sizes of 19-25 nucleotides with at least one 3' overhang of 1 to 5 nucleotides (see, e.g., U.S. Pat. No. 8,372,968). Longer oligonucleotides have also been developed that are processed by the Dicer enzyme to generate active RNAi products (see, e.g., U.S. Pat. No. 8,883,996). Further work produced extended double-stranded oligonucleotides where at least one end of at least one strand is extended beyond a duplex targeting region, including structures where one of the strands includes a thermodynamically-stabilizing tetraloop structure (see, e.g., U.S. Pat. Nos. 8,513,207 and 8,927,705, as well as WO2010033225, which are incorporated by reference herein for their disclosure of these oligonucleotides). Such structures may include single-stranded extensions (on one or both sides of the molecule) as well as double-stranded extensions.

In some embodiments, sequences described herein can be incorporated into, or targeted using, oligonucleotides that comprise separate sense and antisense strands that are both in the range of 17 to 40 nucleotides in length. In some embodiments, oligonucleotides incorporating such sequences are provided that have a tetraloop structure within a 3' extension of their sense strand, and two terminal overhang nucleotides at the 3' end of the separate antisense strand. In some embodiments, the two terminal overhang nucleotides are GG. Typically, one or both of the two terminal GG nucleotides of the antisense strand is or are not complementary to the target.

In some embodiments, oligonucleotides incorporating such sequences are provided that have sense and antisense strands that are both in the range of 21 to 23 nucleotides in length. In some embodiments, a 3' overhang is provided on the sense, antisense, or both sense and antisense strands that is 1 or 2 nucleotides in length. In some embodiments, an oligonucleotide has a guide strand of 23 nucleotides and a passenger strand of 21 nucleotides, in which the 3'-end of passenger strand and 5'-end of guide strand form a blunt end and where the guide strand has a two nucleotide 3' overhang.

In some embodiments, oligonucleotides may be in the range of 21 to 23 nucleotides in length. In some embodiments, oligonucleotides may have an overhang (e.g., of 1, 2, or 3 nucleotides in length) in the 3' end of the sense and/or antisense strands. In some embodiments, oligonucleotides (e.g., siRNAs) may comprise a 21 nucleotide guide strand that is antisense to a target RNA and a complementary passenger strand, in which both strands anneal to form a 19-bp duplex and 2 nucleotide overhangs at either or both 3' ends. See, for example, U.S. Pat. Nos. 9,012,138, 9,012,621, and 9,193,753, the contents of each of which are incorporated herein for their relevant disclosures.

In some embodiments, an oligonucleotide of the invention has a 36 nucleotide sense strand that comprises a region extending beyond the antisense-sense duplex, where the extension region has a stem-tetraloop structure where the stem is a six base pair duplex and where the tetraloop has four nucleotides. In certain of those embodiments, three or four of the tetraloop nucleotides are each conjugated to a monovalent GalNac ligand.

In some embodiments, an oligonucleotide of the invention comprises a 25 nucleotide sense strand and a 27 nucleotide antisense strand that when acted upon by a dicer enzyme results in an antisense strand that is incorporated into the mature RISC.

Other oligonucleotides designs for use with the compositions and methods disclosed herein include: 16-mer siRNAs (see, e.g., Nucleic Acids in Chemistry and Biology. Blackburn (ed.), Royal Society of Chemistry, 2006), shRNAs (e.g., having 19 bp or shorter stems; see, e.g., Moore et al. Methods Mol. Biol. 2010; 629:141-158), blunt siRNAs (e.g., of 19 bps in length; see: e.g., Kraynack and Baker, RNA Vol. 12, p163-176 (2006)), asymmetrical siRNAs (aiRNA; see, e.g., Sun et al., Nat. Biotechnol. 26, 1379-1382 (2008)), asymmetric shorter-duplex siRNA (see, e.g., Chang et al., Mol Ther. 2009 April; 17(4): 725-32), fork siRNAs (see, e.g., Hohjoh, FEBS Letters, Vol 557, issues 1-3; January 2004, p193-198), single-stranded siRNAs (Elsner;

Nature Biotechnology 30, 1063 (2012)), dumbbell-shaped circular siRNAs (see, e.g., Abe et al. J Am Chem Soc 129: 15108-15109 (2007)), and small internally segmented interfering RNA (sisiRNA; see, e.g., Bramsen et al., Nucleic Acids Res. 2007 September; 35(17): 5886-5897). Each of the foregoing references is incorporated by reference in its entirety for the related disclosures therein. Further non-limiting examples of an oligonucleotide structures that may be used in some embodiments to reduce or inhibit the expression of PCSK9 are microRNA (miRNA), short hairpin RNA (shRNA), and short siRNA (see, e.g., Hamilton et al., Embo J., 2002, 21(17): 4671-4679; see also U.S. Application No. 20090099115).

a. Antisense Strands

In some embodiments, an oligonucleotide disclosed herein for targeting PCSK9 comprises an antisense strand comprising or consisting of a sequence as set forth in any one of SEQ ID NOs: 454-906, 1030-1152, or 1193-1232. In some embodiments, an oligonucleotide comprises an antisense strand comprising or consisting of at least 12 (e.g., at least 12, at least 13, at least 14, at least 15, at least 16, at least 17, at least 18, at least 19, at least 20, at least 21, at least 22, or at least 23) contiguous nucleotides of a sequence as set forth in any one of SEQ ID NOs: 454-906, 1030-1152, or 1193-1232.

In some embodiments, a double-stranded oligonucleotide may have an antisense strand of up to 40 nucleotides in length (e.g., up to 40, up to 35, up to 30, up to 27, up to 25, up to 21, up to 19, up to 17, or up to 12 nucleotides in length). In some embodiments, an oligonucleotide may have an antisense strand of at least 12 nucleotides in length (e.g., at least 12, at least 15, at least 19, at least 21, at least 22, at least 25, at least 27, at least 30, at least 35, or at least 38 nucleotides in length). In some embodiments, an oligonucleotide may have an antisense strand in a range of 12 to 40 (e.g., 12 to 40, 12 to 36, 12 to 32, 12 to 28, 15 to 40, 15 to 36, 15 to 32, 15 to 28, 17 to 22, 17 to 25, 19 to 27, 19 to 30, 20 to 40, 22 to 40, 25 to 40, or 32 to 40) nucleotides in length. In some embodiments, an oligonucleotide may have an antisense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In some embodiments, an antisense strand of an oligonucleotide may be referred to as a "guide strand." For example, if an antisense strand can engage with RNA-induced silencing complex (RISC) and bind to an Argonaut protein, or engage with or bind to one or more similar factors, and direct silencing of a target gene, it may be referred to as a guide strand. In some embodiments, a sense strand complementary to a guide strand may be referred to as a "passenger strand."

b. Sense Strands

In some embodiments, an oligonucleotide disclosed herein for targeting PCSK9 comprises or consists of a sense strand sequence as set forth in in any one of SEQ ID NOs: 1 to 453, 907-1029, and 1153-1192. In some embodiments, an oligonucleotide has a sense strand that comprises or consists of at least 12 (e.g., at least 13, at least 14, at least 15, at least 16, at least 17, at least 18, at least 19, at least 20, at least 21, at least 22, or at least 23) contiguous nucleotides of a sequence as set forth in in any one of SEQ ID NOs: 1 to 453, 907-1029, and 1153-1192.

In some embodiments, an oligonucleotide may have a sense strand (or passenger strand) of up to 40 nucleotides in length (e.g., up to 40, up to 36, up to 30, up to 27, up to 25, up to 21, up to 19, up to 17, or up to 12 nucleotides in length). In some embodiments, an oligonucleotide may have a sense strand of at least 12 nucleotides in length (e.g., at least 12, at least 15, at least 19, at least 21, at least 25, at least 27, at least 30, at least 36, or at least 38 nucleotides in length). In some embodiments, an oligonucleotide may have a sense strand in a range of 12 to 40 (e.g., 12 to 40, 12 to 36, 12 to 32, 12 to 28, 15 to 40, 15 to 36, 15 to 32, 15 to 28, 17 to 21, 17 to 25, 19 to 27, 19 to 30, 20 to 40, 22 to 40, 25 to 40, or 32 to 40) nucleotides in length. In some embodiments, an oligonucleotide may have a sense strand of 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

Figure 3:
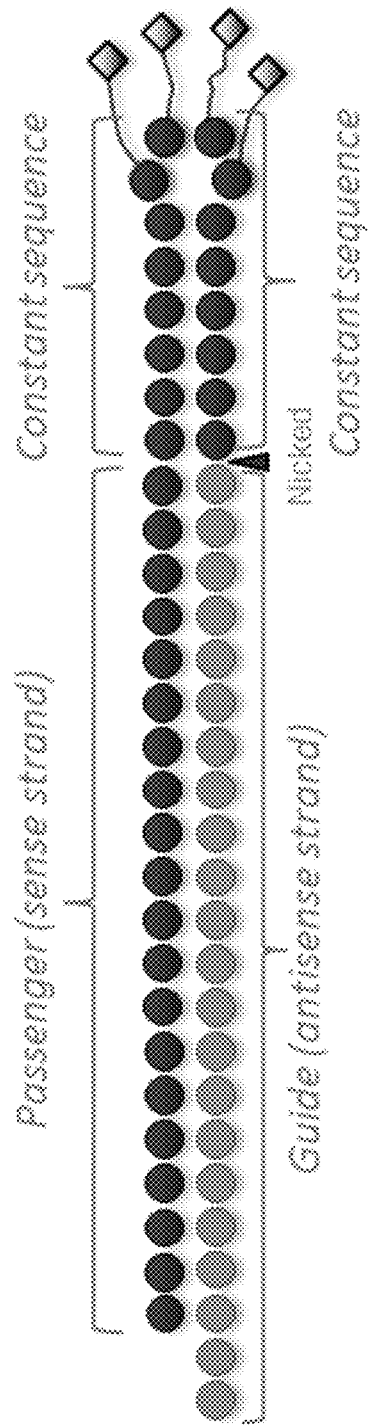
FIG. 3 is a schematic showing a non-limiting example of a double-stranded oligonucleotide with a nicked tetraloop structure that has been conjugated to four GalNAc moieties (diamond shapes).

In some embodiments, a sense strand comprises a stem-loop structure at its 3'-end. In some embodiments, a sense strand comprises a stem-loop structure at its 5'-end. In some embodiments, a stem is a duplex of 2, 3, 4, 5, 6, 7, 8, 9, 10, 11, 12, 13, or 14 base pairs in length. In some embodiments, a stem-loop provides the molecule better protection against degradation (e.g., enzymatic degradation) and facilitates targeting characteristics for delivery to a target cell. For example, in some embodiments, a loop provides added nucleotides on which modification can be made without substantially affecting the gene expression inhibition activity of an oligonucleotide. In certain embodiments, an oligonucleotide is provided herein in which the sense strand comprises (e.g., at its 3'-end) a stem-loop set forth as: $S_1$-L-$S_2$, in which $S_1$ is complementary to $S_2$, and in which L forms a loop between $S_1$ and $S_2$ of up to 10 nucleotides in length (e.g., 3, 4, 5, 6, 7, 8, 9, or 10 nucleotides in length). FIG. 3 depicts a non-limiting example of such an oligonucleotide.

In some embodiments, a loop (L) of a stem-loop is a tetraloop (e.g., within a nicked tetraloop structure). A tetraloop may contain ribonucleotides, deoxyribonucleotides, modified nucleotides, and combinations thereof. Typically, a tetraloop has 4 to 5 nucleotides.

c. Duplex Length

In some embodiments, a duplex formed between a sense and antisense strand is at least 12 (e.g., at least 15, at least 16, at least 17, at least 18, at least 19, at least 20, or at least 21) nucleotides in length. In some embodiments, a duplex formed between a sense and antisense strand is in the range of 12-30 nucleotides in length (e.g., 12 to 30, 12 to 27, 12 to 22, 15 to 25, 18 to 30, 18 to 22, 18 to 25, 18 to 27, 18 to 30, 19 to 30, or 21 to 30 nucleotides in length). In some embodiments, a duplex formed between a sense and antisense strand is 12, 13, 14, 15, 16, 17, 18, 19, 20, 21, 22, 23, 24, 25, 26, 27, 28, 29, or 30 nucleotides in length. In some embodiments a duplex formed between a sense and antisense strand does not span the entire length of the sense strand and/or antisense strand. In some embodiments, a duplex between a sense and antisense strand spans the entire length of either the sense or antisense strands. In certain embodiments, a duplex between a sense and antisense strand spans the entire length of both the sense strand and the antisense strand.

d. Oligonucleotide Ends

In some embodiments, an oligonucleotide provided herein comprises sense and antisense strands, such that there is a 3'-overhang on either the sense strand or the antisense strand, or both the sense and antisense strand. In some embodiments, oligonucleotides provided herein have one 5'-end that is thermodynamically less stable compared to the other 5' end. In some embodiments, an asymmetric oligonucleotide is provided that includes a blunt end at the 3' end of a sense strand and an overhang at the 3' end of an antisense strand. In some embodiments, a 3' overhang on an antisense strand is 1-8 nucleotides in length (e.g., 1, 2, 3, 4, 5, 6, 7, or 8 nucleotides in length).

Typically, an oligonucleotide for RNAi has a two nucleotide overhang on the 3' end of the antisense (guide) strand. However, other overhangs are possible. In some embodiments, an overhang is a 3' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides. However, in some embodiments, the overhang is a 5' overhang comprising a length of between one and six nucleotides, optionally one to five, one to four, one to three, one to two, two to six, two to five, two to four, two to three, three to six, three to five, three to four, four to six, four to five, five to six nucleotides, or one, two, three, four, five or six nucleotides.

In some embodiments, one or more (e.g., 2, 3, 4) terminal nucleotides of the 3' end or 5' end of a sense and/or antisense strand are modified. For example, in some embodiments, one or two terminal nucleotides of the 3' end of an antisense strand are modified. In some embodiments, the last nucleotide at the 3' end of an antisense strand is modified, e.g., comprises 2'-modification, e.g., a 2'-O-methoxyethyl. In some embodiments, the last one or two terminal nucleotides at the 3' end of an antisense strand are complementary to the target. In some embodiments, the last one or two nucleotides at the 3' end of the antisense strand are not complementary to the target. In some embodiments, the 5' end and/or the 3' end of a sense or antisense strand has an inverted cap nucleotide.

e. Mismatches

In some embodiments, there is one or more (e.g., 1, 2, 3, or 4) mismatches between a sense and antisense strand. If there is more than one mismatch between a sense and antisense strand, they may be positioned consecutively (e.g., 2, 3 or more in a row), or interspersed throughout the region of complementarity. In some embodiments, the 3'-terminus of the sense strand contains one or more mismatches. In one embodiment, two mismatches are incorporated at the 3' terminus of the sense strand. In some embodiments, base mismatches or destabilization of segments at the 3'-end of the sense strand of the oligonucleotide improved the potency of synthetic duplexes in RNAi, possibly through facilitating processing by Dicer.

iii. Single-Stranded Oligonucleotides

In some embodiments, an oligonucleotide for reducing PCSK9 expression as described herein is single-stranded. Such structures may include, but are not limited to single-stranded RNAi oligonucleotides. Recent efforts have demonstrated the activity of single-stranded RNAi oligonucleotides (see, e.g., Matsui et al. (May 2016), Molecular Therapy, Vol. 24(5), 946-955). However, in some embodiments, oligonucleotides provided herein are antisense oligonucleotides (ASOs). An antisense oligonucleotide is a single-stranded oligonucleotide that has a nucleobase sequence which, when written in the 5' to 3' direction, comprises the reverse complement of a targeted segment of a particular nucleic acid and is suitably modified (e.g., as a gapmer) so as to induce RNaseH mediated cleavage of its target RNA in cells or (e.g., as a mixmer) so as to inhibit translation of the target mRNA in cells. Antisense oligonucleotides for use in the instant disclosure may be modified in any suitable manner known in the art including, for example, as shown in U.S. Pat. No. 9,567,587, which is incorporated by reference herein for its disclosure regarding modification of antisense oligonucleotides (including, e.g., length, sugar moieties of the nucleobase (pyrimidine, purine), and alterations of the heterocyclic portion of the nucleobase). Further, antisense molecules have been used for decades to reduce expression of specific target genes (see, e.g., Bennett et al.; Pharmacology of Antisense Drugs, Annual Review of Pharmacology and Toxicology, Vol. 57: 81-105).

iv. Oligonucleotide Modifications

Oligonucleotides may be modified in various ways to improve or control specificity, stability, delivery, bioavailability, resistance from nuclease degradation, immunogenicity, base-paring properties, RNA distribution and cellular uptake and other features relevant to therapeutic or research use. See, e.g., Bramsen et al., Nucleic Acids Res., 2009, 37, 2867-2881; Bramsen and Kjems (Frontiers in Genetics, 3 (2012): 1-22). Accordingly, in some embodiments, oligonucleotides of the present disclosure may include one or more suitable modifications. In some embodiments, a modified nucleotide has a modification in its base (or nucleobase), the sugar (e.g., ribose, deoxyribose), or the phosphate group.

The number of modifications on an oligonucleotide and the positions of those nucleotide modifications may influence the properties of an oligonucleotide. For example, oligonucleotides may be delivered in vivo by conjugating them to or encompassing them in a lipid nanoparticle (LNP) or similar carrier. However, when an oligonucleotide is not protected by an LNP or similar carrier (e.g., "naked delivery"), it may be advantageous for at least some of its nucleotides to be modified. Accordingly, in certain embodiments of any of the oligonucleotides provided herein, all or substantially all of the nucleotides of an oligonucleotide are modified. In certain embodiments, more than half of the nucleotides are modified. In certain embodiments, less than half of the nucleotides are modified. Typically, with naked delivery, every nucleotide is modified at the 2'-position of the sugar group of that nucleotide. These modifications may be reversible or irreversible. Typically, the 2' position modification is a 2'-fluoro, 2'-O-methyl, etc. In some embodiments, an oligonucleotide as disclosed herein has a number and type of modified nucleotides sufficient to cause the desired characteristic (e.g., protection from enzymatic degradation, capacity to target a desired cell after in vivo administration, and/or thermodynamic stability).

a. Sugar Modifications

In some embodiments, a modified sugar (also referred to herein as a sugar analog) includes a modified deoxyribose or ribose moiety, e.g., in which one or more modifications occur at the 2', 3', 4', and/or 5' carbon position of the sugar. In some embodiments, a modified sugar may also include non-natural alternative carbon structures such as those present in locked nucleic acids ("LNA") (see, e.g., Koshkin et al. (1998), Tetrahedron 54, 3607-3630), unlocked nucleic acids ("UNA") (see, e.g., Snead et al. (2013), Molecular Therapy—Nucleic Acids, 2, e103), and bridged nucleic acids ("BNA") (see, e.g., Imanishi and Obika (2002), The Royal Society of Chemistry, Chem. Commun., 1653-1659). Koshkin et al., Snead et al., and Imanishi and Obika are incorporated by reference herein for their disclosures relating to sugar modifications.

In some embodiments, a nucleotide modification in a sugar comprises a 2'-modification. In some embodiments, the 2'-modification may be 2'-aminoethyl, 2'-fluoro, 2'-O-methyl, 2'-O-methoxyethyl, or 2'-deoxy-2'-fluoro-β-d-arabinonucleic acid. Typically, the modification is 2'-fluoro, 2'-O-methyl, or 2'-O-methoxyethyl. However, a large variety of 2' position modifications that have been developed for use in oligonucleotides can be employed in oligonucleotides disclosed herein. See, e.g., Bramsen et al., Nucleic Acids Res., 2009, 37, 2867-2881. In some embodiments, a modification in a sugar comprises a modification of the sugar ring, which may comprise modification of one or more carbons of the sugar ring. For example, a modification of a sugar of a nucleotide may comprise a linkage between the 2'-carbon and a 1'-carbon or 4'-carbon of the sugar. For example, the linkage may comprise an ethylene or methylene bridge. In some embodiments, a modified nucleotide has an acyclic sugar that lacks a 2'-carbon to 3'-carbon bond. In some embodiments, a modified nucleotide has a thiol group, e.g., in the 4' position of the sugar.

In some embodiments, the terminal 3'-end group (e.g., a 3'-hydroxyl) is a phosphate group or other group, which can be used, for example, to attach linkers, adapters or labels or for the direct ligation of an oligonucleotide to another nucleic acid.

b. 5' Terminal Phosphates

5'-terminal phosphate groups of oligonucleotides may or in some circumstances enhance the interaction with Argonaut 2. However, oligonucleotides comprising a 5'-phosphate group may be susceptible to degradation via phosphatases or other enzymes, which can limit their bioavailability in vivo. In some embodiments, oligonucleotides include analogs of 5' phosphates that are resistant to such degradation. In some embodiments, a phosphate analog may be oxymethylphosphonate, vinylphosphonate, or malonylphosphonate. In certain embodiments, the 5' end of an oligonucleotide strand is attached to a chemical moiety that mimics the electrostatic and steric properties of a natural 5'-phosphate group ("phosphate mimic") (see, e.g., Prakash et al. (2015), Nucleic Acids Res., Nucleic Acids Res. 2015 Mar. 31; 43(6): 2993-3011, the contents of which relating to phosphate analogs are incorporated herein by reference). Many phosphate mimics have been developed that can be attached to the 5' end (see, e.g., U.S. Pat. No. 8,927,513, the contents of which relating to phosphate analogs are incorporated herein by reference). Other modifications have been developed for the 5' end of oligonucleotides (see, e.g., WO 2011/133871, the contents of which relating to phosphate analogs are incorporated herein by reference). In certain embodiments, a hydroxyl group is attached to the 5' end of the oligonucleotide.

In some embodiments, an oligonucleotide has a phosphate analog at a 4'-carbon position of the sugar (referred to as a "4'-phosphate analog"). See, for example, International Patent Application PCT/US2017/049909, filed on Sep. 1, 2017, U.S. Provisional Application No. 62/383,207, entitled 4'-Phosphate Analogs and Oligonucleotides Comprising the Same, filed on Sep. 2, 2016, and 62/393,401, filed on Sep. 12, 2016, entitled 4'-Phosphate Analogs and Oligonucleotides Comprising the Same, the contents of each of which relating to phosphate analogs are incorporated herein by reference. In some embodiments, an oligonucleotide provided herein comprises a 4'-phosphate analog at a 5'-terminal nucleotide. In some embodiments, a phosphate analog is an oxymethylphosphonate, in which the oxygen atom of the oxymethyl group is bound to the sugar moiety (e.g., at its 4'-carbon) or analog thereof. In other embodiments, a 4'-phosphate analog is a thiomethylphosphonate or an aminomethylphosphonate, in which the sulfur atom of the thiomethyl group or the nitrogen atom of the aminomethyl group is bound to the 4'-carbon of the sugar moiety or analog thereof. In certain embodiments, a 4'-phosphate analog is an oxymethylphosphonate. In some embodiments, an oxymethylphosphonate is represented by the formula —O—$CH_2$—PO(OH)$_2$ or —O—$CH_2$—PO(OR)$_2$, in which R is independently selected from H, $CH_3$, an alkyl group, $CH_2CH_2CN$, $CH_2OCOC(CH_3)_3$, $CH_2OCH_2CH_2Si(CH_3)_3$, or a protecting group. In certain embodiments, the alkyl group is $CH_2CH_3$. More typically, R is independently selected from H, $CH_3$, or $CH_2CH_3$.

c. Modified Internucleoside Linkages

In some embodiments, the oligonucleotide may comprise a modified internucleoside linkage. In some embodiments, phosphate modifications or substitutions may result in an oligonucleotide that comprises at least one (e.g., at least 1, at least 2, at least 3, at least 4, or at least 5) modified internucleotide linkage. In some embodiments, any one of the oligonucleotides disclosed herein comprises 1 to 10 (e.g., 1 to 10, 2 to 8, 4 to 6, 3 to 10, 5 to 10, 1 to 5, 1 to 3 or 1 to 2) modified internucleotide linkages. In some embodiments, any one of the oligonucleotides disclosed herein comprises 1, 2, 3, 4, 5, 6, 7, 8, 9, or 10 modified internucleotide linkages.

A modified internucleotide linkage may be a phosphorodithioate linkage, a phosphorothioate linkage, a phosphotriester linkage, a thionoalkylphosphonate linkage, a thionoalkylphosphotriester linkage, a phosphoramidite linkage, a phosphonate linkage or a boranophosphate linkage. In some embodiments, at least one modified internucleotide linkage of any one of the oligonucleotides as disclosed herein is a phosphorothioate linkage d. Base Modifications In some embodiments, oligonucleotides provided herein have one or more modified nucleobases. In some embodiments, modified nucleobases (also referred to herein as base analogs) are linked at the 1' position of a nucleotide sugar moiety. In certain embodiments, a modified nucleobase is a nitrogenous base. In certain embodiments, a modified nucleobase does not contain a nitrogen atom. See e.g., U.S. Published Patent Application No. 20080274462. In some embodiments, a modified nucleotide comprises a universal base. However, in certain embodiments, a modified nucleotide does not contain a nucleobase (abasic).

In some embodiments, a universal base is a heterocyclic moiety located at the 1' position of a nucleotide sugar moiety in a modified nucleotide, or the equivalent position in a nucleotide sugar moiety substitution that, when present in a duplex, can be positioned opposite more than one type of base without substantially altering the structure of the duplex. In some embodiments, compared to a reference single-stranded nucleic acid (e.g., oligonucleotide) that is fully complementary to a target nucleic acid, a single-stranded nucleic acid containing a universal base forms a duplex with the target nucleic acid that has a lower $T_m$ than a duplex formed with the complementary nucleic acid. However, in some embodiments, compared to a reference single-stranded nucleic acid in which the universal base has been replaced with a base to generate a single mismatch, the single-stranded nucleic acid containing the universal base forms a duplex with the target nucleic acid that has a higher $T_m$ than a duplex formed with the nucleic acid comprising the mismatched base.

Non-limiting examples of universal-binding nucleotides include inosine, 1-β-D-ribofuranosyl-5-nitroindole, and/or 1-β-D-ribofuranosyl-3-nitropyrrole (US Pat. Appl. Publ. No. 20070254362 to Quay et al.; Van Aerschot et al., An acyclic 5-nitroindazole nucleoside analogue as ambiguous nucleoside. Nucleic Acids Res. 1995 Nov. 11; 23(21):4363-70; Loakes et al., 3-Nitropyrrole and 5-nitroindole as universal bases in primers for DNA sequencing and PCR. Nucleic Acids Res. 1995 Jul. 11; 23(13):2361-6; Loakes and Brown, 5-Nitroindole as an universal base analogue. Nucleic Acids Res. 1994 Oct. 11; 22(20):4039-43. Each of the foregoing is incorporated by reference herein for their disclosures relating to base modifications).

e. Reversible Modifications

While certain modifications to protect an oligonucleotide from the in vivo environment before reaching target cells can be made, they can reduce the potency or activity of the oligonucleotide once it reaches the cytosol of the target cell. Reversible modifications can be made such that the molecule retains desirable properties outside of the cell, which are then removed upon entering the cytosolic environment of the cell. Reversible modification can be removed, for example, by the action of an intracellular enzyme or by the chemical conditions inside of a cell (e.g., through reduction by intracellular glutathione).

In some embodiments, a reversibly modified nucleotide comprises a glutathione-sensitive moiety. Typically, nucleic acid molecules have been chemically modified with cyclic disulfide moieties to mask the negative charge created by the internucleotide diphosphate linkages and improve cellular uptake and nuclease resistance. See U.S. Published Application No. 2011/0294869 originally assigned to Traversa Therapeutics, Inc. ("Traversa"), PCT Publication No. WO 2015/188197 to Solstice Biologics, Ltd. ("Solstice"), Meade et al., *Nature Biotechnology*, 2014, 32:1256-1263 ("Meade"), PCT Publication No. WO 2014/088920 to Merck Sharp & Dohme Corp, each of which are incorporated by reference for their disclosures of such modifications. This reversible modification of the internucleotide diphosphate linkages is designed to be cleaved intracellularly by the reducing environment of the cytosol (e.g. glutathione). Earlier examples include neutralizing phosphotriester modifications that were reported to be cleavable inside cells (Dellinger et al. *J. Am. Chem. Soc.* 2003, 125:940-950).

In some embodiments, such a reversible modification allows protection during in vivo administration (e.g., transit through the blood and/or lysosomal/endosomal compartments of a cell) where the oligonucleotide will be exposed to nucleases and other harsh environmental conditions (e.g., pH). When released into the cytosol of a cell where the levels of glutathione are higher compared to extracellular space, the modification is reversed and the result is a cleaved oligonucleotide. Using reversible, glutathione sensitive moieties, it is possible to introduce sterically larger chemical groups into the oligonucleotide of interest as compared to the options available using irreversible chemical modifications. This is because these larger chemical groups will be removed in the cytosol and, therefore, should not interfere with the biological activity of the oligonucleotides inside the cytosol of a cell. As a result, these larger chemical groups can be engineered to confer various advantages to the nucleotide or oligonucleotide, such as nuclease resistance, lipophilicity, charge, thermal stability, specificity, and reduced immunogenicity. In some embodiments, the structure of the glutathione-sensitive moiety can be engineered to modify the kinetics of its release.

In some embodiments, a glutathione-sensitive moiety is attached to the sugar of the nucleotide. In some embodiments, a glutathione-sensitive moiety is attached to the 2'-carbon of the sugar of a modified nucleotide. In some embodiments, the glutathione-sensitive moiety is located at the 5'-carbon of a sugar, particularly when the modified nucleotide is the 5'-terminal nucleotide of the oligonucleotide. In some embodiments, the glutathione-sensitive moiety is located at the 3'-carbon of a sugar, particularly when the modified nucleotide is the 3'-terminal nucleotide of the oligonucleotide. In some embodiments, the glutathione-sensitive moiety comprises a sulfonyl group. See, e.g., International Patent Application PCT/US2017/048239, which published on Mar. 1, 2018 as International Patent Publication WO2018/039364, entitled Compositions Comprising Reversibly Modified Oligonucleotides and Uses Thereof, which was filed on Aug. 23, 2016, the contents of which are incorporated by reference herein for its relevant disclosures.

v. Targeting Ligands

In some embodiments, it may be desirable to target the oligonucleotides of the disclosure to one or more cells or one or more organs. Such a strategy may help to avoid undesirable effects in other organs, or may avoid undue loss of the oligonucleotide to cells, tissue or organs that would not benefit for the oligonucleotide. Accordingly, in some embodiments, oligonucleotides disclosed herein may be modified to facilitate targeting of a particular tissue, cell or organ, e.g., to facilitate delivery of the oligonucleotide to the liver. In certain embodiments, oligonucleotides disclosed herein may be modified to facilitate delivery of the oligonucleotide to the hepatocytes of the liver. In some embodiments, an oligonucleotide comprises a nucleotide that is conjugated to one or more targeting ligands.

A targeting ligand may comprise a carbohydrate, amino sugar, cholesterol, peptide, polypeptide, protein or part of a protein (e.g., an antibody or antibody fragment) or lipid. In some embodiments, a targeting ligand is an aptamer. For example, a targeting ligand may be an RGD peptide that is used to target tumor vasculature or glioma cells, CREKA peptide to target tumor vasculature or stoma, transferrin, lactoferrin, or an aptamer to target transferrin receptors expressed on CNS vasculature, or an anti-EGFR antibody to target EGFR on glioma cells. In certain embodiments, the targeting ligand is one or more GalNAc moieties.

In some embodiments, 1 or more (e.g., 1, 2, 3, 4, 5, or 6) nucleotides of an oligonucleotide are each conjugated to a separate targeting ligand. In some embodiments, 2 to 4 nucleotides of an oligonucleotide are each conjugated to a separate targeting ligand. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the targeting ligands resemble bristles of a toothbrush and the oligonucleotide resembles a toothbrush. For example, an oligonucleotide may comprise a stem-loop at either the 5' or 3' end of the sense strand and 1, 2, 3, or 4 nucleotides of the loop of the stem may be individually conjugated to a targeting ligand, as described, for example, in International Patent Application Publication WO 2016/100401, which was published on Jun. 23, 2016, the relevant contents of which are incorporated herein by reference.

In some embodiments, it is desirable to target an oligonucleotide that reduces the expression of PCSK9 to the hepatocytes of the liver of a subject. Any suitable hepatocyte targeting moiety may be used for this purpose.

GalNAc is a high affinity ligand for asialoglycoprotein receptor (ASGPR), which is primarily expressed on the sinusoidal surface of hepatocyte cells and has a major role in binding, internalization, and subsequent clearance of circulating glycoproteins that contain terminal galactose or N-acetylgalactosamine residues (asialoglycoproteins). Conjugation (either indirect or direct) of GalNAc moieties to oligonucleotides of the instant disclosure may be used to target these oligonucleotides to the ASGPR expressed on these hepatocyte cells.

In some embodiments, an oligonucleotide of the instant disclosure is conjugated directly or indirectly to a monovalent GalNAc. In some embodiments, the oligonucleotide is conjugated directly or indirectly to more than one monovalent GalNAc (i.e., is conjugated to 2, 3, or 4 monovalent GalNAc moieties, and is typically conjugated to 3 or 4 monovalent GalNAc moieties). In some embodiments, an oligonucleotide of the instant disclosure is conjugated to one or more bivalent GalNAc, trivalent GalNAc, or tetravalent GalNAc moieties.

In some embodiments, 1 or more (e.g., 1, 2, 3, 4, 5, or 6) nucleotides of an oligonucleotide are each conjugated to a GalNAc moiety. In some embodiments, 2 to 4 nucleotides of the loop (L) of the stem-loop are each conjugated to a separate GalNAc. In some embodiments, targeting ligands are conjugated to 2 to 4 nucleotides at either ends of the sense or antisense strand (e.g., ligands are conjugated to a 2 to 4 nucleotide overhang or extension on the 5' or 3' end of the sense or antisense strand) such that the GalNAc moieties resemble bristles of a toothbrush and the oligonucleotide resembles a toothbrush. For example, an oligonucleotide may comprise a stem-loop at either the 5' or 3' end of the sense strand and 1, 2, 3, or 4 nucleotides of the loop of the stem may be individually conjugated to a GalNAc moiety. In some embodiments, GalNAc moieties are conjugated to a nucleotide of the sense strand. For example, four GalNAc moieties can be conjugated to nucleotides in the tetraloop of the sense strand, where each GalNAc moiety is conjugated to one nucleotide.

Appropriate methods or chemistry (e.g., click chemistry) can be used to link a targeting ligand to a nucleotide. In some embodiments, a targeting ligand is conjugated to a nucleotide using a click linker. In some embodiments, an acetal-based linker is used to conjugate a targeting ligand to a nucleotide of any one of the oligonucleotides described herein. Acetal-based linkers are disclosed, for example, in International Patent Application Publication Number WO2016100401 A1, which published on Jun. 23, 2016, and the contents of which relating to such linkers are incorporated herein by reference. In some embodiments, the linker is a labile linker. However, in other embodiments, the linker is fairly stable. In some embodiments, a duplex extension (up to 3, 4, 5, or 6 base pairs in length) is provided between a targeting ligand (e.g., a GalNAc moiety) and a double-stranded oligonucleotide.

III. Formulations

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, provided herein are compositions comprising oligonucleotides (e.g., single-stranded or double-stranded oligonucleotides) to reduce the expression of PCSK9. Such compositions can be suitably formulated such that when administered to a subject, either into the immediate environment of a target cell or systemically, a sufficient portion of the oligonucleotides enters the cell to reduce PCSK9 expression. Any of a variety of suitable oligonucleotide formulations can be used to deliver oligonucleotides for the reduction of PCSK9 as disclosed herein. In some embodiments, an oligonucleotide is formulated in buffer solutions such as phosphate-buffered saline solutions, liposomes, micellar structures, and capsids. In some embodiments, naked oligonucleotides or conjugates thereof are formulated in water or in an aqueous solution (e.g., water with pH adjustments). In some embodiments, naked oligonucleotides or conjugates thereof are formulated in basic buffered aqueous solutions (e.g., PBS).

Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine) can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

Accordingly, in some embodiments, a formulation comprises a lipid nanoparticle. In some embodiments, an excipient comprises a liposome, a lipid, a lipid complex, a microsphere, a microparticle, a nanosphere, or a nanoparticle, or may be otherwise formulated for administration to the cells, tissues, organs, or body of a subject in need thereof (see, e.g., Remington: The Science and Practice of Pharmacy, 22nd edition, Pharmaceutical Press, 2013).

In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. For intravenous or subcutaneous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

In some embodiments, a composition may contain at least about 0.1% of the therapeutic agent (e.g., an oligonucleotide for reducing PCSK9 expression) or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Even though a number of embodiments are directed to liver-targeted delivery of any of the oligonucleotides disclosed herein, targeting of other tissues is also contemplated.

IV. Methods of Use i. Reducing PCSK9 Expression in Cells

In some embodiments, methods are provided for delivering to a cell an effective amount any one of oligonucleotides disclosed herein for purposes of reducing expression of PCSK9 in the cell. Methods provided herein are useful in any appropriate cell type. In some embodiments, a cell is any cell that expresses PCSK9 (e.g., liver, lung, kidney, spleen, testis, adipose, and intestinal cells). In some embodiments, the cell is a primary cell that has been obtained from a subject and that may have undergone a limited number of a passages, such that the cell substantially maintains its natural phenotypic properties. In some embodiments, a cell to which the oligonucleotide is delivered is ex vivo or in vitro (i.e., can be delivered to a cell in culture or to an organism in which the cell resides). In specific embodiments, methods are provided for delivering to a cell an effective amount any one of the oligonucleotides disclosed herein for purposes of reducing expression of PCSK9 solely or primarily in hepatocytes.

In some embodiments, oligonucleotides disclosed herein can be introduced using appropriate nucleic acid delivery methods including injection of a solution containing the oligonucleotides, bombardment by particles covered by the oligonucleotides, exposing the cell or organism to a solution containing the oligonucleotides, or electroporation of cell membranes in the presence of the oligonucleotides. Other appropriate methods for delivering oligonucleotides to cells may be used, such as lipid-mediated carrier transport, chemical-mediated transport, and cationic liposome transfection such as calcium phosphate, and others.

The consequences of inhibition can be confirmed by an appropriate assay to evaluate one or more properties of a cell or subject, or by biochemical techniques that evaluate molecules indicative of PCSK9 expression (e.g., RNA, protein). In some embodiments, the extent to which an oligonucleotide provided herein reduces levels of expression of PCSK9 is evaluated by comparing expression levels (e.g., mRNA or protein levels of PCSK9 to an appropriate control (e.g., a level of PCSK9 expression in a cell or population of cells to which an oligonucleotide has not been delivered or to which a negative control has been delivered). In some embodiments, an appropriate control level of PCSK9 expression may be a predetermined level or value, such that a control level need not be measured every time. The predetermined level or value can take a variety of forms. In some embodiments, a predetermined level or value can be single cut-off value, such as a median or mean.

In some embodiments, administration of an oligonucleotide as described herein results in a reduction in the level of PCSK9 expression in a cell. In some embodiments, the reduction in levels of PCSK9 expression may be a reduction to 1% or lower, 5% or lower, 10% or lower, 15% or lower, 20% or lower, 25% or lower, 30% or lower, 35% or lower, 40% or lower, 45% or lower, 50% or lower, 55% or lower, 60% or lower, 70% or lower, 80% or lower, or 90% or lower compared with an appropriate control level of PCSK9. The appropriate control level may be a level of PCSK9 expression in a cell or population of cells that has not been contacted with an oligonucleotide as described herein. In some embodiments, the effect of delivery of an oligonucleotide to a cell according to a method disclosed herein is assessed after a finite period of time. For example, levels of PCSK9 may be analyzed in a cell at least 8 hours, 12 hours, 18 hours, 24 hours; or at least one, two, three, four, five, six, seven, or fourteen days after introduction of the oligonucleotide into the cell.

In some embodiments, an oligonucleotide is delivered in the form of a transgene that is engineered to express in a cell the oligonucleotides disclosed herein (e.g., in the form of an shRNA). In some embodiments, an oligonucleotide is delivered using a transgene that is engineered to express any oligonucleotide disclosed herein. Transgenes may be delivered using viral vectors (e.g., adenovirus, retrovirus, vaccinia virus, poxvirus, adeno-associated virus or herpes simplex virus) or non-viral vectors (e.g., plasmids or synthetic mRNAs). In some embodiments, transgenes can be injected directly to a subject.

ii. Treatment Methods

Aspects of the disclosure relate to methods for reducing PCSK9 expression for the treatment of hypercholesterolemia, atherosclerosis, and/or one or more symptoms or complications thereof in a subject. In some embodiments, the methods may comprise administering to a subject in need thereof an effective amount of any one of the oligonucleotides disclosed herein. In some embodiments, such treatments may be used, for example, to decrease or prevent hypercholesterolemia (high levels of low density lipoprotein (LDL)-cholesterol), atherosclerosis, coronary heart disease (e.g., coronary artery disease), angina, shortness of breath, sweating, nausea, dizziness, shortness of breath, arrhythmias, heart palpitations, stroke (i.e., death of brain cells resulting from insufficient blood and oxygen flow to the brain), feelings of weakness, confusion, difficulty speaking, dizziness, difficulty in walking or standing up straight, blurred vision, numbness of the face, arms, and legs, severe headaches, loss of consciousness, peripheral artery disease, and/or kidney problems (e.g., chronic kidney disease). In some embodiments, such treatments may be used, for example, to treat or prevent one or more symptoms associated with hypercholesterolemia, atherosclerosis, and/or one or more symptoms or complications thereof.

Accordingly, in some embodiments, the present disclosure provides methods of treating a subject at risk of (or susceptible to) hypercholesterolemia, atherosclerosis, and/or one or more symptoms or complications thereof including coronary heart disease (e.g., coronary artery disease), angina, shortness of breath, sweating, nausea, dizziness, shortness of breath, arrhythmias, heart palpitations, stroke (i.e., death of brain cells resulting from insufficient blood and oxygen flow to the brain), feelings of weakness, confusion, difficulty speaking, dizziness, difficulty in walking or standing up straight, blurred vision, numbness of the face, arms, and legs, severe headaches, loss of consciousness, peripheral artery disease, and/or kidney problems (e.g., chronic kidney disease).

In certain aspects, the disclosure provides a method for preventing in a subject, a disease, disorder, symptom, or condition as described herein by administering to the subject a therapeutic agent (e.g., an oligonucleotide or vector or transgene encoding same). In some embodiments, the subject to be treated is a subject who will benefit therapeutically from a reduction in the amount of PCSK9 protein, e.g., in the liver.

Methods described herein typically involve administering to a subject an effective amount of an oligonucleotide, that is, an amount capable of producing a desirable therapeutic result. A therapeutically acceptable amount may be an amount that is capable of treating a disease or disorder. The appropriate dosage for any one subject will depend on certain factors, including the subject's size, body surface area, age, the particular composition to be administered, the active ingredient(s) in the composition, time and route of administration, general health, and other drugs being administered concurrently.

In some embodiments, a subject is administered any one of the compositions disclosed herein either enterally (e.g., orally, by gastric feeding tube, by duodenal feeding tube, via gastrostomy or rectally), parenterally (e.g., subcutaneous injection, intravenous injection or infusion, intra-arterial injection or infusion, intramuscular injection), topically (e.g., epicutaneous, inhalational, via eye drops, or through a mucous membrane), or by direct injection into a target organ (e.g., the liver of a subject). Typically, oligonucleotides disclosed herein are administered intravenously or subcutaneously.

In some embodiments, oligonucleotides are administered at a dose in a range of 0.1 mg/kg to 25 mg/kg (e.g., 1 mg/kg to 5 mg/kg). In some embodiments, oligonucleotides are administered at a dose in a range of 0.1 mg/kg to 5 mg/kg or in a range of 0.5 mg/kg to 5 mg/kg.

As a non-limiting set of examples, the oligonucleotides of the instant disclosure would typically be administered once per year, twice per year, quarterly (once every three months), bi-monthly (once every two months), monthly, or weekly.

In some embodiments, the subject to be treated is a human (e.g., a human patient) or non-human primate or other mammalian subject. Other exemplary subjects include domesticated animals such as dogs and cats; livestock such as horses, cattle, pigs, sheep, goats, and chickens; and animals such as mice, rats, guinea pigs, and hamsters.

EXAMPLES

Example 1: Development of PCSK9 Oligonucleotide Inhibitors Using Human and Mouse Cell-Based Assays Human and mouse-based assays were used to develop candidate oligonucleotides for inhibition of PCSK9 expression. First, a computer-based algorithm was used to generate candidate oligonucleotide sequences (25-27-mer) for PCSK9 inhibition. Cell-based assays and PCR assays were then employed for evaluation of candidate oligonucleotides for their ability to reduce PCSK9 expression.

The computer-based algorithm provided oligonucleotides that were complementary to human PCSK9 mRNA (SEQ ID NO: 1245, Table 1), of which certain sequences were also complementary to Rhesus monkey PCSK9 mRNA (SEQ ID NO: 1246, Table 1).

TABLE 1

Sequences of human and Rhesus monkey PCSK9 mRNA

| Species | GenBank RefSeq # | SEQ ID NO. |
|---|---|---|
| Human | NM_174936.3 | 1245 |
| Rhesus monkey | NM_001112660.1 | 1246 |

Of the oligonucleotides that the algorithm provided, 576 oligonucleotides were selected as candidates for experimental evaluation in a Huh-7 cell-based assay. In this assay, Huh-7 human liver cells stably expressing PCSK9 were transfected with the oligonucleotides. Cells were maintained for a period of time following transfection and then levels of remaining PCSK9 mRNA were interrogated using TAQMAN®-based qPCR assays. Two qPCR assays, a 3' assay and a 5' assay, were used to determine mRNA levels as measured by HEX (housekeeping gene—SFRS9) and FAM probes, respectively. The results of the cell-based assay with the 576 oligonucleotides are shown in FIGS. 1A and 1B. The percent mRNA remaining is shown for each of the 5' assay (circle shapes) and the 3' assay (diamond shapes) in FIG. 1B. Oligonucleotides with the lowest percentage of mRNA remaining compared to mock transfection controls were considered hits. Oligonucleotides with low complementarity to the human genome were used as negative controls.

Based on the activity and locations of these oligonucleotides, hotspots on the human PCSK9 mRNA were defined. A hotspot was identified as a stretch on the human PCSK9 mRNA sequence associated with at least one oligonucleotide resulting in mRNA levels that were less than or equal to 35% in either assay compared with controls. Accordingly, the following hotspots within the human PCSK9 mRNA sequence (NM_174936.3) were identified: 746-783, 2602-2639, 2737-2792, 2880-2923, 2956-2996, 3015-3075, 3099-3178, 3190-3244, 3297-3359, 3649-3446, 3457-3499, and 3532-3715.

The sequences of the hotspots are outlined in Table 2.

TABLE 2

Sequences of Hotspots

| Hotspot Position In Human PCSK9 mRNA | Sequence | SEQ ID NO. |
|---|---|---|
| 746-783 | CGACCTGCTGGAGCTGGCCTTGAA GTTGCCCCATGTCG | 1233 |
| 2602-2639 | AGCCTCCTTGCCTGGAACTCACTC ACTCTGGGTGCCTC | 1234 |
| 2737-2792 | CAATGTGCCGATGTCCGTGGGCAG AATGACTTTTATTGAGCTCTTGTT CCGTGCCA | 1235 |
| 2880-2923 | CGTTGGGGGGTGAGTGTGAAAGGT GCTGATGGCCCTCATCTCCA | 1236 |
| 2956-2996 | GATTAATGGAGGCTTAGCTTTCTG GATGGCATCTAGCCAGA | 1237 |
| 3015-3075 | CCCTGGTGGTCACAGGCTGTGCCT TGGTTTCCTGAGCCACCTTTACTC TGCTCTATGCCAG | 1238 |
| 3099-3178 | TGGCCTGCGGGGAGCCATCACCTA GGACTGACTCGGCAGTGTGCAGTG | 1239 |

TABLE 2-continued

Sequences of Hotspots

| Hotspot Position In Human PCSK9 mRNA | Sequence | SEQ ID NO. |
|---|---|---|
| | GTGCATGCACTGTCTCAGCCAACC CGCTCCAC | |
| 3190-3244 | GTACACATTCGCACCCCTACTTCA CAGAGGAAGAAACCTGGAACCAGA GGGGGCG | 1240 |
| 3297-3359 | GCTCTGAAGCCAAGCCTCTTCTTA CTTCACCCGGCTGGGCTCCTCATT TTTACGGGTAACAGT | 1241 |
| 3469-3446 | AACGATGCCTGCAGGCATGGAACT TTTTCCGTTATCACCCAGGCCT | 1242 |
| 3457-3499 | TTCACTGGCCTGGCGGAGATGCTT CTAAGGCATGGTCGGGGA | 1243 |
| 3532-3715 | GCCCCACCCAAGCAAGCAGACATT TATCTTTTGGGTCTGTCCTCTCTG TTGCCTTTTTACAGCCAACTTTTC TAGACCTGTTTTGCTTTTGTAACT TGAAGATATTTATTCTGGGTTTTG TAGCATTTTTATTAATATGGTGAC TTTTTAAAATAAAAACAAACAAAC GTTGTCCTAACAAAAA | 1244 |

Dose Response Analysis

Figure 2A:
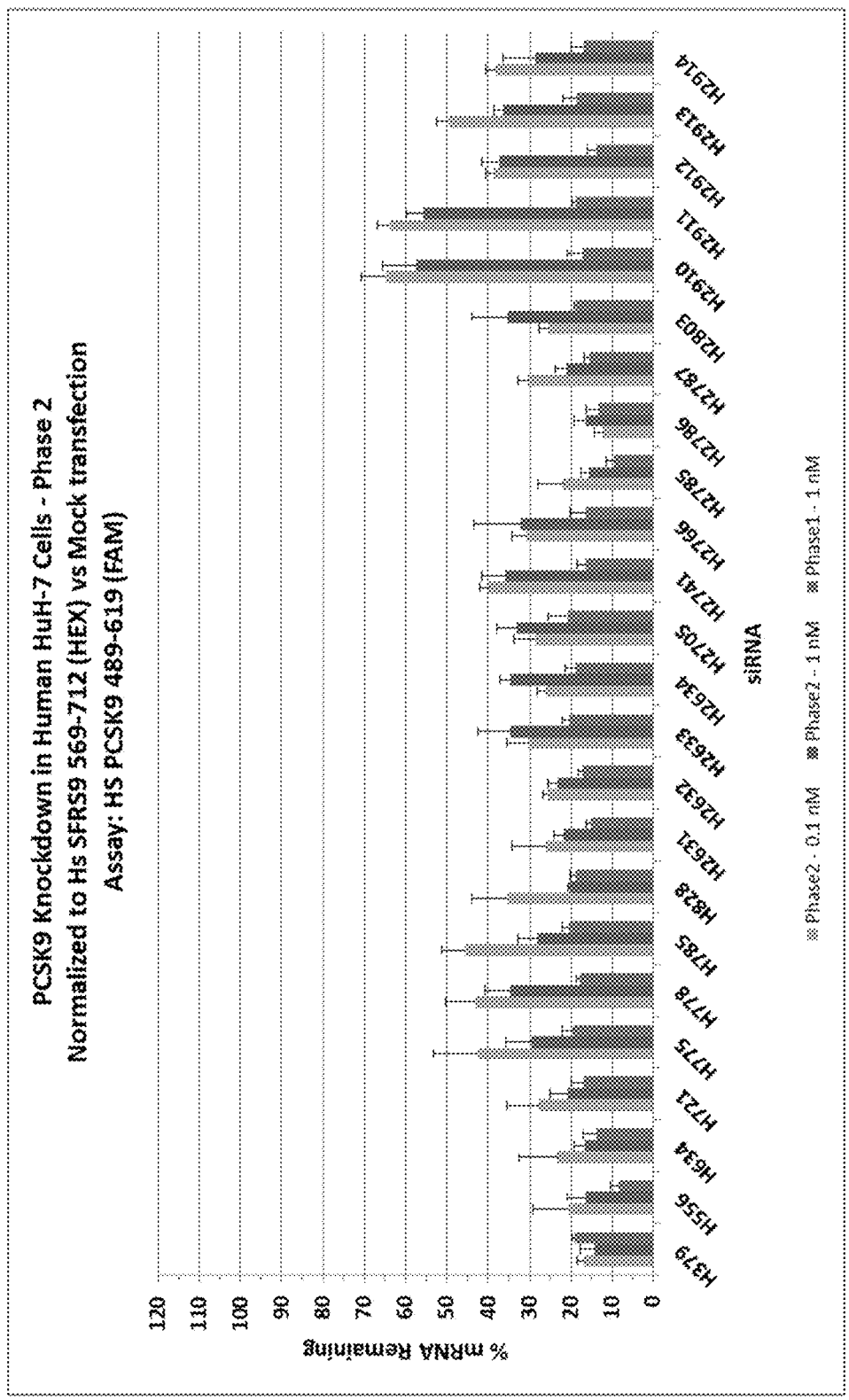
FIGS. 2A-2D are a set of graphs showing the percentage of mRNA remaining after PCSK9 oligonucleotide screening of 96 PCSK9 oligonucleotides at two different concentrations (0.1 nM and 1 nM) in Huh-7 cells. The H number on the X-axis indicates the position in the PCSK9 mRNA mapping to the 5' end of the antisense strand of the oligonucleotides.
Figure 2A:
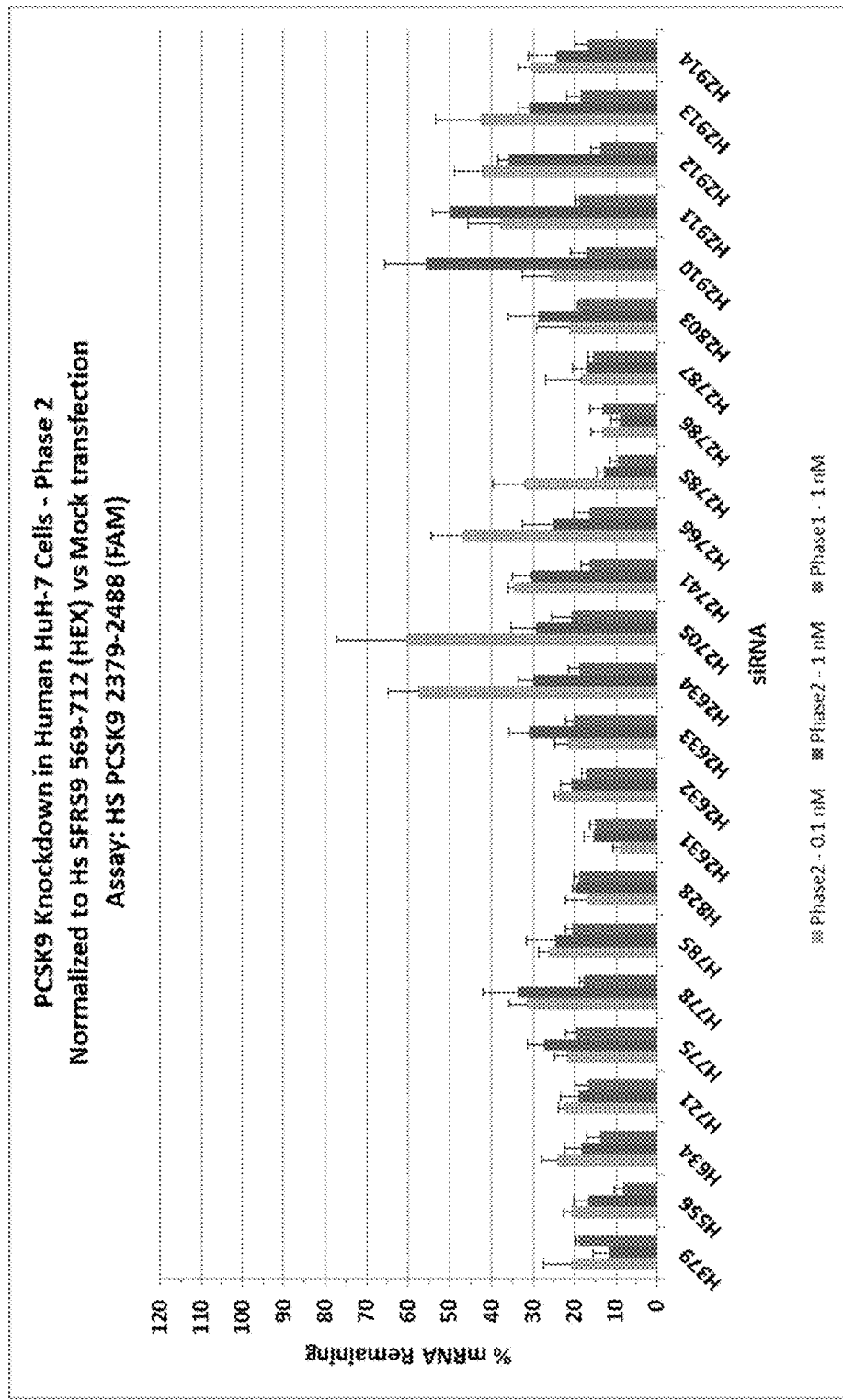
Figure 2B:
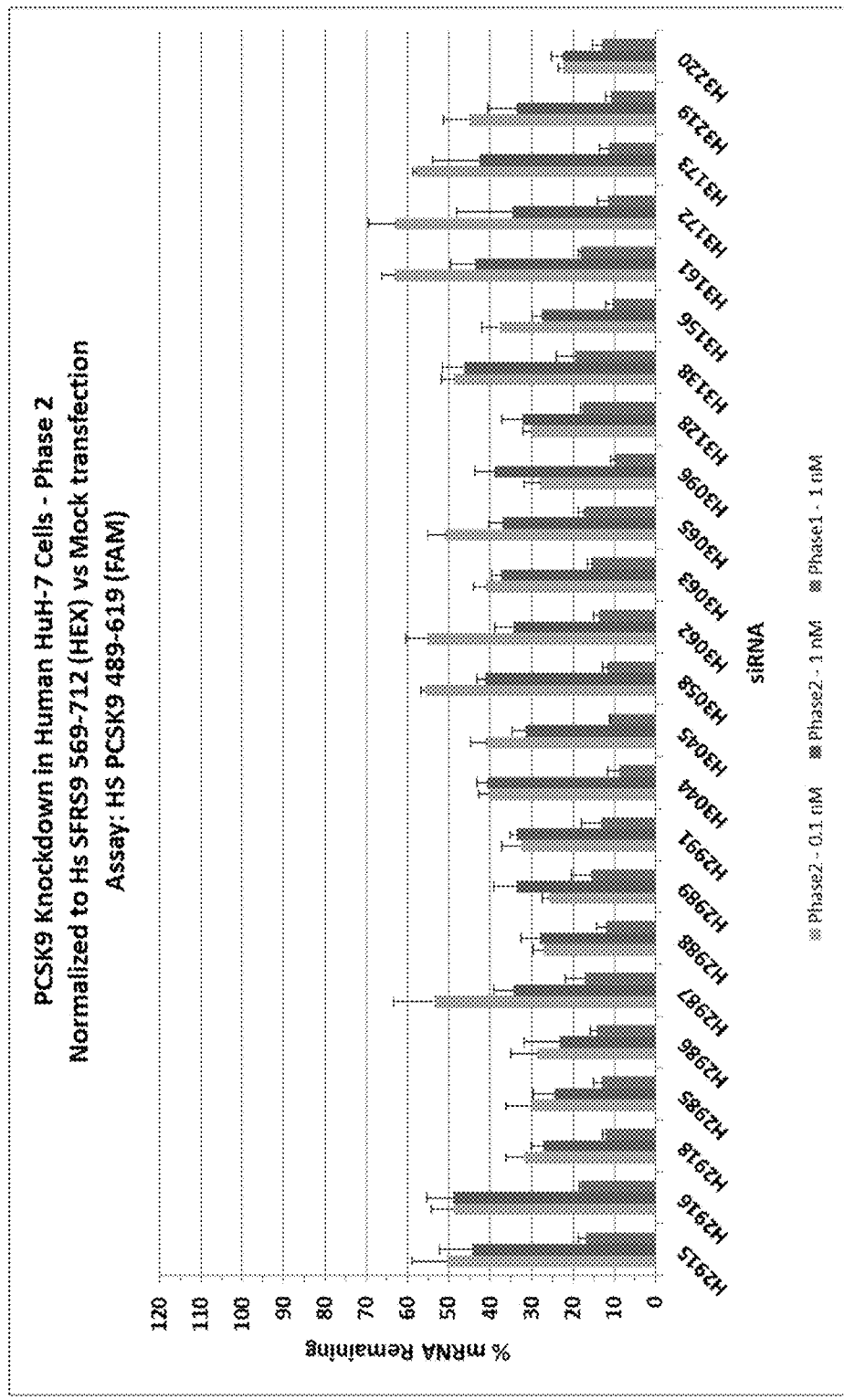
Figure 2B:
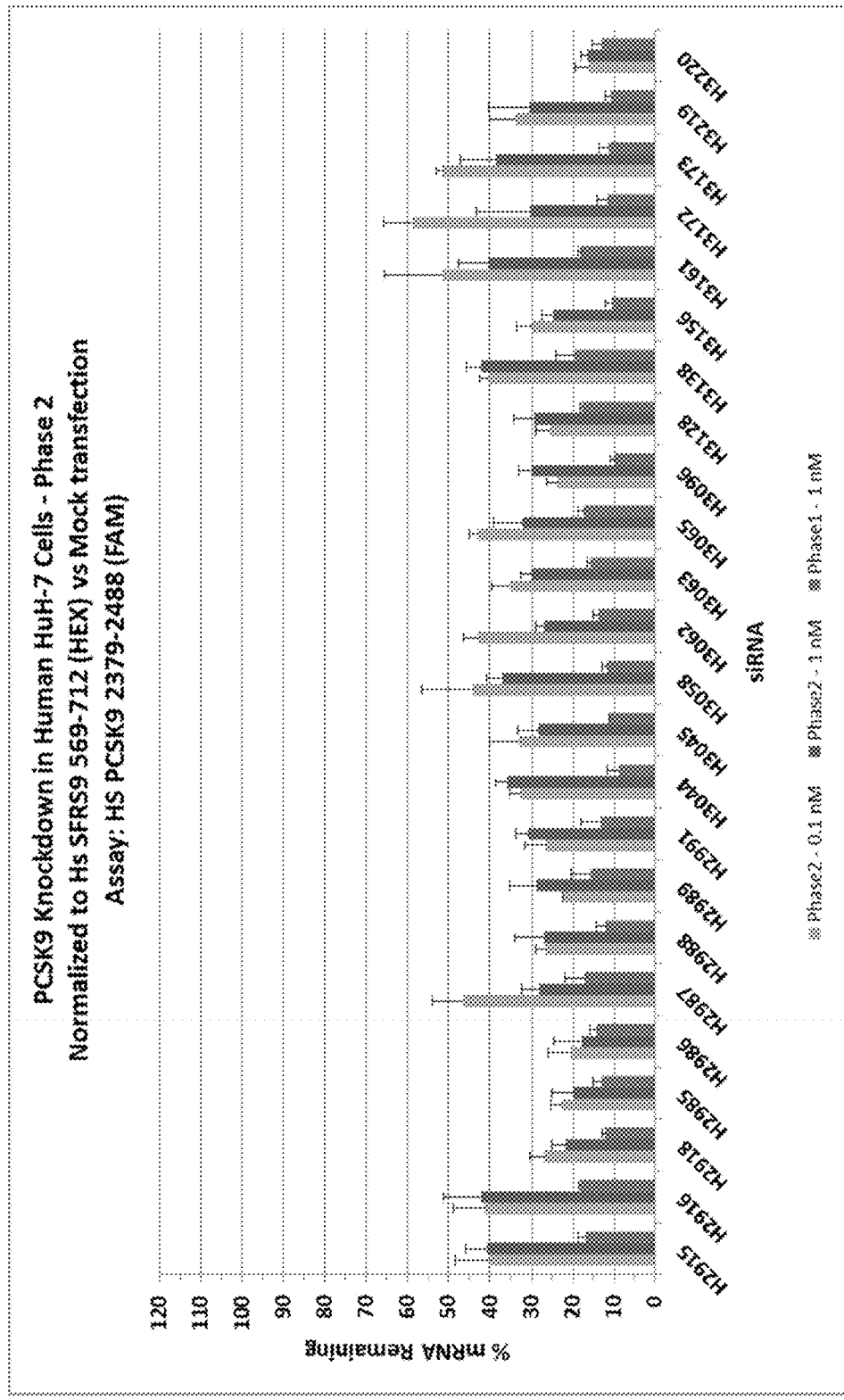
Figure 2C:
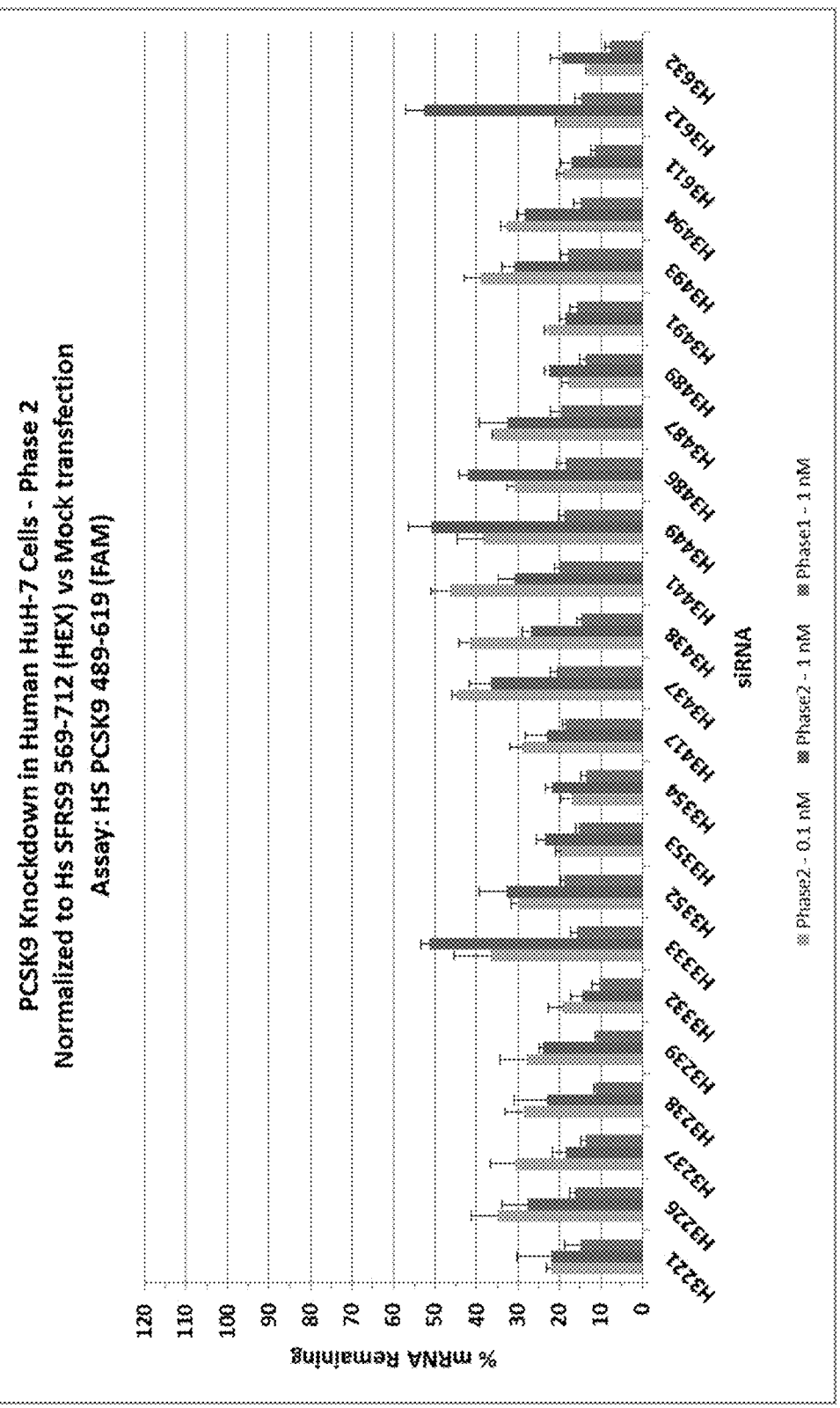
Figure 2C:
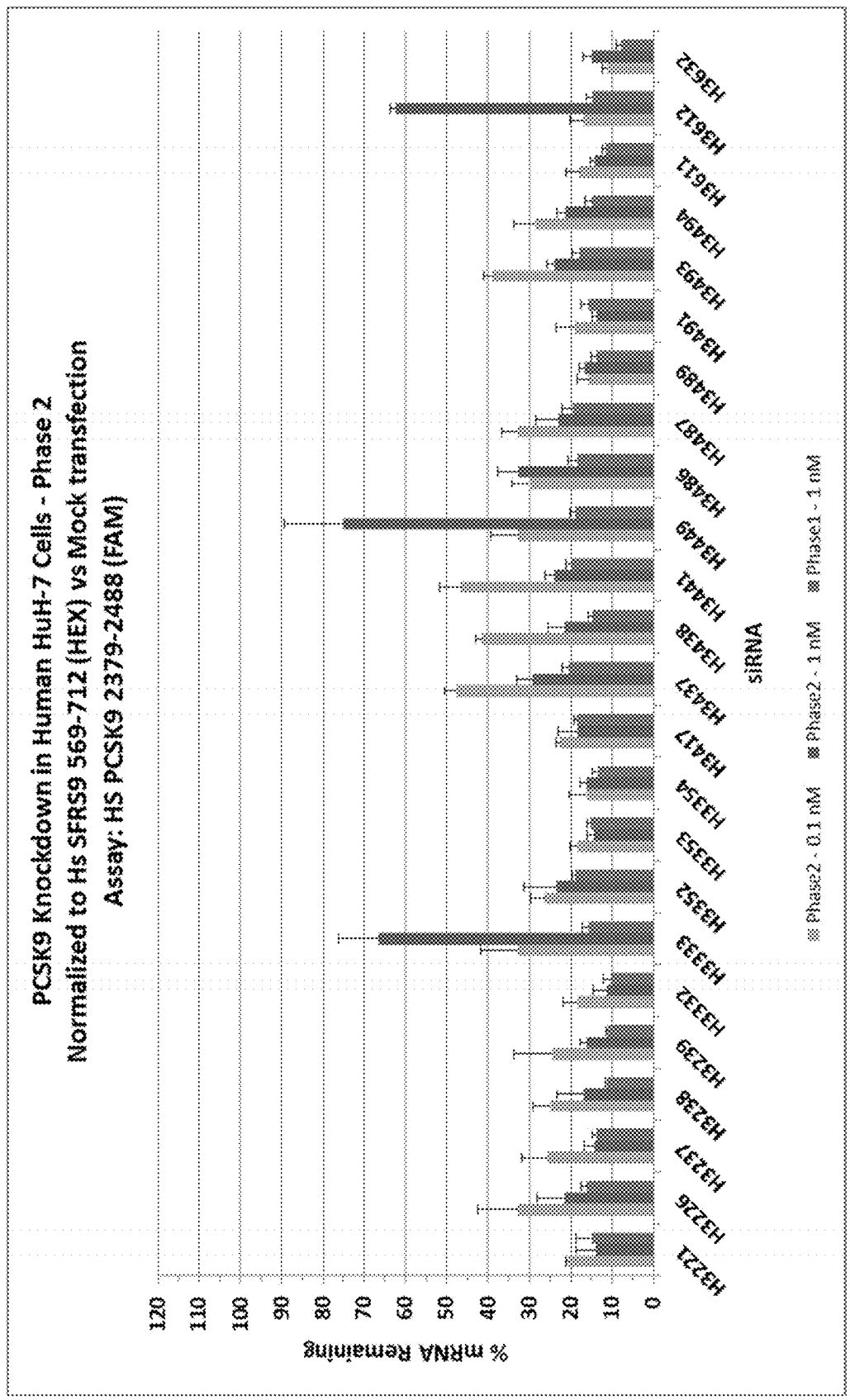
Figure 2D:
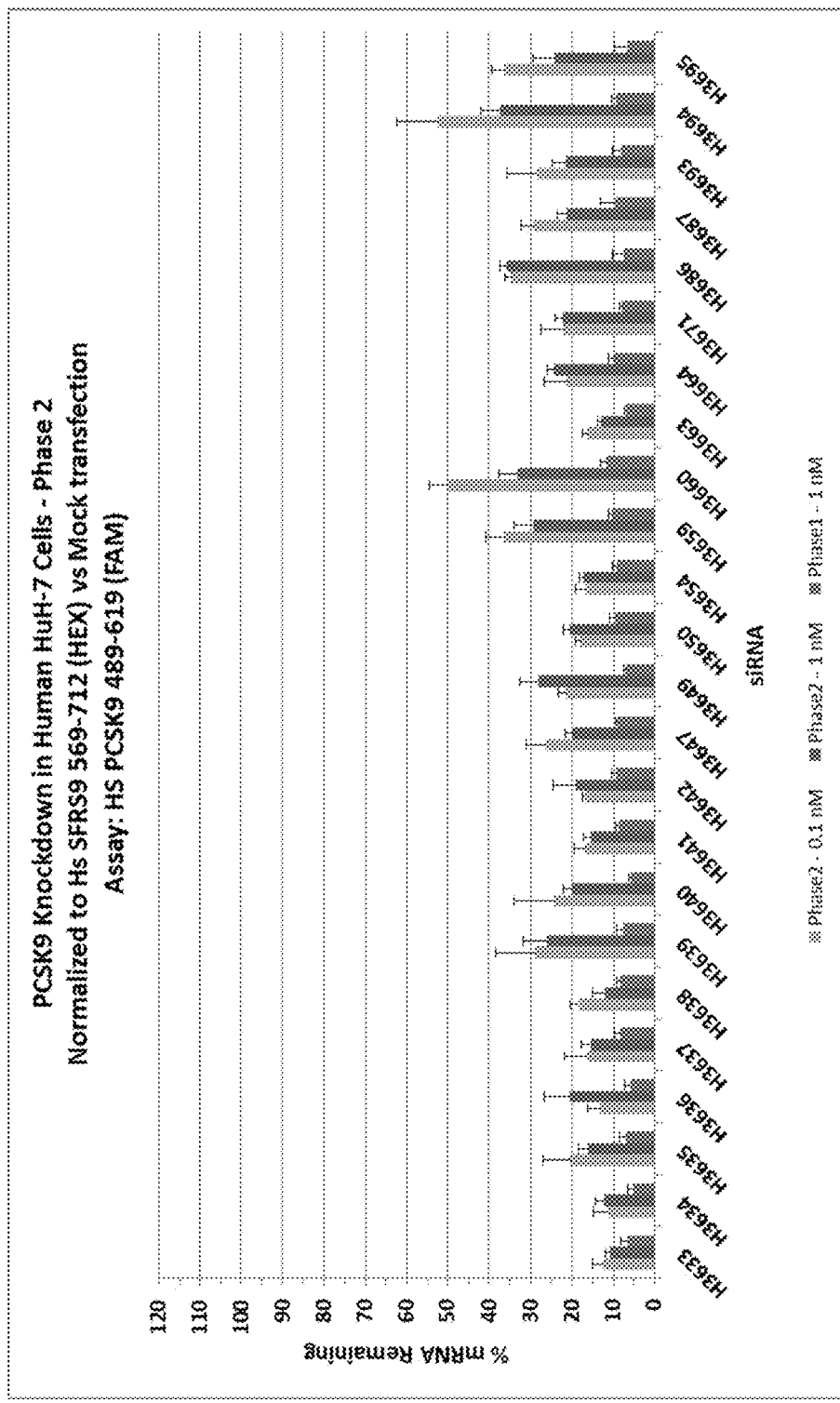
Figure 2D:
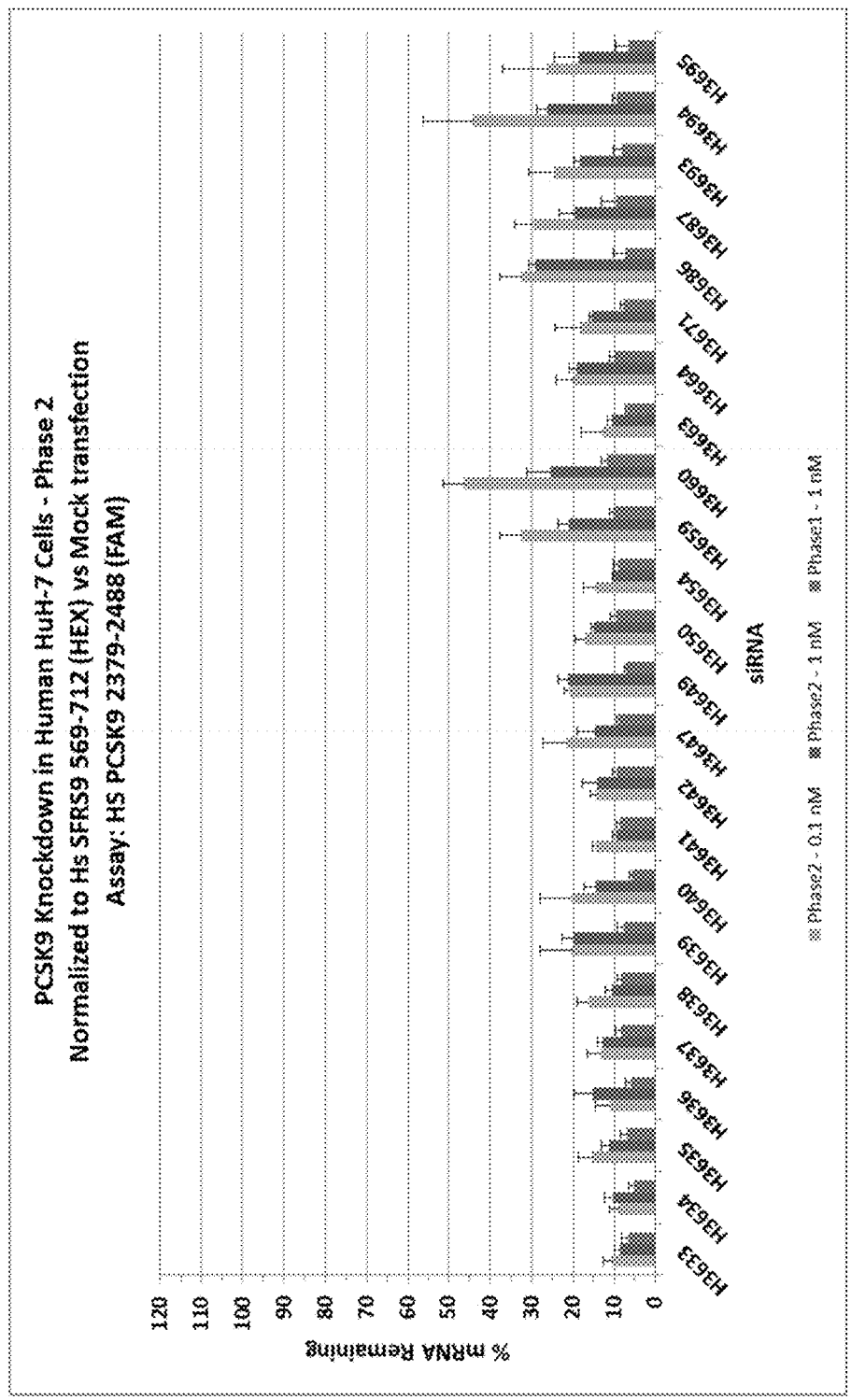

Of the 576 oligonucleotides evaluated in the initial Huh-7 cell-based assay, 96 particularly active oligonucleotides were selected as hits based on their ability to knock down PCSK9 levels and were subjected to a secondary screen (FIGS. 2A and 2B).

In this secondary screen, the candidate oligonucleotides were tested using the same assay as in the primary screen, but at two different concentrations 0.1 nM and 1 nM (FIGS. 2A and 2B). The target mRNA levels were generally normalized based on splicing factor, arginine/serine-rich 9 (SFRS9), a housekeeping gene that provides a stable expression reference across samples, to generate the percent mRNA shown in FIGS. 2A and 2B. The tested oligonucleotides in each of FIGS. 2A and 2B are shown compared to mock transfection control. All 96 oligonucleotides had the same modification pattern, designated M1, which contains a combination of ribonucleotides, deoxyribonucleotides and 2'-O-methyl modified nucleotides. The sequences of the 96 oligonucleotides tested are provided in Table 3.

TABLE 3

Candidate oligonucleotide Sequences for Huh-7 Cell-Based Assay

| Sense SEQ ID NO. | Corresponding Antisense SEQ ID NO. |
|---|---|
| 35, 41, 51, 53, 56-58, 66, 177-180, 187, 192, 196, 201-204, 219-225, 227, 237-241, 243, 248, 249, 257, 261, 262, 264, 266, 268, 274, 280, 281, 288-292, 297, 304-306, 315, 316, 320-322, 328-330, 333, 334, 344, 345, 347, 349, 351, 352, | 488, 494, 504, 506, 509-511, 519, 630-633, 640, 645, 649, 654-657, 672-678, 680, 690-694, 696, 701, 702, 710, 714, 715, 717, 719, 721, 727, 733, 734, 741-745, 750, 757-759, 768, 769, 773-775, 781-783, 786, 787, 797, 798, 800, 802, |

TABLE 3-continued

Candidate oligonucleotide Sequences for Huh-7 Cell-Based Assay

| Sense SEQ ID NO. | Corresponding Antisense SEQ ID NO. |
|---|---|
| 374, 375, 385-395, 400-402, 405, 408-411, 418, 433, 434, 440-442 | 804, 805, 827, 828, 838-848, 853-855, 858, 861-864, 871, 886, 887, 893-895 |

Sense and antisense SEQ ID NO. columns provide the sense strand and respective antisense strand, in relative order, that are hybridized to make each oligonucleotide. For example, sense strand of SEQ ID NO: 35 hybridizes with antisense strand of SEQ ID NO: 488; each of the oligonucleotides tested had the same modification pattern.

At this stage, the most potent sequences from the testing were selected for further analysis. The selected sequences were converted to a nicked tetraloop conjugate structure format (a 36-mer passenger strand with a 22-mer guide strand). See FIG. 3 for a generic tetraloop conjugate structure. Four GalNAc moieties were conjugated to nucleotides in the tetraloop of the sense strand. Conjugation was performed using a click linker. The GalNAc used was as shown below:

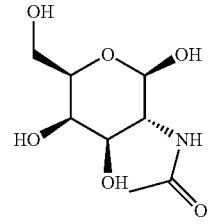

N-Acetyl-b-D-galactosamine (CAS#: 14131-60-3)

These oligonucleotides were then tested as before, and each oligonucleotide was evaluated at two concentrations for its ability to reduce PCSK9 mRNA expression in vitro, using Huh-7 cells, as well as in vivo, using a mouse HDI model.

In Vivo Murine Screening and In Vitro Human Cell Line Screening

Figure 4:
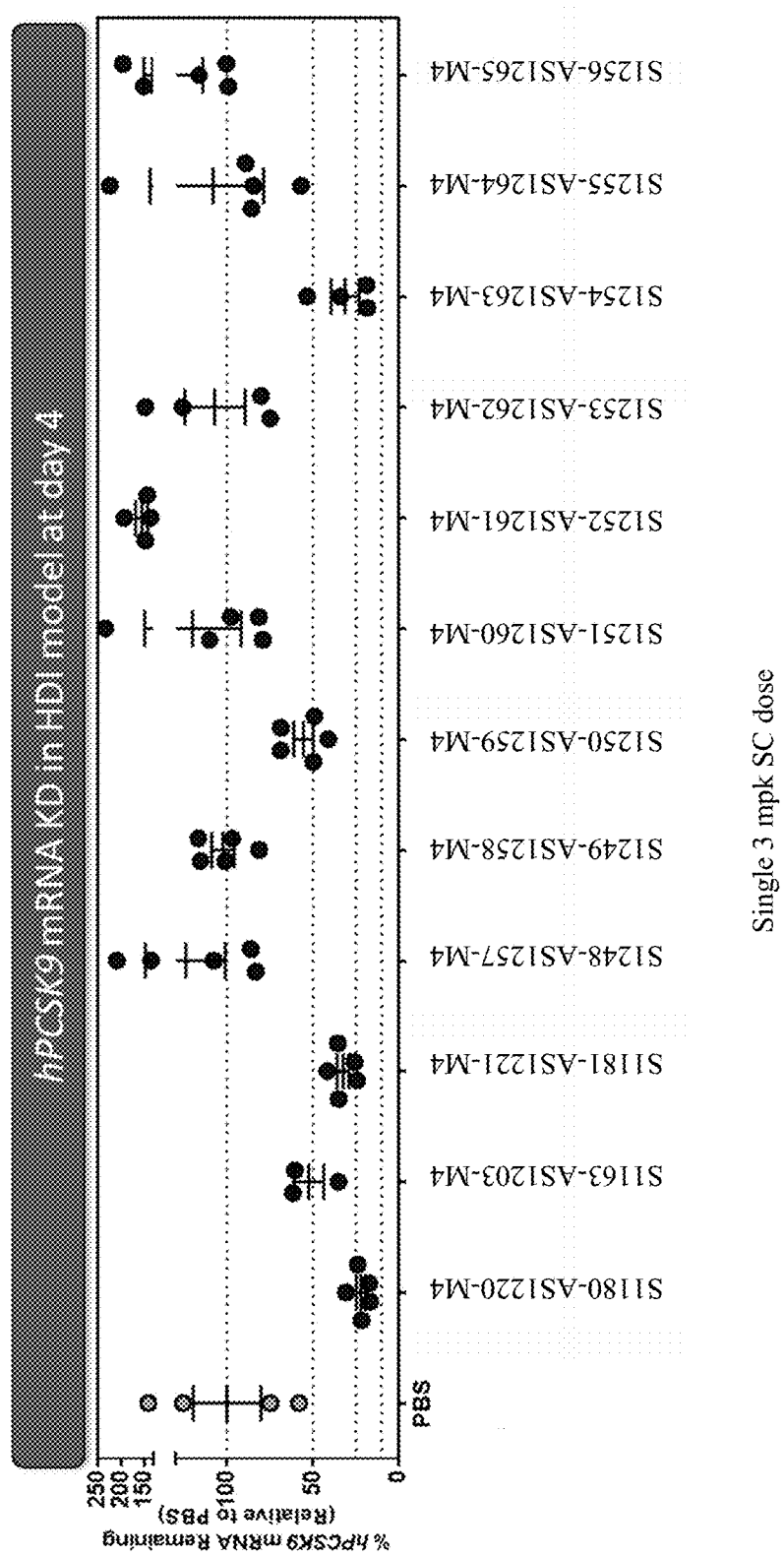
FIG. 4 is a graph showing the results of screening in a mouse hydrodynamic injection (HDI) model using PCSK9 tetraloop conjugates of 12 different base sequences with a single modification pattern. PBS, shown on the far left, was used as a control.

Data from the above in vitro experiments were assessed to identify tetraloops and modification patterns that would improve delivery properties while maintaining activity for reduction of PCSK9 expression in the mouse hepatocytes. As shown in FIG. 4, 12 human PCSK9 tetraloop conjugates with a range of modifications were dosed subcutaneously into mice at a concentration of 3 mg/kg. Animals were administered 2 ml of human PCSK9 plasmid (pcDNA3.1-hPCSK9, total 16 µg) suspended in PBS per animal by tail vein (intravenous) injection on day 3 after the subcutaneous dosing of tetraloop conjugates. Mice were euthanized on day 4 following administration. Liver samples were obtained and RNA was extracted to evaluate PCSK9 mRNA levels by RT-qPCR. The percent PCSK9 mRNA as compared to PBS control mRNA was determined based on these measurements.

Figure 5A:
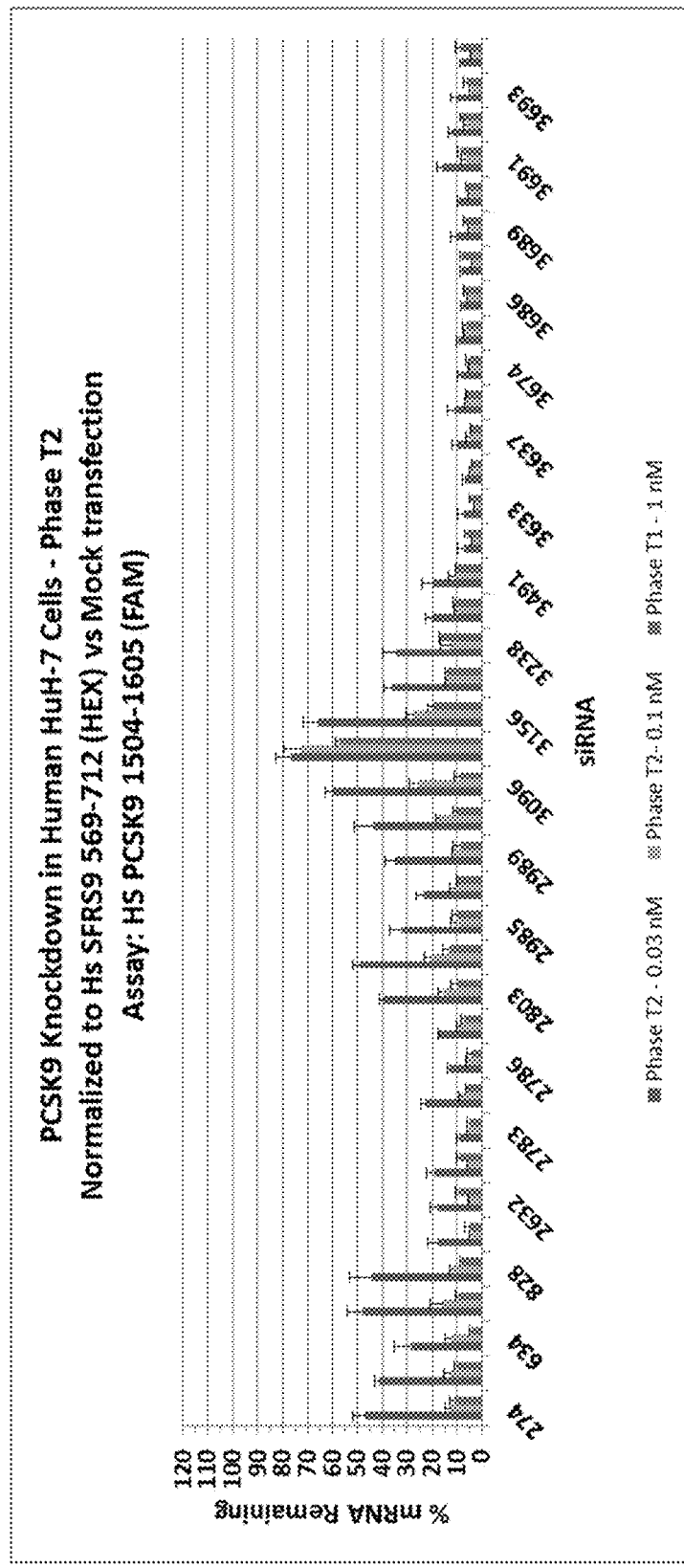
FIGS. 5A-5C are graphs showing the results of screening in Huh-7 cells (FIG. 5A) and in a mouse HDI model (FIGS. 5B and 5C) using PCSK9 oligonucleotides of different base sequences.
Figure 5B:
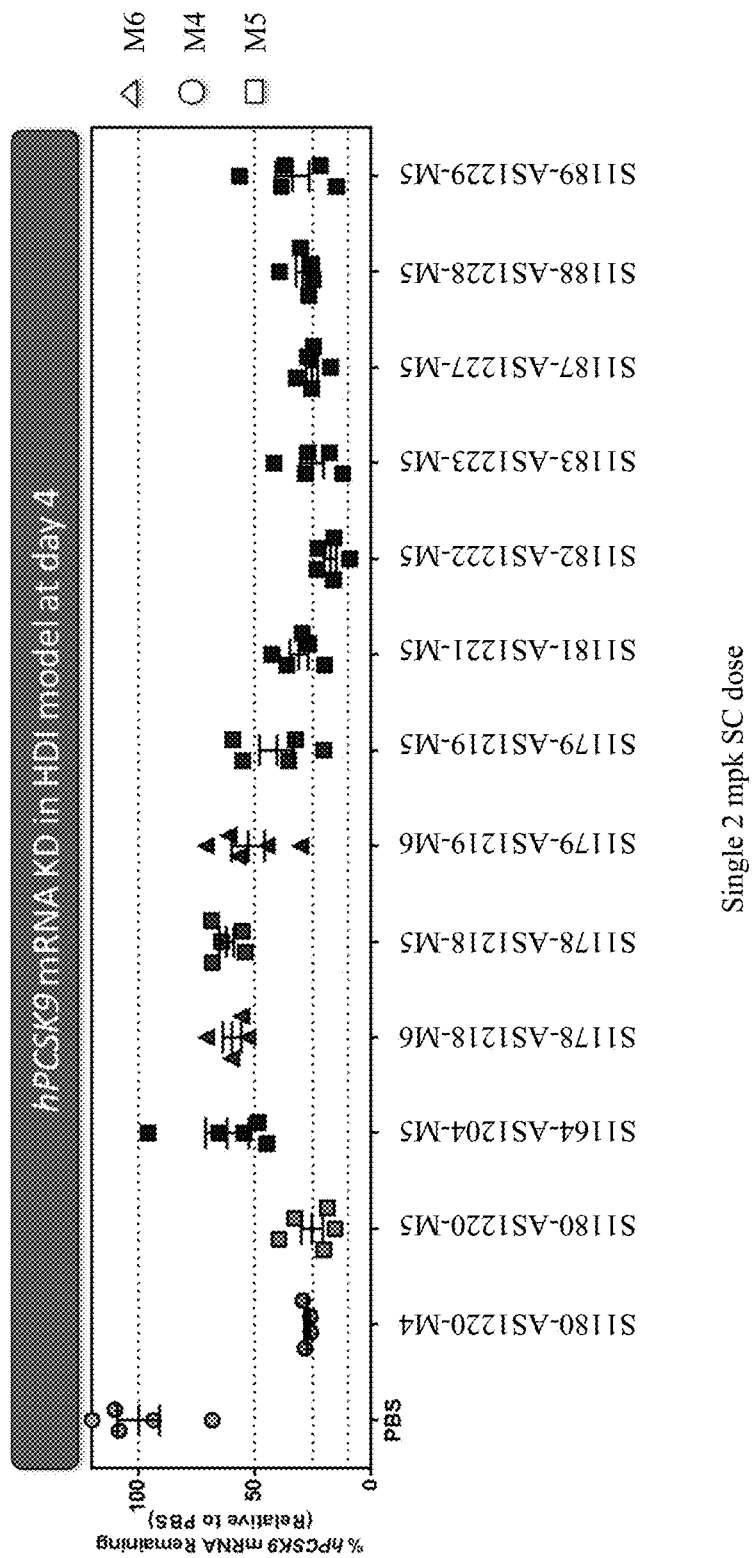
Figure 5C:
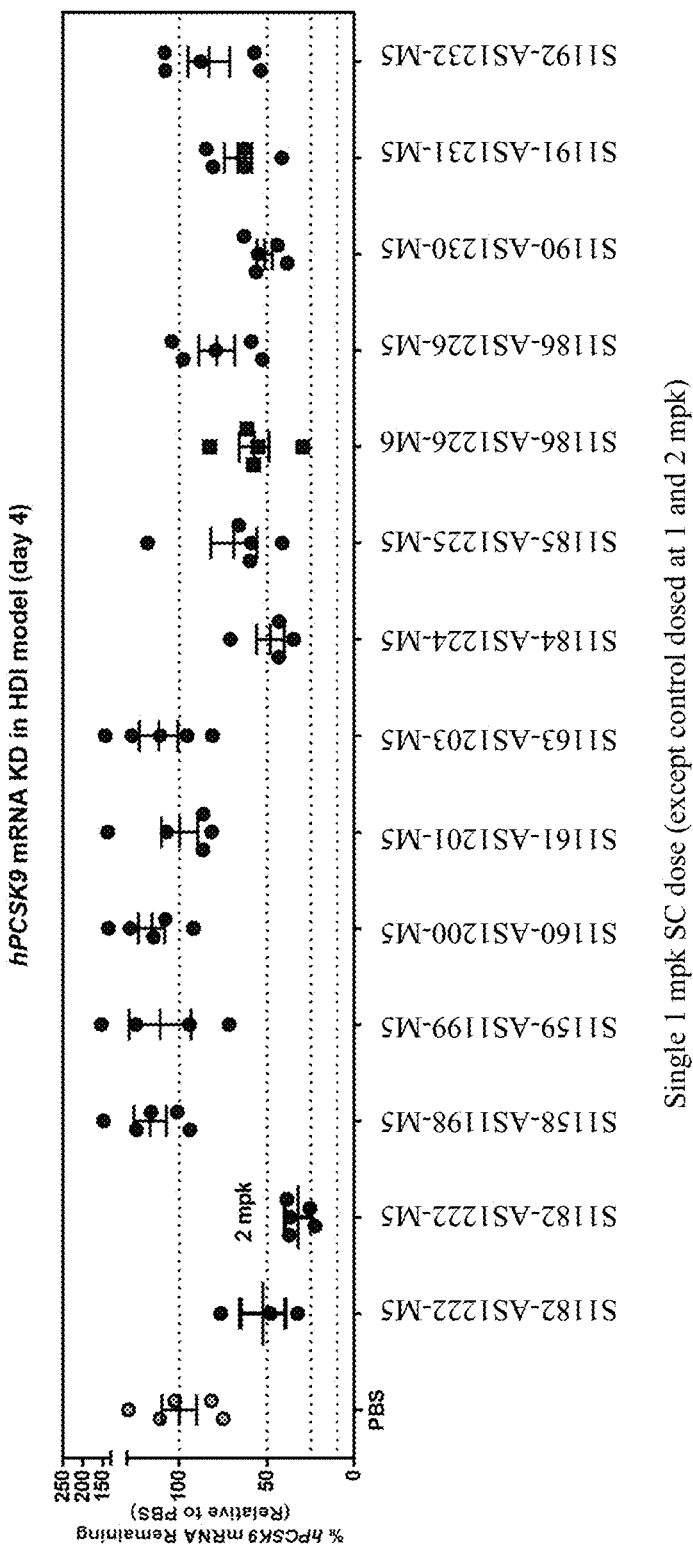

Further tetraloop sequences were tested in human Huh-7 cells at two different concentrations (0.03 nM and 0.1 nM in tetraloop formation; labeled as "Phase T2") (FIG. 5A). From the 40 tetraloop oligonucleotides tested (shown in FIG. 5A), 21 different base sequences were selected to be scaled up as 5'-MOP/GalNAc conjugates for further in vivo testing (FIGS. 5B and 5C). The PCSK9 oligonucleotides were subcutaneously administered to CD-1 mice transiently expressing human PCSK9 mRNA by hydrodynamic injection (HDI) of a human PCSK9 expression plasmid (pcDNA3.1-hPCSK9, total 16 µg). Mice were euthanized on day 4 following administration. Liver samples were obtained and RNA was extracted to evaluate PCSK9 mRNA levels by RT-qPCR. The percent PCSK9 mRNA as compared to PBS control mRNA was determined based on these measurements. As shown in FIGS. 5B-5C, different concentrations (1 mg/kg and 2 mg/kg) were used for the candidate molecules. A candidate of sense sequence SEQ ID NO: 1182 and antisense sequence SEQ ID NO: 1222 may be seen in both FIG. 5B and FIG. 5C.

Figure 6A:
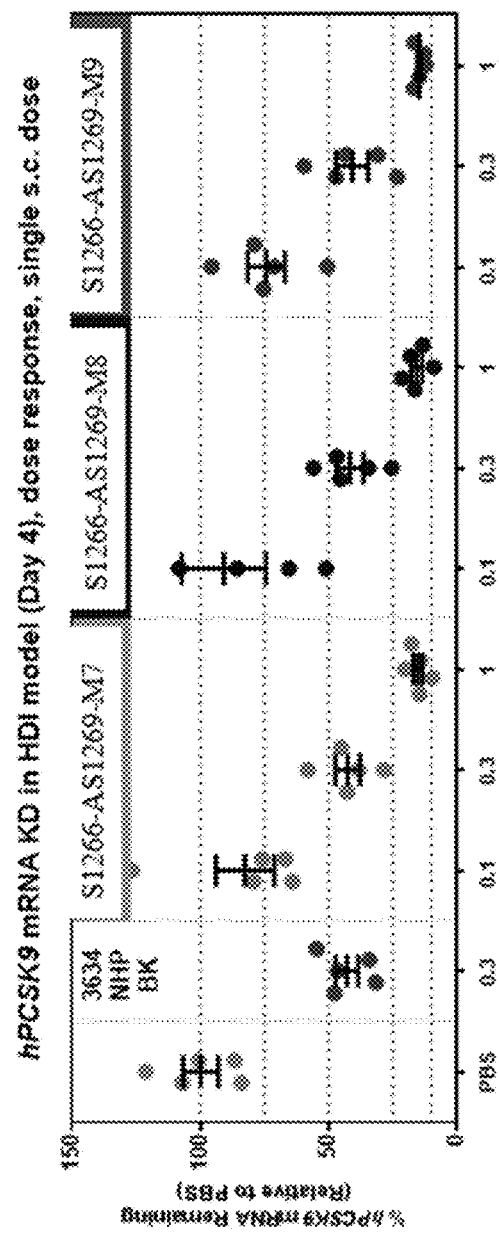
FIGS. 6A and 6B are graphs showing the results of screening in a mouse hydrodynamic injection (HDI) model using three different PCSK9 tetraloop conjugates with varied modification patterns at three different concentrations. PBS, shown on the far left, was used as a control.
Figure 6B:
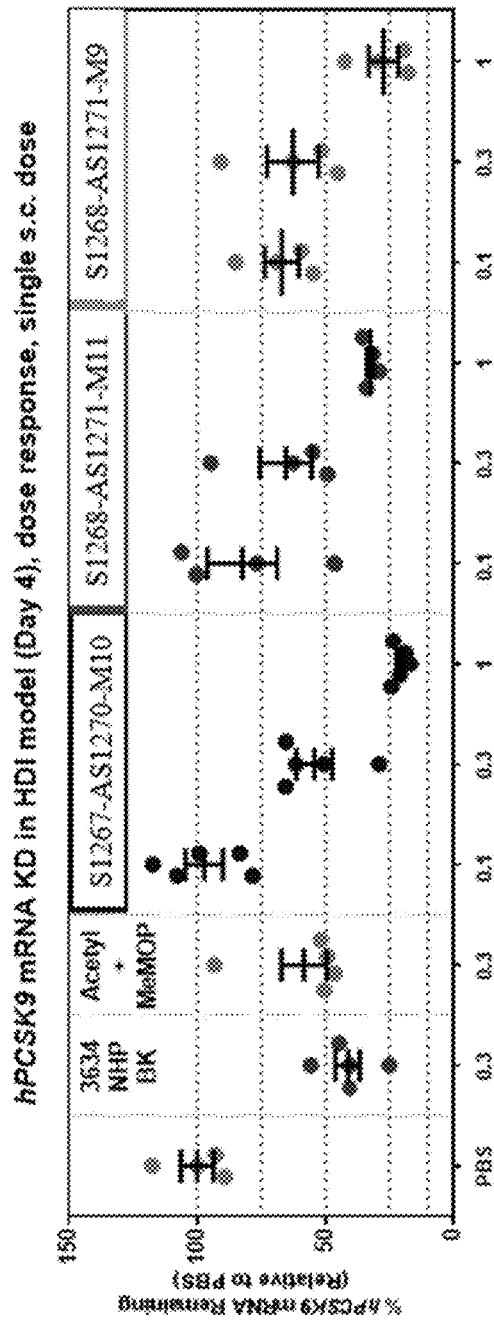

Additional testing of certain PCSK9 oligonucleotides in the mouse HDI model described above was performed using three different PCSK9 tetraloop conjugates with varied modification patterns at three different concentrations (0.1 mg/kg, 0.3 mg/kg, and 1 mg/kg). Results are shown in FIGS. 6A and 6B.

In Vivo Non-Human Primate Screening

Figure 7A:
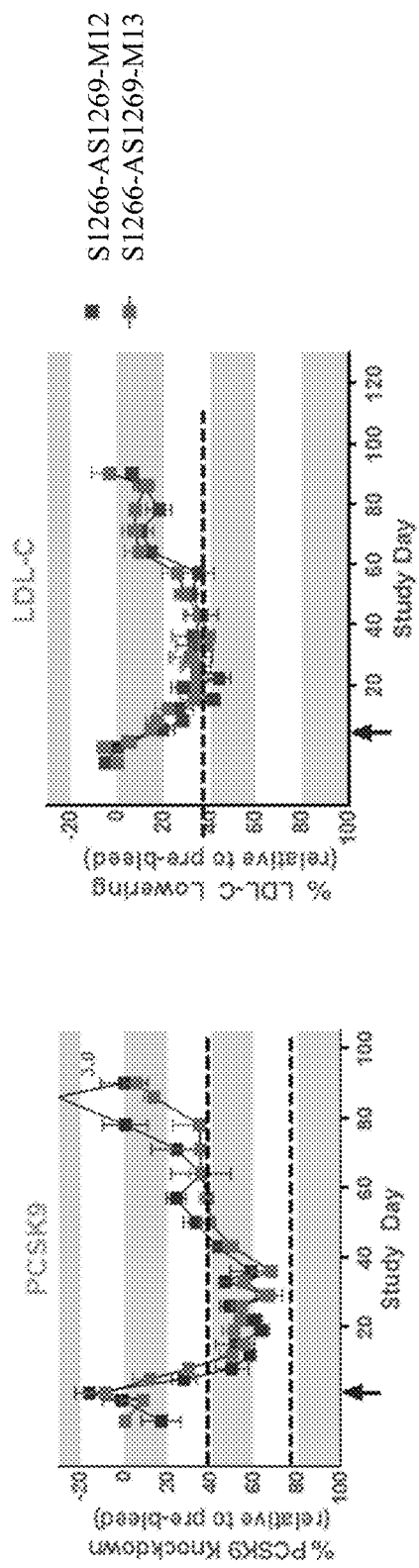
FIGS. 7A-7D are graphs showing an in vivo activity evaluation of PCSK9 oligonucleotides in a tetraloop conjugate in non-human primates. Candidate sequences were tested with different modifications.
Figure 7B:
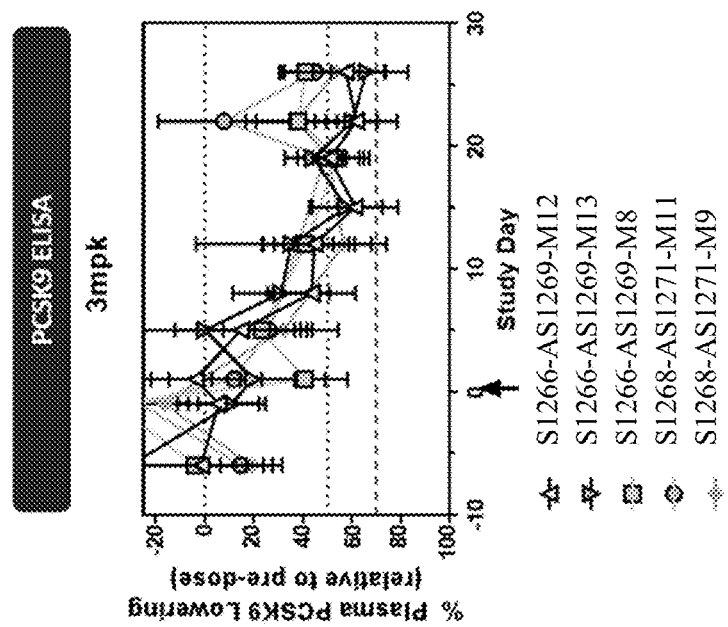
Figure 7C:
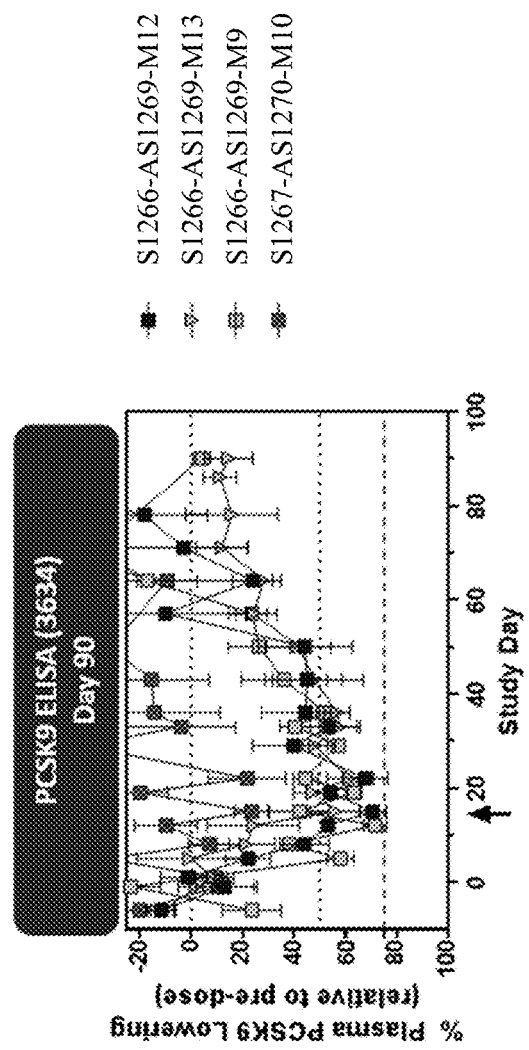
Figure 7D:
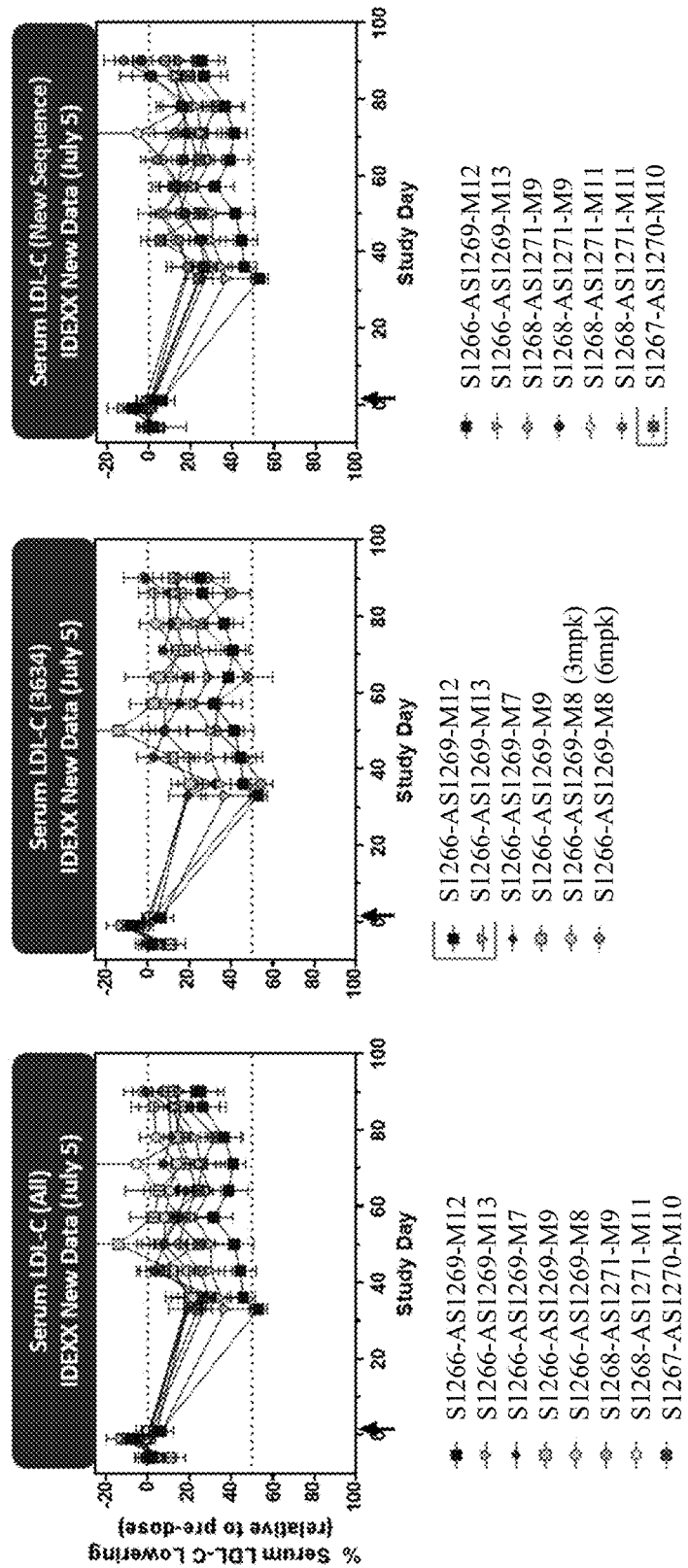

An additional study was performed to evaluate PCSK9 mRNA KD with tetraloop conjugates in non-human primates. Cynomolgus monkeys (n=4 per group) were administered 3 or 6 mg/kg subcutaneously in a single dose. Clinical observations were recorded daily, and blood samples were taken three times prior to the dosing and twice a week until day 36 and weekly through day 90. Serum samples were analyzed for a standard LFT panel (ALT, AST, ALP, and GGT), as well as LDL-c, HDL-c, total cholesterol, and TG. Three sets of sequences (sense and antisense) were tested: S1266-AS1269, S1267-AS1270, and S1268-AS1271 and results are shown in FIGS. 7A-7C. All three sets of sequences were able to reduce plasma levels of PCSK9 relative to the pre-dose levels.

Materials and Methods

Transfection

For the first screen, Lipofectamine RNAiMAX™ was used to complex the oligonucleotides for efficient transfection. Oligonucleotides, RNAiMAX and Opti-MEM incubated together at room temperature for 20 minutes and then 50 µL of this mix was added per well to plates prior to transfection. Media was aspirated from a flask of actively passaging cells and the cells were incubated at 37° C. in the presence of trypsin for 3-5 minutes. After cells no longer adhered to the flask, cell growth media (lacking penicillin and streptomycin) was added to neutralize the trypsin and to suspend the cells. A 10 µL aliquot was removed and cells were counted with a hemocytometer to quantify the cells on a per milliliter basis. A diluted cell suspension was added to the 96-well transfection plates, which already contained the oligonucleotides in Opti-MEM. The transfection plates were then incubated for 24 hours at 37° C. After 24 hours of incubation, media was aspirated from each well.

For subsequent screens and experiments, e.g., the secondary screen, Lipofectamine RNAiMAX was used to complex the oligonucleotides for reverse transfection. The complexes were made by mixing RNAiMAX and siRNAs in OptiMEM medium for 15 minutes. The transfection mixture was transferred to multi-well plates and cell suspension was added to the wells. After 24 hours incubation the cells were washed once with PBS and then processed described above.

Hydrodynamic injection (HDI)

CD-1 female mice were obtained from Charles River Laboratories. All mice were maintained in an AALAC and IACUC approved animal facility at the Dicerna Pharmaceuticals. Animals were divided into appropriate number of study groups and dosed with the test article assigned to that group. Animals were dosed subcutaneously with the PCSK tetraloop conjugates. Animals were administered with 2 ml hPCSK9 plasmid suspended in PBS per animal by tail vein intravenous injection on day 3 after the subcutaneous dosing of tetraloop conjugate. Mice were sacrificed on days 4 via $CO_2$ asphyxiation and liver tissue was collected. Liver tissue was collected by taking two 4 mm punch biopsies and processed to RNA isolation, cDNA synthesis, q-RT PCR, according the manufacturer's protocol. pcDNA3.1-hPCSK9 plasmid encoding the human PCSK9 (NM_174936.3) gene (hPCSK9) was synthesized by Genewiz.

cDNA Synthesis

Cells were lysed for 5 minutes using the iScript RT-qPCR sample preparation buffer from Bio-Rad. The supernatants containing total RNA were then stored at −80° C. or used for reverse transcription using the High Capacity Reverse Transcription kit (Life Technologies) in a 10 microliter reaction. The cDNA was then diluted to 50 µL with nuclease free water and used for quantitative PCR with multiplexed 5′-endonuclease assays and SSoFast qPCR mastermix (Bio-Rad laboratories).

qPCR Assays

For each target, mRNA levels were quantified by two 5′ nuclease assays. In general, several assays are screened for each target. The two assays selected displayed a combination of good efficiency, low limit of detection, and broad 5′→3′ coverage of the gene of interest (GOI). Both assays against one GOI could be combined in one reaction when different fluorophores were used on the respective probes. Thus, the final step in assay validation was to determine the efficiency of the selected assays when they were combined in the same qPCR or "multi-plexed."

Linearized plasmids for both assays in 10-fold dilutions were combined and qPCR was performed. The efficiency of each assay was determined as described above. The accepted efficiency rate was 90-110%.

While validating multi-plexed reactions using linearized plasmid standards, $C_q$ values for the target of interest were also assessed using cDNA as the template. The cDNA, in this case, was derived from RNA isolated on the Corbett (~5 ng/µl in water) from untransfected cells. In this way, the observed $C_q$ values from this sample cDNA were representative of the expected $C_q$ values from a 96-well plate transfection. In cases where $C_q$ values were greater than 30, other cell lines were sought that exhibit higher expression levels of the gene of interest. A library of total RNA isolated from via high-throughput methods on the Corbett from each human and mouse line was generated and used to screen for acceptable levels of target expression.

Description of Oligonucleotide Nomenclature

All oligonucleotides described herein are designated either $SN_1$-$ASN_2$-$MN_3$. The following designations apply:

$N_1$: sequence identifier number of the sense strand sequence $N_2$: sequence identifier number of the antisense strand sequence $N_3$: reference number of modification pattern, in which each number represents a pattern of modified nucleotides in the oligonucleotide.

For example, S1-AS454-M1 represents an oligonucleotide with a sense sequence that is set forth by SEQ ID NO: 1, an antisense sequence that is set forth by SEQ ID NO: 454, and which is adapted to a modification pattern identified as M1.

TABLE 4

Oligonucleotide Sequences

| App Name | Sense Sequence/mRNA seq | S SEQ ID NO | Antisense Sequence | AS SEQ ID NO |
|---|---|---|---|---|
| S1-AS454-M1 | AAGCACCCACACCCUAGAAUGUUTC | 1 | GAAACAUUCUAGGGUGUGGGUGCUUGA | 454 |
| S2-AS455-M1 | AGCACCCACACCCUAGAAGUUUUCC | 2 | GGAAAACUUCUAGGGUGUGGGUGCUUG | 455 |
| S3-AS456-M1 | GCACCCACACCCUAGAAGGUUUCCG | 3 | CGGAAACCUUCUAGGGUGUGGGUGCUU | 456 |
| S4-AS457-M1 | ACCCACACCCUAGAAGGUUUCCGCA | 4 | UGCGGAAACCUUCUAGGGUGUGGGUGC | 457 |
| S5-AS458-M1 | CCCACACCCUAGAAGGUUUUCGCAG | 5 | CUGCGAAAACCUUCUAGGGUGUGGGUG | 458 |
| S6-AS459-M1 | AGUUCAGGGUCUGAGCCUGUAGGAG | 6 | CUCCUACAGGCUCAGACCCUGAACUGA | 459 |
| S7-AS460-M1 | GUUCAGGGUCUGAGCCUGGAGGAGT | 7 | ACUCCUCCAGGCUCAGACCCUGAACUG | 460 |
| S8-AS461-M1 | UUCAGGGUCUGAGCCUGGAUGAGTG | 8 | CACUCAUCCAGGCUCAGACCCUGAACU | 461 |
| S9-AS462-M1 | UCAGGGUCUGAGCCUGGAGUAGUGA | 9 | UCACUACUCCAGGCUCAGACCCUGAAC | 462 |
| S10-AS463-M1 | AGGGUCUGAGCCUGGAGGAUUGAGC | 10 | GCUCAAUCCUCCAGGCUCAGACCCUGA | 463 |
| S11-AS464-M1 | GGUCUGAGCCUGGAGGAGUUAGCCA | 11 | UGGCUAACUCCUCCAGGCUCAGACCCU | 464 |
| S12-AS465-M1 | AGGAUUCCGCGCGCCCCUUUACGCG | 12 | CGCGUAAAGGGGCGCGCGGAAUCCUGG | 465 |
| S13-AS466-M1 | GGAUUCCGCGCGCCCCUUCACGCGC | 13 | GCGCGUGAAGGGGCGCGCGGAAUCCUG | 466 |
| S14-AS467-M1 | UCACGCGCCCUGCUCCUGAACUUCA | 14 | UGAAGUUCAGGAGCAGGGCGCGUGAAG | 467 |
| S15-AS468-M1 | CACGCGCCCUGCUCCUGAAUUUCAG | 15 | CUGAAAUUCAGGAGCAGGGCGCGUGAA | 468 |
| S16-AS469-M1 | CCCUGCUCCUGAACUUCAGUUCCTG | 16 | CAGGAACUGAAGUUCAGGAGCAGGGCG | 469 |
| S17-AS470-M1 | CUGCUCCUGAACUUCAGCUUCUGCA | 17 | UGCAGAAGCUGAAGUUCAGGAGCAGGG | 470 |
| S18-AS471-M1 | UGCUCCUGAACUUCAGCUCUUGCAC | 18 | GUGCAAGAGCUGAAGUUCAGGAGCAGG | 471 |
| S19-AS472-M1 | GCUCCUGAACUUCAGCUCCUGCACA | 19 | UGUGCAGGAGCUGAAGUUCAGGAGCAG | 472 |
| S20-AS473-M1 | CUCCUGAACUUCAGCUCCUUCACAG | 20 | CUGUGAAGGAGCUGAAGUUCAGGAGCA | 473 |
| S21-AS474-M1 | UCCUGAACUUCAGCUCCUGUACAGT | 21 | ACUGUACAGGAGCUGAAGUUCAGGAGC | 474 |
| S22-AS475-M1 | CCUGAACUUCAGCUCCUGCACAGTC | 22 | GACUGUGCAGGAGCUGAAGUUCAGGAG | 475 |
| S23-AS476-M1 | CUGAACUUCAGCUCCUGCAUAGUCC | 23 | GGACUAUGCAGGAGCUGAAGUUCAGGA | 476 |
| S24-AS477-M1 | UGAACUUCAGCUCCUGCACAGUCCT | 24 | AGGACUGUGCAGGAGCUGAAGUUCAGG | 477 |
| S25-AS478-M1 | GAACUUCAGCUCCUGCACAUUCCTC | 25 | GAGGAAUGUGCAGGAGCUGAAGUUCAG | 478 |
| S26-AS479-M1 | AACUUCAGCUCCUGCACAGUCCUCC | 26 | GGAGGACUGUGCAGGAGCUGAAGUUCA | 479 |
| S27-AS480-M1 | ACUUCAGCUCCUGCACAGUUCUCCC | 27 | GGGAGAACUGUGCAGGAGCUGAAGUUC | 480 |
| S28-AS481-M1 | CUUCAGCUCCUGCACAGUCUUCCCC | 28 | GGGGAAGACUGUGCAGGAGCUGAAGUU | 481 |
| S29-AS482-M1 | ACAGUCCUCCCCACCGCAAUGCUCA | 29 | UGAGCAUUGCGGUGGGGAGGACUGUGC | 482 |
| S30-AS483-M1 | CAGUCCUCCCCACCGCAAGUCUCAA | 30 | UUGAGACUUGCGGUGGGGAGGACUGUG | 483 |
| S31-AS484-M1 | GCCUCUAGGUCUCCUCGCCAGGACA | 31 | UGUCCUGGCGAGGAGACCUAGAGGCCG | 484 |
| S32-AS485-M1 | GCCAGGACAGCAACCUCUCUCCUGG | 32 | CCAGGAGAGAGGUUGCUGUCCUGGCGA | 485 |
| S33-AS486-M1 | GGACAGCAACCUCUCCCCUUGCCCT | 33 | AGGGCAAGGGGAGAGGUUGCUGUCCUG | 486 |
| S34-AS487-M1 | CCCCUGGCCCUCAUGGGCAUCGUCA | 34 | UGACGAUGCCCAUGAGGGCCAGGGGAG | 487 |
| S35-AS488-M1 | UGGCCCUCAUGGGCACCGUUAGCUC | 35 | GAGCUAACGGUGCCCAUGAGGGCCAGG | 488 |
| S36-AS489-M1 | GGCCCUCAUGGGCACCGUCAGCUCC | 36 | GGAGCUGACGGUGCCCAUGAGGGCCAG | 489 |
| S37-AS490-M1 | GCCCUCAUGGGCACCGUCAUCUCCA | 37 | UGGAGAUGACGGUGCCCAUGAGGGCCA | 490 |
| S38-AS491-M1 | GCGGUCCUGGUGGCCGCUGUCACTG | 38 | CAGUGACAGCGGCCACCAGGACCGCCU | 491 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S39-AS492-M1 | GGCCUGGCCGAAGCACCCGAGCACG | 39 | CGUGCUCGGGUGCUUCGGCCAGGCCGU | 492 |
| S40-AS493-M1 | ACCCGAGCACGGAACCACAUCCACC | 40 | GGUGGAUGUGGUUCCGUGCUCGGGUGC | 493 |
| S41-AS494-M1 | AGCACGGAACCACAGCCACUUUCCA | 41 | UGGAAAGUGGCUGUGGUUCCGUGCUCG | 494 |
| S42-AS495-M1 | CACGGAACCACAGCCACCUUCCACC | 42 | GGUGGAAGGUGGCUGUGGUUCCGUGCU | 495 |
| S43-AS496-M1 | ACGGAACCACAGCCACCUUUCACCG | 43 | CGGUGAAAGGUGGCUGUGGUUCCGUGC | 496 |
| S44-AS497-M1 | GCCAAGGAUCCGUGGAGGUUGCCUG | 44 | CAGGCAACCUCCACGGAUCCUUGGCGC | 497 |
| S45-AS498-M1 | CCAAGGAUCCGUGGAGGUUUCCUGG | 45 | CCAGGAAACCUCCACGGAUCCUUGGCG | 498 |
| S46-AS499-M1 | AAGGAUCCGUGGAGGUUGCUUGGCA | 46 | UGCCAAGCAACCUCCACGGAUCCUUGG | 499 |
| S47-AS500-M1 | GGAUCCGUGGAGGUUGCCUUGCACC | 47 | GGUGCAAGGCAACCUCCACGGAUCCUU | 500 |
| S48-AS501-M1 | UGGAGGUUGCCUGGCACCUACGUGG | 48 | CCACGUAGGUGCCAGGCAACCUCCACG | 501 |
| S49-AS502-M1 | UGCCUGGCACCUACGUGGUUGUGCT | 49 | AGCACAACCACGUAGGUGCCAGGCAAC | 502 |
| S50-AS503-M1 | GCCUGGCACCUACGUGGUGUUGCUG | 50 | CAGCAACACCACGUAGGUGCCAGGCAA | 503 |
| S51-AS504-M1 | AGGAGGAGACCCACCUCUCUCAGTC | 51 | GACUGAGAGAGGUGGGUCUCCUCCUUC | 504 |
| S52-AS505-M1 | CCUGCAUGUCUUCCAUGGCUUUCUT | 52 | AAGAAAGCCAUGGAAGACAUGCAGGAU | 505 |
| S53-AS506-M1 | UGCAUGUCUUCCAUGGCCUUCUUCC | 53 | GGAAGAAGGCCAUGGAAGACAUGCAGG | 506 |
| S54-AS507-M1 | ACCUGCUGGAGCUGGCCUUUAAGTT | 54 | AACUUAAAGGCCAGCUCCAGCAGGUCG | 507 |
| S55-AS508-M1 | CUGCUGGAGCUGGCCUUGAAGUUGC | 55 | GCAACUUCAAGGCCAGCUCCAGCAGGU | 508 |
| S56-AS509-M1 | UGCUGGAGCUGGCCUUGAAUUUGCC | 56 | GGCAAAUUCAAGGCCAGCUCCAGCAGG | 509 |
| S57-AS510-M1 | UGGAGCUGGCCUUGAAGUUUCCCCA | 57 | UGGGGAAACUUCAAGGCCAGCUCCAGC | 510 |
| S58-AS511-M1 | GGCCUUGAAGUUGCCCCAUUUCGAC | 58 | GUCGAAAUGGGGCAACUUCAAGGCCAG | 511 |
| S59-AS512-M1 | GCCUUGAAGUUGCCCCAUGUCGACT | 59 | AGUCGACAUGGGGCAACUUCAAGGCCA | 512 |
| S60-AS513-M1 | CCUUGAAGUUGCCCCAUGUUGACTA | 60 | UAGUCAACAUGGGGCAACUUCAAGGCC | 513 |
| S61-AS514-M1 | CUUGAAGUUGCCCCAUGUCUACUAC | 61 | GUAGUAGACAUGGGGCAACUUCAAGGC | 514 |
| S62-AS515-M1 | ACUCCUCUGUCUUUGCCCAUAGCAT | 62 | AUGCUAUGGGCAAAGACAGAGGAGUCC | 515 |
| S63-AS516-M1 | CUCCUCUGUCUUUGCCCAGAGCATC | 63 | GAUGCUCUGGGCAAAGACAGAGGAGUC | 516 |
| S64-AS517-M1 | UCCUCUGUCUUUGCCCAGAUCAUCC | 64 | GGAUGAUCUGGGCAAAGACAGAGGAGU | 517 |
| S65-AS518-M1 | CCUCUGUCUUUGCCCAGAGUAUCCC | 65 | GGGAUACUCUGGGCAAAGACAGAGGAG | 518 |
| S66-AS519-M1 | UCUGUCUUUGCCCAGAGCAUCCCGT | 66 | ACGGGAUGCUCUGGGCAAAGACAGAGG | 519 |
| S67-AS520-M1 | CUGUCUUUGCCCAGAGCAUUCCGTG | 67 | CACGGAAUGCUCUGGGCAAAGACAGAG | 520 |
| S68-AS521-M1 | GUCUUUGCCCAGAGCAUCCUGUGGA | 68 | UCCACAGGAUGCUCUGGGCAAAGACAG | 521 |
| S69-AS522-M1 | UCUUUGCCCAGAGCAUCCCUUGGAA | 69 | UUCCAAGGGAUGCUCUGGGCAAAGACA | 522 |
| S70-AS523-M1 | UUUGCCCAGAGCAUCCCGUUGAACC | 70 | GGUUCAACGGGAUGCUCUGGGCAAAGA | 523 |
| S71-AS524-M1 | AGAGCAUCCCGUGGAACCUUGAGCG | 71 | CGCUCAAGGUUCCACGGGAUGCUCUGG | 524 |
| S72-AS525-M1 | GAGCAUCCCGUGGAACCUGUAGCGG | 72 | CCGCUACAGGUUCCACGGGAUGCUCUG | 525 |
| S73-AS526-M1 | AGCAUCCCGUGGAACCUGGAGCGGA | 73 | UCCGCUCCAGGUUCCACGGGAUGCUCU | 526 |
| S74-AS527-M1 | GCAUCCCGUGGAACCUGGAUCGGAT | 74 | AUCCGAUCCAGGUUCCACGGGAUGCUC | 527 |
| S75-AS528-M1 | CAUCCCGUGGAACCUGGAGUGGATT | 75 | AAUCCACUCCAGGUUCCACGGGAUGCU | 528 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S76-AS529-M1 | AUCCCGUGGAACCUGGAGCUGAUTA | 76 | UAAUCAGCUCCAGGUUCCACGGGAUGC | 529 |
| S77-AS530-M1 | UCCCGUGGAACCUGGAGCGUAUUAC | 77 | GUAAUACGCUCCAGGUUCCACGGGAUG | 530 |
| S78-AS531-M1 | CCCGUGGAACCUGGAGCGGAUUACC | 78 | GGUAAUCCGCUCCAGGUUCCACGGGAU | 531 |
| S79-AS532-M1 | CCGUGGAACCUGGAGCGGAUUACCC | 79 | GGGUAAUCCGCUCCAGGUUCCACGGGA | 532 |
| S80-AS533-M1 | CUGGAGCGGAUUACCCCUCUACGGT | 80 | ACCGUAGAGGGGUAAUCCGCUCCAGGU | 533 |
| S81-AS534-M1 | UGGAGCGGAUUACCCCUCCACGGTA | 81 | UACCGUGGAGGGGUAAUCCGCUCCAGG | 534 |
| S82-AS535-M1 | GGAGCGGAUUACCCCUCCAUGGUAC | 82 | GUACCAUGGAGGGGUAAUCCGCUCCAG | 535 |
| S83-AS536-M1 | GAGCGGAUUACCCCUCCACUGUACC | 83 | GGUACAGUGGAGGGGUAAUCCGCUCCA | 536 |
| S84-AS537-M1 | AGCGGAUUACCCCUCCACGUUACCG | 84 | CGGUAACGUGGAGGGGUAAUCCGCUCC | 537 |
| S85-AS538-M1 | CGGAUUACCCCUCCACGGUACCGGG | 85 | CCCGGUACCGUGGAGGGGUAAUCCGCU | 538 |
| S86-AS539-M1 | GGAUUACCCCUCCACGGUAUCGGGC | 86 | GCCCGAUACCGUGGAGGGGUAAUCCGC | 539 |
| S87-AS540-M1 | UCCACGGUACCGGGCGGAUUAAUAC | 87 | GUAUUAAUCCGCCCGGUACCGUGGAGG | 540 |
| S88-AS541-M1 | CGGAGGCAGCCUGGUGGAGUUGUAT | 88 | AUACAACUCCACCAGGCUGCCUCCGUC | 541 |
| S89-AS542-M1 | AGACACCAGCAUACAGAGUUACCAC | 89 | GUGGUAACUCUGUAUGCUGGUGUCUAG | 542 |
| S90-AS543-M1 | GCAUACAGAGUGACCACCGUGAAAT | 90 | AUUUCACGGUGGUCACUCUGUAUGCUG | 543 |
| S91-AS544-M1 | CGAGAAUGUGCCCGAGGAGUACGGG | 91 | CCCGUACUCCUCGGGCACAUUCUCGAA | 544 |
| S92-AS545-M1 | GAGAAUGUGCCCGAGGAGGACGGGA | 92 | UCCCGUCCUCCUCGGGCACAUUCUCGA | 545 |
| S93-AS546-M1 | AGAAUGUGCCCGAGGAGGAUGGGAC | 93 | GUCCCAUCCUCCUCGGGCACAUUCUCG | 546 |
| S94-AS547-M1 | GCAAGUGUGACAGUCAUGGUACCCA | 94 | UGGGUACCAUGACUGUCACACUUGCUG | 547 |
| S95-AS548-M1 | CAAGUGUGACAGUCAUGGCACCCAC | 95 | GUGGGUGCCAUGACUGUCACACUUGCU | 548 |
| S96-AS549-M1 | AAGUGUGACAGUCAUGGCAUCCACC | 96 | GGUGGAUGCCAUGACUGUCACACUUGC | 549 |
| S97-AS550-M1 | CGCAGCCUGCGCGUGCUCAACUGCC | 97 | GGCAGUUGAGCACGCGCAGGCUGCGCA | 550 |
| S98-AS551-M1 | GCAGCCUGCGCGUGCUCAAUUGCCA | 98 | UGGCAAUUGAGCACGCGCAGGCUGCGC | 551 |
| S99-AS552-M1 | AGCCUGGGGCCACUGGUUGUGCT | 99 | AGCACAACCAGUGGCCCCACAGGCUGG | 552 |
| S100-AS553-M1 | CCUCUACUCCCCAGCCUCAUCUCCC | 100 | GGGAGAUGAGGCUGGGGAGUAGAGGCA | 553 |
| S101-AS554-M1 | CAGCCUCAGCUCCCGAGGUUAUCAC | 101 | GUGAUAACCUCGGGAGCUGAGGCUGGG | 554 |
| S102-AS555-M1 | GCCACCAAUGCCCAAGACCAGCCGG | 102 | CCGGCUGGUCUUGGGCAUUGGUGGCCC | 555 |
| S103-AS556-M1 | AUGCCCAAGACCAGCCGGUUACCCT | 103 | AGGGUAACCGGCUGGUCUUGGGCAUUG | 556 |
| S104-AS557-M1 | UGCCCAAGACCAGCCGGUGACCCTG | 104 | CAGGGUCACCGGCUGGUCUUGGGCAUU | 557 |
| S105-AS558-M1 | GUCACAGAGUGGGACAUCAUAGGCT | 105 | AGCCUAUGAUGUCCCACUCUGUGACAC | 558 |
| S106-AS559-M1 | GAGUGGGACAUCACAGGCUUCUGCC | 106 | GGCAGAAGCCUGUGAUGUCCCACUCUG | 559 |
| S107-AS560-M1 | UGGGACAUCACAGGCUGCUUCCCAC | 107 | GUGGGAAGCAGCCUGUGAUGUCCCACU | 560 |
| S108-AS561-M1 | GGGACAUCACAGGCUGCUGUCCACG | 108 | CGUGGACAGCAGCCUGUGAUGUCCCAC | 561 |
| S109-AS562-M1 | CUCACCCUGGCCGAGUUGAUGCAGA | 109 | UCUGCAUCAACUCGGCCAGGGUGAGCU | 562 |
| S110-AS563-M1 | ACCCUGGCCGAGUUGAGGCAGAGAC | 110 | GUCUCUGCCUCAACUCGGCCAGGGUGA | 563 |
| S111-AS564-M1 | ACUUCUCUGCCAAAGAUGUUAUCAA | 111 | UUGAUAACAUCUUUGGCAGAGAAGUGG | 564 |
| S112-AS565-M1 | CCCAUGGGGCAGGUUGGCAUCUGTT | 112 | AACAGAUGCCAACCUGCCCCAUGGGUG | 565 |
| S113-AS566-M1 | UGGGGCAGGUUGGCAGCUGUUUUGC | 113 | GCAAAACAGCUGCCAACCUGCCCCAUG | 566 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S114-AS567-M1 | CUGUUUUGCAGGACUGUAUUGUCAG | 114 | CUGACAAUACAGUCCUGCAAAACAGCU | 567 |
| S115-AS568-M1 | UUUUGCAGGACUGUAUGGUUAGCAC | 115 | GUGCUAACCAUACAGUCCUGCAAAACA | 568 |
| S116-AS569-M1 | CAGGACUGUAUGGUCAGCAUACUCG | 116 | CGAGUAUGCUGACCAUACAGUCCUGCA | 569 |
| S117-AS570-M1 | GGACUGUAUGGUCAGCACAUUCGGG | 117 | CCCGAAUGUGCUGACCAUACAGUCCUG | 570 |
| S118-AS571-M1 | CGCUGCGCCCCAGAUGAGGAGCUGC | 118 | GCAGCUCCUCAUCUGGGGCGCAGCGGG | 571 |
| S119-AS572-M1 | GCGCCCCAGAUGAGGAGCUUCUGAG | 119 | CUCAGAAGCUCCUCAUCUGGGGCGCAG | 572 |
| S120-AS573-M1 | CCCCAGAUGAGGAGCUGCUUAGCUG | 120 | CAGCUAAGCAGCUCCUCAUCUGGGGCG | 573 |
| S121-AS574-M1 | CCCAGAUGAGGAGCUGCUGAGCUGC | 121 | GCAGCUCAGCAGCUCCUCAUCUGGGGC | 574 |
| S122-AS575-M1 | CCAGAUGAGGAGCUGCUGAUCUGCT | 122 | AGCAGAUCAGCAGCUCCUCAUCUGGGG | 575 |
| S123-AS576-M1 | CGGCGGGGCGAGCGCAUGGAGGCCC | 123 | GGGCCUCCAUGCGCUCGCCCCGCCGCU | 576 |
| S124-AS577-M1 | GGCGGGGCGAGCGCAUGGAUGCCCA | 124 | UGGGCAUCCAUGCGCUCGCCCCGCCGC | 577 |
| S125-AS578-M1 | GGCGAGCGCAUGGAGGCCCAAGGGG | 125 | CCCCUUGGGCCUCCAUGCGCUCGCCCC | 578 |
| S126-AS579-M1 | CUGGUCUGCCGGGCCCACAACGCUU | 126 | AAGCGUUGUGGGCCCGGCAGACCAGCU | 579 |
| S127-AS580-M1 | UGCCUGCUACCCCAGGCCAACUGCA | 127 | UGCAGUUGGCCUGGGGUAGCAGGCAGC | 580 |
| S128-AS581-M1 | GCCUGCUACCCCAGGCCAAUUGCAG | 128 | CUGCAAUUGGCCUGGGGUAGCAGGCAG | 581 |
| S129-AS582-M1 | CCCAGGCCAACUGCAGCGUUCACAC | 129 | GUGUGAACGCUGCAGUUGGCCUGGGGU | 582 |
| S130-AS583-M1 | GGCCCCUCAGGAGCAGGUGACCGTG | 130 | CACGGUCACCUGCUCCUGAGGGGCCGG | 583 |
| S131-AS584-M1 | UGACCGUGGCCUGCGAGGAUGGCUG | 131 | CAGCCAUCCUCGCAGGCCACGGUCACC | 584 |
| S132-AS585-M1 | GCGAGGAGGGCUGGACCCUUACUGG | 132 | CCAGUAAGGGUCCAGCCCUCCUCGCAG | 585 |
| S133-AS586-M1 | CGAGGAGGGCUGGACCCUGACUGGC | 133 | GCCAGUCAGGGUCCAGCCCUCCUCGCA | 586 |
| S134-AS587-M1 | GGGCUGGACCCUGACUGGCUGCAGT | 134 | ACUGCAGCCAGUCAGGGUCCAGCCCUC | 587 |
| S135-AS588-M1 | GGCUGGACCCUGACUGGCUUCAGTG | 135 | CACUGAAGCCAGUCAGGGUCCAGCCCU | 588 |
| S136-AS589-M1 | UGGACCCUGACUGGCUGCAUUGCCC | 136 | GGGCAAUGCAGCCAGUCAGGGUCCAGC | 589 |
| S137-AS590-M1 | GGCUGCAGUGCCCUCCCUGUGACCT | 137 | AGGUCACAGGGAGGGCACUGCAGCCAG | 590 |
| S138-AS591-M1 | UCCCUGGGACCUCCCACGUUCUGGG | 138 | CCCAGAACGUGGGAGGUCCCAGGGAGG | 591 |
| S139-AS592-M1 | CCCUGGGACCUCCCACGUCUUGGGG | 139 | CCCCAAGACGUGGGAGGUCCCAGGGAG | 592 |
| S140-AS593-M1 | GGGCCUACGCCGUAGACAAUACGTG | 140 | CACGUAUUGUCUACGGCGUAGGCCCCC | 593 |
| S141-AS594-M1 | GACGUCAGCACUACAGGCAUCACCA | 141 | UGGUGAUGCCUGUAGUGCUGACGUCCC | 594 |
| S142-AS595-M1 | CAGCACUACAGGCAGCACCAGCGAA | 142 | UUCGCUGGUGCUGCCUGUAGUGCUGAC | 595 |
| S143-AS596-M1 | AGCACUACAGGCAGCACCAUCGAAG | 143 | CUUCGAUGGUGCUGCCUGUAGUGCUGA | 596 |
| S144-AS597-M1 | GCACUACAGGCAGCACCAGUGAAGG | 144 | CCUUCACUGGUGCUGCCUGUAGUGCUG | 597 |
| S145-AS598-M1 | GGGGCCGUGACAGCCGUUGUCAUCT | 145 | AGAUGACAACGGCUGUCACGGCCCCUU | 598 |
| S146-AS599-M1 | GGAGCUCCAGUGACAGCCCUAUCCC | 146 | GGGAUAGGGCUGUCACUGGAGCUCCUG | 599 |
| S147-AS600-M1 | AGGAUGGUGUCUGGGGAGUGUCAA | 147 | UUGACACUCCCCAGACACCCAUCCUGG | 600 |
| S148-AS601-M1 | UGGGUGUCUGGGGAGGGUCAAGGGC | 148 | GCCCUUGACCCUCCCCAGACACCCAUC | 601 |
| S149-AS602-M1 | GGGUGUCUGGGGAGGGUCAAGGGCT | 149 | AGCCCUUGACCCUCCCCAGACACCCAU | 602 |
| S150-AS603-M1 | GGUGUCUGGGGAGGGUCAAUGGCUG | 150 | CAGCCAUUGACCCUCCCCAGACACCCA | 603 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S151-AS604-M1 | AGGGUCAAGGGCUGGGGCUUAGCTT | 151 | AAGCUAAGCCCCAGCCCUUGACCCUCC | 604 |
| S152-AS605-M1 | GGGUCAAGGGCUGGGGCUGAGCUTT | 152 | AAAGCUCAGCCCCAGCCCUUGACCCUC | 605 |
| S153-AS606-M1 | GACUUGUCCCUCUCUCAGCUCUCCA | 153 | UGGAGAGCUGAGAGAGGGACAAGUCGG | 606 |
| S154-AS607-M1 | ACUUGUCCCUCUCUCAGCCUUCCAT | 154 | AUGGAAGGCUGAGAGAGGGACAAGUCG | 607 |
| S155-AS608-M1 | CUUGUCCCUCUCUCAGCCCUCCATG | 155 | CAUGGAGGGCUGAGAGAGGGACAAGUC | 608 |
| S156-AS609-M1 | UUGUCCCUCUCUCAGCCCUUCAUGG | 156 | CCAUGAAGGGCUGAGAGAGGGACAAGU | 609 |
| S157-AS610-M1 | UCCCUCUCUCAGCCCUCCAUGGCCT | 157 | AGGCCAUGGAGGGCUGAGAGAGGGACA | 610 |
| S158-AS611-M1 | UGGCCUGGCACGAGGGGAUUGGGAT | 158 | AUCCCAAUCCCCUCGUGCCAGGCCAUG | 611 |
| S159-AS612-M1 | UGGCACGAGGGGAUGGGGAUGCUTC | 159 | GAAGCAUCCCCAUCCCCUCGUGCCAGG | 612 |
| S160-AS613-M1 | CGAGGGGAUGGGGAUGCUUUCGCCT | 160 | AGGCGAAAGCAUCCCCAUCCCCUCGUG | 613 |
| S161-AS614-M1 | GAGGGGAUGGGGAUGCUUCUGCCTT | 161 | AAGGCAGAAGCAUCCCCAUCCCCUCGU | 614 |
| S162-AS615-M1 | GGGAUGGGGAUGCUUCCGCUUUUCC | 162 | GGAAAAGCGGAAGCAUCCCCAUCCCCU | 615 |
| S163-AS616-M1 | AUGGGGAUGCUUCCGCCUUUCCGGG | 163 | CCCGGAAAGGCGGAAGCAUCCCCAUCC | 616 |
| S164-AS617-M1 | UGGGGAUGCUUCCGCCUUUUCGGGG | 164 | CCCCGAAAAGGCGGAAGCAUCCCCAUC | 617 |
| S165-AS618-M1 | GGGGAUGCUUCCGCCUUUCGGGGC | 165 | GCCCCAGAAAGGCGGAAGCAUCCCCAU | 618 |
| S166-AS619-M1 | GGGAUGCUUCCGCCUUUCCUGGGCT | 166 | AGCCCAGGAAAGGCGGAAGCAUCCCCA | 619 |
| S167-AS620-M1 | CCCUUGAGUGGGGCAGCCUUCUUGC | 167 | GCAAGAAGGCUGCCCCACUCAAGGGCC | 620 |
| S168-AS621-M1 | UGAGUGGGGCAGCCUCCUUUCCUGG | 168 | CCAGGAAAGGAGGCUGCCCCACUCAAG | 621 |
| S169-AS622-M1 | GGGGCAGCCUCCUUGCCUGUAACTC | 169 | GAGUUACAGGCAAGGAGGCUGCCCCAC | 622 |
| S170-AS623-M1 | GGCAGCCUCCUUGCCUGGAACUCAC | 170 | GUGAGUUCCAGGCAAGGAGGCUGCCCC | 623 |
| S171-AS624-M1 | GCAGCCUCCUUGCCUGGAAUUCACT | 171 | AGUGAAUUCCAGGCAAGGAGGCUGCCC | 624 |
| S172-AS625-M1 | AGCCUCCUUGCCUGGAACUUACUCA | 172 | UGAGUAAGUUCCAGGCAAGGAGGCUGC | 625 |
| S173-AS626-M1 | GCCUCCUUGCCUGGAACUCACUCAC | 173 | GUGAGUGAGUUCCAGGCAAGGAGGCUG | 626 |
| S174-AS627-M1 | CCUCCUUGCCUGGAACUCAUUCACT | 174 | AGUGAAUGAGUUCCAGGCAAGGAGGCU | 627 |
| S175-AS628-M1 | CUCCUUGCCUGGAACUCACUCACTC | 175 | GAGUGAGUGAGUUCCAGGCAAGGAGGC | 628 |
| S176-AS629-M1 | UCCUUGCCUGGAACUCACUUACUCT | 176 | AGAGUAAGUGAGUUCCAGGCAAGGAGG | 629 |
| S177-AS630-M1 | CCUUGCCUGGAACUCACUCACUCTG | 177 | CAGAGUGAGUGAGUUCCAGGCAAGGAG | 630 |
| S178-AS631-M1 | CUUGCCUGGAACUCACUCAUUCUGG | 178 | CCAGAAUGAGUGAGUUCCAGGCAAGGA | 631 |
| S179-AS632-M1 | UUGCCUGGAACUCACUCACUCUGGG | 179 | CCCAGAGUGAGUGAGUUCCAGGCAAGG | 632 |
| S180-AS633-M1 | UGCCUGGAACUCACUCACUUUGGGT | 180 | ACCCAAAGUGAGUGAGUUCCAGGCAAG | 633 |
| S181-AS634-M1 | UCUGGGUGCCUCCUCCCCAUGUGGA | 181 | UCCACAUGGGGAGGAGGCACCCAGAGU | 634 |
| S182-AS635-M1 | CCCAGGUGGAGGUGCCAGGAAGCUC | 182 | GAGCUUCCUGGCACCUCCACCUGGGGA | 635 |
| S183-AS636-M1 | CCAGGAAGCUCCCUCCCUCACUGTG | 183 | CACAGUGAGGGAGGGAGCUUCCUGGCA | 636 |
| S184-AS637-M1 | GGAAGCUCCCUCCCUCACUUUGGGG | 184 | CCCCAAAGUGAGGGAGGGAGCUUCCUG | 637 |
| S185-AS638-M1 | AGCUCCCUCCCUCACUGUGUGGCAT | 185 | AUGCCACACAGUGAGGGAGGGAGCUUC | 638 |
| S186-AS639-M1 | GCUCCCUCCCUCACUGUGGUGCATT | 186 | AAUGCACCACAGUGAGGGAGGGAGCUU | 639 |
| S187-AS640-M1 | GGGGCAUUUCACCAUUCAAACAGGT | 187 | ACCUGUUUGAAUGGUGAAAUGCCCCAC | 640 |
| S188-AS641-M1 | GGGCAUUUCACCAUUCAAAUAGGTC | 188 | GACCUAUUUGAAUGGUGAAAUGCCCCA | 641 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S189-AS642-M1 | CACCAUUCAAACAGGUCGAUCUGTG | 189 | CACAGAUCGACCUGUUUGAAUGGUGAA | 642 |
| S190-AS643-M1 | ACCAUUCAAACAGGUCGAGUUGUGC | 190 | GCACAACUCGACCUGUUUGAAUGGUGA | 643 |
| S191-AS644-M1 | UGCUCGGGUGCUGCCAGCUUCUCCC | 191 | GGGAGAAGCUGGCAGCACCCGAGCACA | 644 |
| S192-AS645-M1 | CGGGUGCUGCCAGCUGCUCUCAATG | 192 | CAUUGAGAGCAGCUGGCAGCACCCGAG | 645 |
| S193-AS646-M1 | GGGUGCUGCCAGCUGCUCCUAAUGT | 193 | ACAUUAGGAGCAGCUGGCAGCACCCGA | 646 |
| S194-AS647-M1 | GCCAGCUGCUCCCAAUGUGUCGATG | 194 | CAUCGACACAUUGGGAGCAGCUGGCAG | 647 |
| S195-AS648-M1 | CCAGCUGCUCCCAAUGUGCUGAUGT | 195 | ACAUCAGCACAUUGGGAGCAGCUGGCA | 648 |
| S196-AS649-M1 | UGCCGAUGUCCGUGGGCAGAAUGAC | 196 | GUCAUUCUGCCCACGGACAUCGGCACA | 649 |
| S197-AS650-M1 | GCAGAAUGACUUUUAUUGAUCUCTT | 197 | AAGAGAUCAAUAAAAGUCAUUCUGCCC | 650 |
| S198-AS651-M1 | CAGAAUGACUUUUAUUGAGUUCUTG | 198 | CAAGAACUCAAUAAAAGUCAUUCUGCC | 651 |
| S199-AS652-M1 | AGAAUGACUUUUAUUGAGCUCUUGT | 199 | ACAAGAGCUCAAUAAAAGUCAUUCUGC | 652 |
| S200-AS653-M1 | GAAUGACUUUUAUUGAGCUUUUGTT | 200 | AACAAAAGCUCAAUAAAAGUCAUUCUG | 653 |
| S201-AS654-M1 | AAUGACUUUUAUUGAGCUCUUGUTC | 201 | GAACAAGAGCUCAAUAAAAGUCAUUCU | 654 |
| S202-AS655-M1 | AUGACUUUUAUUGAGCUCUUGUUCC | 202 | GGAACAAGAGCUCAAUAAAAGUCAUUC | 655 |
| S203-AS656-M1 | UGACUUUUAUUGAGCUCUUUUCCG | 203 | CGGAAAAAGAGCUCAAUAAAAGUCAUU | 656 |
| S204-AS657-M1 | CUUGUUCCGUGCCAGGCAUUCAAUC | 204 | GAUUGAAUGCCUGGCACGGAACAAGAG | 657 |
| S205-AS658-M1 | CCAGGCAUUCAAUCCUCAGUUCUCC | 205 | GGAGAACUGAGGAUUGAAUGCCUGGCA | 658 |
| S206-AS659-M1 | CAUUCAAUCCUCAGGUCUCUACCAA | 206 | UUGGUAGAGACCUGAGGAUUGAAUGCC | 659 |
| S207-AS660-M1 | AUUCAAUCCUCAGGUCUCCACCAAG | 207 | CUUGGUGGAGACCUGAGGAUUGAAUGC | 660 |
| S208-AS661-M1 | UUCAAUCCUCAGGUCUCCAUCAAGG | 208 | CCUUGAUGGAGACCUGAGGAUUGAAUG | 661 |
| S209-AS662-M1 | CCUCAGGUCUCCACCAAGGAGGCAG | 209 | CUGCCUCCUUGGUGGAGACCUGAGGAU | 662 |
| S210-AS663-M1 | CUCAGGUCUCCACCAAGGAUGCAGG | 210 | CCUGCAUCCUUGGUGGAGACCUGAGGA | 663 |
| S211-AS664-M1 | GCGGUAGGGCUGCAGGGAUAAACA | 211 | UGUUUAUCCCUGCAGCCCCUACCGCCC | 664 |
| S212-AS665-M1 | CGGUAGGGCUGCAGGGACAAACAT | 212 | AUGUUUGUCCCUGCAGCCCCUACCGCC | 665 |
| S213-AS666-M1 | GGUAGGGCUGCAGGGACAAACAUC | 213 | GAUGUUUGUCCCUGCAGCCCCUACCGC | 666 |
| S214-AS667-M1 | UAGGGGCUGCAGGGACAAAUAUCGT | 214 | ACGAUAUUUGUCCCUGCAGCCCCUACC | 667 |
| S215-AS668-M1 | AGGGGCUGCAGGGACAAACAUCGTT | 215 | AACGAUGUUUGUCCCUGCAGCCCCUAC | 668 |
| S216-AS669-M1 | GGGGCUGCAGGGACAAACAUCGUTG | 216 | CAACGAUGUUUGUCCCUGCAGCCCCUA | 669 |
| S217-AS670-M1 | GGGCUGCAGGGACAAACAUUGUUGG | 217 | CCAACAAUGUUUGUCCCUGCAGCCCCU | 670 |
| S218-AS671-M1 | GGCUGCAGGGACAAACAUCUUUGGG | 218 | CCCAAAGAUGUUUGUCCCUGCAGCCCC | 671 |
| S219-AS672-M1 | GGGGUGAGUGUGAAAGGUGUUGATG | 219 | CAUCAACACCUUUCACACUCACCCCCC | 672 |
| S220-AS673-M1 | GGGUGAGUGUGAAAGGUGCUGAUGG | 220 | CCAUCAGCACCUUUCACACUCACCCCC | 673 |
| S221-AS674-M1 | GGUGAGUGUGAAAGGUGCUUAUGGC | 221 | GCCAUAAGCACCUUUCACACUCACCCC | 674 |
| S222-AS675-M1 | GUGAGUGUGAAAGGUGCUGAUGGCC | 222 | GGCCAUCAGCACCUUUCACACUCACCC | 675 |
| S223-AS676-M1 | UGAGUGUGAAAGGUGCUGAUGGCCC | 223 | GGGCCAUCAGCACCUUUCACACUCACC | 676 |
| S224-AS677-M1 | GAGUGUGAAAGGUGCUGAUUGCCCT | 224 | AGGGCAAUCAGCACCUUUCACACUCAC | 677 |
| S225-AS678-M1 | AGUGUGAAAGGUGCUGAUGUCCCTC | 225 | GAGGGACAUCAGCACCUUUCACACUCA | 678 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S226-AS679-M1 | GUGUGAAAGGUGCUGAUGGUCCUCA | 226 | UGAGGACCAUCAGCACCUUUCACACUC | 679 |
| S227-AS680-M1 | UGUGAAAGGUGCUGAUGGCUCUCAT | 227 | AUGAGAGCCAUCAGCACCUUUCACACU | 680 |
| S228-AS681-M1 | GUGAAAGGUGCUGAUGGCCUUCATC | 228 | GAUGAAGGCCAUCAGCACCUUUCACAC | 681 |
| S229-AS682-M1 | UGAAAGGUGCUGAUGGCCCUCAUCT | 229 | AGAUGAGGGCCAUCAGCACCUUUCACA | 682 |
| S230-AS683-M1 | GAAAGGUGCUGAUGGCCCUUAUCTC | 230 | GAGAUAAGGGCCAUCAGCACCUUUCAC | 683 |
| S231-AS684-M1 | CUCAUCUCCAGCUAACUGUUGAGAA | 231 | UUCUCAACAGUUAGCUGGAGAUGAGGG | 684 |
| S232-AS685-M1 | CCAGCUAACUGUGGAGAAGUCCCTG | 232 | CAGGGACUUCUCCACAGUUAGCUGGAG | 685 |
| S233-AS686-M1 | CAGCUAACUGUGGAGAAGCUCCUGG | 233 | CCAGGAGCUUCUCCACAGUUAGCUGGA | 686 |
| S234-AS687-M1 | AGCUAACUGUGGAGAAGCCUCUGGG | 234 | CCCAGAGGCUUCUCCACAGUUAGCUGG | 687 |
| S235-AS688-M1 | GCUAACUGUGGAGAAGCCCUUGGGG | 235 | CCCCAAGGGCUUCUCCACAGUUAGCUG | 688 |
| S236-AS689-M1 | GGGCUCCCUGAUUAAUGGAUGCUTA | 236 | UAAGCAUCCAUUAAUCAGGGAGCCCCC | 689 |
| S237-AS690-M1 | AUGGAGGCUUAGCUUUCUGUAUGGC | 237 | GCCAUACAGAAAGCUAAGCCUCCAUUA | 690 |
| S238-AS691-M1 | UGGAGGCUUAGCUUUCUGGAUGGCA | 238 | UGCCAUCCAGAAAGCUAAGCCUCCAUU | 691 |
| S239-AS692-M1 | GGAGGCUUAGCUUUCUGGAUGGCAT | 239 | AUGCCAUCCAGAAAGCUAAGCCUCCAU | 692 |
| S240-AS693-M1 | GAGGCUUAGCUUUCUGGAUUGCATC | 240 | GAUGCAAUCCAGAAAGCUAAGCCUCCA | 693 |
| S241-AS694-M1 | AGGCUUAGCUUUCUGGAUGUCAUCT | 241 | AGAUGACAUCCAGAAAGCUAAGCCUCC | 694 |
| S242-AS695-M1 | GGCUUAGCUUUCUGGAUGGUAUCTA | 242 | UAGAUACCAUCCAGAAAGCUAAGCCUC | 695 |
| S243-AS696-M1 | GCUUAGCUUUCUGGAUGGCAUCTAG | 243 | CUAGAUGCCAUCCAGAAAGCUAAGCCU | 696 |
| S244-AS697-M1 | GACAGGUGCGCCCCUGGUGUUCACA | 244 | UGUGAACACCAGGGGCGCACCUGUCUC | 697 |
| S245-AS698-M1 | GCGCCCCUGGUGGUCACAGUCUGTG | 245 | CACAGACUGUGACCACCAGGGGCGCAC | 698 |
| S246-AS699-M1 | CCCCUGGUGGUCACAGGCUUUGCCT | 246 | AGGCAAAGCCUGUGACCACCAGGGGCG | 699 |
| S247-AS700-M1 | CCCUGGUGGUCACAGGCUGUGCCTT | 247 | AAGGCACAGCCUGUGACCACCAGGGGC | 700 |
| S248-AS701-M1 | GUGGUCACAGGCUGUGCCUUGGUTT | 248 | AAACCAAGGCACAGCCUGUGACCACCA | 701 |
| S249-AS702-M1 | UGGUCACAGGCUGUGCCUUUGUUTC | 249 | GAAACAAAGGCACAGCCUGUGACCACC | 702 |
| S250-AS703-M1 | GGUCACAGGCUGUGCCUUGUUUUCC | 250 | GGAAAACAAGGCACAGCCUGUGACCAC | 703 |
| S251-AS704-M1 | GUCACAGGCUGUGCCUUGGUUUCCT | 251 | AGGAAACCAAGGCACAGCCUGUGACCA | 704 |
| S252-AS705-M1 | GGCUGUGCCUUGGUUUCCUUAGCCA | 252 | UGGCUAAGGAAACCAAGGCACAGCCUG | 705 |
| S253-AS706-M1 | GCUGUGCCUUGGUUUCCUGAGCCAC | 253 | GUGGCUCAGGAAACCAAGGCACAGCCU | 706 |
| S254-AS707-M1 | CUGUGCCUUGGUUUCCUGAUCCACC | 254 | GGUGGAUCAGGAAACCAAGGCACAGCC | 707 |
| S255-AS708-M1 | UGUGCCUUGGUUUCCUGAGUCACCT | 255 | AGGUGACUCAGGAAACCAAGGCACAGC | 708 |
| S256-AS709-M1 | GUGCCUUGGUUUCCUGAGCUACCTT | 256 | AAGGUAGCUCAGGAAACCAAGGCACAG | 709 |
| S257-AS710-M1 | UGCCUUGGUUUCCUGAGCCACCUTT | 257 | AAAGGUGGCUCAGGAAACCAAGGCACA | 710 |
| S258-AS711-M1 | GCCUUGGUUUCCUGAGCCAUCUUTA | 258 | UAAAGAUGGCUCAGGAAACCAAGGCAC | 711 |
| S259-AS712-M1 | CCUUGGUUUCCUGAGCCACUUUUAC | 259 | GUAAAAGUGGCUCAGGAAACCAAGGCA | 712 |
| S260-AS713-M1 | CUUGGUUUCCUGAGCCACCUUUACT | 260 | AGUAAAGGUGGCUCAGGAAACCAAGGC | 713 |
| S261-AS714-M1 | UUGGUUUCCUGAGCCACCUUUACTC | 261 | GAGUAAAGGUGGCUCAGGAAACCAAGG | 714 |
| S262-AS715-M1 | UGGUUUCCUGAGCCACCUUUACUCT | 262 | AGAGUAAAGGUGGCUCAGGAAACCAAG | 715 |
| S263-AS716-M1 | GGUUUCCUGAGCCACCUUUACUCTG | 263 | CAGAGUAAAGGUGGCUCAGGAAACCAA | 716 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S264-AS717-M1 | GUUUCCUGAGCCACCUUUAUUCUGC | 264 | GCAGAAUAAAGGUGGCUCAGGAAACCA | 717 |
| S265-AS718-M1 | CUGAGCCACCUUUACUCUGUUCUAU | 265 | AUAGAACAGAGUAAAGGUGGCUCAGGA | 718 |
| S266-AS719-M1 | CCAGGCUGUGCUAGCAACAUCCAAA | 266 | UUUGGAUGUUGCUAGCACAGCCUGGCA | 719 |
| S267-AS720-M1 | CUGCGGGGAGCCAUCACCUAGGACU | 267 | AGUCCUAGGUGAUGGCUCCCCGCAGGC | 720 |
| S268-AS721-M1 | UGCGGGGAGCCAUCACCUAUGACUG | 268 | CAGUCAUAGGUGAUGGCUCCCCGCAGG | 721 |
| S269-AS722-M1 | GCGGGGAGCCAUCACCUAGUACUGA | 269 | UCAGUACUAGGUGAUGGCUCCCCGCAG | 722 |
| S270-AS723-M1 | CGGGGAGCCAUCACCUAGGACUGAC | 270 | GUCAGUCCUAGGUGAUGGCUCCCCGCA | 723 |
| S271-AS724-M1 | GGGGAGCCAUCACCUAGGAUUGACU | 271 | AGUCAAUCCUAGGUGAUGGCUCCCCGC | 724 |
| S272-AS725-M1 | GCCAUCACCUAGGACUGACUCGGCA | 272 | UGCCGAGUCAGUCCUAGGUGAUGGCUC | 725 |
| S273-AS726-M1 | CCAUCACCUAGGACUGACUUGGCAG | 273 | CUGCCAAGUCAGUCCUAGGUGAUGGCU | 726 |
| S274-AS727-M1 | CAUCACCUAGGACUGACUCUGCAGU | 274 | ACUGCAGAGUCAGUCCUAGGUGAUGGC | 727 |
| S275-AS728-M1 | CUAGGACUGACUCGGCAGUUUGCAG | 275 | CUGCAAACUGCCGAGUCAGUCCUAGGU | 728 |
| S276-AS729-M1 | UGACUCGGCAGUGUGCAGUUGUGCA | 276 | UGCACAACUGCACACUGCCGAGUCAGU | 729 |
| S277-AS730-M1 | GACUCGGCAGUGUGCAGUGUUGCAU | 277 | AUGCAACACUGCACACUGCCGAGUCAG | 730 |
| S278-AS731-M1 | CUCGGCAGUGUGCAGUGGUUCAUGC | 278 | GCAUGAACCACUGCACACUGCCGAGUC | 731 |
| S279-AS732-M1 | UCGGCAGUGUGCAGUGGUGUAUGCA | 279 | UGCAUACACCACUGCACACUGCCGAGU | 732 |
| S280-AS733-M1 | CGGCAGUGUGCAGUGGUGCAUGCAC | 280 | GUGCAUGCACCACUGCACACUGCCGAG | 733 |
| S281-AS734-M1 | GUGUGCAGUGGUGCAUGCAUUGUCT | 281 | AGACAAUGCAUGCACCACUGCACACUG | 734 |
| S282-AS735-M1 | UGUGCAGUGGUGCAUGCACUGUCUC | 282 | GAGACAGUGCAUGCACCACUGCACACU | 735 |
| S283-AS736-M1 | GUGCAGUGGUGCAUGCACUUUCUCA | 283 | UGAGAAGUGCAUGCACCACUGCACAC | 736 |
| S284-AS737-M1 | UGCAGUGGUGCAUGCACUGUCUCAG | 284 | CUGAGACAGUGCAUGCACCACUGCACA | 737 |
| S285-AS738-M1 | GCAGUGGUGCAUGCACUGUUUCAGC | 285 | GCUGAAACAGUGCAUGCACCACUGCAC | 738 |
| S286-AS739-M1 | CAGUGGUGCAUGCACUGUCUCAGCC | 286 | GGCUGAGACAGUGCAUGCACCACUGCA | 739 |
| S287-AS740-M1 | AGUGGUGCAUGCACUGUCUUAGCCA | 287 | UGGCUAAGACAGUGCAUGCACCACUGC | 740 |
| S288-AS741-M1 | UGCAUGCACUGUCUCAGCCAACCCG | 288 | CGGGUUGGCUGAGACAGUGCAUGCACC | 741 |
| S289-AS742-M1 | GCAUGCACUGUCUCAGCCAACCCGC | 289 | GCGGGUUGGCUGAGACAGUGCAUGCAC | 742 |
| S290-AS743-M1 | CAUUCGCACCCCUACUUCAUAGAGG | 290 | CCUCUAUGAAGUAGGGGUGCGAAUGUG | 743 |
| S291-AS744-M1 | AUUCGCACCCCUACUUCACAGAGGA | 291 | UCCUCUGUGAAGUAGGGGUGCGAAUGU | 744 |
| S292-AS745-M1 | UUCGCACCCCUACUUCACAUAGGAA | 292 | UUCCUAUGUGAAGUAGGGGUGCGAAUG | 745 |
| S293-AS746-M1 | UCGCACCCCUACUUCACAGAGGAAG | 293 | CUUCCUCUGUGAAGUAGGGGUGCGAAU | 746 |
| S294-AS747-M1 | CGCACCCCUACUUCACAGAUGAAGA | 294 | UCUUCAUCUGUGAAGUAGGGGUGCGAA | 747 |
| S295-AS748-M1 | GCACCCCUACUUCACAGAGUAAGAA | 295 | UUCUUACUCUGUGAAGUAGGGGUGCGA | 748 |
| S296-AS749-M1 | CACCCCUACUUCACAGAGGAAGAAA | 296 | UUUCUUCCUCUGUGAAGUAGGGGUGCG | 749 |
| S297-AS750-M1 | ACCCCUACUUCACAGAGGAAGAAAC | 297 | GUUUCUUCCUCUGUGAAGUAGGGGUGC | 750 |
| S298-AS751-M1 | CCCCUACUUCACAGAGGAAUAAACC | 298 | GGUUUAUUCCUCUGUGAAGUAGGGGUG | 751 |
| S299-AS752-M1 | CCCUACUUCACAGAGGAAGAAACCU | 299 | AGGUUUCUUCCUCUGUGAAGUAGGGGU | 752 |
| S300-AS753-M1 | CUUCACAGAGGAAGAAACCUGGAAC | 300 | GUUCCAGGUUUCUUCCUCUGUGAAGUA | 753 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S301-AS754-M1 | UUCACAGAGGAAGAAACCUUGAACC | 301 | GGUUCAAGGUUUCUUCCUCUGUGAAGU | 754 |
| S302-AS755-M1 | UCACAGAGGAAGAAACCUGUAACCA | 302 | UGGUUACAGGUUUCUUCCUCUGUGAAG | 755 |
| S303-AS756-M1 | CACAGAGGAAGAAACCUGGAACCAG | 303 | CUGGUUCCAGGUUUCUUCCUCUGUGAA | 756 |
| S304-AS757-M1 | ACAGAGGAAGAAACCUGGAACCAGA | 304 | UCUGGUUCCAGGUUUCUUCCUCUGUGA | 757 |
| S305-AS758-M1 | CAGAGGAAGAAACCUGGAAUCAGAG | 305 | CUCUGAUUCCAGGUUUCUUCCUCUGUG | 758 |
| S306-AS759-M1 | AGAGGAAGAAACCUGGAACUAGAGG | 306 | CCUCUAGUUCCAGGUUUCUUCCUCUGU | 759 |
| S307-AS760-M1 | GAGGAAGAAACCUGGAACCAGAGGG | 307 | CCCUCUGGUUCCAGGUUUCUUCCUCUG | 760 |
| S308-AS761-M1 | AGGAAGAAACCUGGAACCAUAGGGG | 308 | CCCCUAUGGUUCCAGGUUUCUUCCUCU | 761 |
| S309-AS762-M1 | GCAGAUUGGGCUGGCUCUGAAGCCA | 309 | UGGCUUCAGAGCCAGCCCAAUCUGCGU | 762 |
| S310-AS763-M1 | CAGAUUGGGCUGGCUCUGAAGCCAA | 310 | UUGGCUUCAGAGCCAGCCCAAUCUGCG | 763 |
| S311-AS764-M1 | AGAUUGGGCUGGCUCUGAAUCCAAG | 311 | CUUGGAUUCAGAGCCAGCCCAAUCUGC | 764 |
| S312-AS765-M1 | UGGGCUGGCUCUGAAGCCAAGCCUC | 312 | GAGGCUUGGCUUCAGAGCCAGCCCAAU | 765 |
| S313-AS766-M1 | GGGCUGGCUCUGAAGCCAAUCCUCT | 313 | AGAGGAUUGGCUUCAGAGCCAGCCCAA | 766 |
| S314-AS767-M1 | GAAGCCAAGCCUCUUCUUAUUUCAC | 314 | GUGAAAUAAGAAGAGGCUUGGCUUCAG | 767 |
| S315-AS768-M1 | AAGCCUCUUCUUACUUCACUCGGCT | 315 | AGCCGAGUGAAGUAAGAAGAGGCUUGG | 768 |
| S316-AS769-M1 | AGCCUCUUCUUACUUCACCUGGCTG | 316 | CAGCCAGGUGAAGUAAGAAGAGGCUUG | 769 |
| S317-AS770-M1 | GCCUCUUCUUACUUCACCCUGCUGG | 317 | CCAGCAGGGUGAAGUAAGAAGAGGCUU | 770 |
| S318-AS771-M1 | CCCGGCUGGGCUCCUCAUUUUUACG | 318 | CGUAAAAAUGAGGAGCCCAGCCGGGUG | 771 |
| S319-AS772-M1 | CCGGCUGGGCUCCUCAUUUUUACGG | 319 | CCGUAAAAAUGAGGAGCCCAGCCGGGU | 772 |
| S320-AS773-M1 | CGGCUGGGCUCCUCAUUUUUACGGG | 320 | CCCGUAAAAAUGAGGAGCCCAGCCGGG | 773 |
| S321-AS774-M1 | GGCUGGGCUCCUCAUUUUUACGGGT | 321 | ACCCGUAAAAAUGAGGAGCCCAGCCGG | 774 |
| S322-AS775-M1 | GCUGGGCUCCUCAUUUUUAUGGGTA | 322 | UACCCAUAAAAAUGAGGAGCCCAGCCG | 775 |
| S323-AS776-M1 | ACGGGUAACAGUGAGGCUGUGAAGG | 323 | CCUUCACAGCCUCACUGUUACCCGUAA | 776 |
| S324-AS777-M1 | AGCUCGGUGAGUGAUGGCAUAACGA | 324 | UCGUUAUGCCAUCACUCACCGAGCUUC | 777 |
| S325-AS778-M1 | GCUCGGUGAGUGAUGGCAGAACGAT | 325 | AUCGUUCUGCCAUCACUCACCGAGCUU | 778 |
| S326-AS779-M1 | CUCGGUGAGUGAUGGCAGAACGATG | 326 | CAUCGUUCUGCCAUCACUCACCGAGCU | 779 |
| S327-AS780-M1 | UCGGUGAGUGAUGGCAGAAUGAUGC | 327 | GCAUCAUUCUGCCAUCACUCACCGAGC | 780 |
| S328-AS781-M1 | CGGUGAGUGAUGGCAGAACUAUGCC | 328 | GGCAUAGUUCUGCCAUCACUCACCGAG | 781 |
| S329-AS782-M1 | AUGCCUGCAGGCAUGGAACUUUUUC | 329 | GAAAAAGUUCCAUGCCUGCAGGCAUCG | 782 |
| S330-AS783-M1 | UGCCUGCAGGCAUGGAACUUUUUCC | 330 | GGAAAAGUUCCAUGCCUGCAGGCAUC | 783 |
| S331-AS784-M1 | GCCUGCAGGCAUGGAACUUUUUCCG | 331 | CGGAAAAGUUCCAUGCCUGCAGGCAU | 784 |
| S332-AS785-M1 | CCUGCAGGCAUGGAACUUUUUCCGT | 332 | ACGGAAAAGUUCCAUGCCUGCAGGCA | 785 |
| S333-AS786-M1 | CUGCAGGCAUGGAACUUUUUCCGTT | 333 | AACGGAAAAGUUCCAUGCCUGCAGGC | 786 |
| S334-AS787-M1 | AUGGAACUUUUUCCGUUAUUACCCA | 334 | UGGGUAAUAACGGAAAAGUUCCAUGC | 787 |
| S335-AS788-M1 | UUUUUCCGUUAUCACCCAGUCCUGA | 335 | UCAGGACUGGGUGAUAACGGAAAAGU | 788 |
| S336-AS789-M1 | UUUUCCGUUAUCACCCAGGUCUGAT | 336 | AUCAGACCUGGGUGAUAACGGAAAAG | 789 |
| S337-AS790-M1 | UUUCCGUUAUCACCCAGGCUUGATT | 337 | AAUCAAGCCUGGGUGAUAACGGAAAA | 790 |
| S338-AS791-M1 | UUCCGUUAUCACCCAGGCCUGAUCC | 338 | GAAUCAGGCCUGGGUGAUAACGGAAAA | 791 |

TABLE 4-continued

Oligonucleotide Sequences

| App Name | Sense Sequence/mRNA seq | S SEQ ID NO | Antisense Sequence | AS SEQ ID NO |
| --- | --- | --- | --- | --- |
| S339-AS792-M1 | UCCGUUAUCACCCAGGCCUUAUUCA | 339 | UGAAUAAGGCCUGGGUGAUAACGGAAA | 792 |
| S340-AS793-M1 | CCGUUAUCACCCAGGCCUGAUUCAC | 340 | GUGAAUCAGGCCUGGGUGAUAACGGAA | 793 |
| S341-AS794-M1 | CGUUAUCACCCAGGCCUGAUUCACT | 341 | AGUGAAUCAGGCCUGGGUGAUAACGGA | 794 |
| S342-AS795-M1 | CACCCAGGCCUGAUUCACUUGCCUG | 342 | CAGGCAAGUGAAUCAGGCCUGGGUGAU | 795 |
| S343-AS796-M1 | ACCCAGGCCUGAUUCACUGUCCUGG | 343 | CCAGGACAGUGAAUCAGGCCUGGGUGA | 796 |
| S344-AS797-M1 | UGGCCUGGCGGAGAUGCUUUUAAGG | 344 | CCUUAAAAGCAUCUCCGCCAGGCCAGU | 797 |
| S345-AS798-M1 | GGCCUGGCGGAGAUGCUUCUAAGGC | 345 | GCCUUAGAAGCAUCUCCGCCAGGCCAG | 798 |
| S346-AS799-M1 | GCCUGGCGGAGAUGCUUCUAAGGCA | 346 | UGCCUUAGAAGCAUCUCCGCCAGGCCA | 799 |
| S347-AS800-M1 | CCUGGCGGAGAUGCUUCUAAGGCAT | 347 | AUGCCUUAGAAGCAUCUCCGCCAGGCC | 800 |
| S348-AS801-M1 | CUGGCGGAGAUGCUUCUAAUGCAUG | 348 | CAUGCAUUAGAAGCAUCUCCGCCAGGC | 801 |
| S349-AS802-M1 | UGGCGGAGAUGCUUCUAAGUCAUGG | 349 | CCAUGACUUAGAAGCAUCUCCGCCAGG | 802 |
| S350-AS803-M1 | GGCGGAGAUGCUUCUAAGGUAUGGT | 350 | ACCAUACCUUAGAAGCAUCUCCGCCAG | 803 |
| S351-AS804-M1 | GCGGAGAUGCUUCUAAGGCAUGGTC | 351 | GACCAUGCCUUAGAAGCAUCUCCGCCA | 804 |
| S352-AS805-M1 | CGGAGAUGCUUCUAAGGCAUGGUCG | 352 | CGACCAUGCCUUAGAAGCAUCUCCGCC | 805 |
| S353-AS806-M1 | GGAGAUGCUUCUAAGGCAUUGUCGG | 353 | CCGACAAUGCCUUAGAAGCAUCUCCGC | 806 |
| S354-AS807-M1 | GAGAUGCUUCUAAGGCAUGUUCGGG | 354 | CCCGAACAUGCCUUAGAAGCAUCUCCG | 807 |
| S355-AS808-M1 | GGAGAGGGCCAACAACUGUUCCUCC | 355 | GGAGGAACAGUUGUUGGCCCUCUCCCC | 808 |
| S356-AS809-M1 | GCCAACAACUGUCCCUCCUUGAGCA | 356 | UGCUCAAGGAGGGACAGUUGUUGGCCC | 809 |
| S357-AS810-M1 | CCAACAACUGUCCCUCCUUUAGCAC | 357 | GUGCUAAAGGAGGGACAGUUGUUGGCC | 810 |
| S358-AS811-M1 | UUGAGCACCAGCCCCACCCAAGCAA | 358 | UUGCUUGGGUGGGGCUGGUGCUCAAGG | 811 |
| S359-AS812-M1 | UGAGCACCAGCCCCACCCAAGCAAG | 359 | CUUGCUUGGGUGGGGCUGGUGCUCAAG | 812 |
| S360-AS813-M1 | GAGCACCAGCCCCACCCAAUCAAGC | 360 | GCUUGAUUGGGUGGGGCUGGUGCUCAA | 813 |
| S361-AS814-M1 | AGCACCAGCCCCACCCAAGUAAGCA | 361 | UGCUUACUUGGGUGGGGCUGGUGCUCA | 814 |
| S362-AS815-M1 | ACCCAAGCAAGCAGACAUUUAUCTT | 362 | AAGAUAAAUGUCUGCUUGCUUGGGUGG | 815 |
| S363-AS816-M1 | CCCAAGCAAGCAGACAUUUAUCUTT | 363 | AAAGAUAAAUGUCUGCUUGCUUGGGUG | 816 |
| S364-AS817-M1 | CCAAGCAAGCAGACAUUUAUCUUTT | 364 | AAAAGAUAAAUGUCUGCUUGCUUGGGU | 817 |
| S365-AS818-M1 | CAAGCAAGCAGACAUUUAUUUUUTG | 365 | CAAAAAUAAAUGUCUGCUUGCUUGGG | 818 |
| S366-AS819-M1 | AAGCAAGCAGACAUUUAUCUUUUGG | 366 | CCAAAAGAUAAAUGUCUGCUUGCUUGG | 819 |
| S367-AS820-M1 | AGCAAGCAGACAUUUAUCUUUUGGG | 367 | CCCAAAAGAUAAAUGUCUGCUUGCUUG | 820 |
| S368-AS821-M1 | GCAAGCAGACAUUUAUCUUUUGGGT | 368 | ACCCAAAAGAUAAAUGUCUGCUUGCUU | 821 |
| S369-AS822-M1 | AAGCAGACAUUUAUCUUUUGGUCT | 369 | AGACCAAAAGAUAAAUGUCUGCUUGC | 822 |
| S370-AS823-M1 | AGCAGACAUUUAUCUUUUGUGUCTG | 370 | CAGACACAAAAGAUAAAUGUCUGCUUG | 823 |
| S371-AS824-M1 | GCAGACAUUUAUCUUUUGGUUCUGT | 371 | ACAGAACCAAAAGAUAAAUGUCUGCUU | 824 |
| S372-AS825-M1 | UGUUGCCUUUUUACAGCCAACUUTT | 372 | AAAAGUUGGCUGUAAAAAGGCAACAGA | 825 |
| S373-AS826-M1 | GUUGCCUUUUUACAGCCAAUUUUTC | 373 | GAAAAAUUGGCUGUAAAAAGGCAACAG | 826 |
| S374-AS827-M1 | UUUACAGCCAACUUUUCUAUACCTG | 374 | CAGGUAUAGAAAAGUUGGCUGUAAAAA | 827 |
| S375-AS828-M1 | UUACAGCCAACUUUUCUAGACCUGT | 375 | ACAGGUCUAGAAAAGUUGGCUGUAAAA | 828 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S376-AS829-M1 | UUUUCUAGACCUGUUUUGCUUUUGT | 376 | ACAAAAGCAAAACAGGUCUAGAAAAGU | 829 |
| S377-AS830-M1 | UUUCUAGACCUGUUUUGCUUUUGTA | 377 | UACAAAAGCAAAACAGGUCUAGAAAAG | 830 |
| S378-AS831-M1 | UUCUAGACCUGUUUUGCUUUUGUAA | 378 | UUACAAAAGCAAAACAGGUCUAGAAAA | 831 |
| S379-AS832-M1 | UCUAGACCUGUUUUGCUUUUGUAAC | 379 | GUUACAAAAGCAAAACAGGUCUAGAAA | 832 |
| S380-AS833-M1 | CUAGACCUGUUUUGCUUUUUUAACT | 380 | AGUUAAAAAGCAAAACAGGUCUAGAA | 833 |
| S381-AS834-M1 | UAGACCUGUUUUGCUUUUGUAACTT | 381 | AAGUUACAAAGCAAAACAGGUCUAGA | 834 |
| S382-AS835-M1 | AGACCUGUUUUGCUUUUGUAACUTG | 382 | CAAGUUACAAAAGCAAAACAGGUCUAG | 835 |
| S383-AS836-M1 | GACCUGUUUUGCUUUUGUAACUUGA | 383 | UCAAGUUACAAAAGCAAAACAGGUCUA | 836 |
| S384-AS837-M1 | ACCUGUUUUGCUUUUGUAAUUUGAA | 384 | UUCAAUUACAAAAGCAAAACAGGUCU | 837 |
| S385-AS838-M1 | CCUGUUUUGCUUUUGUAACUUGAAG | 385 | CUUCAAGUUACAAAAGCAAAACAGGUC | 838 |
| S386-AS839-M1 | CUGUUUUGCUUUUGUAACUUGAAGA | 386 | UCUUCAAGUUACAAAAGCAAAACAGGU | 839 |
| S387-AS840-M1 | UGUUUUGCUUUUGUAACUUUAAGAT | 387 | AUCUUAAAGUUACAAAAGCAAAACAGG | 840 |
| S388-AS841-M1 | GUUUUGCUUUUGUAACUUGAAGATA | 388 | UAUCUUCAAGUUACAAAAGCAAAACAG | 841 |
| S389-AS842-M1 | UUUUGCUUUUGUAACUUGAAGAUAT | 389 | AUAUCUUCAAGUUACAAAAGCAAAACA | 842 |
| S390-AS843-M1 | UUUGCUUUUGUAACUUGAAUAUAUU | 390 | AAUAUAUUCAAGUUACAAAAGCAAAAC | 843 |
| S391-AS844-M1 | UUGCUUUUGUAACUUGAAGAUAUUU | 391 | AAAUAUCUUCAAGUUACAAAAGCAAAA | 844 |
| S392-AS845-M1 | UGCUUUUGUAACUUGAAGAUAUUUA | 392 | UAAAUAUCUUCAAGUUACAAAAGCAAA | 845 |
| S393-AS846-M1 | GCUUUUGUAACUUGAAGAUAUUUAT | 393 | AUAAAUAUCUUCAAGUUACAAAAGCAA | 846 |
| S394-AS847-M1 | CUUUUGUAACUUGAAGAUAUUUAUU | 394 | AAUAAAUAUCUUCAAGUUACAAAAGCA | 847 |
| S395-AS848-M1 | UUUUGUAACUUGAAGAUAUUUAUUC | 395 | GAAUAAAUAUCUUCAAGUUACAAAAGC | 848 |
| S396-AS849-M1 | UUUGUAACUUGAAGAUAUUUAUUCT | 396 | AGAAUAAAUAUCUUCAAGUUACAAAAG | 849 |
| S397-AS850-M1 | UUGUAACUUGAAGAUAUUUAUUCTG | 397 | CAGAAUAAAUAUCUUCAAGUUACAAAA | 850 |
| S398-AS851-M1 | UGUAACUUGAAGAUAUUUAUUCUGG | 398 | CCAGAAUAAAUAUCUUCAAGUUACAAA | 851 |
| S399-AS852-M1 | GUAACUUGAAGAUAUUUAUUCUGGG | 399 | CCCAGAAUAAAUAUCUUCAAGUUACAA | 852 |
| S400-AS853-M1 | UAACUUGAAGAUAUUUAUUUGGGT | 400 | ACCCAAAAUAAAUAUCUUCAAGUUACA | 853 |
| S401-AS854-M1 | ACUUGAAGAUAUUUAUUCUUGGUUT | 401 | AAACCAAGAAUAAAUAUCUUCAAGUUA | 854 |
| S402-AS855-M1 | CUUGAAGAUAUUUAUUCUGUGUUUT | 402 | AAAACACAGAAUAAAUAUCUUCAAGUU | 855 |
| S403-AS856-M1 | UUGAAGAUAUUUAUUCUGGUUUUTG | 403 | CAAAACCAGAAUAAAUAUCUUCAAGU | 856 |
| S404-AS857-M1 | GAAGAUAUUUAUUCUGGGUUUUGTA | 404 | UACAAAACCCAGAAUAAAUAUCUUCAA | 857 |
| S405-AS858-M1 | AAGAUAUUUAUUCUGGGUUUUGUAG | 405 | CUACAAAACCCAGAAUAAAUAUCUUCA | 858 |
| S406-AS859-M1 | AUAUUUAUUCUGGGUUUUGUAGCAT | 406 | AUGCUACAAAACCCAGAAUAAAUAUCU | 859 |
| S407-AS860-M1 | UAUUUAUUCUGGGUUUUGUAGCATT | 407 | AAUGCUACAAAACCCAGAAUAAAUAUC | 860 |
| S408-AS861-M1 | AUUUAUUCUGGGUUUUGUAUCAUTT | 408 | AAAUGAUACAAAACCCAGAAUAAAUAU | 861 |
| S409-AS862-M1 | UUUAUUCUGGGUUUUGUAGUAUUTT | 409 | AAAAUACUACAAAACCCAGAAUAAAUA | 862 |
| S410-AS863-M1 | AUUCUGGGUUUUGUAGCAUUUUUAT | 410 | AUAAAAUGCUACAAAACCCAGAAUAA | 863 |
| S411-AS864-M1 | UUCUGGGUUUUGUAGCAUUUUUATT | 411 | AAUAAAAUGCUACAAAACCCAGAAUA | 864 |
| S412-AS865-M1 | UCUGGGUUUUGUAGCAUUUUUAUTA | 412 | UAAUAAAAUGCUACAAAACCCAGAAU | 865 |
| S413-AS866-M1 | CUGGGUUUUGUAGCAUUUUUAUUAA | 413 | UUAAUAAAAUGCUACAAAACCCAGAA | 866 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S414-AS867-M1 | UGGGUUUUGUAGCAUUUUUAUUAAT | 414 | AUUAAUAAAAAUGCUACAAAACCCAGA | 867 |
| S415-AS868-M1 | GGGUUUUGUAGCAUUUUUAUUAATA | 415 | UAUUAAUAAAAAUGCUACAAAACCCAG | 868 |
| S416-AS869-M1 | GGUUUUGUAGCAUUUUUAUUAAUAT | 416 | AUAUUAAUAAAAAUGCUACAAAACCCA | 869 |
| S417-AS870-M1 | GUUUUGUAGCAUUUUUAUUAAUAUG | 417 | CAUAUUAAUAAAAAUGCUACAAAACCC | 870 |
| S418-AS871-M1 | UUUUGUAGCAUUUUUAUUAAUAUGG | 418 | CCAUAUUAAUAAAAAUGCUACAAAACC | 871 |
| S419-AS872-M1 | UUUGUAGCAUUUUUAUUAAUAUGGT | 419 | ACCAUAUUAAUAAAAAUGCUACAAAAC | 872 |
| S420-AS873-M1 | UUGUAGCAUUUUUAUUAAUAUGGTG | 420 | CACCAUAUUAAUAAAAAUGCUACAAAA | 873 |
| S421-AS874-M1 | UGUAGCAUUUUUAUUAAUAUGGUGA | 421 | UCACCAUAUUAAUAAAAAUGCUACAAA | 874 |
| S422-AS875-M1 | GUAGCAUUUUUAUUAAUAUUGUGAC | 422 | GUCACAAUAUUAAUAAAAAUGCUACAA | 875 |
| S423-AS876-M1 | UAGCAUUUUUAUUAAUAUGUUGACT | 423 | AGUCAACAUAUUAAUAAAAAUGCUACA | 876 |
| S424-AS877-M1 | AGCAUUUUUAUUAAUAUGGUGACTT | 424 | AAGUCACCAUAUUAAUAAAAAUGCUAC | 877 |
| S425-AS878-M1 | GCAUUUUUAUUAAUAUGGUUACUTT | 425 | AAAGUAACCAUAUUAAUAAAAAUGCUA | 878 |
| S426-AS879-M1 | CAUUUUUAUUAAUAUGGUGACUUTT | 426 | AAAAGUCACCAUAUUAAUAAAAAUGCU | 879 |
| S427-AS880-M1 | AUUUUUAUUAAUAUGGUGAUUUUTT | 427 | AAAAAUCACCAUAUUAAUAAAAAUGC | 880 |
| S428-AS881-M1 | UUUUUAUUAAUAUGGUGACUUUUTA | 428 | UAAAAGUCACCAUAUUAAUAAAAAUG | 881 |
| S429-AS882-M1 | UUUUAUUAAUAUGGUGACUUUUUAA | 429 | UUAAAAGUCACCAUAUUAAUAAAAAU | 882 |
| S430-AS883-M1 | UUUAUUAAUAUGGUGACUUUUUAAA | 430 | UUUAAAAGUCACCAUAUUAAUAAAAA | 883 |
| S431-AS884-M1 | UUAUUAAUAUGGUGACUUUUUAAAA | 431 | UUUUAAAAGUCACCAUAUUAAUAAAA | 884 |
| S432-AS885-M1 | UAUUAAUAUGGUGACUUUUUAAAAT | 432 | AUUUUAAAAGUCACCAUAUUAAUAAA | 885 |
| S433-AS886-M1 | AUUAAUAUGGUGACUUUUUAAAATA | 433 | UAUUUUAAAAGUCACCAUAUUAAUAA | 886 |
| S434-AS887-M1 | UUAAUAUGGUGACUUUUUAAAAUAA | 434 | UUAUUUUAAAAGUCACCAUAUUAAUA | 887 |
| S435-AS888-M1 | UAAUAUGGUGACUUUUUAAAAUAAA | 435 | UUUAUUUUAAAAGUCACCAUAUUAAU | 888 |
| S436-AS889-M1 | AAUAUGGUGACUUUUUAAAAUAAAA | 436 | UUUUAUUUUAAAAGUCACCAUAUUAA | 889 |
| S437-AS890-M1 | AUAUGGUGACUUUUUAAAAUAAAAA | 437 | UUUUUAUUUUAAAAGUCACCAUAUUA | 890 |
| S438-AS891-M1 | UAUGGUGACUUUUUAAAAUAAAAAC | 438 | GUUUUUAUUUUAAAAGUCACCAUAUU | 891 |
| S439-AS892-M1 | AUGGUGACUUUUUAAAAUAAAAACA | 439 | UGUUUUUAUUUUAAAAGUCACCAUAU | 892 |
| S440-AS893-M1 | UGGUGACUUUUUAAAAUAAAAACAA | 440 | UUGUUUUUAUUUUAAAAGUCACCAUA | 893 |
| S441-AS894-M1 | GGUGACUUUUUAAAAUAAAAACAAA | 441 | UUUGUUUUUAUUUUAAAAGUCACCAU | 894 |
| S442-AS895-M1 | GUGACUUUUUAAAAUAAAAACAAAC | 442 | GUUUGUUUUUAUUUUAAAAGUCACCA | 895 |
| S443-AS896-M1 | UGACUUUUUAAAAUAAAAAUAAACA | 443 | UGUUUAUUUUUAUUUUAAAAGUCACC | 896 |
| S444-AS897-M1 | GACUUUUUAAAAUAAAAACAAACAA | 444 | UUGUUUGUUUUUAUUUUAAAAGUCAC | 897 |
| S445-AS898-M1 | ACUUUUUAAAAUAAAAACAAACAAA | 445 | UUUGUUUGUUUUUAUUUUAAAAGUCA | 898 |
| S446-AS899-M1 | UUUUAAAAUAAAAACAAACAAACGT | 446 | ACGUUUGUUUGUUUUUAUUUUAAAAG | 899 |
| S447-AS900-M1 | UUUAAAAUAAAAACAAACAAACGTT | 447 | AACGUUUGUUUGUUUUUAUUUUAAAA | 900 |
| S448-AS901-M1 | UUAAAAUAAAAACAAACAAACGUTG | 448 | CAACGUUUGUUUGUUUUUAUUUUAAA | 901 |
| S449-AS902-M1 | UAAAAUAAAAACAAACAAAUGUUGT | 449 | ACAACAUUUGUUUGUUUUUAUUUUAAA | 902 |
| S450-AS903-M1 | AAAACAAACAAACGUUGUUCUAAC | 450 | GUUAGAACAACGUUUGUUUGUUUUUAU | 903 |

TABLE 4-continued

Oligonucleotide Sequences

| App Name | Sense Sequence/mRNA seq | S SEQ ID NO | Antisense Sequence | AS SEQ ID NO |
| --- | --- | --- | --- | --- |
| S451-AS904-M1 | CAAACAAACGUUGUCCUAAUAAAAA | 451 | UUUUUAUUAGGACAACGUUUGUUUGUU | 904 |
| S452-AS905-M1 | AAACAAACGUUGUCCUAACAAAAAA | 452 | UUUUUUGUUAGGACAACGUUUGUUUGU | 905 |
| S453-AS906-M1 | AACAAACGUUGUCCUAACAAAAAAA | 453 | UUUUUUUGUUAGGACAACGUUUGUUUG | 906 |
| S907-AS1030-M1 | CUCCAGGCGGUCCUGGUGGUCGCUG | 907 | CAGCGACCACCAGGACCGCCUGGAGCU | 1030 |
| S908-AS1031-M1 | UCCAGGCGGUCCUGGUGGCUGCUGC | 908 | GCAGCAGCCACCAGGACCGCCUGGAGC | 1031 |
| S909-AS1032-M1 | GCCGCUGCCACUGCUGCUGUUGCUG | 909 | CAGCAACAGCAGCAGUGGCAGCGGCCA | 1032 |
| S910-AS1033-M1 | CCGCUGCCACUGCUGCUGCUGCUGC | 910 | GCAGCAGCAGCAGCAGUGGCAGCGGCC | 1033 |
| S911-AS1034-M1 | GCCCGUGCGCAGGAGGACGAGGACG | 911 | CGUCCUCGUCCUCCUGCGCACGGGCGC | 1034 |
| S912-AS1035-M1 | CCCGUGCGCAGGAGGACGAUGACGG | 912 | CCGUCAUCGUCCUCCUGCGCACGGGCG | 1035 |
| S913-AS1036-M1 | CCGUGCGCAGGAGGACGAGUACGGC | 913 | GCCGUACUCGUCCUCCUGCGCACGGGC | 1036 |
| S914-AS1037-M1 | CGUGCGCAGGAGGACGAGGACGGCG | 914 | CGCCGUCCUCGUCCUCCUGCGCACGGG | 1037 |
| S915-AS1038-M1 | GUGCGCAGGAGGACGAGGAUGGCGA | 915 | UCGCCAUCCUCGUCCUCCUGCGCACGG | 1038 |
| S916-AS1039-M1 | UGCGCAGGAGGACGAGGACUGCGAC | 916 | GUCGCAGUCCUCGUCCUCCUGCGCACG | 1039 |
| S917-AS1040-M1 | GCGCAGGAGGACGAGGACGUCGACT | 917 | AGUCGACGUCCUCGUCCUCCUGCGCAC | 1040 |
| S918-AS1041-M1 | GGAGGACGAGGACGGCGACUACGAG | 918 | CUCGUAGUCGCCGUCCUCGUCCUCCUG | 1041 |
| S919-AS1042-M1 | GCGUUCCGAGGAGGACGGCUUGGCC | 919 | GGCCAAGCCGUCCUCCUCGGAACGCAA | 1042 |
| S920-AS1043-M1 | CGUUCCGAGGAGGACGGCCUGGCCG | 920 | CGGCCAGGCCGUCCUCCUCGGAACGCA | 1043 |
| S921-AS1044-M1 | GUUCCGAGGAGGACGGCCUUGCCGA | 921 | UCGGCAAGGCCGUCCUCCUCGGAACGC | 1044 |
| S922-AS1045-M1 | UUCCGAGGAGGACGGCCUGUCCGAA | 922 | UUCGGACAGGCCGUCCUCCUCGGAACG | 1045 |
| S923-AS1046-M1 | UCCGAGGAGGACGGCCUGGUCGAAG | 923 | CUUCGACCAGGCCGUCCUCCUCGGAAC | 1046 |
| S924-AS1047-M1 | CCGAGGAGGACGGCCUGGCUGAAGC | 924 | GCUUCAGCCAGGCCGUCCUCCUCGGAA | 1047 |
| S925-AS1048-M1 | CGAGGAGGACGGCCUGGCCUAAGCA | 925 | UGCUUAGGCCAGGCCGUCCUCCUCGGA | 1048 |
| S926-AS1049-M1 | GAGGAGGACGGCCUGGCCGAAGCAC | 926 | GUGCUUCGGCCAGGCCGUCCUCCUCGG | 1049 |
| S927-AS1050-M1 | GCCACCUUCCACCGCUGCGUCAAGG | 927 | CCUUGACGCAGCGGUGGAAGGUGGCUG | 1050 |
| S928-AS1051-M1 | CCACCUUCCACCGCUGCGCUAAGGA | 928 | UCCUUAGCGCAGCGGUGGAAGGUGGCU | 1051 |
| S929-AS1052-M1 | CACCUUCCACCGCUGCGCCAAGGAT | 929 | AUCCUUGGCGCAGCGGUGGAAGGUGGC | 1052 |
| S930-AS1053-M1 | ACCUUCCACCGCUGCGCCAAGGATC | 930 | GAUCCUUGGCGCAGCGGUGGAAGGUGG | 1053 |
| S931-AS1054-M1 | AGCGCACUGCCCGCCGCCUUCAGGC | 931 | GCCUGAAGGCGGCGGGCAGUGCGCUCU | 1054 |
| S932-AS1055-M1 | GCGCACUGCCCGCCGCCUGUAGGCC | 932 | GGCCUACAGGCGGCGGGCAGUGCGCUC | 1055 |
| S933-AS1056-M1 | CGCACUGCCCGCCGCCUGCAGGCCC | 933 | GGGCCUGCAGGCGGCGGGCAGUGCGCU | 1056 |
| S934-AS1057-M1 | GCACUGCCCGCCGCCUGCAUGCCCA | 934 | UGGGCAUGCAGGCGGCGGGCAGUGCGC | 1057 |
| S935-AS1058-M1 | CACUGCCCGCCGCCUGCAGUCCCAG | 935 | CUGGGACUGCAGGCGGCGGGCAGUGCG | 1058 |
| S936-AS1059-M1 | ACUGCCCGCCGCCUGCAGGUCCAGG | 936 | CCUGGACCUGCAGGCGGCGGGCAGUGC | 1059 |
| S937-AS1060-M1 | CUGCCCGCCGCCUGCAGGCUCAGGC | 937 | GCCUGAGCCUGCAGGCGGCGGGCAGUG | 1060 |
| S938-AS1061-M1 | UGCCCGCCGCCUGCAGGCCUAGGCT | 938 | AGCCUAGGCCUGCAGGCGGCGGGCAGU | 1061 |
| S939-AS1062-M1 | GCCCGCCGCCUGCAGGCCCAGGCTG | 939 | CAGCCUGGGCCUGCAGGCGGCGGGCAG | 1062 |
| S940-AS1063-M1 | CCCGCCGCCUGCAGGCCCAUGCUGC | 940 | GCAGCAUGGGCCUGCAGGCGGCGGGCA | 1063 |
| S941-AS1064-M1 | UGGCGACCUGCUGGAGCUGUCCUUG | 941 | CAAGGACAGCUCCAGCAGGUCGCCACU | 1064 |

TABLE 4-continued

Oligonucleotide Sequences

| App Name | Sense Sequence/mRNA seq | S SEQ ID NO | Antisense Sequence | AS SEQ ID NO |
| --- | --- | --- | --- | --- |
| S942-AS1065-M1 | GGCGACCUGCUGGAGCUGGUCUUGA | 942 | UCAAGACCAGCUCCAGCAGGUCGCCAC | 1065 |
| S943-AS1066-M1 | GCGACCUGCUGGAGCUGGCUUUGAA | 943 | UUCAAAGCCAGCUCCAGCAGGUCGCCA | 1066 |
| S944-AS1067-M1 | CGACCUGCUGGAGCUGGCCUUGAAG | 944 | CUUCAAGGCCAGCUCCAGCAGGUCGCC | 1067 |
| S945-AS1068-M1 | GAGGCAGCCUGGUGGAGGUUUAUCT | 945 | AGAUAAACCUCCACCAGGCUGCCUCCG | 1068 |
| S946-AS1069-M1 | AGGCAGCCUGGUGGAGGUGUAUCTC | 946 | GAGAUACACCUCCACCAGGCUGCCUCC | 1069 |
| S947-AS1070-M1 | UGUGCCCGAGGAGGACGGGACCCGC | 947 | GCGGGUCCCGUCCUCCUCGGGCACAUU | 1070 |
| S948-AS1071-M1 | GUGCCCGAGGAGGACGGGAUCCGCT | 948 | AGCGGAUCCCGUCCUCCUCGGGCACAU | 1071 |
| S949-AS1072-M1 | UGCCCGAGGAGGACGGGACUCGCTT | 949 | AAGCGAGUCCCGUCCUCCUCGGGCACA | 1072 |
| S950-AS1073-M1 | GCCCGAGGAGGACGGGACCUGCUTC | 950 | GAAGCAGGUCCCGUCCUCCUCGGGCAC | 1073 |
| S951-AS1074-M1 | CCCGAGGAGGACGGGACCCUCUUCC | 951 | GGAAGAGGGUCCCGUCCUCCUCGGGCA | 1074 |
| S952-AS1075-M1 | CCGAGGAGGACGGGACCCGUUUCCA | 952 | UGGAAACGGGUCCCGUCCUCCUCGGGC | 1075 |
| S953-AS1076-M1 | CGAGGAGGACGGGACCCGCUUCCAC | 953 | GUGGAAGCGGGUCCCGUCCUCCUCGGG | 1076 |
| S954-AS1077-M1 | GGCAGGGGUGGUCAGCGGCUGGGAT | 954 | AUCCCAGCCGCUGACCACCCUGCCAG | 1077 |
| S955-AS1078-M1 | GCAGGGGUGGUCAGCGGCCUGGAUG | 955 | CAUCCAGGCCGCUGACCACCCCUGCCA | 1078 |
| S956-AS1079-M1 | CAGGGGUGGUCAGCGGCCGUGAUGC | 956 | GCAUCACGGCCGCUGACCACCCCUGCC | 1079 |
| S957-AS1080-M1 | GUGCUGCUGCCCCUGGCGGUUGGGT | 957 | ACCCAACCGCCAGGGGCAGCAGCACCA | 1080 |
| S958-AS1081-M1 | UGCUGCUGCCCCUGGCGGGUGGGTA | 958 | UACCCACCCGCCAGGGGCAGCAGCACC | 1081 |
| S959-AS1082-M1 | GCUGCUGCCCCUGGCGGGUUGGUAC | 959 | GUACCAACCCGCCAGGGGCAGCAGCAC | 1082 |
| S960-AS1083-M1 | CUGCUGCCCCUGGCGGGUGUGUACA | 960 | UGUACACACCCGCCAGGGGCAGCAGCA | 1083 |
| S961-AS1084-M1 | UGCUGCCCCUGGCGGGUGGUUACAG | 961 | CUGUAACCACCCGCCAGGGGCAGCAGC | 1084 |
| S962-AS1085-M1 | GCUGCCCCUGGCGGGUGGGUACAGC | 962 | GCUGUACCCACCCGCCAGGGGCAGCAG | 1085 |
| S963-AS1086-M1 | CUGCCCCUGGCGGGUGGGUACAGCC | 963 | GGCUGUACCCACCCGCCAGGGGCAGCA | 1086 |
| S964-AS1087-M1 | UGCCCCUGGCGGGUGGGUAUAGCCG | 964 | CGGCUAUACCCACCCGCCAGGGGCAGC | 1087 |
| S965-AS1088-M1 | GCCCCUGGCGGGUGGGUACAGCCGC | 965 | GCGGCUGUACCCACCCGCCAGGGGCAG | 1088 |
| S966-AS1089-M1 | UCAACGCCGCCUGCCAGCGUCUGGC | 966 | GCCAGACGCUGGCAGGCGGCGUUGAGG | 1089 |
| S967-AS1090-M1 | CAACGCCGCCUGCCAGCGCUUGGCG | 967 | CGCCAAGCGCUGGCAGGCGGCGUUGAG | 1090 |
| S968-AS1091-M1 | AACGCCGCCUGCCAGCGCCUGGCGA | 968 | UCGCCAGGCGCUGGCAGGCGGCGUUGA | 1091 |
| S969-AS1092-M1 | ACGCCGCCUGCCAGCGCCUUGCGAG | 969 | CUCGCAAGGCGCUGGCAGGCGGCGUUG | 1092 |
| S970-AS1093-M1 | CGCCGCCUGCCAGCGCCUGUCGAGG | 970 | CCUCGACAGGCGCUGGCAGGCGGCGUU | 1093 |
| S971-AS1094-M1 | GCCGCCUGCCAGCGCCUGGUGAGGG | 971 | CCCUCACCAGGCGCUGGCAGGCGGCGU | 1094 |
| S972-AS1095-M1 | CCGCCUGCCAGCGCCUGGCUAGGGC | 972 | GCCCUAGCCAGGCGCUGGCAGGCGGCG | 1095 |
| S973-AS1096-M1 | CGCCUGCCAGCGCCUGGCGAGGGCT | 973 | AGCCCUCGCCAGGCGCUGGCAGGCGGC | 1096 |
| S974-AS1097-M1 | GCCUGCCAGCGCCUGGCGAUGGCTG | 974 | CAGCCAUCGCCAGGCGCUGGCAGGCGG | 1097 |
| S975-AS1098-M1 | CCAGCGCCUGGCGAGGGCUUGGGTC | 975 | GACCCAAGCCCUCGCCAGGCGCUGGCA | 1098 |
| S976-AS1099-M1 | CAGCGCCUGGCGAGGGCUGUGGUCG | 976 | CGACCACAGCCCUCGCCAGGCGCUGGC | 1099 |
| S977-AS1100-M1 | AGCGCCUGGCGAGGGCUGGUGUCGT | 977 | ACGACACCAGCCCUCGCCAGGCGCUGG | 1100 |
| S978-AS1101-M1 | GCGCCUGGCGAGGGCUGGGUUCGTG | 978 | CACGAACCCAGCCCUCGCCAGGCGCUG | 1101 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S979-AS1102-M1 | CGCCUGGCGAGGGCUGGGGUCGUGC | 979 | GCACGACCCCAGCCCUCGCCAGGCGCU | 1102 |
| S980-AS1103-M1 | GCGAGGGCUGGGGUCGUGCUGGUCA | 980 | UGACCAGCACGACCCCAGCCCUCGCCA | 1103 |
| S981-AS1104-M1 | AUGCCUGCCUCUACUCCCCAGCCUC | 981 | GAGGCUGGGGAGUAGAGGCAGGCAUCG | 1104 |
| S982-AS1105-M1 | GCCUCUACUCCCCAGCCUCAGCUCC | 982 | GGAGCUGAGGCUGGGGAGUAGAGGCAG | 1105 |
| S983-AS1106-M1 | GACCUCUUUGCCCCAGGGGAGGACA | 983 | UGUCCUCCCCUGGGGCAAAGAGGUCCA | 1106 |
| S984-AS1107-M1 | CUUUGCCCCAGGGGAGGACAUCAUU | 984 | AAUGAUGUCCUCCCCUGGGGCAAAGAG | 1107 |
| S985-AS1108-M1 | UUUGCCCCAGGGGAGGACAUCAUTG | 985 | CAAUGAUGUCCUCCCCUGGGGCAAAGA | 1108 |
| S986-AS1109-M1 | UUGCCCCAGGGGAGGACAUUAUUGG | 986 | CCAAUAAUGUCCUCCCCUGGGGCAAAG | 1109 |
| S987-AS1110-M1 | UGCCCCAGGGGAGGACAUCAUUGGT | 987 | ACCAAUGAUGUCCUCCCCUGGGGCAAA | 1110 |
| S988-AS1111-M1 | GCCCCAGGGGAGGACAUCAUUGGTG | 988 | CACCAAUGAUGUCCUCCCCUGGGGCAA | 1111 |
| S989-AS1112-M1 | ACACGGAUGGCCACAGCCGUCGCCC | 989 | GGGCGACGGCUGUGGCCAUCCGUGUAG | 1112 |
| S990-AS1113-M1 | CUCCAGGAGUGGGAAGCGGUGGGGC | 990 | GCCCCACCGCUUCCCACUCCUGGAGAA | 1113 |
| S991-AS1114-M1 | UCCAGGAGUGGGAAGCGGCUGGGCG | 991 | CGCCCAGCCGCUUCCCACUCCUGGAGA | 1114 |
| S992-AS1115-M1 | CCAGGAGUGGGAAGCGGCGUGGCGA | 992 | UCGCCACGCCGCUUCCCACUCCUGGAG | 1115 |
| S993-AS1116-M1 | CAGGAGUGGGAAGCGGCGGUGCGAG | 993 | CUCGCACCGCCGCUUCCCACUCCUGGA | 1116 |
| S994-AS1117-M1 | AGGAGUGGGAAGCGGCGGGUCGAGC | 994 | GCUCGACCCGCCGCUUCCCACUCCUGG | 1117 |
| S995-AS1118-M1 | GGAGUGGGAAGCGGCGGGGUGAGCG | 995 | CGCUCACCCCGCCGCUUCCCACUCCUG | 1118 |
| S996-AS1119-M1 | GAGUGGGAAGCGGCGGGGCUAGCGC | 996 | GCGCUAGCCCCGCCGCUUCCCACUCCU | 1119 |
| S997-AS1120-M1 | AGUGGGAAGCGGCGGGGCGAGCGCA | 997 | UGCGCUCGCCCCGCCGCUUCCCACUCC | 1120 |
| S998-AS1121-M1 | GAAGCGGCGGGGCGAGCGCAUGGAG | 998 | CUCCAUGCGCUCGCCCCGCCGCUUCCC | 1121 |
| S999-AS1122-M1 | AAGCGGCGGGGCGAGCGCAUGGAGG | 999 | CCUCCAUGCGCUCGCCCCGCCGCUUCC | 1122 |
| S1000-AS1123-M1 | AGCGGCGGGGCGAGCGCAUUGAGGG | 1000 | GCCUCAAUGCGCUCGCCCCGCCGCUUC | 1123 |
| S1001-AS1124-M1 | GGUGCUGCCUGCUACCCCAUGCCAA | 1001 | UUGGCAUGGGGUAGCAGGCAGCACCUG | 1124 |
| S1002-AS1125-M1 | GUGCUGCCUGCUACCCCAGUCCAAC | 1002 | GUUGGACUGGGGUAGCAGGCAGCACCU | 1125 |
| S1003-AS1126-M1 | UGCUGCCUGCUACCCCAGGUCAACT | 1003 | AGUUGACCUGGGGUAGCAGGCAGCACC | 1126 |
| S1004-AS1127-M1 | GGGCCACGUCCUCACAGGCUGCAGC | 1004 | GCUGCAGCCUGUGAGGACGUGGCCCUG | 1127 |
| S1005-AS1128-M1 | GGCCACGUCCUCACAGGCUUCAGCT | 1005 | AGCUGAAGCCUGUGAGGACGUGGCCCU | 1128 |
| S1006-AS1129-M1 | GCCACGUCCUCACAGGCUGUAGCTC | 1006 | GAGCUACAGCCUGUGAGGACGUGGCCC | 1129 |
| S1007-AS1130-M1 | GGCUGCAGCUCCCACUGGGAGGUGG | 1007 | CCACCUCCCAGUGGGAGCUGCAGCCUG | 1130 |
| S1008-AS1131-M1 | GCUGCAGCUCCCACUGGGAUGUGGA | 1008 | UCCACAUCCCAGUGGGAGCUGCAGCCU | 1131 |
| S1009-AS1132-M1 | CUGCAGCUCCCACUGGGAGUUGGAG | 1009 | CUCCAACUCCCAGUGGGAGCUGCAGCC | 1132 |
| S1010-AS1133-M1 | UGCAGCUCCCACUGGGAGGUGGAGG | 1010 | CCUCCACCUCCCAGUGGGAGCUGCAGC | 1133 |
| S1011-AS1134-M1 | GCAGCUCCCACUGGGAGGUUGAGGA | 1011 | UCCUCAACCUCCCAGUGGGAGCUGCAG | 1134 |
| S1012-AS1135-M1 | CAGCUCCCACUGGGAGGUGUAGGAC | 1012 | GUCCUACACCUCCCAGUGGGAGCUGCA | 1135 |
| S1013-AS1136-M1 | AGCUCCCACUGGGAGGUGGAGGACC | 1013 | GGUCCUCCACCUCCCAGUGGGAGCUGC | 1136 |
| S1014-AS1137-M1 | GCUCCCACUGGGAGGUGGAUGACCT | 1014 | AGGUCAUCCACCUCCCAGUGGGAGCUG | 1137 |
| S1015-AS1138-M1 | CUCCCACUGGGAGGUGGAGUACCTT | 1015 | AAGGUACUCCACCUCCCAGUGGGAGCU | 1138 |
| S1016-AS1139-M1 | UCCCACUGGGAGGUGGAGGACCUTG | 1016 | CAAGGUCCUCCACCUCCCAGUGGGAGC | 1139 |

TABLE 4-continued

Oligonucleotide Sequences

| App Name | Sense Sequence/mRNA seq | S SEQ ID NO | Antisense Sequence | AS SEQ ID NO |
| --- | --- | --- | --- | --- |
| S1017-AS1140-M1 | UGGCACCCACAAGCCGCCUUUGCUG | 1017 | CAGCAAAGGCGGCUUGUGGGUGCCAAG | 1140 |
| S1018-AS1141-M1 | GGCACCCACAAGCCGCCUGUGCUGA | 1018 | UCAGCACAGGCGGCUUGUGGGUGCCAA | 1141 |
| S1019-AS1142-M1 | AGCCGCCUGUGCUGAGGCCACGAGG | 1019 | CCUCGUGGCCUCAGCACAGGCGGCUUG | 1142 |
| S1020-AS1143-M1 | GCCGCCUGUGCUGAGGCCAUGAGGT | 1020 | ACCUCAUGGCCUCAGCACAGGCGGCUU | 1143 |
| S1021-AS1144-M1 | CCGCCUGUGCUGAGGCCACUAGGTC | 1021 | GACCUAGUGGCCUCAGCACAGGCGGCU | 1144 |
| S1022-AS1145-M1 | GGGCCACAGGGAGGCCAGCAUCCAC | 1022 | GUGGAUGCUGGCCUCCCUGUGGCCCAC | 1145 |
| S1023-AS1146-M1 | GGCCACAGGGAGGCCAGCAUCCACG | 1023 | CGUGGAUGCUGGCCUCCCUGUGGCCCA | 1146 |
| S1024-AS1147-M1 | GCCACAGGGAGGCCAGCAUUCACGC | 1024 | GCGUGAAUGCUGGCCUCCCUGUGGCCC | 1147 |
| S1025-AS1148-M1 | CGGCCCCUCAGGAGCAGGUUACCGT | 1025 | ACGGUAACCUGCUCCUGAGGGGCCGGG | 1148 |
| S1026-AS1149-M1 | UGCUGCCGGAGCCGGCACCUGGCGC | 1026 | GCGCCAGGUGCCGGCUCCGGCAGCAGA | 1149 |
| S1027-AS1150-M1 | UCACAGGCUGCUGCCCACGUGGCUG | 1027 | CAGCCACGUGGGCAGCAGCCUGUGAUG | 1150 |
| S1028-AS1151-M1 | CACAGGCUGCUGCCCACGUUGCUGG | 1028 | CCAGCAACGUGGGCAGCAGCCUGUGAU | 1151 |
| S1029-AS1152-M1 | GCUUCCUGCUGCCAUGCCCUAGGTC | 1029 | GACCUAGGGCAUGGCAGCAGGAAGCGU | 1152 |
| S1153-AS1193-M2 | AACUUCAGCUCCUGCACAGUGCAGCCGAAAGGCUGC | 1153 | ACUGUGCAGGAGCUGAAGUUCA | 1193 |
| S1154-AS1194-M2 | UGGCCCUCAUGGGCACCGUUGCAGCCGAAAGGCUGC | 1154 | AACGGUGCCCAUGAGGGCCAGG | 1194 |
| S1155-AS1195-M2 | AGGAGGAGACCCACCUCUCUGCAGCCGAAAGGCUGC | 1155 | AGAGAGGUGGGUCUCCUCCUUC | 1195 |
| S1156-AS1196-M2 | UGCUGGAGCUGGCCUUGAAUGCAGCCGAAAGGCUGC | 1156 | AUUCAAGGCCAGCUCCAGCAGG | 1196 |
| S1157-AS1197-M2 | UCUGUCUUUGCCCAGAGCAUGCAGCCGAAAGGCUGC | 1157 | AUGCUCUGGGCAAAGACAGAGG | 1197 |
| S1158-AS1198-M2 | CUGUCUUUGCCCAGAGCAUUGCAGCCGAAAGGCUGC | 1158 | AAUGCUCUGGGCAAAGACAGAG | 1198 |
| S1159-AS1199-M2 | CUUGCCUGGAACUCACUCAUGCAGCCGAAAGGCUGC | 1159 | AUGAGUGAGUUCCAGGCAAGGA | 1199 |
| S1160-AS1200-M2 | UUGCCUGGAACUCACUCACUGCAGCCGAAAGGCUGC | 1160 | AGUGAGUGAGUUCCAGGCAAGG | 1200 |
| S1161-AS1201-M2 | AGAAUGACUUUUAUUGAGCUGCAGCCGAAAGGCUGC | 1161 | AGCUCAAUAAAAGUCAUUCUGC | 1201 |
| S1162-AS1202-M2 | GAAUGACUUUUAUUGAGCUUGCAGCCGAAAGGCUGC | 1162 | AAGCUCAAUAAAAGUCAUUCUG | 1202 |
| S1163-AS1203-M2 | AUGACUUUUAUUGAGCUCUUGCAGCCGAAAGGCUGC | 1163 | AAGAGCUCAAUAAAAGUCAUUC | 1203 |
| S1164-AS1204-M2 | UGACUUUUAUUGAGCUCUUUGCAGCCGAAAGGCUGC | 1164 | AAAGAGCUCAAUAAAAGUCAUU | 1204 |
| S1165-AS1205-M2 | CUUGUUCCGUGCCAGGCAUUGCAGCCGAAAGGCUGC | 1165 | AAUGCCUGGCACGGAACAAGAG | 1205 |
| S1166-AS1206-M2 | UGUGAAAGGUGCUGAUGGCUGCAGCCGAAAGGCUGC | 1166 | AGCCAUCAGCACCUUUCACACU | 1206 |
| S1167-AS1207-M2 | AUGGAGGCUUAGCUUUCUGUGCAGCCGAAAGGCUGC | 1167 | ACAGAAAGCUAAGCCUCCAUUA | 1207 |
| S1168-AS1208-M2 | GAGGCUUAGCUUUCUGGAUUGCAGCCGAAAGGCUGC | 1168 | AAUCCAGAAAGCUAAGCCUCCA | 1208 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S1169-AS1209-M2 | AGGCUUAGCUUUCUGGAUGUGCAGC CGAAAGGCUGC | 1169 | ACAUCCAGAAAGCUAAGCCUCC | 1209 |
| S1170-AS1210-M2 | GCUUAGCUUUCUGGAUGGCAGCAGC CGAAAGGCUGC | 1170 | UGCCAUCCAGAAAGCUAAGCCU | 1210 |
| S1171-AS1211-M2 | CCAGGCUGUGCUAGCAACAUGCAGC CGAAAGGCUGC | 1171 | AUGUUGCUAGCACAGCCUGGCA | 1211 |
| S1172-AS1212-M2 | UGCGGGGAGCCAUCACCUAUGCAGC CGAAAGGCUGC | 1172 | AUAGGUGAUGGCUCCCCGCAGG | 1212 |
| S1173-AS1213-M2 | CGGCAGUGUGCAGUGGUGCAGCAGC CGAAAGGCUGC | 1173 | UGCACCACUGCACACUGCCGAG | 1213 |
| S1174-AS1214-M2 | ACAGAGGAAGAAACCUGGAAGCAGC CGAAAGGCUGC | 1174 | UUCCAGGUUUCUUCCUCUGUGA | 1214 |
| S1175-AS1215-M2 | CAGAGGAAGAAACCUGGAAUGCAGC CGAAAGGCUGC | 1175 | AUUCCAGGUUUCUUCCUCUGUG | 1215 |
| S1176-AS1216-M2 | AGAGGAAGAAACCUGGAACUGCAGC CGAAAGGCUGC | 1176 | AGUUCCAGGUUUCUUCCUCUGU | 1216 |
| S1177-AS1217-M2 | UGGCGGAGAUGCUUCUAAGUGCAGC CGAAAGGCUGC | 1177 | ACUUAGAAGCAUCUCCGCCAGG | 1217 |
| S1178-AS1218-M2 | UUACAGCCAACUUUUCUAGAGCAGC CGAAAGGCUGC | 1178 | UCUAGAAAAGUUGGCUGUAAAA | 1218 |
| S1179-AS1219-M2 | CUGUUUUGCUUUUGUAACUUGCAGC CGAAAGGCUGC | 1179 | AAGUUACAAAAGCAAACAGGU | 1219 |
| S1180-AS1220-M2 | UGUUUUGCUUUUGUAACUUGCAGC CGAAAGGCUGC | 1180 | AAAGUUACAAAAGCAAACAGG | 1220 |
| S1181-AS1221-M2 | UUUGCUUUUGUAACUUGAAUGCAGC CGAAAGGCUGC | 1181 | AUUCAAGUUACAAAAGCAAAC | 1221 |
| S1182-AS1222-M2 | UUUGUAGCAUUUUUAUUAAUGCAGC CGAAAGGCUGC | 1182 | AUUAAUAAAAAUGCUACAAAAC | 1222 |
| S1183-AS1223-M2 | UGUAGCAUUUUUAUUAAUAUGCAGC CGAAAGGCUGC | 1183 | AUAUUAAUAAAAAUGCUACAAA | 1223 |
| S1184-AS1224-M2 | GUAGCAUUUUUAUUAAUAUUGCAGC CGAAAGGCUGC | 1184 | AAUAUUAAUAAAAAUGCUACAA | 1224 |
| S1185-AS1225-M2 | AUUAAUAUGGUGACUUUUUAGCAGC CGAAAGGCUGC | 1185 | UAAAAAGUCACCAUAUUAAUAA | 1225 |
| S1186-AS1226-M2 | UUAAUAUGGUGACUUUUUAAGCAGC CGAAAGGCUGC | 1186 | UUAAAAAGUCACCAUAUUAAUA | 1226 |
| S1187-AS1227-M2 | AAUAUGGUGACUUUUUAAAAGCAGC CGAAAGGCUGC | 1187 | UUUUAAAAAGUCACCAUAUUAA | 1227 |
| S1188-AS1228-M2 | AUAUGGUGACUUUUUAAAAUGCAGC CGAAAGGCUGC | 1188 | AUUUUAAAAAGUCACCAUAUUA | 1228 |
| S1189-AS1229-M2 | UAUGGUGACUUUUUAAAAUAGCAGC CGAAAGGCUGC | 1189 | UAUUUUAAAAAGUCACCAUAUU | 1229 |
| S1190-AS1230-M2 | AUGGUGACUUUUUAAAAUAAGCAGC CGAAAGGCUGC | 1190 | UUAUUUUAAAAAGUCACCAUAU | 1230 |
| S1191-AS1231-M2 | UGGUGACUUUUUAAAAUAAAGCAGC CGAAAGGCUGC | 1191 | UUUAUUUUAAAAAGUCACCAUA | 1231 |
| S1192-AS1232-M2 | GUGACUUUUUAAAAUAAAAGCAGC CGAAAGGCUGC | 1192 | UUUUUAUUUUAAAAAGUCACCA | 1232 |
| S1153-AS1193-M3 | AACUUCAGCUCCUGCACAGUGCAGC CGAAAGGCUGC | 1153 | ACUGUGCAGGAGCUGAAGUUCA | 1193 |

TABLE 4-continued

Oligonucleotide Sequences

| App Name | Sense Sequence/mRNA seq | S SEQ ID NO | Antisense Sequence | AS SEQ ID NO |
| --- | --- | --- | --- | --- |
| S1154-AS1194-M3 | UGGCCCUCAUGGGCACCGUUGCAGCCGAAAGGCUGC | 1154 | AACGGUGCCCAUGAGGGCCAGG | 1194 |
| S1155-AS1195-M3 | AGGAGGAGACCCACCUCUCUGCAGCCGAAAGGCUGC | 1155 | AGAGAGGUGGGUCUCCUCCUUC | 1195 |
| S1156-AS1196-M3 | UGCUGGAGCUGGCCUUGAAUGCAGCCGAAAGGCUGC | 1156 | AUUCAAGGCCAGCUCCAGCAGG | 1196 |
| S1157-AS1197-M3 | UCUGUCUUUGCCCAGAGCAUGCAGCCGAAAGGCUGC | 1157 | AUGCUCUGGGCAAAGACAGAGG | 1197 |
| S1158-AS1198-M3 | CUGUCUUUGCCCAGAGCAUUGCAGCCGAAAGGCUGC | 1158 | AAUGCUCUGGGCAAAGACAGAG | 1198 |
| S1159-AS1199-M3 | CUUGCCUGGAACUCACUCAUGCAGCCGAAAGGCUGC | 1159 | AUGAGUGAGUUCCAGGCAAGGA | 1199 |
| S1160-AS1200-M3 | UUGCCUGGAACUCACUCACUGCAGCCGAAAGGCUGC | 1160 | AGUGAGUGAGUUCCAGGCAAGG | 1200 |
| S1161-AS1201-M3 | AGAAUGACUUUUAUUGAGCUGCAGCCGAAAGGCUGC | 1161 | AGCUCAAUAAAAGUCAUUCUGC | 1201 |
| S1162-AS1202-M3 | GAAUGACUUUUAUUGAGCUUGCAGCCGAAAGGCUGC | 1162 | AAGCUCAAUAAAAGUCAUUCUG | 1202 |
| S1163-AS1203-M3 | AUGACUUUUAUUGAGCUCUUGCAGCCGAAAGGCUGC | 1163 | AAGAGCUCAAUAAAAGUCAUUC | 1203 |
| S1164-AS1204-M3 | UGACUUUUAUUGAGCUCUUUGCAGCCGAAAGGCUGC | 1164 | AAAGAGCUCAAUAAAAGUCAUU | 1204 |
| S1165-AS1205-M3 | CUUGUUCCGUGCCAGGCAUUGCAGCCGAAAGGCUGC | 1165 | AAUGCCUGGCACGGAACAAGAG | 1205 |
| S1166-AS1206-M3 | UGUGAAAGGUGCUGAUGGCUGCAGCCGAAAGGCUGC | 1166 | AGCCAUCAGCACCUUUCACACU | 1206 |
| S1167-AS1207-M3 | AUGGAGGCUUAGCUUUCUGUGCAGCCGAAAGGCUGC | 1167 | ACAGAAAGCUAAGCCUCCAUUA | 1207 |
| S1168-AS1208-M3 | GAGGCUUAGCUUUCUGGAUUGCAGCCGAAAGGCUGC | 1168 | AAUCCAGAAAGCUAAGCCUCCA | 1208 |
| S1169-AS1209-M3 | AGGCUUAGCUUUCUGGAUGUGCAGCCGAAAGGCUGC | 1169 | ACAUCCAGAAAGCUAAGCCUCC | 1209 |
| S1170-AS1210-M3 | GCUUAGCUUUCUGGAUGGCAGCAGCCGAAAGGCUGC | 1170 | UGCCAUCCAGAAAGCUAAGCCU | 1210 |
| S1171-AS1211-M3 | CCAGGCUGUGCUAGCAACAUGCAGCCGAAAGGCUGC | 1171 | AUGUUGCUAGCACAGCCUGGCA | 1211 |
| S1172-AS1212-M3 | UGCGGGGAGCCAUCACCUAUGCAGCCGAAAGGCUGC | 1172 | AUAGGUGAUGGCUCCCCGCAGG | 1212 |
| S1173-AS1213-M3 | CGGCAGUGUGCAGUGGUGCAGCAGCCGAAAGGCUGC | 1173 | UGCACCACUGCACACUGCCGAG | 1213 |
| S1174-AS1214-M3 | ACAGAGGAAGAAACCUGGAAGCAGCCGAAAGGCUGC | 1174 | UUCCAGGUUUCUUCCUCUGUGA | 1214 |
| S1175-AS1215-M3 | CAGAGGAAGAAACCUGGAAUGCAGCCGAAAGGCUGC | 1175 | AUUCCAGGUUUCUUCCUCUGUG | 1215 |
| S1176-AS1216-M3 | AGAGGAAGAAACCUGGAACUGCAGCCGAAAGGCUGC | 1176 | AGUUCCAGGUUUCUUCCUCUGU | 1216 |
| S1177-AS1217-M3 | UGGCGGAGAUGCUUCUAAGUGCAGCCGAAAGGCUGC | 1177 | ACUUAGAAGCAUCUCCGCCAGG | 1217 |
| S1178-AS1218-M3 | UUACAGCCAACUUUUCUAGAGCAGCCGAAAGGCUGC | 1178 | UCUAGAAAAGUUGGCUGUAAAA | 1218 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S1179-AS1219-M3 | CUGUUUUGCUUUUGUAACUUGCAGCCGAAAGGCUGC | 1179 | AAGUUACAAAAGCAAAACAGGU | 1219 |
| S1180-AS1220-M3 | UGUUUUGCUUUUGUAACUUGCAGCCGAAAGGCUGC | 1180 | AAAGUUACAAAAGCAAAACAGG | 1220 |
| S1181-AS1221-M3 | UUUGCUUUUGUAACUUGAAUGCAGCCGAAAGGCUGC | 1181 | AUUCAAGUUACAAAAGCAAAAC | 1221 |
| S1182-AS1222-M3 | UUUGUAGCAUUUUUAUUAAUGCAGCCGAAAGGCUGC | 1182 | AUUAAUAAAAAUGCUACAAAAC | 1222 |
| S1183-AS1223-M3 | UGUAGCAUUUUUAUUAAUAUGCAGCCGAAAGGCUGC | 1183 | AUAUUAAUAAAAAUGCUACAAA | 1223 |
| S1184-AS1224-M3 | GUAGCAUUUUUAUUAAUAUUGCAGCCGAAAGGCUGC | 1184 | AAUAUUAAUAAAAAUGCUACAA | 1224 |
| S1185-AS1225-M3 | AUUAAUAUGGUGACUUUUUAGCAGCCGAAAGGCUGC | 1185 | UAAAAAGUCACCAUAUUAAUAA | 1225 |
| S1186-AS1226-M3 | UUAAUAUGGUGACUUUUUAAGCAGCCGAAAGGCUGC | 1186 | UUAAAAAGUCACCAUAUUAAUA | 1226 |
| S1187-AS1227-M3 | AAUAUGGUGACUUUUUAAAAGCAGCCGAAAGGCUGC | 1187 | UUUUAAAAGUCACCAUAUUAA | 1227 |
| S1188-AS1228-M3 | AUAUGGUGACUUUUUAAAAUGCAGCCGAAAGGCUGC | 1188 | AUUUUAAAAGUCACCAUAUUA | 1228 |
| S1189-AS1229-M3 | UAUGGUGACUUUUUAAAAUAGCAGCCGAAAGGCUGC | 1189 | UAUUUUAAAAGUCACCAUAUU | 1229 |
| S1190-AS1230-M3 | AUGGUGACUUUUUAAAAUAAGCAGCCGAAAGGCUGC | 1190 | UUAUUUUAAAAGUCACCAUAU | 1230 |
| S1191-AS1231-M3 | UGGUGACUUUUUAAAAUAAAGCAGCCGAAAGGCUGC | 1191 | UUUAUUUUAAAAGUCACCAUA | 1231 |
| S1192-AS1232-M3 | GUGACUUUUUAAAAUAAAAGCAGCCGAAAGGCUGC | 1192 | UUUUUAUUUUAAAAGUCACCA | 1232 |
| S1180-AS1220-M4 | UGUUUUGCUUUUGUAACUUGCAGCCGAAAGGCUGC | 1180 | AAAGUUACAAAAGCAAAACAGG | 1220 |
| S1163-AS1203-M4 | AUGACUUUUAUUGAGCUCUUGCAGCCGAAAGGCUGC | 1163 | AAGAGCUCAAUAAAAGUCAUUC | 1203 |
| S1181-AS1221-M4 | UUUGCUUUUGUAACUUGAAUGCAGCCGAAAGGCUGC | 1181 | AUUCAAGUUACAAAAGCAAAAC | 1221 |
| S1248-AS1257-M4 | GCUGGGCUCCUCAUUUUUAUGCAGCCGAAAGGCUGC | 1248 | AUAAAAAUGAGGAGCCCAGCGG | 1257 |
| S1249-AS1258-M4 | GCUGGCGGAGAUGCUUCUAAGCAGCCGAAAGGCUGC | 1249 | UUAGAAGCAUCUCCGCCAGCGG | 1258 |
| S1250-AS1259-M4 | UUUACAGCCAACUUUUCUAUGCAGCCGAAAGGCUGC | 1250 | AUAGAAAAGUUGGCUGUAAAGG | 1259 |
| S1251-AS1260-M4 | GGCUGGGCUCCUCAUUUUUAGCAGCCGAAAGGCUGC | 1251 | UAAAAAUGAGGAGCCCAGCCGG | 1260 |
| S1252-AS1261-M4 | AGCACGGAACCACAGCCACUGCAGCCGAAAGGCUGC | 1252 | AGUGGCUGUGGUUCCGUGCUGG | 1261 |
| S1253-AS1262-M4 | AAUGACUUUUAUUGAGCUCUGCAGCCGAAAGGCUGC | 1253 | AGAGCUCAAUAAAAGUCAUUGG | 1262 |
| S1254-AS1263-M4 | UUUGUAGCAUUUUUAUUAAGCAGCCGAAAGGCUGC | 1254 | UUAAUAAAAAUGCUACAAAAGG | 1263 |
| S1255-AS1264-M4 | GCUUGCCUGGAACUCACUCAGCAGCCGAAAGGCUGC | 1255 | UGAGUGAGUUCCAGGCAAGCGG | 1264 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S1256-AS1265-M4 | UGGAGGCUUAGCUUUCUGGAGCAGC CGAAAGGCUGC | 1256 | UCCAGAAAGCUAAGCCUCCAGG | 1265 |
| S1180-AS1220-M4 | UGUUUUGCUUUUGUAACUUUGCAGC CGAAAGGCUGC | 1180 | AAAGUUACAAAAGCAAAACAGG | 1220 |
| S1180-AS1220-M5 | UGUUUUGCUUUUGUAACUUUGCAGC CGAAAGGCUGC | 1180 | AAAGUUACAAAAGCAAAACAGG | 1220 |
| S1164-AS1204-M5 | UGACUUUAUUGAGCUCUUUGCAGC CGAAAGGCUGC | 1164 | AAAGAGCUCAAUAAAAGUCAUU | 1204 |
| S1178-AS1218-M6 | UUACAGCCAACUUUUCUAGAGCAGC CGAAAGGCUGC | 1178 | UCUAGAAAAGUUGGCUGUAAAA | 1218 |
| S1178-AS1218-M5 | UUACAGCCAACUUUUCUAGAGCAGC CGAAAGGCUGC | 1178 | UCUAGAAAAGUUGGCUGUAAAA | 1218 |
| S1179-AS1219-M6 | CUGUUUUGCUUUUGUAACUUGCAGC CGAAAGGCUGC | 1179 | AAGUUACAAAAGCAAAACAGGU | 1219 |
| S1179-AS1219-M5 | CUGUUUUGCUUUUGUAACUUGCAGC CGAAAGGCUGC | 1179 | AAGUUACAAAAGCAAAACAGGU | 1219 |
| S1181-AS1221-M5 | UUUGCUUUUGUAACUUGAAUGCAGC CGAAAGGCUGC | 1181 | AUUCAAGUUACAAAAGCAAAAC | 1221 |
| S1182-AS1222-M5 | UUUGUAGCAUUUUUAUUAAUGCAGC CGAAAGGCUGC | 1182 | AUUAAUAAAAAUGCUACAAAAC | 1222 |
| S1183-AS1223-M5 | UGUAGCAUUUUUAUUAAUAUGCAGC CGAAAGGCUGC | 1183 | AUAUUAAUAAAAAUGCUACAAA | 1223 |
| S1187-AS1227-M5 | AAUAUGGUGACUUUUUAAAAGCAGC CGAAAGGCUGC | 1187 | UUUUAAAAAGUCACCAUAUUAA | 1227 |
| S1188-AS1228-M5 | AUAUGGUGACUUUUUAAAAUGCAGC CGAAAGGCUGC | 1188 | AUUUUAAAAAGUCACCAUAUUA | 1228 |
| S1189-AS1229-M5 | UAUGGUGACUUUUUAAAAUAGCAGC CGAAAGGCUGC | 1189 | UAUUUUAAAAAGUCACCAUAUU | 1229 |
| S1158-AS1198-M5 | CUGUCUUUGCCCAGAGCAUUGCAGC CGAAAGGCUGC | 1158 | AAUGCUCUGGGCAAAGACAGAG | 1198 |
| S1159-AS1199-M5 | CUUGCCUGGAACUCACUCAUGCAGC CGAAAGGCUGC | 1159 | AUGAGUGAGUUCCAGGCAAGGA | 1199 |
| S1160-AS1200-M5 | UUGCCUGGAACUCACUCACUGCAGC CGAAAGGCUGC | 1160 | AGUGAGUGAGUUCCAGGCAAGG | 1200 |
| S1161-AS1201-M5 | AGAAUGACUUUAUUGAGCUGCAGC CGAAAGGCUGC | 1161 | AGCUCAAUAAAAGUCAUUCUGC | 1201 |
| S1163-AS1203-M5 | AUGACUUUAUUGAGCUCUUGCAGC CGAAAGGCUGC | 1163 | AAGAGCUCAAUAAAAGUCAUUC | 1203 |
| S1184-AS1224-M5 | GUAGCAUUUUUAUUAAUAUUGCAGC CGAAAGGCUGC | 1184 | AAUAUUAAUAAAAAUGCUACAA | 1224 |
| S1185-AS1225-M5 | AUUAAUAUGGUGACUUUUUAGCAGC CGAAAGGCUGC | 1185 | UAAAAAGUCACCAUAUUAAUAA | 1225 |
| S1186-AS1226-M6 | UUAAUAUGGUGACUUUUUAGCAGC CGAAAGGCUGC | 1186 | UUAAAAAGUCACCAUAUUAAUA | 1226 |
| S1186-AS1226-M5 | UUAAUAUGGUGACUUUUUAGCAGC CGAAAGGCUGC | 1186 | UUAAAAAGUCACCAUAUUAAUA | 1226 |
| S1190-AS1230-M5 | AUGGUGACUUUUUAAAAUAAGCAGC CGAAAGGCUGC | 1190 | UUAUUUUAAAAAGUCACCAUAU | 1230 |
| S1191-AS1231-M5 | UGGUGACUUUUUAAAAUAAAGCAGC CGAAAGGCUGC | 1191 | UUUAUUUUAAAAAGUCACCAUA | 1231 |

TABLE 4-continued

Oligonucleotide Sequences

| App Name | Sense Sequence/mRNA seq | S SEQ ID NO | Antisense Sequence | AS SEQ ID NO |
|---|---|---|---|---|
| S1192-AS1232-M5 | GUGACUUUUUAAAAUAAAAAGCAGCCGAAAGGCUGC | 1192 | UUUUUAUUUUAAAAAGUCACCA | 1232 |
| S1266-AS1269-M7 | UGUUUUGCUUUUGUAACUU[U/A]GCAGCCGAAAGGCUGC | 1266 | [U/A]AAGUUACAAAAGCAAAACAGG | 1269 |
| S1266-AS1269-M8 | UGUUUUGCUUUUGUAACUU[U/A]GCAGCCGAAAGGCUGC | 1266 | [U/A]AAGUUACAAAAGCAAAACAGG | 1269 |
| S1266-AS1269-M9 | UGUUUUGCUUUUGUAACUU[U/A]GCAGCCGAAAGGCUGC | 1266 | [U/A]AAGUUACAAAAGCAAAACAGG | 1269 |
| S1267-AS1270-M10 | UUUUGUAACUUGAAGAUAUAGCAGCCGAAAGGCUGC | 1267 | UAUAUCUUCAAGUUACAAAAGG | 1270 |
| S1268-AS1271-M11 | CUGGGUUUUGUAGCAUUUUAGCAGCCGAAAGGCUGC | 1268 | UAAAAUGCUACAAAACCCAGGG | 1271 |
| S1268-AS1271-M9 | CUGGGUUUUGUAGCAUUUUAGCAGCCGAAAGGCUGC | 1268 | UAAAAUGCUACAAAACCCAGGG | 1271 |
| S1266-AS1269-M12 | UGUUUUGCUUUUGUAACUU[U/A]GCAGCCGAAAGGCUGC | 1266 | [U/A]AAGUUACAAAAGCAAAACAGG | 1269 |
| S1266-AS1269-M13 | UGUUUUGCUUUUGUAACUU[U/A]GCAGCCGAAAGGCUGC | 1266 | [U/A]AAGUUACAAAAGCAAAACAGG | 1269 |

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. An oligonucleotide for reducing expression of PCSK9, the oligonucleotide comprising an antisense strand comprising a sequence as set forth in any one of SEQ ID NOs: 1219-1222, 1231-1232, and 1269-1271, and a sense strand comprising a sequence as set forth in any one of SEQ ID NOs: 1179-1182, 1191-1192, and 1266-1268, wherein the sense strand forms a duplex region with the antisense strand.

2. The oligonucleotide of claim 1, wherein the antisense strand is up to 27 nucleotides in length.

3. An oligonucleotide for reducing expression of PCSK9, the oligonucleotide comprises a pair of antisense strand and sense strand,
   wherein the antisense strand is 21 to 27 nucleotides in length comprising a sequence as set forth in any one of SEQ ID NOs: 1219-1222, 1231-1232, and 1269-1271, and has a region of complementarity to PCSK9,
   wherein the sense strand comprises at its 3'-end a stem-loop set forth as: $S_1$-L-$S_2$, wherein $S_1$ is complementary to $S_2$, and wherein L forms a loop between $S_1$ and $S_2$ of 3 to 5 nucleotides in length,
   and wherein the antisense strand and the sense strand form a duplex structure of at least 19 nucleotides in length but are not covalently linked.

4. The oligonucleotide of claim 3, wherein the sense strand comprises a sequence as set forth in any one of SEQ ID NOs: 1179-1182, 1191-1192, and 1266-1268.

5. The oligonucleotide of claim 1, wherein the oligonucleotide comprises a 3'-overhang sequence of two nucleotides in length, wherein the 3'-overhang sequence is present on the antisense strand.

6. An oligonucleotide for reducing expression of PCSK9, wherein the antisense strand consists of a sequence as set forth in any one of SEQ ID NOs: 1219-1222, 1231-1232, and 1269-1271, and wherein the sense strand consists of a sequence as set forth in any one of SEQ ID NOs: 1179-1182, 1191-1192, and 1266-1268;
   and
   wherein the oligonucleotide comprises at least one modified nucleotide, wherein the modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid.

7. The oligonucleotide of claim 6, wherein the oligonucleotide comprises at least one modified internucleotide linkage, and wherein the at least one modified internucleotide linkage is a phosphorothioate linkage.

8. The oligonucleotide of claim 6, wherein the 4'-carbon of the sugar of the 5'-nucleotide of the antisense strand comprises a phosphate analog, and wherein the phosphate analog is oxymethylphosphonate, vinylphosphonate, or malonylphosphonate.

9. The oligonucleotide of claim 6, wherein at least one nucleotide of the oligonucleotide is conjugated to one or more targeting ligands, and wherein each targeting ligand comprises a N-acetylgalactosamine (GalNAc) moiety.

10. A composition comprising the oligonucleotide of claim 6 and an excipient.

11. The oligonucleotide of claim 3, wherein the oligonucleotide comprises at least one modified nucleotide, wherein the modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid.

12. The oligonucleotide of claim 3, wherein the oligonucleotide comprises at least one modified internucleotide linkage, and wherein the at least one modified internucleotide linkage is a phosphorothioate linkage.

13. The oligonucleotide of claim 3, wherein the 4'-carbon of the sugar of the 5'-nucleotide of the antisense strand comprises a phosphate analog, and wherein the phosphate analog is oxymethylphosphonate, vinylphosphonate, or malonylphosphonate.

14. The oligonucleotide of claim 3, wherein at least one nucleotide of the oligonucleotide is conjugated to one or more targeting ligands, and wherein each targeting ligand comprises a N-acetylgalactosamine (GalNAc) moiety.

15. A composition comprising the oligonucleotide of claim 3 and an excipient.

16. The oligonucleotide of claim 1, wherein the oligonucleotide comprises at least one modified nucleotide, wherein the modified nucleotide comprises a 2'-modification selected from: 2'-aminoethyl, 2'-fluoro, 2'-O-methyl, 2'-O-methoxyethyl, and 2'-deoxy-2'-fluoro-β-d-arabinonucleic acid.

17. The oligonucleotide of claim 1, wherein the oligonucleotide comprises at least one modified internucleotide linkage, and wherein the at least one modified internucleotide linkage is a phosphorothioate linkage.

18. The oligonucleotide of claim 1, wherein the 4'-carbon of the sugar of the 5'-nucleotide of the antisense strand comprises a phosphate analog, and wherein the phosphate analog is oxymethylphosphonate, vinylphosphonate, or malonylphosphonate.

19. The oligonucleotide of claim 1, wherein at least one nucleotide of the oligonucleotide is conjugated to one or more targeting ligands, and wherein each targeting ligand comprises a N-acetylgalactosamine (GalNAc) moiety.

20. A composition comprising the oligonucleotide of claim 1 and an excipient.

* * * * *

SEQUENCE LISTING

<160> NUMBER OF SEQ ID NOS: 1271

<210> SEQ ID NO 1
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1
aagcacccac acccuagaau guutc                                              25

<210> SEQ ID NO 2
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 2
agcacccaca cccuagaagu uuccc                                              25

<210> SEQ ID NO 3
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 3
gcacccacac ccuagaaggu uuccg                                              25

<210> SEQ ID NO 4
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 4
acccacaccc uagaagguuu ccgca                                              25

<210> SEQ ID NO 5
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 5
cccacacccu agaagguuuu cgcag                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 6
aguucagggu cugagccugu aggag                                              25

<210> SEQ ID NO 7
<211> LENGTH: 25
<212> TYPE: DNA
<213> ORGANISM: Artificial Sequence

```
<220> FEATURE:
<223> OTHER INFORMATION: Synthetic Nucleic Acid

<400> SEQUENCE: 7
guucaggguc ugagccugga ggagt                                          25

<210> SEQ ID NO 8
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 8
uucagggucu gagccuggau gagtg                                          25

<210> SEQ ID NO 9
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 9
ucaggguctg agccuggagu aguga                                          25

<210> SEQ ID NO 10
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 10
agggucugag ccuggaggau ugagc                                          25

<210> SEQ ID NO 11
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 11
ggucugagcc uggaggaguu agcca                                          25

<210> SEQ ID NO 12
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 12
aggauuccgc gcgccccuuu acgcg                                          25

<210> SEQ ID NO 13
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 13
ggauuccgcg cgccccuuca cgcgc                                          25
```

```
<210> SEQ ID NO 14
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 14
ucacgcgccc ugcuccugaa cuuca                                          25

<210> SEQ ID NO 15
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 15
cacgcgcccu gcuccugaau uucag                                          25

<210> SEQ ID NO 16
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 16
cccugcuccu gaacuucagu ucctg                                          25

<210> SEQ ID NO 17
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 17
cugcuccuga acuucagcuu cugca                                          25

<210> SEQ ID NO 18
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 18
ugcuccugaa cuucagcucu ugcac                                          25

<210> SEQ ID NO 19
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 19
gcuccugaac uucagcuccu gcaca                                          25

<210> SEQ ID NO 20
<211> LENGTH: 25
<212> TYPE: DNA
<213> ORGANISM: Artificial Sequence
<220> FEATURE:
<223> OTHER INFORMATION: Synthetic Nucleic Acid
```

<400> SEQUENCE: 20
cuccugaacu ucagcuccuu cacag                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 21
uccugaacuu cagcuccugu acagt                                          25

<210> SEQ ID NO 22
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 22
ccugaacuuc agcuccugca cagtc                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 23
cugaacuuca gcuccugcau agucc                                          25

<210> SEQ ID NO 24
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 24
ugaacuucag cuccugcaca gucct                                          25

<210> SEQ ID NO 25
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 25
gaacuucagc uccugcacau ucctc                                          25

<210> SEQ ID NO 26
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 26
aacuucagcu ccugcacagu ccucc                                          25

<210> SEQ ID NO 27

<210> SEQ ID NO 27
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 27
acuucagcuc cugcacaguu cuccc                                              25

<210> SEQ ID NO 28
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 28
cuucagcucc ugcacagucu uccccc                                             25

<210> SEQ ID NO 29
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 29
acagaccucc ccaccgcaau gcuca                                              25

<210> SEQ ID NO 30
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 30
caguccuccc caccgcaagu cucaa                                              25

<210> SEQ ID NO 31
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 31
gccucuaggu cuccucgcca ggaca                                              25

<210> SEQ ID NO 32
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 32
gccaggacag caaccucucu ccugg                                              25

<210> SEQ ID NO 33
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 33
ggacagcaac cucucccuu gccct                                          25

<210> SEQ ID NO 34
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 34
ccccuggccc ucaugggcau cguca                                         25

<210> SEQ ID NO 35
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 35
uggcccucau gggcaccguu agcuc                                         25

<210> SEQ ID NO 36
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 36
ggcccucaug gcaccguca gcucc                                          25

<210> SEQ ID NO 37
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 37
gcccucaugg gcaccgucau cucca                                         25

<210> SEQ ID NO 38
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 38
gcgguccugg uggccgcugu cactg                                         25

<210> SEQ ID NO 39
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 39
ggccuggccg aagcacccga gcacg                                         25

<210> SEQ ID NO 40
<211> LENGTH: 25
<212> TYPE: DNA

<213> ORGANISM: Artificial Sequence
<220> FEATURE:
<223> OTHER INFORMATION: Synthetic Nucleic Acid

<400> SEQUENCE: 40
acccgagcac ggaaccacau ccacc                                              25

<210> SEQ ID NO 41
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 41
agcacggaac cacagccacu uucca                                              25

<210> SEQ ID NO 42
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 42
cacggaacca cagccaccuu ccacc                                              25

<210> SEQ ID NO 43
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 43
acggaaccac agccaccuuu caccg                                              25

<210> SEQ ID NO 44
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 44
gccaaggauc cguggagguu gcctg                                              25

<210> SEQ ID NO 45
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 45
ccaaggaucc guggagguuu ccugg                                              25

<210> SEQ ID NO 46
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 46
aaggauccgu ggagguugcu uggca                                              25

<210> SEQ ID NO 47
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 47
ggauccgugg agguugccuu gcacc                                          25

<210> SEQ ID NO 48
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 48
uggagguugc cuggcaccua cgugg                                          25

<210> SEQ ID NO 49
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 49
ugccuggcac cuacgugguu gugct                                          25

<210> SEQ ID NO 50
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 50
gccuggcacc uacguggugu ugctg                                          25

<210> SEQ ID NO 51
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 51
aggaggagac ccaccucucu cagtc                                          25

<210> SEQ ID NO 52
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 52
ccugcauguc uuccauggcu uuctt                                          25

<210> SEQ ID NO 53
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 53
ugcaugucuu ccauggccuu cuucc        25

<210> SEQ ID NO 54
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 54
accugcugga gcuggccuuu aaguu        25

<210> SEQ ID NO 55
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 55
cugcuggagc uggccuugaa guugc        25

<210> SEQ ID NO 56
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 56
ugcuggagcu ggccuugaau uugcc        25

<210> SEQ ID NO 57
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 57
uggagcuggc cuugaaguuu cccca        25

<210> SEQ ID NO 58
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 58
ggccuugaag uugccccauu ucgac        25

<210> SEQ ID NO 59
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 59
gccuugaagu ugccccaugu cgact        25

-continued

```
<210> SEQ ID NO 60
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 60
ccuugaaguu gccccauguu gacta                                              25

<210> SEQ ID NO 61
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 61
cuugaaguug ccccaugucu acuac                                              25

<210> SEQ ID NO 62
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 62
acuccucugu cuuugcccau agcat                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 63
cuccucuguc uuugcccaga gcatc                                              25

<210> SEQ ID NO 64
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 64
uccucugucu ugcccagau caucc                                               25

<210> SEQ ID NO 65
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 65
ccucugucuu ugcccagagu auccc                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic Nucleic Acid
```

<400> SEQUENCE: 66
ucugucuuug cccagagcau cccgt                                       25

<210> SEQ ID NO 67
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 67
cugucuuugc ccagagcauu ccgtg                                       25

<210> SEQ ID NO 68
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 68
gucuuugccc agagcauccu gugga                                       25

<210> SEQ ID NO 69
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 69
ucuuugccca gagcauccccu uggaa                                      25

<210> SEQ ID NO 70
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 70
uuugcccaga gcaucccguu gaacc                                       25

<210> SEQ ID NO 71
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 71
agagcauccc guggaaccuu gagcg                                       25

<210> SEQ ID NO 72
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 72 gagcauccccg uggaaccugu agcgg                                      25

<210> SEQ ID NO 73
<211> LENGTH: 25

```
<212> TYPE: DNA
<213> ORGANISM: Artificial Sequence
<220> FEATURE:
<223> OTHER INFORMATION: Synthetic Nucleic Acid

<400> SEQUENCE: 73
agcaucccgu ggaaccugga gcgga                                              25

<210> SEQ ID NO 74
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 74
gcaucccgug gaaccuggau cggat                                              25

<210> SEQ ID NO 75
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 75
caucccgugg aaccuggagu ggatt                                              25

<210> SEQ ID NO 76
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 76
aucccgugga accuggagcu gauta                                              25

<210> SEQ ID NO 77
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 77
ucccguggaa ccuggagcgu auuac                                              25

<210> SEQ ID NO 78
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 78
cccguggaac cuggagcgga uuacc                                              25

<210> SEQ ID NO 79
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 79
```
ccguggaacc uggagcggau uaccc                                            25

<210> SEQ ID NO 80
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 80
cuggagcgga uuaccccucu acggt                                            25

<210> SEQ ID NO 81
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 81
uggagcggau accccucca cggta                                             25

<210> SEQ ID NO 82
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 82
ggagcggauu accccuccau gguac                                            25

<210> SEQ ID NO 83
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 83
gagcggauua ccccuccacu guacc                                            25

<210> SEQ ID NO 84
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 84
agcggauuac cccuccacgu uaccg                                            25

<210> SEQ ID NO 85
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 85
cggauuaccc cuccacggua ccggg                                            25

<210> SEQ ID NO 86
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 86
ggauuacccc uccacgguau cgggc                                    25

<210> SEQ ID NO 87
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 87
uccacgguac cgggcggauu aauac                                    25

<210> SEQ ID NO 88
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 88
cggaggcagc cugguggagu uguat                                    25

<210> SEQ ID NO 89
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 89
agacaccagc auacagaguu accac                                    25

<210> SEQ ID NO 90
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 90
gcauacagag ugaccaccgu gaaat                                    25

<210> SEQ ID NO 91
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 91
cgagaaugug cccgaggagu acggg                                    25

<210> SEQ ID NO 92
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 92
gagaaugugc ccgaggagga cggga                                    25

<210> SEQ ID NO 93
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 93
agaaugugcc cgaggaggau gggac                                              25

<210> SEQ ID NO 94
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 94
gcaaguguga cagucauggu accca                                              25

<210> SEQ ID NO 95
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 95
caagugugac agucauggca cccac                                              25

<210> SEQ ID NO 96
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 96
aagugugaca gucauggcau ccacc                                              25

<210> SEQ ID NO 97
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 97
cgcagccugc gcgugcucaa cugcc                                              25

<210> SEQ ID NO 98
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 98
gcagccugcg cgugcucaau ugcca                                              25

<210> SEQ ID NO 99
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 99
agccuguggg gccacugguu gugct                                          25

<210> SEQ ID NO 100
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 100
ccucuacucc ccagccucau cuccc                                          25

<210> SEQ ID NO 101
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 101
cagccucagc ucccgagguu aucac                                          25

<210> SEQ ID NO 102
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 102
gccaccaaug cccaagacca gccgg                                          25

<210> SEQ ID NO 103
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 103
augcccaaga ccagccgguu accct                                          25

<210> SEQ ID NO 104
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 104
ugcccaagac cagccgguga ccctg                                          25

<210> SEQ ID NO 105
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 105
gucacagagu gggacaucau aggct                                          25

<210> SEQ ID NO 106

<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 106
gagugggaca ucacaggcuu cugcc                                           25

<210> SEQ ID NO 107
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 107
ugggacauca caggcugcuu cccac                                           25

<210> SEQ ID NO 108
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 108
gggacaucac aggcugcugu ccacg                                           25

<210> SEQ ID NO 109
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 109
cucacccugg ccgaguugau gcaga                                           25

<210> SEQ ID NO 110
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 110
acccuggccg aguugaggca gagac                                           25

<210> SEQ ID NO 111
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 111
acuucucugc caaagauguu aucaa                                           25

<210> SEQ ID NO 112
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 112 cccaugggc agguuggcau cugtt 25

<210> SEQ ID NO 113
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 113
uggggcaggu uggcagcugu uuugc 25

<210> SEQ ID NO 114
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 114
cuguuuugca ggacuguauu gucag 25

<210> SEQ ID NO 115
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 115
uuuugcagga cuguaugguu agcac 25

<210> SEQ ID NO 116
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 116
caggacugua uggucagcau acucg 25

<210> SEQ ID NO 117
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 117
ggacuguaug gucagcacau ucggg 25

<210> SEQ ID NO 118
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 118
cgcugcgccc cagaugagga gcugc 25

<210> SEQ ID NO 119
<211> LENGTH: 25
<212> TYPE: DNA

<213> ORGANISM: Artificial Sequence
<220> FEATURE:
<223> OTHER INFORMATION: Synthetic Nucleic Acid

<400> SEQUENCE: 119
gcgccccaga ugaggagcuu cugag                                              25

<210> SEQ ID NO 120
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 120
ccccagauga ggagcugcuu agctg                                              25

<210> SEQ ID NO 121
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 121
cccagaugag gagcugcuga gcugc                                              25

<210> SEQ ID NO 122
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 122
ccagaugagg agcugcugau cugct                                              25

<210> SEQ ID NO 123
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 123
cggcggggcg agcgcaugga ggccc                                              25

<210> SEQ ID NO 124
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 124
ggcggggcga gcgcauggau gccca                                              25

<210> SEQ ID NO 125
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 125
ggcgagcgca uggaggccca agggg                                              25

<210> SEQ ID NO 126
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 126
cuggucugcc gggcccacaa cgcuu                                        25

<210> SEQ ID NO 127
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 127
ugccugcuac cccaggccaa cugca                                        25

<210> SEQ ID NO 128
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 128
gccugcuacc ccaggccaau ugcag                                        25

<210> SEQ ID NO 129
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 129
cccaggccaa cugcagcguu cacac                                        25

<210> SEQ ID NO 130
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 130
ggccccucag gagcagguga ccgtg                                        25

<210> SEQ ID NO 131
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 131
ugaccguggc cugcgaggau ggctg                                        25

<210> SEQ ID NO 132
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 132
gcgaggaggg cuggacccuu acugg                                    25

<210> SEQ ID NO 133
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 133
cgaggagggc uggacccuga cuggc                                    25

<210> SEQ ID NO 134
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 134
gggcuggacc cugacuggcu gcagt                                    25

<210> SEQ ID NO 135
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 135
ggcuggaccc ugacuggcuu cagtg                                    25

<210> SEQ ID NO 136
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 136
uggacccuga cuggcugcau ugccc                                    25

<210> SEQ ID NO 137
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 137
ggcugcagug cccucccugu gacct                                    25

<210> SEQ ID NO 138
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 138
ucccugggac cucccacguu cuggg                                    25

```
<210> SEQ ID NO 139
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 139
cccugggacc ucccacgucu ugggg                                              25

<210> SEQ ID NO 140
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 140
gggccuacgc cguagacaau acgtg                                              25

<210> SEQ ID NO 141
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 141
gacgucagca cuacaggcau cacca                                              25

<210> SEQ ID NO 142
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 142
cagcacuaca ggcagcacca gcgaa                                              25

<210> SEQ ID NO 143
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 143
agcacuacag gcagcaccau cgaag                                              25

<210> SEQ ID NO 144
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 144
gcacuacagg cagcaccagu gaagg                                              25

<210> SEQ ID NO 145
<211> LENGTH: 25
<212> TYPE: DNA
<213> ORGANISM: Artificial Sequence
<220> FEATURE:
<223> OTHER INFORMATION: Synthetic Nucleic Acid
```

```
<400> SEQUENCE: 145
ggggccguga cagccguugu cauct                                              25

<210> SEQ ID NO 146
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 146
ggagcuccag ugacagcccu auccc                                              25

<210> SEQ ID NO 147
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 147
aggaugggug ucuggggagu gucaa                                              25

<210> SEQ ID NO 148
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 148 uggugucug gggaggguca agggc                                               25

<210> SEQ ID NO 149
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 149
gggugucugg ggaggguucaa gggct                                             25

<210> SEQ ID NO 150
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 150
ggugucuggg gagggucaau ggctg                                              25

<210> SEQ ID NO 151
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 151
agggucaagg gcuggggcuu agcuu                                              25

<210> SEQ ID NO 152
<211> LENGTH: 25
```

```
<212> TYPE: DNA
<213> ORGANISM: Artificial Sequence
<220> FEATURE:
<223> OTHER INFORMATION: Synthetic Nucleic Acid

<400> SEQUENCE: 152
gggucaaggg cuggggcuga gcutt                                           25

<210> SEQ ID NO 153
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 153
gacugucccc ucucucagcu cucca                                           25

<210> SEQ ID NO 154
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 154
acuugucccu cucucagccu uccat                                           25

<210> SEQ ID NO 155
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 155
cuugucccuc ucucagcccu ccatg                                           25

<210> SEQ ID NO 156
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 156
uugucccucu cucagcccuu caugg                                           25

<210> SEQ ID NO 157
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 157
ucccucucuc agcccuccau ggcct                                           25

<210> SEQ ID NO 158
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 158
```
uggccuggca cgaggggauu gggat                                              25

<210> SEQ ID NO 159
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 159
uggcacgagg ggaugggggau gcutc                                             25

<210> SEQ ID NO 160
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 160
cgaggggaug gggaugcuuu cgcct                                              25

<210> SEQ ID NO 161
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 161
gaggggaugg ggaugcuucu gcctt                                              25

<210> SEQ ID NO 162
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 162
gggaugggga ugcuuccgcu uuucc                                              25

<210> SEQ ID NO 163
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 163
auggggaugc uuccgccuuu ccggg                                              25

<210> SEQ ID NO 164
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 164 ugggggaugcu uccgccuuuu cgggg                                             25

<210> SEQ ID NO 165
<211> LENGTH: 25
<212> TYPE: DNA
<213> ORGANISM: Artificial Sequence

```
<220> FEATURE:
<223> OTHER INFORMATION: Synthetic Nucleic Acid

<400> SEQUENCE: 165
ggggaugcuu ccgccuuucu ggggc                                    25

<210> SEQ ID NO 166
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 166
gggaugcuuc cgccuuuccu gggct                                    25

<210> SEQ ID NO 167
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 167
cccuugagug gggcagccuu cuugc                                    25

<210> SEQ ID NO 168
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 168
ugaguggggc agccuccuuu ccugg                                    25

<210> SEQ ID NO 169
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 169
ggggcagccu ccuugccugu aactc                                    25

<210> SEQ ID NO 170
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 170
ggcagccucc uugccuggaa cucac                                    25

<210> SEQ ID NO 171
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 171
gcagccuccu ugccuggaau ucact                                    25
```

<210> SEQ ID NO 172
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 172
agccuccuug ccuggaacuu acuca                                          25

<210> SEQ ID NO 173
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 173
gccuccuugc cuggaacuca cucac                                          25

<210> SEQ ID NO 174
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 174
ccuccuugcc uggaacucau ucact                                          25

<210> SEQ ID NO 175
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 175
cuccuugccu ggaacucacu cactc                                          25

<210> SEQ ID NO 176
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 176
uccuugccug gaacucacuu acuct                                          25

<210> SEQ ID NO 177
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 177
ccuugccugg aacucacuca cuctg                                          25

<210> SEQ ID NO 178
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 178
cuugccugga acucacucau ucugg						25

<210> SEQ ID NO 179
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 179
uugccuggaa cucacucacu cuggg						25

<210> SEQ ID NO 180
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 180
ugccuggaac ucacucacuu ugggt						25

<210> SEQ ID NO 181
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 181
ucugggugcc uccuccccau gugga						25

<210> SEQ ID NO 182
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 182
cccaggugga ggugccagga agcuc						25

<210> SEQ ID NO 183
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 183
ccaggaagcu cccucccuca cugtg						25

<210> SEQ ID NO 184
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 184
ggaagcuccc ucccucacuu ugggg						25

<210> SEQ ID NO 185

```
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 185
agcucccucc cucacugugu ggcat                                              25

<210> SEQ ID NO 186
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 186
gcucccuccc ucacuguggu gcatt                                              25

<210> SEQ ID NO 187
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 187
ggggcauuuc accauucaaa caggt                                              25

<210> SEQ ID NO 188
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 188
gggcauuuca ccauucaaau aggtc                                              25

<210> SEQ ID NO 189
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 189
caccauucaa acaggucgau cugtg                                              25

<210> SEQ ID NO 190
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 190
accauucaaa caggucgagu ugugc                                              25

<210> SEQ ID NO 191
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 191
```
ugcucggguG cugccagcuu cuccc            25

```
<210> SEQ ID NO 192
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 192
```
cgggugcugc cagcugcucu caatg            25

```
<210> SEQ ID NO 193
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 193
```
gggugcugcc agcugcuccu aaugt            25

```
<210> SEQ ID NO 194
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 194
```
gccagcugcu cccaaugugu cgatg            25

```
<210> SEQ ID NO 195
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 195
```
ccagcugcuc ccaaugugcu gaugt            25

```
<210> SEQ ID NO 196
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 196
```
ugccgauguc cgugggcaga augac            25

```
<210> SEQ ID NO 197
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 197
```
gcagaaugac uuuuauugau cuctt            25

```
<210> SEQ ID NO 198
<211> LENGTH: 25
<212> TYPE: DNA
```

```
<213> ORGANISM: Artificial Sequence
<220> FEATURE:
<223> OTHER INFORMATION: Synthetic Nucleic Acid

<400> SEQUENCE: 198
cagaaugacu uuuauugagu ucutg                                    25

<210> SEQ ID NO 199
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 199
agaaugacuu uuauugagcu cuugt                                    25

<210> SEQ ID NO 200
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 200
gaaugacuuu uauugagcuu uugtt                                    25

<210> SEQ ID NO 201
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 201
aaugacuuuu auugagcucu ugutc                                    25

<210> SEQ ID NO 202
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 202
augacuuuua uugagcucuu guucc                                    25

<210> SEQ ID NO 203
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 203
ugacuuuuau ugagcucuuu uuccg                                    25

<210> SEQ ID NO 204
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 204
cuuguuccgu gccaggcauu caatc                                    25
```

<210> SEQ ID NO 205
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 205
ccaggcauuc aauccucagu ucucc                                              25

<210> SEQ ID NO 206
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 206
cauucaaucc ucaggucucu accaa                                              25

<210> SEQ ID NO 207
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 207
auucaauccu caggucucca ccaag                                              25

<210> SEQ ID NO 208
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 208
uucaauccuc aggucuccau caagg                                              25

<210> SEQ ID NO 209
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 209
ccucaggucu ccaccaagga ggcag                                              25

<210> SEQ ID NO 210
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 210
cucaggucuc caccaaggau gcagg                                              25

<210> SEQ ID NO 211
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 211
gcgguagggg cugcagggau aaaca                                    25

<210> SEQ ID NO 212
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 212
cgguaggggc ugcagggaca aacat                                    25

<210> SEQ ID NO 213
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 213
gguaggggcu gcagggacaa acatc                                    25

<210> SEQ ID NO 214
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 214
uaggggcugc agggacaaau aucgt                                    25

<210> SEQ ID NO 215
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 215
aggggcugca gggacaaaca ucgtt                                    25

<210> SEQ ID NO 216
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 216
ggggcugcag ggacaaacau cgutg                                    25

<210> SEQ ID NO 217
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 217
gggcugcagg gacaaacauu guugg                                    25

```
<210> SEQ ID NO 218
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 218
ggcugcaggg acaaacaucu uuggg                                        25

<210> SEQ ID NO 219
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 219
ggggugagug ugaaaggugu ugaug                                        25

<210> SEQ ID NO 220
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 220
gggugagugu gaaaggugcu gaugg                                        25

<210> SEQ ID NO 221
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 221
ggugagugug aaaggugcuu auggc                                        25

<210> SEQ ID NO 222
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 222
gugaguguga aaggugcuga uggcc                                        25

<210> SEQ ID NO 223
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 223
ugagugugaa aggugcugau ggccc                                        25

<210> SEQ ID NO 224
<211> LENGTH: 25
<212> TYPE: DNA
<213> ORGANISM: Artificial Sequence
<220> FEATURE:
<223> OTHER INFORMATION: Synthetic Nucleic Acid
```

```
<400> SEQUENCE: 224
gagugugaaa ggugcugauu gccct                                              25

<210> SEQ ID NO 225
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 225
agugugaaag gugcugaugu ccctc                                              25

<210> SEQ ID NO 226
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 226
gugugaaagg ugcugauggu ccuca                                              25

<210> SEQ ID NO 227
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 227
ugugaaaggu gcugauggcu cucat                                              25

<210> SEQ ID NO 228
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 228
gugaaaggug cugauggccu ucatc                                              25

<210> SEQ ID NO 229
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 229
ugaaaggugc ugauggcccu cauct                                              25

<210> SEQ ID NO 230
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 230
gaaaggugcu gauggcccuu auctc                                              25

<210> SEQ ID NO 231
<211> LENGTH: 25
```

```
<212> TYPE: DNA
<213> ORGANISM: Artificial Sequence
<220> FEATURE:
<223> OTHER INFORMATION: Synthetic Nucleic Acid

<400> SEQUENCE: 231
cucaucucca gcuaacuguu gagaa                                              25

<210> SEQ ID NO 232
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 232
ccagcuaacu guggagaagu ccctg                                              25

<210> SEQ ID NO 233
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 233
cagcuaacug uggagaagcu ccugg                                              25

<210> SEQ ID NO 234
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 234
agcuaacugu ggagaagccu cuggg                                              25

<210> SEQ ID NO 235
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 235
gcuaacugug gagaagcccu ugggg                                              25

<210> SEQ ID NO 236
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 236
gggcucccug auuaauggau gcuta                                              25

<210> SEQ ID NO 237
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 237
```
auggaggcuu agcuuucugu auggc                                              25

<210> SEQ ID NO 238
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 238
uggaggcuua gcuuucugga uggca                                              25

<210> SEQ ID NO 239
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 239
ggaggcuuag cuuucuggau ggcat                                              25

<210> SEQ ID NO 240
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 240
gaggcuuagc uuucuggauu gcatc                                              25

<210> SEQ ID NO 241
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 241
aggcuuagcu uucuggaugu cauct                                              25

<210> SEQ ID NO 242
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 242
ggcuuagcuu ucuggauggu aucta                                              25

<210> SEQ ID NO 243
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 243
gcuuagcuuu cuggauggca ucuag                                              25

<210> SEQ ID NO 244
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 244
gacaggugcg ccccuggugu ucaca                              25

<210> SEQ ID NO 245
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 245
gcgccccugg uggucacagu cugtg                              25

<210> SEQ ID NO 246
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 246
ccccuggugg ucacaggcuu ugcct                              25

<210> SEQ ID NO 247
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 247
cccugguggu cacaggcugu gcctt                              25

<210> SEQ ID NO 248
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 248
guggucacag gcugugccuu ggutt                              25

<210> SEQ ID NO 249
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 249
uggucacagg cugugccuuu guutc                              25

<210> SEQ ID NO 250
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 250
ggucacaggc ugugccuugu uuucc                              25

```
<210> SEQ ID NO 251
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 251
gucacaggcu gugccuuggu uucct                                              25

<210> SEQ ID NO 252
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 252
ggcugugccu ugguuuccuu agcca                                              25

<210> SEQ ID NO 253
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 253
gcugugccuu gguuccuga gccac                                               25

<210> SEQ ID NO 254
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 254
cugugccuug guuccugau ccacc                                               25

<210> SEQ ID NO 255
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 255
ugugccuugg uuuccugagu cacct                                              25

<210> SEQ ID NO 256
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 256
gugccuuggu uuccugagcu acctt                                              25

<210> SEQ ID NO 257
<211> LENGTH: 25
<212> TYPE: DNA
<213> ORGANISM: Artificial Sequence
<220> FEATURE:
<223> OTHER INFORMATION: Synthetic Nucleic Acid
```

```
<400> SEQUENCE: 257 ugccugguu uccugagcca ccutt                                              25

<210> SEQ ID NO 258
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 258
gccuugguuu ccugagccau cuuta                                             25

<210> SEQ ID NO 259
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 259
ccuugguuuc cugagccacu uuuac                                             25

<210> SEQ ID NO 260
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 260
cuugguuucc ugagccaccu uuact                                             25

<210> SEQ ID NO 261
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 261
uugguuuccu gagccaccuu uactc                                             25

<210> SEQ ID NO 262
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 262
ugguuuccug agccaccuuu acuct                                             25

<210> SEQ ID NO 263
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 263
gguuuccuga gccaccuuua cuctg                                             25

<210> SEQ ID NO 264
```

```
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 264
guuuccugag ccaccuuuau ucugc                                            25

<210> SEQ ID NO 265
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 265
cugagccacc uuuacucugu ucuat                                            25

<210> SEQ ID NO 266
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 266
ccaggcugug cuagcaacau ccaaa                                            25

<210> SEQ ID NO 267
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 267
cugcggggag ccaucaccua ggact                                            25

<210> SEQ ID NO 268
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 268
ugcggggagc caucaccuau gactg                                            25

<210> SEQ ID NO 269
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 269
gcggggagcc aucaccuagu acuga                                            25

<210> SEQ ID NO 270
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 270
```

-continued cggggagcca ucaccuagga cugac                                              25

<210> SEQ ID NO 271
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 271
ggggagccau caccuaggau ugact                                              25

<210> SEQ ID NO 272
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 272
gccaucaccu aggacugacu cggca                                              25

<210> SEQ ID NO 273
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 273
ccaucaccua ggacugacuu ggcag                                              25

<210> SEQ ID NO 274
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 274
caucaccuag gacugacucu gcagt                                              25

<210> SEQ ID NO 275
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 275
cuaggacuga cucggcaguu ugcag                                              25

<210> SEQ ID NO 276
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 276
ugacucggca gugugcaguu gugca                                              25

<210> SEQ ID NO 277
<211> LENGTH: 25
<212> TYPE: DNA

```
<213> ORGANISM: Artificial Sequence
<220> FEATURE:
<223> OTHER INFORMATION: Synthetic Nucleic Acid

<400> SEQUENCE: 277
gacucggcag ugugcagugu ugcat                                    25

<210> SEQ ID NO 278
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 278
cucggcagug ugcagugguu caugc                                    25

<210> SEQ ID NO 279
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 279
ucggcagugu gcaguggugu augca                                    25

<210> SEQ ID NO 280
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 280
cggcagugug caguggugca ugcac                                    25

<210> SEQ ID NO 281
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 281
gugugcagug gugcaugcau uguct                                    25

<210> SEQ ID NO 282
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 282
ugugcagugg ugcaugcacu guctc                                    25

<210> SEQ ID NO 283
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 283
gugcaguggu gcaugcacuu ucuca                                    25
```

<210> SEQ ID NO 284
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 284
ugcaguggug caugcacugu cucag                                             25

<210> SEQ ID NO 285
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 285
gcaguggugc augcacuguu ucagc                                             25

<210> SEQ ID NO 286
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 286
caguggugca ugcacugucu cagcc                                             25

<210> SEQ ID NO 287
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 287
aguggugcau gcacugucuu agcca                                             25

<210> SEQ ID NO 288
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 288
ugcaugcacu gucucagcca acccg                                             25

<210> SEQ ID NO 289
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 289
gcaugcacug ucucagccaa cccgc                                             25

<210> SEQ ID NO 290
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 290
cauucgcacc ccuacuucau agagg                                          25

<210> SEQ ID NO 291
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 291
auucgcaccc cuacuucaca gagga                                          25

<210> SEQ ID NO 292
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 292
uucgcacccc uacuucacau aggaa                                          25

<210> SEQ ID NO 293
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 293 ucgcacccu acuucacaga ggaag                                           25

<210> SEQ ID NO 294
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 294 cgcacccua cuucacagau gaaga                                           25

<210> SEQ ID NO 295
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 295
gcaccccuac uucacagagu aagaa                                          25

<210> SEQ ID NO 296
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 296
caccccuacu ucacagagga agaaa                                          25

```
<210> SEQ ID NO 297
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 297
accccuacuu cacagaggaa gaaac                                              25

<210> SEQ ID NO 298
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 298
ccccuacuuc acagaggaau aaacc                                              25

<210> SEQ ID NO 299
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 299
cccuacuuca cagaggaaga aacct                                              25

<210> SEQ ID NO 300
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 300
cuucacagag gaagaaaccu ggaac                                              25

<210> SEQ ID NO 301
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 301
uucacagagg aagaaaccuu gaacc                                              25

<210> SEQ ID NO 302
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 302
ucacagagga agaaaccugu aacca                                              25

<210> SEQ ID NO 303
<211> LENGTH: 25
<212> TYPE: DNA
<213> ORGANISM: Artificial Sequence
<220> FEATURE:
<223> OTHER INFORMATION: Synthetic Nucleic Acid
```

<400> SEQUENCE: 303
cacagaggaa gaaaccugga accag                                    25

<210> SEQ ID NO 304
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 304
acagaggaag aaaccuggaa ccaga                                    25

<210> SEQ ID NO 305
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 305
cagaggaaga aaccuggaau cagag                                    25

<210> SEQ ID NO 306
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 306
agaggaagaa accuggaacu agagg                                    25

<210> SEQ ID NO 307
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 307
gaggaagaaa ccuggaacca gaggg                                    25

<210> SEQ ID NO 308
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 308
aggaagaaac cuggaaccau agggg                                    25

<210> SEQ ID NO 309
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 309
gcagauuggg cuggcucuga agcca                                    25

<210> SEQ ID NO 310
<211> LENGTH: 25

```
<212> TYPE: DNA
<213> ORGANISM: Artificial Sequence
<220> FEATURE:
<223> OTHER INFORMATION: Synthetic Nucleic Acid

<400> SEQUENCE: 310
cagauugggc uggcucugaa gccaa                                              25

<210> SEQ ID NO 311
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 311
agauugggcu ggcucugaau ccaag                                              25

<210> SEQ ID NO 312
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 312
ugggcuggcu cugaagccaa gccuc                                              25

<210> SEQ ID NO 313
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 313
gggcuggcuc ugaagccaau ccuct                                              25

<210> SEQ ID NO 314
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 314
gaagccaagc cucuucuuau uucac                                              25

<210> SEQ ID NO 315
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 315
aagccucuuc uuacuucacu cggct                                              25

<210> SEQ ID NO 316
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 316
```
agccucuucu uacuucaccu ggctg                     25

<210> SEQ ID NO 317
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 317
gccucuucuu acuucacccu gcugg                     25

<210> SEQ ID NO 318
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 318
cccggcuggg cuccucauuu uuacg                     25

<210> SEQ ID NO 319
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 319
ccggcugggc uccucauuuu uacgg                     25

<210> SEQ ID NO 320
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 320
cggcugggcu ccucauuuuu acggg                     25

<210> SEQ ID NO 321
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 321
ggcugggcuc cucauuuuua cgggt                     25

<210> SEQ ID NO 322
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 322
gcugggcucc ucauuuuuau gggta                     25

<210> SEQ ID NO 323
<211> LENGTH: 25
<212> TYPE: DNA
<213> ORGANISM: Artificial Sequence

```
<220> FEATURE:
<223> OTHER INFORMATION: Synthetic Nucleic Acid

<400> SEQUENCE: 323 acgguaaca gugaggcugu gaagg                                           25

<210> SEQ ID NO 324
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 324
agcucgguga gugauggcau aacga                                          25

<210> SEQ ID NO 325
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 325
gcucggugag ugauggcaga acgat                                          25

<210> SEQ ID NO 326
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 326
cucggugagu gauggcagaa cgatg                                          25

<210> SEQ ID NO 327
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 327
ucggugagug auggcagaau gaugc                                          25

<210> SEQ ID NO 328
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 328
cggugaguga uggcagaacu augcc                                          25

<210> SEQ ID NO 329
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 329
augccugcag gcauggaacu uuutc                                          25
```

<210> SEQ ID NO 330
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 330
ugccugcagg cauggaacuu uuucc                                              25

<210> SEQ ID NO 331
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 331
gccugcaggc auggaacuuu uuccg                                              25

<210> SEQ ID NO 332
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 332
ccugcaggca uggaacuuuu uccgt                                              25

<210> SEQ ID NO 333
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 333
cugcaggcau ggaacuuuuu ccgtt                                              25

<210> SEQ ID NO 334
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 334
auggaacuuu uuccguuauu accca                                              25

<210> SEQ ID NO 335
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 335
uuuuuccguu aucacccagu ccuga                                              25

<210> SEQ ID NO 336
<211> LENGTH: 25
<212> TYPE: DNA
<213> ORGANISM: Artificial Sequence
<220> FEATURE:
<223> OTHER INFORMATION: Synthetic Nucleic Acid -continued

<400> SEQUENCE: 336
uuuuccguua ucacccaggu cugat                                    25

<210> SEQ ID NO 337
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 337
uuuccguuau cacccaggcu ugatt                                    25

<210> SEQ ID NO 338
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 338
uuccguuauc acccaggccu gautc                                    25

<210> SEQ ID NO 339
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 339
uccguuauca cccaggccuu auuca                                    25

<210> SEQ ID NO 340
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 340
ccguuaucac ccaggccuga uucac                                    25

<210> SEQ ID NO 341
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 341
cguuaucacc caggccugau ucact                                    25

<210> SEQ ID NO 342
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 342
cacccaggcc ugauucacuu gcctg                                    25

<210> SEQ ID NO 343

<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 343
acccaggccu gauucacugu ccugg                                              25

<210> SEQ ID NO 344
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 344
uggccuggcg gagaugcuuu uaagg                                              25

<210> SEQ ID NO 345
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 345
ggccuggcgg agaugcuucu aaggc                                              25

<210> SEQ ID NO 346
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 346
gccuggcgga gaugcuucua aggca                                              25

<210> SEQ ID NO 347
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 347
ccuggcggag augcuucuaa ggcat                                              25

<210> SEQ ID NO 348
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 348
cuggcggaga ugcuucuaau gcatg                                              25

<210> SEQ ID NO 349
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 349
uggcggagau gcuucuaagu caugg                                          25

<210> SEQ ID NO 350
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 350
ggcggagaug cuucuaaggu auggt                                          25

<210> SEQ ID NO 351
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 351
gcggagaugc uucuaaggca uggtc                                          25

<210> SEQ ID NO 352
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 352
cggagaugcu ucuaaggcau ggucg                                          25

<210> SEQ ID NO 353
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 353
ggagaugcuu cuaaggcauu gucgg                                          25

<210> SEQ ID NO 354
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 354
gagaugcuuc uaaggcaugu ucggg                                          25

<210> SEQ ID NO 355
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 355
ggagagggcc aacaacuguu ccucc                                          25

<210> SEQ ID NO 356
<211> LENGTH: 25
<212> TYPE: DNA

```
<213> ORGANISM: Artificial Sequence
<220> FEATURE:
<223> OTHER INFORMATION: Synthetic Nucleic Acid

<400> SEQUENCE: 356
gccaacaacu gucccuccuu gagca                                          25

<210> SEQ ID NO 357
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 357
ccaacaacug ucccuccuuu agcac                                          25

<210> SEQ ID NO 358
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 358
uugagcacca gccccaccca agcaa                                          25

<210> SEQ ID NO 359
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 359
ugagcaccag ccccacccaa gcaag                                          25

<210> SEQ ID NO 360
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 360
gagcaccagc cccacccaau caagc                                          25

<210> SEQ ID NO 361
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 361
agcaccagcc ccacccaagu aagca                                          25

<210> SEQ ID NO 362
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 362
acccaagcaa gcagacauuu auctt                                          25
```

<210> SEQ ID NO 363
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 363
cccaagcaag cagacauuua ucutt                                              25

<210> SEQ ID NO 364
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 364
ccaagcaagc agacauuuau cuutt                                              25

<210> SEQ ID NO 365
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 365
caagcaagca gacauuuauu uutg                                               25

<210> SEQ ID NO 366
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 366
aagcaagcag acauuuaucu uugg                                               25

<210> SEQ ID NO 367
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 367
agcaagcaga cauuuaucuu uggg                                               25

<210> SEQ ID NO 368
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 368
gcaagcagac auuuaucuuu gggt                                               25

<210> SEQ ID NO 369
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 369
aagcagacau uuaucuuuuu gguct                                  25

<210> SEQ ID NO 370
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 370
agcagacauu uaucuuuugu guctg                                  25

<210> SEQ ID NO 371
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 371
gcagacauuu aucuuuuggu ucugt                                  25

<210> SEQ ID NO 372
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 372
uguugccuuu uuacagccaa cuutt                                  25

<210> SEQ ID NO 373
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 373
guugccuuuu uacagccaau uuutc                                  25

<210> SEQ ID NO 374
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 374
uuuacagcca acuuuucuau acctg                                  25

<210> SEQ ID NO 375
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 375
uuacagccaa cuuuucuaga ccugt                                  25

```
<210> SEQ ID NO 376
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 376
uuuucuagac cuguuuugcu uuugt                                     25

<210> SEQ ID NO 377
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 377
uuucuagacc uguuuugcuu uugta                                     25

<210> SEQ ID NO 378
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 378
uucuagaccu guuuugcuuu uguaa                                     25

<210> SEQ ID NO 379
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 379
ucuagaccug uuuugcuuuu guaac                                     25

<210> SEQ ID NO 380
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 380
cuagaccugu uugcuuuuu uaact                                      25

<210> SEQ ID NO 381
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 381
uagaccuguu uugcuuuugu aactt                                     25

<210> SEQ ID NO 382
<211> LENGTH: 25
<212> TYPE: DNA
<213> ORGANISM: Artificial Sequence
<220> FEATURE:
<223> OTHER INFORMATION: Synthetic Nucleic Acid
```

```
<400> SEQUENCE: 382
agaccuguuu ugcuuuugua acutg                                    25

<210> SEQ ID NO 383
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 383
gaccuguuuu gcuuuuguaa cuuga                                    25

<210> SEQ ID NO 384
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 384 accuguuug cuuuuguaau uugaa                                     25

<210> SEQ ID NO 385
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 385 ccuguuugc uuuuguaacu ugaag                                     25

<210> SEQ ID NO 386
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 386 cuguuugcu uuguaacuu gaaga                                      25

<210> SEQ ID NO 387
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 387 uguuugcuu uguaacuuu aagat                                      25

<210> SEQ ID NO 388
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 388 guuugcuuu uguaacuuga agata                                     25

<210> SEQ ID NO 389
<211> LENGTH: 25
```

```
<212> TYPE: DNA
<213> ORGANISM: Artificial Sequence
<220> FEATURE:
<223> OTHER INFORMATION: Synthetic Nucleic Acid

<400> SEQUENCE: 389
uuuugcuuuu guaacuugaa gauat                                              25

<210> SEQ ID NO 390
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 390
uuugcuuuug uaacuugaau auatt                                              25

<210> SEQ ID NO 391
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 391
uugcuuuugu aacugaaga uautt                                               25

<210> SEQ ID NO 392
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 392
ugcuuuugua acugaagau auuta                                               25

<210> SEQ ID NO 393
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 393
gcuuuuguaa cuugaagaua uuuat                                              25

<210> SEQ ID NO 394
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 394
cuuuuguaac uugaagauau uuatt                                              25

<210> SEQ ID NO 395
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 395
```
uuuuguaacu ugaagauauu uautc					25

<210> SEQ ID NO 396
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 396
uuuguaacuu gaagauauuu auuct					25

<210> SEQ ID NO 397
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 397
uuguaacuug aagauauuua uuctg					25

<210> SEQ ID NO 398
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 398
uguaacuuga agauauuuau ucugg					25

<210> SEQ ID NO 399
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 399
guaacuugaa gauauuuauu cuggg					25

<210> SEQ ID NO 400
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 400
uaacuugaag auauuuauuu ugggt					25

<210> SEQ ID NO 401
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 401
acuugaagau auuuauucuu ggutt					25

<210> SEQ ID NO 402
<211> LENGTH: 25
<212> TYPE: DNA
<213> ORGANISM: Artificial Sequence

```
<220> FEATURE:
<223> OTHER INFORMATION: Synthetic Nucleic Acid

<400> SEQUENCE: 402
cuugaagaua uuuauucugu guutt                                          25

<210> SEQ ID NO 403
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 403
uugaagauau uuauucuggu uuutg                                          25

<210> SEQ ID NO 404
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 404
gaagauauuu auucuggguu uugta                                          25

<210> SEQ ID NO 405
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 405
aagauauuua uucuggguuu uguag                                          25

<210> SEQ ID NO 406
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 406
auauuuauuc uggguuuugu agcat                                          25

<210> SEQ ID NO 407
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 407
uauuuauucu ggguuuugua gcatt                                          25

<210> SEQ ID NO 408
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 408
auuuauucug gguuuuguau cautt                                          25
```

<210> SEQ ID NO 409
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 409
uuuauucugg guuuuguagu auutt                                              25

<210> SEQ ID NO 410
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 410
auucuggguu uuguagcauu uuuat                                              25

<210> SEQ ID NO 411
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 411
uucuggguuu uguagcauuu uuatt                                              25

<210> SEQ ID NO 412
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 412
ucuggguuuu guagcauuuu uauta                                              25

<210> SEQ ID NO 413
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 413
cuggguuuug uagcauuuuu auuaa                                              25

<210> SEQ ID NO 414
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 414
uggguuuugu agcauuuuua uuaat                                              25

<210> SEQ ID NO 415
<211> LENGTH: 25
<212> TYPE: DNA
<213> ORGANISM: Artificial Sequence
<220> FEATURE:
<223> OTHER INFORMATION: Synthetic Nucleic Acid -continued

<400> SEQUENCE: 415
ggguuuugua gcauuuuuau uaata                                      25

<210> SEQ ID NO 416
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 416
gguuuuguag cauuuuauu aauat                                       25

<210> SEQ ID NO 417
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 417 guuuguagc auuuuauua auatg                                        25

<210> SEQ ID NO 418
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 418
uuuuguagca uuuuauuaa uaugg                                       25

<210> SEQ ID NO 419
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 419
uuuguagcau uuuauuaau auggt                                       25

<210> SEQ ID NO 420
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 420
uuguagcauu uuauuaaua uggtg                                       25

<210> SEQ ID NO 421
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 421
uguagcauuu uauuaauau gguga                                       25

<210> SEQ ID NO 422

```
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 422
guagcauuuu uauuaauauu gugac                                              25

<210> SEQ ID NO 423
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 423
uagcauuuuu auuaauaugu ugact                                              25

<210> SEQ ID NO 424
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 424
agcauuuuua uuaauauggu gactt                                              25

<210> SEQ ID NO 425
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 425
gcauuuuuau uaauaugguu acutt                                              25

<210> SEQ ID NO 426
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 426 cauuuuauu aauaugguga cuutt                                               25

<210> SEQ ID NO 427
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 427 auuuuauua auauggugau uuutt                                               25

<210> SEQ ID NO 428
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 428
```
uuuuuauuaa uauggugacu uuuta                                              25

<210> SEQ ID NO 429
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 429
uuuuauuaau auggugacuu uuuaa                                              25

<210> SEQ ID NO 430
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 430
uuuauuaaua uggugacuuu uuaaa                                              25

<210> SEQ ID NO 431
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 431
uuauuaauau ggugacuuuu uaaaa                                              25

<210> SEQ ID NO 432
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 432
uauuaauaug gugacuuuuu aaaat                                              25

<210> SEQ ID NO 433
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 433
auuaauaugg ugacuuuuua aaata                                              25

<210> SEQ ID NO 434
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 434
uuaauauggu gacuuuuuaa aauaa                                              25

<210> SEQ ID NO 435
<211> LENGTH: 25
<212> TYPE: DNA

```
<213> ORGANISM: Artificial Sequence
<220> FEATURE:
<223> OTHER INFORMATION: Synthetic Nucleic Acid

<400> SEQUENCE: 435
uaauauggug acuuuuuaaa auaaa                                          25

<210> SEQ ID NO 436
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 436
aauaugguga cuuuuuaaaa uaaaa                                          25

<210> SEQ ID NO 437
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 437
auauggugac uuuuuaaaau aaaaa                                          25

<210> SEQ ID NO 438
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 438
uauggugacu uuuuaaaaua aaaac                                          25

<210> SEQ ID NO 439
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 439
auggugacuu uuuaaaauaa aaaca                                          25

<210> SEQ ID NO 440
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 440
uggugacuuu uuaaaauaaa aacaa                                          25

<210> SEQ ID NO 441
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 441
ggugacuuuu uaaaauaaaa acaaa                                          25
```

<210> SEQ ID NO 442
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 442
gugacuuuuu aaauaaaaa caaac                                  25

<210> SEQ ID NO 443
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 443
ugacuuuuua aauaaaaau aaaca                                  25

<210> SEQ ID NO 444
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 444
gacuuuuuaa aauaaaaaca aacaa                                 25

<210> SEQ ID NO 445
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 445
acuuuuuaaa auaaaaacaa acaaa                                 25

<210> SEQ ID NO 446
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 446
uuuuaaaaua aaacaaaca aacgt                                  25

<210> SEQ ID NO 447
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 447
uuuaaaauaa aacaaacaa acgtt                                  25

<210> SEQ ID NO 448
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 448
uuaaaauaaa aacaaacaaa cgutg                                25

<210> SEQ ID NO 449
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 449
uaaaauaaaa acaaacaaau guugt                                25

<210> SEQ ID NO 450
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 450
aaaaacaaac aaacguuguu cuaac                                25

<210> SEQ ID NO 451
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 451
caaacaaacg uuguccuaau aaaaa                                25

<210> SEQ ID NO 452
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 452
aaacaaacgu uguccuaaca aaaaa                                25

<210> SEQ ID NO 453
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 453
aacaaacguu guccuaacaa aaaaa                                25

<210> SEQ ID NO 454
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 454
gaaacauucu aggguguggg ugcuuga                              27

```
<210> SEQ ID NO 455
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 455
ggaaaacuuc uaggugugg gugcuug                                              27

<210> SEQ ID NO 456
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 456
cggaaaccuu cuagggugug ggugcuu                                             27

<210> SEQ ID NO 457
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 457
ugcggaaacc uucuagggug ugggugc                                             27

<210> SEQ ID NO 458
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 458
cugcgaaaac cuucuagggu gugggug                                             27

<210> SEQ ID NO 459
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 459
cuccuacagg cucagacccu gaacuga                                             27

<210> SEQ ID NO 460
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 460
acuccuccag gcucagaccc ugaacug                                             27

<210> SEQ ID NO 461
<211> LENGTH: 27
<212> TYPE: DNA
<213> ORGANISM: Artificial Sequence
<220> FEATURE:
<223> OTHER INFORMATION: Synthetic Nucleic Acid
```

```
<400> SEQUENCE: 461
cacucaucca ggcucagacc cugaacu                                              27

<210> SEQ ID NO 462
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 462
ucacuacucc aggcucagac ccugaac                                              27

<210> SEQ ID NO 463
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 463
gcucaauccu ccaggcucag acccuga                                              27

<210> SEQ ID NO 464
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 464
uggcuaacuc cuccaggcuc agacccu                                              27

<210> SEQ ID NO 465
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 465
cgcguaaagg ggcgcgcgga auccugg                                              27

<210> SEQ ID NO 466
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 466
gcgcgugaag gggcgcgcgg aauccug                                              27

<210> SEQ ID NO 467
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 467
ugaaguucag gagcagggcg cgugaag                                              27

<210> SEQ ID NO 468
<211> LENGTH: 27
```

```
<212> TYPE: DNA
<213> ORGANISM: Artificial Sequence
<220> FEATURE:
<223> OTHER INFORMATION: Synthetic Nucleic Acid

<400> SEQUENCE: 468
cugaaauuca ggagcagggc gcgugaa                                          27

<210> SEQ ID NO 469
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 469
caggaacuga aguucaggag cagggcg                                          27

<210> SEQ ID NO 470
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 470
ugcagaagcu gaaguucagg agcaggg                                          27

<210> SEQ ID NO 471
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 471
gugcaagagc ugaaguucag gagcagg                                          27

<210> SEQ ID NO 472
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 472
ugugcaggag cugaaguuca ggagcag                                          27

<210> SEQ ID NO 473
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 473
cugugaagga gcugaaguuc aggagca                                          27

<210> SEQ ID NO 474
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 474
```
acuguacagg agcugaaguu caggagc                                           27

<210> SEQ ID NO 475
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 475
gacugugcag gagcugaagu ucaggag                                           27

<210> SEQ ID NO 476
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 476
ggacuaugca ggagcugaag uucagga                                           27

<210> SEQ ID NO 477
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 477
aggacugugc aggagcugaa guucagg                                           27

<210> SEQ ID NO 478
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 478
gaggaaugug caggagcuga aguucag                                           27

<210> SEQ ID NO 479
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 479
ggaggacugu gcaggagcug aaguuca                                           27

<210> SEQ ID NO 480
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 480
gggagaacug ugcaggagcu gaaguuc                                           27

<210> SEQ ID NO 481
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 481
ggggaagacu gugcaggagc ugaaguu                                            27

<210> SEQ ID NO 482
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 482
ugagcauugc ggugggagg acugugc                                             27

<210> SEQ ID NO 483
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 483
uugagacuug cggugggag gacugug                                             27

<210> SEQ ID NO 484
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 484
uguccuggcg aggagaccua gaggccg                                            27

<210> SEQ ID NO 485
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 485
ccaggagaga gguugcuguc cuggcga                                            27

<210> SEQ ID NO 486
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 486
agggcaaggg gagagguugc uguccug                                            27

<210> SEQ ID NO 487
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 487
ugacgaugcc caugagggcc aggggag                                            27
```

```
<210> SEQ ID NO 488
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 488
gagcuaacgg ugcccaugag ggccagg                                          27

<210> SEQ ID NO 489
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 489
ggagcugacg gugcccauga gggccag                                          27

<210> SEQ ID NO 490
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 490
uggagaugac ggugcccaug agggcca                                          27

<210> SEQ ID NO 491
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 491
cagugacagc ggccaccagg accgccu                                          27

<210> SEQ ID NO 492
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 492
cgugcucggg ugcuucggcc aggccgu                                          27

<210> SEQ ID NO 493
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 493 ggugaugug guuccgugcu cgggugc                                           27

<210> SEQ ID NO 494
<211> LENGTH: 27
<212> TYPE: DNA
<213> ORGANISM: Artificial Sequence
<220> FEATURE:
<223> OTHER INFORMATION: Synthetic Nucleic Acid
```

```
<400> SEQUENCE: 494
uggaaagugg cugugguucc gugcucg                                               27

<210> SEQ ID NO 495
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 495
gguggaaggu ggcuguggu uccgugcu                                               27

<210> SEQ ID NO 496
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 496
cggugaaagg uggcuguggu uccgugc                                               27

<210> SEQ ID NO 497
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 497
caggcaaccu ccacggaucc uuggcgc                                               27

<210> SEQ ID NO 498
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 498
ccaggaaacc uccacggauc cuuggcg                                               27

<210> SEQ ID NO 499
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 499
ugccaagcaa ccuccacgga uccuugg                                               27

<210> SEQ ID NO 500
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 500
ggugcaaggc aaccuccacg gauccuu                                               27

<210> SEQ ID NO 501
```

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 501
ccacguaggu gccaggcaac cuccacg                                          27

<210> SEQ ID NO 502
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 502
agcacaacca cguaggugcc aggcaac                                          27

<210> SEQ ID NO 503
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 503
cagcaacacc acguaggugc caggcaa                                          27

<210> SEQ ID NO 504
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 504
gacugagaga ggugggucuc cuccuuc                                          27

<210> SEQ ID NO 505
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 505
aagaaagcca uggaagacau gcaggau                                          27

<210> SEQ ID NO 506
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 506
ggaagaaggc cauggaagac augcagg                                          27

<210> SEQ ID NO 507
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 507
```

-continued aacuuaaagg ccagcuccag caggucg 27

<210> SEQ ID NO 508
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 508
gcaacuucaa ggccagcucc agcaggu 27

<210> SEQ ID NO 509
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 509
ggcaaauuca aggccagcuc cagcagg 27

<210> SEQ ID NO 510
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 510 ugggaaacu ucaaggccag cuccagc 27

<210> SEQ ID NO 511
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 511
gucgaaaugg ggcaacuuca aggccag 27

<210> SEQ ID NO 512
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 512
agucgacaug gggcaacuuc aaggcca 27

<210> SEQ ID NO 513
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 513
uagucaacau ggggcaacuu caaggcc 27

<210> SEQ ID NO 514
<211> LENGTH: 27
<212> TYPE: DNA

```
<213> ORGANISM: Artificial Sequence
<220> FEATURE:
<223> OTHER INFORMATION: Synthetic Nucleic Acid

<400> SEQUENCE: 514
guaguagaca ugggcaacu ucaaggc                                          27

<210> SEQ ID NO 515
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 515
augcuauggg caaagacaga ggagucc                                         27

<210> SEQ ID NO 516
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 516
gaugcucugg gcaaagacag aggaguc                                         27

<210> SEQ ID NO 517
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 517
ggaugaucug ggcaaagaca gaggagu                                         27

<210> SEQ ID NO 518
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 518
gggauacucu gggcaaagac agaggag                                         27

<210> SEQ ID NO 519
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 519
acgggaugcu cugggcaaag acagagg                                         27

<210> SEQ ID NO 520
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 520
cacggaaugc ucugggcaaa gacagag                                         27
```

<210> SEQ ID NO 521
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 521
uccacaggau gcucgggca aagacag            27

<210> SEQ ID NO 522
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 522
uuccaaggga ugcucgggc aaagaca            27

<210> SEQ ID NO 523
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 523
gguucaacgg gaugcucugg gcaaaga            27

<210> SEQ ID NO 524
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 524
cgcucaaggu uccacgggau gcucugg            27

<210> SEQ ID NO 525
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 525
ccgcuacagg uuccacggga ugcucug            27

<210> SEQ ID NO 526
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 526
uccgcuccag guuccacggg augcucu            27

<210> SEQ ID NO 527
<211> LENGTH: 27
<212> TYPE: DNA
<213> ORGANISM: Artificial Sequence
<220> FEATURE:

```
<223> OTHER INFORMATION: Synthetic Nucleic Acid

<400> SEQUENCE: 527
auccgaucca gguuccacgg gaugcuc                                27

<210> SEQ ID NO 528
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 528
aauccacucc agguuccacg ggaugcu                                27

<210> SEQ ID NO 529
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 529
uaaucagcuc cagguuccac gggaugc                                27

<210> SEQ ID NO 530
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 530
guaauacgcu ccagguucca cgggaug                                27

<210> SEQ ID NO 531
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 531
gguaauccgc uccagguucc acgggau                                27

<210> SEQ ID NO 532
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 532
ggguaauccg cuccagguuc cacggga                                27

<210> SEQ ID NO 533
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 533
accguagagg gguaauccgc uccaggu                                27
```

```
<210> SEQ ID NO 534
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 534
uaccguggag ggguaauccg cuccagg                                          27

<210> SEQ ID NO 535
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 535
guaccaugga gggguaaucc gcuccag                                          27

<210> SEQ ID NO 536
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 536
gguacagugg aggggua auc cgcucca                                         27

<210> SEQ ID NO 537
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 537
cgguaacgug gaggguaau ccgcucc                                           27

<210> SEQ ID NO 538
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 538
cccgguaccg uggaggggua auccgcu                                          27

<210> SEQ ID NO 539
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 539
gcccgauacc guggaggggu aauccgc                                          27

<210> SEQ ID NO 540
<211> LENGTH: 27
<212> TYPE: DNA
<213> ORGANISM: Artificial Sequence
<220> FEATURE:
<223> OTHER INFORMATION: Synthetic Nucleic Acid
```

<400> SEQUENCE: 540
guauuaaucc gcccgguacc guggagg 27

<210> SEQ ID NO 541
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 541
auacaacucc accaggcugc cuccguc 27

<210> SEQ ID NO 542
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 542
gugguaacuc uguaugcugg ugucuag 27

<210> SEQ ID NO 543
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 543
auuucacggu ggucacucug uaugcug 27

<210> SEQ ID NO 544
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 544
cccguacucc ucgggcacau ucucgaa 27

<210> SEQ ID NO 545
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 545
ucccguccuc cucgggcaca uucucga 27

<210> SEQ ID NO 546
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 546
gucccauccu ccucgggcac auucucg 27

<210> SEQ ID NO 547
<211> LENGTH: 27

```
<212> TYPE: DNA
<213> ORGANISM: Artificial Sequence
<220> FEATURE:
<223> OTHER INFORMATION: Synthetic Nucleic Acid

<400> SEQUENCE: 547
uggguaccau gacugucaca cuugcug                                               27

<210> SEQ ID NO 548
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 548
gugggugcca ugacugucac acuugcu                                               27

<210> SEQ ID NO 549
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 549
gguggaugcc augacuguca cacuugc                                               27

<210> SEQ ID NO 550
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 550
ggcaguugag cacgcgcagg cugcgca                                               27

<210> SEQ ID NO 551
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 551
uggcaauuga gcacgcgcag gcugcgc                                               27

<210> SEQ ID NO 552
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 552
agcacaacca guggcccac aggcugg                                                27

<210> SEQ ID NO 553
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 553
```
gggagaugag gcuggggagu agaggca                                              27

<210> SEQ ID NO 554
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 554
gugauaaccu cgggagcuga ggcuggg                                              27

<210> SEQ ID NO 555
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 555
ccggcugguc uugggcauug guggccc                                              27

<210> SEQ ID NO 556
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 556
aggguaaccg gcuggucuug ggcauug                                              27

<210> SEQ ID NO 557
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 557
cagggucacc ggcuggucuu gggcauu                                              27

<210> SEQ ID NO 558
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 558
agccuaugau gucccacucu gugacac                                              27

<210> SEQ ID NO 559
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 559
ggcagaagcc ugugaugucc cacucug                                              27

<210> SEQ ID NO 560
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 560
gugggaagca gccugugaug ucccacu                                              27

<210> SEQ ID NO 561
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 561
cguggacagc agccugugau gucccac                                              27

<210> SEQ ID NO 562
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 562
ucugcaucaa cucggccagg gugagcu                                              27

<210> SEQ ID NO 563
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 563
gucucugccu caacucggcc aggguga                                              27

<210> SEQ ID NO 564
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 564
uugauaacau cuuuggcaga gaagugg                                              27

<210> SEQ ID NO 565
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 565
aacagaugcc aaccugcccc augggug                                              27

<210> SEQ ID NO 566
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 566
gcaaaacagc ugccaaccug ccccaug                                              27
```

```
<210> SEQ ID NO 567
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 567
cugacaauac aguccugcaa aacagcu                                          27

<210> SEQ ID NO 568
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 568
gugcuaacca uacaguccug caaaaca                                          27

<210> SEQ ID NO 569
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 569
cgaguaugcu gaccauacag uccugca                                          27

<210> SEQ ID NO 570
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 570
cccgaaugug cugaccauac aguccug                                          27

<210> SEQ ID NO 571
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 571
gcagcuccuc aucuggggcg cagcggg                                          27

<210> SEQ ID NO 572
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 572
cucagaagcu ccucaucugg ggcgcag                                          27

<210> SEQ ID NO 573
<211> LENGTH: 27
<212> TYPE: DNA
<213> ORGANISM: Artificial Sequence
<220> FEATURE:
<223> OTHER INFORMATION: Synthetic Nucleic Acid
```

```
<400> SEQUENCE: 573
cagcuaagca gcuccucauc ugggcg                                27

<210> SEQ ID NO 574
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 574
gcagcucagc agcuccucau cuggggc                               27

<210> SEQ ID NO 575
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 575
agcagaucag cagcuccuca ucugggg                               27

<210> SEQ ID NO 576
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 576
gggccuccau gcgcucgccc cgccgcu                               27

<210> SEQ ID NO 577
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 577
ugggcaucca ugcgcucgcc ccgccgc                               27

<210> SEQ ID NO 578
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 578
ccccuugggc cuccaugcgc ucgcccc                               27

<210> SEQ ID NO 579
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 579
aagcguugug ggcccggcag accagcu                               27

<210> SEQ ID NO 580
```

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 580
ugcaguuggc cugggguagc aggcagc                                              27

<210> SEQ ID NO 581
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 581
cugcaauugg ccugggguag caggcag                                              27

<210> SEQ ID NO 582
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 582
gugugaacgc ugcaguuggc cuggggu                                              27

<210> SEQ ID NO 583
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 583
cacggucacc ugcuccugag gggccgg                                              27

<210> SEQ ID NO 584
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 584
cagccauccu cgcaggccac ggucacc                                              27

<210> SEQ ID NO 585
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 585
ccaguaaggg uccagcccuc cucgcag                                              27

<210> SEQ ID NO 586
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 586
```
gccagucagg guccagcccu ccucgca					27

<210> SEQ ID NO 587
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 587
acugcagcca gucaggaucc agcccuc					27

<210> SEQ ID NO 588
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 588
cacugaagcc agucaggguc cagcccu					27

<210> SEQ ID NO 589
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 589
gggcaaugca gccagucagg guccagc					27

<210> SEQ ID NO 590
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 590
aggucacagg gagggcacug cagccag					27

<210> SEQ ID NO 591
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 591
cccagaacgu gggagguccc agggagg					27

<210> SEQ ID NO 592
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 592
ccccaagacg ugggaggucc cagggag					27

<210> SEQ ID NO 593
<211> LENGTH: 27
<212> TYPE: DNA

```
<213> ORGANISM: Artificial Sequence
<220> FEATURE:
<223> OTHER INFORMATION: Synthetic Nucleic Acid

<400> SEQUENCE: 593
cacguauugu cuacggcgua ggccccc                                          27

<210> SEQ ID NO 594
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 594
uggugaugcc uguagugcug acguccc                                          27

<210> SEQ ID NO 595
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 595
uucgcuggug cugccuguag ugcugac                                          27

<210> SEQ ID NO 596
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 596
cuucgauggu gcugccugua gugcuga                                          27

<210> SEQ ID NO 597
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 597
ccuucacugg ugcugccugu agugcug                                          27

<210> SEQ ID NO 598
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 598
agaugacaac ggcugucacg gccccuu                                          27

<210> SEQ ID NO 599
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 599
gggauagggc ugucacugga gcuccug                                          27
```

<210> SEQ ID NO 600
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 600
uugacacucc ccagacaccc auccugg                                          27

<210> SEQ ID NO 601
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 601
gcccuugacc cuccccagac acccauc                                          27

<210> SEQ ID NO 602
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 602
agcccuugac ccuccccaga cacccau                                          27

<210> SEQ ID NO 603
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 603
cagccauuga cccucccag acaccca                                           27

<210> SEQ ID NO 604
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 604
aagcuaagcc ccagcccuug acccucc                                          27

<210> SEQ ID NO 605
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 605
aaagcucagc cccagcccuu gacccuc                                          27

<210> SEQ ID NO 606
<211> LENGTH: 27
<212> TYPE: DNA
<213> ORGANISM: Artificial Sequence
<220> FEATURE:

<223> OTHER INFORMATION: Synthetic Nucleic Acid

<400> SEQUENCE: 606
uggagagcug agagagggac aagucgg         27

<210> SEQ ID NO 607
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 607
auggaaggcu gagagaggga caagucg         27

<210> SEQ ID NO 608
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 608
cauggagggc ugagagaggg acaaguc         27

<210> SEQ ID NO 609
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 609
ccaugaaggg cugagagagg gacaagu         27

<210> SEQ ID NO 610
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 610
aggccaugga gggcugagag agggaca         27

<210> SEQ ID NO 611
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 611
aucccaaucc ccucgugcca ggccaug         27

<210> SEQ ID NO 612
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 612
gaagcauccc caucccucg ugccagg         27

```
<210> SEQ ID NO 613
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 613
aggcgaaagc auccccaucc ccucgug                                          27

<210> SEQ ID NO 614
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 614
aaggcagaag cauccccauc cccucgu                                          27

<210> SEQ ID NO 615
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 615
ggaaaagcgg aagcauccccc auccccu                                         27

<210> SEQ ID NO 616
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 616
cccggaaagg cggaagcauc cccaucc                                          27

<210> SEQ ID NO 617
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 617
ccccgaaaag gcggaagcau ccccauc                                          27

<210> SEQ ID NO 618
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 618
gccccagaaa ggcggaagca uccccau                                          27

<210> SEQ ID NO 619
<211> LENGTH: 27
<212> TYPE: DNA
<213> ORGANISM: Artificial Sequence
<220> FEATURE:
<223> OTHER INFORMATION: Synthetic Nucleic Acid
```

-continued

```
<400> SEQUENCE: 619
agcccaggaa aggcggaagc auccca                                27

<210> SEQ ID NO 620
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 620
gcaagaaggc ugccccacuc aagggcc                               27

<210> SEQ ID NO 621
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 621
ccaggaaagg aggcugcccc acucaag                               27

<210> SEQ ID NO 622
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 622
gaguuacagg caaggaggcu gccccac                               27

<210> SEQ ID NO 623
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 623
gugaguucca ggcaaggagg cugcccc                               27

<210> SEQ ID NO 624
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 624
agugaauucc aggcaaggag gcugccc                               27

<210> SEQ ID NO 625
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 625
ugaguaaguu ccaggcaagg aggcugc                               27

<210> SEQ ID NO 626
<211> LENGTH: 27
```

```
<212> TYPE: DNA
<213> ORGANISM: Artificial Sequence
<220> FEATURE:
<223> OTHER INFORMATION: Synthetic Nucleic Acid

<400> SEQUENCE: 626
gugagugagu uccaggcaag gaggcug                                              27

<210> SEQ ID NO 627
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 627
agugaaugag uuccaggcaa ggaggcu                                              27

<210> SEQ ID NO 628
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 628
gagugaguga guuccaggca aggaggc                                              27

<210> SEQ ID NO 629
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 629
agaguaagug aguuccaggc aaggagg                                              27

<210> SEQ ID NO 630
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 630
cagagugagu gaguuccagg caaggag                                              27

<210> SEQ ID NO 631
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 631
ccagaaugag ugaguuccag gcaagga                                              27

<210> SEQ ID NO 632
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 632
```
cccagaguga gugaguucca ggcaagg					27

<210> SEQ ID NO 633
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 633
acccaaagug agugaguucc aggcaag					27

<210> SEQ ID NO 634
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 634
uccacauggg gaggaggcac ccagagu					27

<210> SEQ ID NO 635
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 635
gagcuuccug gcaccuccac cugggga					27

<210> SEQ ID NO 636
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 636
cacagugagg gagggagcuu ccuggca					27

<210> SEQ ID NO 637
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 637
ccccaaagug agggagggag cuuccug					27

<210> SEQ ID NO 638
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 638
augccacaca gugagggagg gagcuuc					27

<210> SEQ ID NO 639
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 639
aaugcaccac agugagggag ggagcuu                                      27

<210> SEQ ID NO 640
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 640
accuguuuga auggugaaau gccccac                                      27

<210> SEQ ID NO 641
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 641
gaccuauuug aauggugaaa ugcccca                                      27

<210> SEQ ID NO 642
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 642
cacagaucga ccuguuugaa uggugaa                                      27

<210> SEQ ID NO 643
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 643
gcacaacucg accuguuuga augguga                                      27

<210> SEQ ID NO 644
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 644
gggagaagcu ggcagcaccc gagcaca                                      27

<210> SEQ ID NO 645
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 645
cauugagagc agcuggcagc acccgag                                      27
```

```
<210> SEQ ID NO 646
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 646
acauuaggag cagcuggcag cacccga                                        27

<210> SEQ ID NO 647
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 647
caucgacaca uugggagcag cuggcag                                        27

<210> SEQ ID NO 648
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 648
acaucagcac auugggagca gcuggca                                        27

<210> SEQ ID NO 649
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 649
gucauucugc ccacggacau cggcaca                                        27

<210> SEQ ID NO 650
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 650
aagagaucaa uaaaagucau ucugccc                                        27

<210> SEQ ID NO 651
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 651
caagaacuca auaaaaguca uucugcc                                        27

<210> SEQ ID NO 652
<211> LENGTH: 27
<212> TYPE: DNA
<213> ORGANISM: Artificial Sequence
<220> FEATURE:
<223> OTHER INFORMATION: Synthetic Nucleic Acid
```

<400> SEQUENCE: 652
acaagagcuc aauaaaaguc auucugc                              27

<210> SEQ ID NO 653
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 653
aacaaaagcu caauaaaagu cauucug                              27

<210> SEQ ID NO 654
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 654
gaacaagagc ucaauaaaag ucauucu                              27

<210> SEQ ID NO 655
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 655
ggaacaagag cucaauaaaa gucauuc                              27

<210> SEQ ID NO 656
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 656 cggaaaaga gcucaauaaa agucauu                               27

<210> SEQ ID NO 657
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 657
gauugaaugc cuggcacgga acaagag                              27

<210> SEQ ID NO 658
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 658
ggagaacuga ggauugaaug ccuggca                              27

<210> SEQ ID NO 659

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 659
uugguagaga ccugaggauu gaaugcc                                              27

<210> SEQ ID NO 660
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 660
cuugguggag accugaggau ugaaugc                                              27

<210> SEQ ID NO 661
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 661
ccuugaugga gaccugagga uugaaug                                              27

<210> SEQ ID NO 662
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 662
cugccuccuu gguggagacc ugaggau                                              27

<210> SEQ ID NO 663
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 663
ccugcauccu ugguggagac cugagga                                              27

<210> SEQ ID NO 664
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 664
uguuuauccc ugcagcsccu accgccc                                              27

<210> SEQ ID NO 665
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 665
```
auguuugucc cugcagcccc uaccgcc                                               27

<210> SEQ ID NO 666
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 666
gauguuuguc ccugcagccc cuaccgc                                               27

<210> SEQ ID NO 667
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 667
acgauauuug ucccugcagc cccuacc                                               27

<210> SEQ ID NO 668
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 668
aacgauguuu gucccugcag ccccuac                                               27

<210> SEQ ID NO 669
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 669
caacgauguu ugucccugca gccccua                                               27

<210> SEQ ID NO 670
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 670
ccaacaaugu uugucccugc agccccu                                               27

<210> SEQ ID NO 671
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 671
cccaaagaug uuugucccug cagcccc                                               27

<210> SEQ ID NO 672
<211> LENGTH: 27
<212> TYPE: DNA

<213> ORGANISM: Artificial Sequence
<220> FEATURE:
<223> OTHER INFORMATION: Synthetic Nucleic Acid

<400> SEQUENCE: 672
caucaacacc uuucacacuc acccccc                                              27

<210> SEQ ID NO 673
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 673
ccaucagcac cuuucacacu cacccccc                                             27

<210> SEQ ID NO 674
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 674
gccauaagca ccuuucacac ucacccc                                              27

<210> SEQ ID NO 675
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 675
ggccaucagc accuuucaca cucaccc                                              27

<210> SEQ ID NO 676
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 676
gggccaucag caccuuucac acucacc                                              27

<210> SEQ ID NO 677
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 677
agggcaauca gcaccuuuca cacucac                                              27

<210> SEQ ID NO 678
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 678
gagggacauc agcaccuuuc acacuca                                              27

<210> SEQ ID NO 679
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 679
ugaggaccau cagcaccuuu cacacuc                                27

<210> SEQ ID NO 680
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 680
augagagcca ucagcaccuu ucacacu                                27

<210> SEQ ID NO 681
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 681
gaugaaggcc aucagcaccu uucacac                                27

<210> SEQ ID NO 682
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 682
agaugagggc caucagcacc uuucaca                                27

<210> SEQ ID NO 683
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 683
gagauaaggg ccaucagcac cuuucac                                27

<210> SEQ ID NO 684
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 684
uucucaacag uuagcuggag augaggg                                27

<210> SEQ ID NO 685
<211> LENGTH: 27
<212> TYPE: DNA
<213> ORGANISM: Artificial Sequence
<220> FEATURE:

<223> OTHER INFORMATION: Synthetic Nucleic Acid

<400> SEQUENCE: 685
cagggacuuc uccacaguua gcuggag					27

<210> SEQ ID NO 686
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 686
ccaggagcuu cuccacaguu agcugga					27

<210> SEQ ID NO 687
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 687
cccagaggcu ucuccacagu uagcugg					27

<210> SEQ ID NO 688
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 688
ccccaagggc uucuccacag uuagcug					27

<210> SEQ ID NO 689
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 689
uaagcaucca uuaaucaggg agccccc					27

<210> SEQ ID NO 690
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 690
gccauacaga aagcuaagcc uccauua					27

<210> SEQ ID NO 691
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 691
ugccauccag aaagcuaagc cuccauu					27

<210> SEQ ID NO 692
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 692
augccaucca gaaagcuaag ccuccau                               27

<210> SEQ ID NO 693
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 693
gaugcaaucc agaaagcuaa gccucca                               27

<210> SEQ ID NO 694
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 694
agaugacauc cagaaagcua agccucc                               27

<210> SEQ ID NO 695
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 695
uagauaccau ccagaaagcu aagccuc                               27

<210> SEQ ID NO 696
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 696
cuagaugcca uccagaaagc uaagccu                               27

<210> SEQ ID NO 697
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 697
ugugaacacc aggggcgcac cugucuc                               27

<210> SEQ ID NO 698
<211> LENGTH: 27
<212> TYPE: DNA
<213> ORGANISM: Artificial Sequence
<220> FEATURE:
<223> OTHER INFORMATION: Synthetic Nucleic Acid

```
<400> SEQUENCE: 698
cacagacugu gaccaccagg ggcgcac                                              27

<210> SEQ ID NO 699
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 699
aggcaaagcc ugugaccacc aggggcg                                              27

<210> SEQ ID NO 700
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 700
aaggcacagc cugugaccac caggggc                                              27

<210> SEQ ID NO 701
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 701
aaaccaaggc acagccugug accacca                                              27

<210> SEQ ID NO 702
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 702
gaaacaaagg cacagccugu gaccacc                                              27

<210> SEQ ID NO 703
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 703
ggaaaacaag gcacagccug ugaccac                                              27

<210> SEQ ID NO 704
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 704
aggaaaccaa ggcacagccu gugacca                                              27

<210> SEQ ID NO 705
<211> LENGTH: 27
```

```
<212> TYPE: DNA
<213> ORGANISM: Artificial Sequence
<220> FEATURE:
<223> OTHER INFORMATION: Synthetic Nucleic Acid

<400> SEQUENCE: 705
uggcuaagga aaccaaggca cagccug                                           27

<210> SEQ ID NO 706
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 706
guggcucagg aaaccaaggc acagccu                                           27

<210> SEQ ID NO 707
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 707
gguggaucag gaaaccaagg cacagcc                                           27

<210> SEQ ID NO 708
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 708
aggugacuca ggaaaccaag gcacagc                                           27

<210> SEQ ID NO 709
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 709
aagguagcuc aggaaaccaa ggcacag                                           27

<210> SEQ ID NO 710
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 710
aaagguggcu caggaaacca aggcaca                                           27

<210> SEQ ID NO 711
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 711
```
uaaagauggc ucaggaaacc aaggcac                                                 27

<210> SEQ ID NO 712
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 712 guaaagugg cucaggaaac caaggca                                                  27

<210> SEQ ID NO 713
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 713
aguaaaggug gcucaggaaa ccaaggc                                                 27

<210> SEQ ID NO 714
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 714
gaguaaaggu ggcucaggaa accaagg                                                 27

<210> SEQ ID NO 715
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 715
agaguaaagg uggcucagga aaccaag                                                 27

<210> SEQ ID NO 716
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 716
cagaguaaag guggcucagg aaaccaa                                                 27

<210> SEQ ID NO 717
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 717
gcagaauaaa gguggcucag gaaacca                                                 27

<210> SEQ ID NO 718
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 718
auagaacaga guaaaggugg cucagga                                        27

<210> SEQ ID NO 719
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 719
uuuggauguu gcuagcacag ccuggca                                        27

<210> SEQ ID NO 720
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 720
aguccuaggu gauggcuccc cgcaggc                                        27

<210> SEQ ID NO 721
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 721
cagucauagg ugauggcucc ccgcagg                                        27

<210> SEQ ID NO 722
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 722
ucaguacuag gugauggcuc cccgcag                                        27

<210> SEQ ID NO 723
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 723
gucaguccua ggugauggcu ccccgca                                        27

<210> SEQ ID NO 724
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 724
agucaauccu aggugauggc uccccgc                                        27
```

<210> SEQ ID NO 725
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 725
ugccgaguca guccuaggug auggcuc        27

<210> SEQ ID NO 726
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 726
cugccaaguc aguccuaggu gauggcu        27

<210> SEQ ID NO 727
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 727
acugcagagu caguccuagg ugauggc        27

<210> SEQ ID NO 728
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 728
cugcaaacug ccgagucagu ccuaggu        27

<210> SEQ ID NO 729
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 729
ugcacaacug cacacugccg agucagu        27

<210> SEQ ID NO 730
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 730
augcaacacu gcacacugcc gagucag        27

<210> SEQ ID NO 731
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 731
gcaugaacca cugcacacug ccgaguc                                   27

<210> SEQ ID NO 732
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 732
ugcauacacc acugcacacu gccgagu                                   27

<210> SEQ ID NO 733
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 733
gugcaugcac cacugcacac ugccgag                                   27

<210> SEQ ID NO 734
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 734
agacaaugca ugcaccacug cacacug                                   27

<210> SEQ ID NO 735
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 735
gagacagugc augcaccacu gcacacu                                   27

<210> SEQ ID NO 736
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 736
ugagaaagug caugcaccac ugcacac                                   27

<210> SEQ ID NO 737
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 737
cugagacagu gcaugcacca cugcaca                                   27

<210> SEQ ID NO 738

<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 738
gcugaaacag ugcaugcacc acugcac                                            27

<210> SEQ ID NO 739
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 739
ggcugagaca gugcaugcac cacugca                                            27

<210> SEQ ID NO 740
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 740
uggcuaagac agugcaugca ccacugc                                            27

<210> SEQ ID NO 741
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 741
cggguuggcu gagacagugc augcacc                                            27

<210> SEQ ID NO 742
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 742
gcggguuggc ugagacagug caugcac                                            27

<210> SEQ ID NO 743
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 743
ccucuaugaa guaggggugc gaaugug                                            27

<210> SEQ ID NO 744
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 744
uccucuguga aguaggggug cgaaugu                                27

<210> SEQ ID NO 745
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 745
uuccuaugug aaguaggggu gcgaaug                                27

<210> SEQ ID NO 746
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 746
cuuccucugu gaaguagggg ugcgaau                                27

<210> SEQ ID NO 747
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 747
ucuucaucug ugaaguaggg gugcgaa                                27

<210> SEQ ID NO 748
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 748
uucuuacucu gugaaguagg ggugcga                                27

<210> SEQ ID NO 749
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 749
uuucuuccuc ugugaaguag gggugcg                                27

<210> SEQ ID NO 750
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 750
guuucuuccu cugugaagua ggggugc                                27

<210> SEQ ID NO 751
<211> LENGTH: 27
<212> TYPE: DNA

```
<213> ORGANISM: Artificial Sequence
<220> FEATURE:
<223> OTHER INFORMATION: Synthetic Nucleic Acid

<400> SEQUENCE: 751
gguuuauucc ucugugaagu aggggug                                27

<210> SEQ ID NO 752
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 752
agguuucuuc cucugugaag uaggggu                                27

<210> SEQ ID NO 753
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 753
guuccagguu ucuuccucug ugaagua                                27

<210> SEQ ID NO 754
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 754
gguucaaggu uucuuccucu gugaagu                                27

<210> SEQ ID NO 755
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 755
ugguuacagg uuucuuccuc ugugaag                                27

<210> SEQ ID NO 756
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 756
cugguuccag guuucuuccu cugugaa                                27

<210> SEQ ID NO 757
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 757
ucugguucca gguuucuucc ucuguga                                27
```

<210> SEQ ID NO 758
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 758
cucugauucc agguuucuuc cucugug                                27

<210> SEQ ID NO 759
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 759
ccucuaguuc cagguuucuu ccucugu                                27

<210> SEQ ID NO 760
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 760
cccucugguu ccagguuucu uccucug                                27

<210> SEQ ID NO 761
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 761
ccccuauggu uccagguuuc uuccucu                                27

<210> SEQ ID NO 762
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 762
uggcuucaga gccagcccaa ucugcgu                                27

<210> SEQ ID NO 763
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 763
uuggcuucag agccagccca aucugcg                                27

<210> SEQ ID NO 764
<211> LENGTH: 27
<212> TYPE: DNA
<213> ORGANISM: Artificial Sequence
<220> FEATURE:

```
<223> OTHER INFORMATION: Synthetic Nucleic Acid

<400> SEQUENCE: 764
cuuggauuca gagccagccc aaucugc                                              27

<210> SEQ ID NO 765
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 765
gaggcuuggc uucagagcca gcccaau                                              27

<210> SEQ ID NO 766
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 766
agaggauugg cuucagagcc agcccaa                                              27

<210> SEQ ID NO 767
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 767
gugaaauaag aagaggcuug gcuucag                                              27

<210> SEQ ID NO 768
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 768
agccgaguga aguaagaaga ggcuugg                                              27

<210> SEQ ID NO 769
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 769
cagccaggug aaguaagaag aggcuug                                              27

<210> SEQ ID NO 770
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 770
ccagcagggu gaaguaagaa gaggcuu                                              27
```

```
<210> SEQ ID NO 771
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 771
cguaaaaaug aggagcccag ccgggug                                     27

<210> SEQ ID NO 772
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 772
ccguaaaaau gaggagccca gccgggu                                     27

<210> SEQ ID NO 773
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 773
cccguaaaaa ugaggagccc agccggg                                     27

<210> SEQ ID NO 774
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 774
acccguaaaa augaggagcc cagccgg                                     27

<210> SEQ ID NO 775
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 775
uacccauaaa aaugaggagc ccagccg                                     27

<210> SEQ ID NO 776
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 776
ccuucacagc cucacuguua cccguaa                                     27

<210> SEQ ID NO 777
<211> LENGTH: 27
<212> TYPE: DNA
<213> ORGANISM: Artificial Sequence
<220> FEATURE:
<223> OTHER INFORMATION: Synthetic Nucleic Acid
```

```
<400> SEQUENCE: 777
ucguuaugcc aucacucacc gagcuuc                                          27

<210> SEQ ID NO 778
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 778
aucguucugc caucacucac cgagcuu                                          27

<210> SEQ ID NO 779
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 779
caucguucug ccaucacuca ccgagcu                                          27

<210> SEQ ID NO 780
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 780
gcaucauucu gccaucacuc accgagc                                          27

<210> SEQ ID NO 781
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 781
ggcauaguuc ugccaucacu caccgag                                          27

<210> SEQ ID NO 782
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 782
gaaaaaguuc caugccugca ggcaucg                                          27

<210> SEQ ID NO 783
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 783
ggaaaaaguu ccaugccugc aggcauc                                          27

<210> SEQ ID NO 784
<211> LENGTH: 27
```

```
<212> TYPE: DNA
<213> ORGANISM: Artificial Sequence
<220> FEATURE:
<223> OTHER INFORMATION: Synthetic Nucleic Acid

<400> SEQUENCE: 784
cggaaaaagu uccaugccug caggcau                                           27

<210> SEQ ID NO 785
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 785
acggaaaaag uuccaugccu gcaggca                                           27

<210> SEQ ID NO 786
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 786
aacggaaaaa guuccaugcc ugcaggc                                           27

<210> SEQ ID NO 787
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 787
uggguaauaa cggaaaaagu uccaugc                                           27

<210> SEQ ID NO 788
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 788
ucaggacugg gugauaacgg aaaaagu                                           27

<210> SEQ ID NO 789
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 789
aucagaccug ggugauaacg gaaaaag                                           27

<210> SEQ ID NO 790
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 790
```
aaucaagccu ggguugauaac ggaaaaa                                          27

<210> SEQ ID NO 791
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 791
gaaucaggcc ugggugauaa cggaaaa                                           27

<210> SEQ ID NO 792
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 792
ugaauaaggc cugggugaua acggaaa                                           27

<210> SEQ ID NO 793
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 793
gugaaucagg ccugggugau aacggaa                                           27

<210> SEQ ID NO 794
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 794
agugaaucag gccuggguga uaacgga                                           27

<210> SEQ ID NO 795
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 795
caggcaagug aaucaggccu gggugau                                           27

<210> SEQ ID NO 796
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 796
ccaggacagu gaaucaggcc uggguga                                           27

<210> SEQ ID NO 797
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 797
ccuuaaaagc aucuccgcca ggccagu                                              27

<210> SEQ ID NO 798
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 798
gccuuagaag caucuccgcc aggccag                                              27

<210> SEQ ID NO 799
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 799
ugccuuagaa gcaucuccgc caggcca                                              27

<210> SEQ ID NO 800
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 800
augccuuaga agcaucuccg ccaggcc                                              27

<210> SEQ ID NO 801
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 801
caugcauuag aagcaucucc gccaggc                                              27

<210> SEQ ID NO 802
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 802
ccaugacuua gaagcaucuc cgccagg                                              27

<210> SEQ ID NO 803
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 803
accauaccuu agaagcaucu ccgccag                                              27
```

<210> SEQ ID NO 804
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 804
gaccaugccu uagaagcauc uccgcca                                          27

<210> SEQ ID NO 805
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 805
cgaccaugcc uuagaagcau cuccgcc                                          27

<210> SEQ ID NO 806
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 806
ccgacaaugc cuuagaagca ucuccgc                                          27

<210> SEQ ID NO 807
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 807
cccgaacaug ccuuagaagc aucuccg                                          27

<210> SEQ ID NO 808
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 808
ggaggaacag uuguuggccc ucucccc                                          27

<210> SEQ ID NO 809
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 809
ugcucaagga gggacaguug uuggccc                                          27

<210> SEQ ID NO 810
<211> LENGTH: 27
<212> TYPE: DNA
<213> ORGANISM: Artificial Sequence
<220> FEATURE:
<223> OTHER INFORMATION: Synthetic Nucleic Acid -continued

<400> SEQUENCE: 810
gugcuaaagg agggacaguu guuggcc					27

<210> SEQ ID NO 811
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 811
uugcuugggu ggggcuggug cucaagg					27

<210> SEQ ID NO 812
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 812
cuugcuuggg uggggcuggu gcucaag					27

<210> SEQ ID NO 813
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 813
gcuugauugg gugggcugg ugcucaa					27

<210> SEQ ID NO 814
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 814
ugcuuacuug ggugggcug gugcuca					27

<210> SEQ ID NO 815
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 815
aagauaaaug ucugcuugcu ugggugg					27

<210> SEQ ID NO 816
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 816
aaagauaaau gucugcuugc uugggug					27

<210> SEQ ID NO 817

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 817
aaaagauaaa ugucugcuug cuugggu                                        27

<210> SEQ ID NO 818
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 818 caaaaauaa augucugcuu gcuuggg                                         27

<210> SEQ ID NO 819
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 819
ccaaaagaua aaugucugcu ugcuugg                                        27

<210> SEQ ID NO 820
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 820
cccaaaagau aaugucugc uugcuug                                         27

<210> SEQ ID NO 821
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 821
acccaaaaga uaaaugucug cuugcuu                                        27

<210> SEQ ID NO 822
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 822
agaccaaaaa gauaaauguc ugcuugc                                        27

<210> SEQ ID NO 823
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 823
```
cagacacaaa agauaaaugu cugcuug                                           27

<210> SEQ ID NO 824
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 824
acagaaccaa aagauaaaug ucugcuu                                           27

<210> SEQ ID NO 825
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 825
aaaaguuggc uguaaaaagg caacaga                                           27

<210> SEQ ID NO 826
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 826
gaaaaauugg cuguaaaaag gcaacag                                           27

<210> SEQ ID NO 827
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 827
cagguauaga aaaguuggcu guaaaaa                                           27

<210> SEQ ID NO 828
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 828
acaggucuag aaaaguuggc uguaaaa                                           27

<210> SEQ ID NO 829
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 829
acaaaagcaa aacaggucua gaaaagu                                           27

<210> SEQ ID NO 830
<211> LENGTH: 27
<212> TYPE: DNA

-continued

```
<213> ORGANISM: Artificial Sequence
<220> FEATURE:
<223> OTHER INFORMATION: Synthetic Nucleic Acid

<400> SEQUENCE: 830
uacaaaagca aaacaggucu agaaaag                                            27

<210> SEQ ID NO 831
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 831
uuacaaaagc aaacagguc uagaaaa                                             27

<210> SEQ ID NO 832
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 832
guuacaaaag caaacaggu cuagaaa                                             27

<210> SEQ ID NO 833
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 833
aguuaaaaaa gcaaacagg ucuagaa                                             27

<210> SEQ ID NO 834
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 834
aaguuacaaa agcaaaacag gucuaga                                            27

<210> SEQ ID NO 835
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 835
caaguuacaa aagcaaaaca ggucuag                                            27

<210> SEQ ID NO 836
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 836
ucaaguuaca aaagcaaaac aggucua                                            27
```

```
<210> SEQ ID NO 837
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 837
uucaaauuac aaaagcaaaa caggucu                                       27

<210> SEQ ID NO 838
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 838
cuucaaguua caaaagcaaa acagguc                                       27

<210> SEQ ID NO 839
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 839
ucuucaaguu acaaaagcaa aacaggu                                       27

<210> SEQ ID NO 840
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 840
aucuuaaagu acaaaagca aaacagg                                        27

<210> SEQ ID NO 841
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 841
uaucuucaag uuacaaaagc aaaacag                                       27

<210> SEQ ID NO 842
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 842
auaucuucaa guuacaaaag caaaaca                                       27

<210> SEQ ID NO 843
<211> LENGTH: 27
<212> TYPE: DNA
<213> ORGANISM: Artificial Sequence
<220> FEATURE:
```

<223> OTHER INFORMATION: Synthetic Nucleic Acid

<400> SEQUENCE: 843
aauauauuca aguuacaaaa gcaaaac                                27

<210> SEQ ID NO 844
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 844
aaauaucuuc aaguuacaaa agcaaaa                                27

<210> SEQ ID NO 845
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 845
uaaauaucuu caaguuacaa aagcaaa                                27

<210> SEQ ID NO 846
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 846
auaaauaucu ucaaguuaca aaagcaa                                27

<210> SEQ ID NO 847
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 847
aauaaauauc uucaaguuac aaaagca                                27

<210> SEQ ID NO 848
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 848
gaauaaauau cuucaaguua caaaagc                                27

<210> SEQ ID NO 849
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 849
agaauaaaua ucuucaaguu acaaaag                                27

```
<210> SEQ ID NO 850
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 850
cagaauaaau aucuucaagu uacaaaa                                       27

<210> SEQ ID NO 851
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 851
ccagaauaaa uaucuucaag uuacaaa                                       27

<210> SEQ ID NO 852
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 852
cccagaauaa auaucuucaa guuacaa                                       27

<210> SEQ ID NO 853
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 853
acccaaaaua aauaucuuca aguuaca                                       27

<210> SEQ ID NO 854
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 854
aaaccaagaa uaaauaucuu caaguua                                       27

<210> SEQ ID NO 855
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 855
aaaacacaga auaaauaucu ucaaguu                                       27

<210> SEQ ID NO 856
<211> LENGTH: 27
<212> TYPE: DNA
<213> ORGANISM: Artificial Sequence
<220> FEATURE:
<223> OTHER INFORMATION: Synthetic Nucleic Acid
```

```
<400> SEQUENCE: 856
caaaaaccag aauaaauauc uucaagu                                              27

<210> SEQ ID NO 857
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 857
uacaaaaccc agaauaaaua ucuucaa                                              27

<210> SEQ ID NO 858
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 858
cuacaaaacc cagaauaaau aucuuca                                              27

<210> SEQ ID NO 859
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 859
augcuacaaa acccagaaua aauaucu                                              27

<210> SEQ ID NO 860
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 860
aaugcuacaa aacccagaau aaauauc                                              27

<210> SEQ ID NO 861
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 861
aaaugauaca aaacccagaa uaaauau                                              27

<210> SEQ ID NO 862
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 862
aaaauacuac aaaacccaga auaaaua                                              27

<210> SEQ ID NO 863
<211> LENGTH: 27
```

```
<212> TYPE: DNA
<213> ORGANISM: Artificial Sequence
<220> FEATURE:
<223> OTHER INFORMATION: Synthetic Nucleic Acid

<400> SEQUENCE: 863
auaaaaaugc uacaaaaccc agaauaa                                       27

<210> SEQ ID NO 864
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 864
aauaaaaaug cuacaaaacc cagaaua                                       27

<210> SEQ ID NO 865
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 865
uaauaaaaau gcuacaaaac ccagaau                                       27

<210> SEQ ID NO 866
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 866
uuaauaaaaa ugcuacaaaa cccagaa                                       27

<210> SEQ ID NO 867
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 867
auuaauaaaa augcuacaaa acccaga                                       27

<210> SEQ ID NO 868
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 868
uauuaauaaa aaugcuacaa aacccag                                       27

<210> SEQ ID NO 869
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 869
```
auauuaauaa aaaugcuaca aaaccca                                              27

<210> SEQ ID NO 870
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 870
cauauuaaua aaaugcuac aaaccc                                                27

<210> SEQ ID NO 871
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 871
ccauauuaau aaaaaugcua caaaacc                                              27

<210> SEQ ID NO 872
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 872
accauauuaa uaaaaaugcu acaaaac                                              27

<210> SEQ ID NO 873
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 873
caccauauua auaaaaaugc uacaaaa                                              27

<210> SEQ ID NO 874
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 874
ucaccauauu aauaaaaaug cuacaaa                                              27

<210> SEQ ID NO 875
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 875
gucacaauau uaauaaaaau gcuacaa                                              27

<210> SEQ ID NO 876
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 876
agucaacaua uuaauaaaaa ugcuaca                                27

<210> SEQ ID NO 877
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 877
aagucaccau auuaauaaaa augcuac                                27

<210> SEQ ID NO 878
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 878
aaaguaacca uauuaauaaa aaugcua                                27

<210> SEQ ID NO 879
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 879
aaaagucacc auauuaauaa aaaugcu                                27

<210> SEQ ID NO 880
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 880
aaaaaaucac cauauuaaua aaaaugc                                27

<210> SEQ ID NO 881
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 881
uaaaaaguca ccauauuaau aaaaaug                                27

<210> SEQ ID NO 882
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 882
uuaaaaaguc accauauuaa uaaaaau                                27
```

```
<210> SEQ ID NO 883
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 883
uuuaaaaagu caccauauua auaaaaa                                          27

<210> SEQ ID NO 884
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 884
uuuuaaaaag ucaccauauu aauaaaa                                          27

<210> SEQ ID NO 885
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 885
auuuuaaaaa gucaccauau uaauaaa                                          27

<210> SEQ ID NO 886
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 886
uauuuuaaaa agucaccaua uuaauaa                                          27

<210> SEQ ID NO 887
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 887
uuauuuuaaa aagucaccau auuaaua                                          27

<210> SEQ ID NO 888
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 888
uuuauuuuaa aaagucacca uauuaau                                          27

<210> SEQ ID NO 889
<211> LENGTH: 27
<212> TYPE: DNA
<213> ORGANISM: Artificial Sequence
<220> FEATURE:
<223> OTHER INFORMATION: Synthetic Nucleic Acid
```

```
<400> SEQUENCE: 889
uuuuauuuua aaaagucacc auauuaa                                              27

<210> SEQ ID NO 890
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 890
uuuuuauuuu aaaagucac cauauua                                               27

<210> SEQ ID NO 891
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 891
guuuuuauuu uaaaaaguca ccauauu                                              27

<210> SEQ ID NO 892
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 892
uguuuuuauu uuaaaaaguc accauau                                              27

<210> SEQ ID NO 893
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 893
uuguuuuuau uuuaaaaagu caccaua                                              27

<210> SEQ ID NO 894
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 894 uuuguuuua uuuuaaaaag ucaccau                                               27

<210> SEQ ID NO 895
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 895
guuuguuuuu auuuuaaaaa gucacca                                              27

<210> SEQ ID NO 896
```

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 896
uguuuauuuu uauuuaaaa agucacc                                          27

<210> SEQ ID NO 897
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 897
uuguuuguuu uuauuuaaa aagucac                                          27

<210> SEQ ID NO 898
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 898
uuuguuuguu uuuauuuaa aaaguca                                          27

<210> SEQ ID NO 899
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 899
acguuuguuu guuuuauuu uaaaaag                                          27

<210> SEQ ID NO 900
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 900
aacguuuguu uguuuuauu uuaaaaa                                          27

<210> SEQ ID NO 901
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 901
caacguuugu uuguuuuau uuuaaaa                                          27

<210> SEQ ID NO 902
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 902
```
acaacauuug uuguuuuua uuuuaaa                                              27

<210> SEQ ID NO 903
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 903
guuagaacaa cguuuguuug uuuuuau                                             27

<210> SEQ ID NO 904
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 904
uuuuuauuag gacaacguuu guugguu                                             27

<210> SEQ ID NO 905
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 905
uuuuuuguua ggacaacguu uguuugu                                             27

<210> SEQ ID NO 906
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 906
uuuuuuuguu aggacaacgu uuguuug                                             27

<210> SEQ ID NO 907
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 907
cuccaggcgg uccugguggu cgctg                                               25

<210> SEQ ID NO 908
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 908
uccaggcggu ccugguggcu gcugc                                               25

<210> SEQ ID NO 909
<211> LENGTH: 25
<212> TYPE: DNA

```
<213> ORGANISM: Artificial Sequence
<220> FEATURE:
<223> OTHER INFORMATION: Synthetic Nucleic Acid

<400> SEQUENCE: 909
gccgcugcca cugcugcugu ugcug                                          25

<210> SEQ ID NO 910
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 910
ccgcugccac ugcugcugcu gcugc                                          25

<210> SEQ ID NO 911
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 911
gcccgugcgc aggaggacga ggacg                                          25

<210> SEQ ID NO 912
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 912
cccgugcgca ggaggacgau gacgg                                          25

<210> SEQ ID NO 913
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 913
ccgugcgcag gaggacgagu acggc                                          25

<210> SEQ ID NO 914
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 914
cgugcgcagg aggacgagga cggcg                                          25

<210> SEQ ID NO 915
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 915
gugcgcagga ggacgaggau ggcga                                          25
```

<210> SEQ ID NO 916
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 916
ugcgcaggag gacgaggacu gcgac                                              25

<210> SEQ ID NO 917
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 917
gcgcaggagg acgaggacgu cgact                                              25

<210> SEQ ID NO 918
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 918
ggaggacgag gacggcgacu acgag                                              25

<210> SEQ ID NO 919
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 919
gcguuccgag gaggacggcu uggcc                                              25

<210> SEQ ID NO 920
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 920
cguuccgagg aggacggccu ggccg                                              25

<210> SEQ ID NO 921
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 921
guuccgagga ggacggccuu gccga                                              25

<210> SEQ ID NO 922
<211> LENGTH: 25
<212> TYPE: DNA
<213> ORGANISM: Artificial Sequence
<220> FEATURE:

<223> OTHER INFORMATION: Synthetic Nucleic Acid

<400> SEQUENCE: 922
uuccgaggag dacggccugu ccgaa                                      25

<210> SEQ ID NO 923
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 923
uccgaggagg acggccuggu cgaag                                      25

<210> SEQ ID NO 924
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 924
ccgaggagga cggccuggcu gaagc                                      25

<210> SEQ ID NO 925
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 925
cgaggaggac ggccuggccu aagca                                      25

<210> SEQ ID NO 926
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 926
gaggaggacg gccuggccga agcac                                      25

<210> SEQ ID NO 927
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 927
gccaccuucc accgcugcgu caagg                                      25

<210> SEQ ID NO 928
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 928
ccaccuucca ccgcugcgcu aagga                                      25

```
<210> SEQ ID NO 929
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 929
caccuuccac cgcugcgcca aggat                                              25

<210> SEQ ID NO 930
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 930
accuuccacc gcugcgccaa ggatc                                              25

<210> SEQ ID NO 931
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 931
agcgcacugc ccgccgccuu caggc                                              25

<210> SEQ ID NO 932
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 932
gcgcacugcc cgccgccugu aggcc                                              25

<210> SEQ ID NO 933
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 933
cgcacugccc gccgccugca ggccc                                              25

<210> SEQ ID NO 934
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 934
gcacugcccg ccgccugcau gccca                                              25

<210> SEQ ID NO 935
<211> LENGTH: 25
<212> TYPE: DNA
<213> ORGANISM: Artificial Sequence
<220> FEATURE:
<223> OTHER INFORMATION: Synthetic Nucleic Acid
```

```
<400> SEQUENCE: 935
cacugcccgc cgccugcagu cccag                                           25

<210> SEQ ID NO 936
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 936
acugcccgcc gccugcaggu ccagg                                           25

<210> SEQ ID NO 937
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 937
cugcccgccg ccugcaggcu caggc                                           25

<210> SEQ ID NO 938
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 938
ugcccgccgc cugcaggccu aggct                                           25

<210> SEQ ID NO 939
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 939
gcccgccgcc ugcaggccca ggctg                                           25

<210> SEQ ID NO 940
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 940
cccgccgccu gcaggcccau gcugc                                           25

<210> SEQ ID NO 941
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 941
uggcgaccug cuggagcugu ccutg                                           25

<210> SEQ ID NO 942
<211> LENGTH: 25
```

```
<212> TYPE: DNA
<213> ORGANISM: Artificial Sequence
<220> FEATURE:
<223> OTHER INFORMATION: Synthetic Nucleic Acid

<400> SEQUENCE: 942
ggcgaccugc uggagcuggu cuuga                                      25

<210> SEQ ID NO 943
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 943
gcgaccugcu ggagcuggcu uugaa                                      25

<210> SEQ ID NO 944
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 944
cgaccugcug gagcuggccu ugaag                                      25

<210> SEQ ID NO 945
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 945
gaggcagccu gguggagguu uauct                                      25

<210> SEQ ID NO 946
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 946
aggcagccug guggaggugu auctc                                      25

<210> SEQ ID NO 947
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 947
ugugcccgag gaggacggga cccgc                                      25

<210> SEQ ID NO 948
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 948
```
gugcccgagg aggacgggau ccgct                                              25

<210> SEQ ID NO 949
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 949
ugcccgagga ggacgggacu cgctt                                              25

<210> SEQ ID NO 950
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 950
gcccgaggag gacgggaccu gcutc                                              25

<210> SEQ ID NO 951
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 951
cccgaggagg acgggacccu cuucc                                              25

<210> SEQ ID NO 952
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 952
ccgaggagga cgggacccgu uucca                                              25

<210> SEQ ID NO 953
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 953
cgaggaggac gggacccgcu uccac                                              25

<210> SEQ ID NO 954
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 954
ggcaggggug gucagcggcu gggat                                              25

<210> SEQ ID NO 955
<211> LENGTH: 25
<212> TYPE: DNA
<213> ORGANISM: Artificial Sequence

```
<220> FEATURE:
<223> OTHER INFORMATION: Synthetic Nucleic Acid

<400> SEQUENCE: 955
gcaggggugg ucagcggccu ggaug                                 25

<210> SEQ ID NO 956
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 956
cagggguggu cagcggccgu gaugc                                 25

<210> SEQ ID NO 957
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 957
gugcugcugc cccuggcggu ugggt                                 25

<210> SEQ ID NO 958
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 958
ugcugcugcc ccuggcgggu gggta                                 25

<210> SEQ ID NO 959
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 959
gcugcugccc cuggcggguu gguac                                 25

<210> SEQ ID NO 960
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 960
cugcugcccc uggcgggugu guaca                                 25

<210> SEQ ID NO 961
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 961
ugcugccccu ggcggguggu uacag                                 25
```

<210> SEQ ID NO 962
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 962
gcugccccug gcggugggu acagc                                              25

<210> SEQ ID NO 963
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 963
cugccccugg cggugggua cagcc                                              25

<210> SEQ ID NO 964
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 964
ugccccuggc ggguggguau agccg                                             25

<210> SEQ ID NO 965
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 965
gccccuggcg gguggguaca gccgc                                             25

<210> SEQ ID NO 966
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 966
ucaacgccgc cugccagcgu cuggc                                             25

<210> SEQ ID NO 967
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 967
caacgccgcc ugccagcgcu uggcg                                             25

<210> SEQ ID NO 968
<211> LENGTH: 25
<212> TYPE: DNA
<213> ORGANISM: Artificial Sequence
<220> FEATURE:
<223> OTHER INFORMATION: Synthetic Nucleic Acid

```
<400> SEQUENCE: 968
aacgccgccu gccagcgccu ggcga                                              25

<210> SEQ ID NO 969
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 969
acgccgccug ccagcgccuu gcgag                                              25

<210> SEQ ID NO 970
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 970
cgccgccugc cagcgccugu cgagg                                              25

<210> SEQ ID NO 971
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 971
gccgccugcc agcgccuggu gaggg                                              25

<210> SEQ ID NO 972
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 972
ccgccugcca gcgccuggcu agggc                                              25

<210> SEQ ID NO 973
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 973
cgccugccag cgccuggcga gggct                                              25

<210> SEQ ID NO 974
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 974
gccugccagc gccuggcgau ggctg                                              25

<210> SEQ ID NO 975
```

```
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 975
ccagcgccug gcgagggcuu gggtc                                              25

<210> SEQ ID NO 976
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 976
cagcgccugg cgagggcugu ggucg                                              25

<210> SEQ ID NO 977
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 977
agcgccuggc gagggcuggu gucgt                                              25

<210> SEQ ID NO 978
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 978
gcgccuggcg agggcugggu ucgtg                                              25

<210> SEQ ID NO 979
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 979
cgccuggcga gggcuggggu cgugc                                              25

<210> SEQ ID NO 980
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 980
gcgagggcug gggucgugcu gguca                                              25

<210> SEQ ID NO 981
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 981
```
augccugccu cuacucccca gccuc                                    25

<210> SEQ ID NO 982
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 982
gccucuacuc cccagccuca gcucc                                    25

<210> SEQ ID NO 983
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 983
gaccucuuug ccccagggga ggaca                                    25

<210> SEQ ID NO 984
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 984
cuuugcccca ggggaggaca ucatt                                    25

<210> SEQ ID NO 985
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 985
uuugccccag gggaggacau cautg                                    25

<210> SEQ ID NO 986
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 986
uugccccagg ggaggacauu auugg                                    25

<210> SEQ ID NO 987
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 987
ugccccaggg gaggacauca uuggt                                    25

<210> SEQ ID NO 988
<211> LENGTH: 25
<212> TYPE: DNA

```
<213> ORGANISM: Artificial Sequence
<220> FEATURE:
<223> OTHER INFORMATION: Synthetic Nucleic Acid

<400> SEQUENCE: 988
gccccagggg aggacaucau uggtg                                        25

<210> SEQ ID NO 989
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 989
acacggaugg ccacagccgu cgccc                                        25

<210> SEQ ID NO 990
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 990
cuccaggagu gggaagcggu ggggc                                        25

<210> SEQ ID NO 991
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 991
uccaggagug ggaagcggcu gggcg                                        25

<210> SEQ ID NO 992
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 992
ccaggagugg gaagcggcgu ggcga                                        25

<210> SEQ ID NO 993
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 993
caggaguggg aagcggcggu gcgag                                        25

<210> SEQ ID NO 994
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 994
aggaguggga agcggcgggu cgagc                                        25
```

<210> SEQ ID NO 995
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 995
ggagugggaa gcggcggggu gagcg                                    25

<210> SEQ ID NO 996
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 996
gagugggaag cggcggggcu agcgc                                    25

<210> SEQ ID NO 997
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 997
agugggaagc ggcggggcga gcgca                                    25

<210> SEQ ID NO 998
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 998
gaagcggcgg ggcgagcgca uggag                                    25

<210> SEQ ID NO 999
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 999
aagcggcggg gcgagcgcau ggagg                                    25

<210> SEQ ID NO 1000
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1000
agcggcgggg cgagcgcauu gaggc                                    25

<210> SEQ ID NO 1001
<211> LENGTH: 25
<212> TYPE: DNA
<213> ORGANISM: Artificial Sequence
<220> FEATURE:

```
<223> OTHER INFORMATION: Synthetic Nucleic Acid

<400> SEQUENCE: 1001
ggugcugccu gcuaccccau gccaa                                              25

<210> SEQ ID NO 1002
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1002
gugcugccug cuaccccagu ccaac                                              25

<210> SEQ ID NO 1003
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1003
ugcugccugc uaccccaggu caact                                              25

<210> SEQ ID NO 1004
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1004
gggccacguc cucacaggcu gcagc                                              25

<210> SEQ ID NO 1005
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1005
ggccacgucc ucacaggcuu cagct                                              25

<210> SEQ ID NO 1006
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1006
gccacguccu cacaggcugu agctc                                              25

<210> SEQ ID NO 1007
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1007
ggcugcagcu cccacuggga ggugg                                              25
```

```
<210> SEQ ID NO 1008
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1008
gcugcagcuc ccacugggau gugga                                  25

<210> SEQ ID NO 1009
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1009
cugcagcucc cacugggagu uggag                                  25

<210> SEQ ID NO 1010
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1010
ugcagcuccc acugggaggu ggagg                                  25

<210> SEQ ID NO 1011
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1011
gcagcuccca cugggagguu gagga                                  25

<210> SEQ ID NO 1012
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1012
cagcucccac ugggaggugu aggac                                  25

<210> SEQ ID NO 1013
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1013
agcucccacu gggaggugga ggacc                                  25

<210> SEQ ID NO 1014
<211> LENGTH: 25
<212> TYPE: DNA
<213> ORGANISM: Artificial Sequence
<220> FEATURE:
<223> OTHER INFORMATION: Synthetic Nucleic Acid
```

```
<400> SEQUENCE: 1014
gcucccacug ggaggugggau gacct                                    25

<210> SEQ ID NO 1015
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1015
cucccacugg gagguggagu acctt                                     25

<210> SEQ ID NO 1016
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1016
ucccacuggg agguggagga ccutg                                     25

<210> SEQ ID NO 1017
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1017
uggcacccac aagccgccuu ugctg                                     25

<210> SEQ ID NO 1018
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1018
ggcacccaca agccgccugu gcuga                                     25

<210> SEQ ID NO 1019
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1019
agccgccugu gcugaggcca cgagg                                     25

<210> SEQ ID NO 1020
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1020
gccgccugug cugaggccau gaggt                                     25

<210> SEQ ID NO 1021
<211> LENGTH: 25
```

<212> TYPE: DNA
<213> ORGANISM: Artificial Sequence
<220> FEATURE:
<223> OTHER INFORMATION: Synthetic Nucleic Acid

<400> SEQUENCE: 1021
ccgccugugc ugaggccacu aggtc                                              25

<210> SEQ ID NO 1022
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1022
gggccacagg gaggccagca uccac                                              25

<210> SEQ ID NO 1023
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1023
ggccacaggg aggccagcau ccacg                                              25

<210> SEQ ID NO 1024
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1024
gccacaggga ggccagcauu cacgc                                              25

<210> SEQ ID NO 1025
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1025 cggcccuca ggagcagguu accgt                                               25

<210> SEQ ID NO 1026
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1026
ugcugccgga gccggcaccu ggcgc                                              25

<210> SEQ ID NO 1027
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1027

-continued ucacaggcug cugcccacgu ggcug                                          25

<210> SEQ ID NO 1028
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1028
cacaggcugc ugcccacguu gcugg                                          25

<210> SEQ ID NO 1029
<211> LENGTH: 25
<212> TYPE: DNA
<213> ORGANISM: Artificial Sequence
<220> FEATURE:
<223> OTHER INFORMATION: Synthetic Nucleic Acid

<400> SEQUENCE: 1029
gcuuccugcu gccaugcccu aggtc                                          25

<210> SEQ ID NO 1030
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1030
cagcgaccac caggaccgcc uggagcu                                        27

<210> SEQ ID NO 1031
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1031
gcagcagcca ccaggaccgc cuggagc                                        27

<210> SEQ ID NO 1032
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1032
cagcaacagc agcaguggca gcggcca                                        27

<210> SEQ ID NO 1033
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1033
gcagcagcag cagcaguggc agcggcc                                        27

<210> SEQ ID NO 1034
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 1034
cguccucguc cuccugcgca cgggcgc                                          27

<210> SEQ ID NO 1035
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1035
ccgucaucgu ccuccugcgc acgggcg                                          27

<210> SEQ ID NO 1036
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1036
gccguacucg uccuccugcg cacggc                                           27

<210> SEQ ID NO 1037
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1037
cgccguccuc guccuccugc gcacggg                                          27

<210> SEQ ID NO 1038
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1038
ucgccauccu cguccuccug cgcacgg                                          27

<210> SEQ ID NO 1039
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1039
gucgcagucc ucguccuccu gcgcacg                                          27

<210> SEQ ID NO 1040
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1040
agucgacguc cucguccucc ugcgcac                                          27
```

<210> SEQ ID NO 1041
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1041
cucguagucg ccguccucgu ccuccug                               27

<210> SEQ ID NO 1042
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1042
ggccaagccg uccuccucgg aacgcaa                               27

<210> SEQ ID NO 1043
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1043
cggccaggcc guccuccucg gaacgca                               27

<210> SEQ ID NO 1044
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1044
ucggcaaggc cguccuccuc ggaacgc                               27

<210> SEQ ID NO 1045
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1045
uucggacagg ccguccuccu cggaacg                               27

<210> SEQ ID NO 1046
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1046
cuucgaccag gccguccucc ucggaac                               27

<210> SEQ ID NO 1047
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1047
gcuucagcca ggccguccuc cucggaa                                    27

<210> SEQ ID NO 1048
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1048
ugcuuaggcc aggccguccu ccucgga                                    27

<210> SEQ ID NO 1049
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1049
gugcuucggc caggccrucc uccucgg                                    27

<210> SEQ ID NO 1050
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1050
ccuugacgca gcgguggaag guggcug                                    27

<210> SEQ ID NO 1051
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1051
uccuuagcgc agcgguggaa gguggcu                                    27

<210> SEQ ID NO 1052
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1052
auccuuggcg cagcggugga aggugge                                    27

<210> SEQ ID NO 1053
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1053
gauccuuggc gcagcggugg aaggugg                                    27

<210> SEQ ID NO 1054

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1054
gccugaaggc ggcgggcagu gcgcucu                                              27

<210> SEQ ID NO 1055
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1055
ggccuacagg cggcgggcag ugcgcuc                                              27

<210> SEQ ID NO 1056
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1056
gggccugcag gcggcgggca gugcgcu                                              27

<210> SEQ ID NO 1057
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1057
ugggcaugca ggcggcgggc agugcgc                                              27

<210> SEQ ID NO 1058
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1058
cugggacugc aggcggcggg cagugcg                                              27

<210> SEQ ID NO 1059
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1059
ccuggaccug caggcggcgg gcagugc                                              27

<210> SEQ ID NO 1060
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1060
```
gccugagccu gcaggcggcg ggcagug                                              27

<210> SEQ ID NO 1061
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1061
agccuaggcc ugcaggcggc gggcagu                                              27

<210> SEQ ID NO 1062
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1062
cagccugggc cugcaggcgg cgggcag                                              27

<210> SEQ ID NO 1063
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1063
gcagcauggg ccugcaggcg gcgggca                                              27

<210> SEQ ID NO 1064
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1064
caaggacagc uccagcaggu cgccacu                                              27

<210> SEQ ID NO 1065
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1065
ucaagaccag cuccagcagg ucgccac                                              27

<210> SEQ ID NO 1066
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1066
uucaaagcca gcuccagcag gucgcca                                              27

<210> SEQ ID NO 1067
<211> LENGTH: 27
<212> TYPE: DNA

```
<213> ORGANISM: Artificial Sequence
<220> FEATURE:
<223> OTHER INFORMATION: Synthetic Nucleic Acid

<400> SEQUENCE: 1067
cuucaaggcc agcuccagca ggucgcc                                27

<210> SEQ ID NO 1068
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1068
agauaaaccu ccaccaggcu gccuccg                                27

<210> SEQ ID NO 1069
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1069
gagauacacc uccaccaggc ugccucc                                27

<210> SEQ ID NO 1070
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1070 gcggucccg uccuccucgg gcacauu                                 27

<210> SEQ ID NO 1071
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1071
agcggauccc guccuccucg ggcacau                                27

<210> SEQ ID NO 1072
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1072
aagcgagucc cguccuccuc gggcaca                                27

<210> SEQ ID NO 1073
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1073
gaagcagguc ccguccuccu cgggcac                                27
```

```
<210> SEQ ID NO 1074
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1074
ggaagagggu cccguccucc ucgggca                                27

<210> SEQ ID NO 1075
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1075
uggaaacggg ucccguccuc cucgggc                                27

<210> SEQ ID NO 1076
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1076
guggaagcgg gucccguccu ccucggg                                27

<210> SEQ ID NO 1077
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1077
aucccagccg cugaccaccc cugccag                                27

<210> SEQ ID NO 1078
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1078
cauccaggcc gcugaccacc ccugcca                                27

<210> SEQ ID NO 1079
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1079
gcaucacggc cgcugaccac cccugcc                                27

<210> SEQ ID NO 1080
<211> LENGTH: 27
<212> TYPE: DNA
<213> ORGANISM: Artificial Sequence
<220> FEATURE:
```

<223> OTHER INFORMATION: Synthetic Nucleic Acid

<400> SEQUENCE: 1080
acccaaccgc caggggcagc agcacca                                          27

<210> SEQ ID NO 1081
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1081
uacccacccg ccaggggcag cagcacc                                          27

<210> SEQ ID NO 1082
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1082
guaccaaccc gccaggggca gcagcac                                          27

<210> SEQ ID NO 1083
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1083
uguacacacc cgccaggggc agcagca                                          27

<210> SEQ ID NO 1084
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1084
cuguaaccac ccgccagggg cagcagc                                          27

<210> SEQ ID NO 1085
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1085
gcuguaccca cccgccaggg gcagcag                                          27

<210> SEQ ID NO 1086
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1086
ggcuguaccc acccgccagg ggcagca                                          27

```
<210> SEQ ID NO 1087
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1087
cggcuauacc cacccgccag gggcagc                                            27

<210> SEQ ID NO 1088
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1088
gcggcuguac ccacccgcca ggggcag                                            27

<210> SEQ ID NO 1089
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1089
gccagacgcu ggcaggcggc guugagg                                            27

<210> SEQ ID NO 1090
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1090
cgccaagcgc uggcaggcgg cguugag                                            27

<210> SEQ ID NO 1091
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1091
ucgccaggcg cuggcaggcg gcguuga                                            27

<210> SEQ ID NO 1092
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1092
cucgcaaggc gcuggcaggc ggcguug                                            27

<210> SEQ ID NO 1093
<211> LENGTH: 27
<212> TYPE: DNA
<213> ORGANISM: Artificial Sequence
<220> FEATURE:
<223> OTHER INFORMATION: Synthetic Nucleic Acid
```

<400> SEQUENCE: 1093
ccucgacagg cgcuggcagg cggcguu                                27

<210> SEQ ID NO 1094
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1094
cccucaccag gcgcuggcag gcggcgu                                27

<210> SEQ ID NO 1095
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1095
gcccuagcca ggcgcuggca ggcggcg                                27

<210> SEQ ID NO 1096
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1096
agcccucgcc aggcgcuggc aggcggc                                27

<210> SEQ ID NO 1097
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1097
cagccaucgc caggcgcugg caggcgg                                27

<210> SEQ ID NO 1098
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1098
gacccaagcc cucgccaggc gcuggca                                27

<210> SEQ ID NO 1099
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1099
cgaccacagc ccucgccagg cgcuggc                                27

<210> SEQ ID NO 1100
<211> LENGTH: 27

```
<212> TYPE: DNA
<213> ORGANISM: Artificial Sequence
<220> FEATURE:
<223> OTHER INFORMATION: Synthetic Nucleic Acid

<400> SEQUENCE: 1100
acgacaccag cccucgccag gcgcugg                                              27

<210> SEQ ID NO 1101
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1101
cacgaaccca gcccucgcca ggcgcug                                              27

<210> SEQ ID NO 1102
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1102
gcacgacccc agcccucgcc aggcgcu                                              27

<210> SEQ ID NO 1103
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1103
ugaccagcac gaccccagcc cucgcca                                              27

<210> SEQ ID NO 1104
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1104
gaggcugggg aguagaggca ggcaucg                                              27

<210> SEQ ID NO 1105
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1105
ggagcugagg cugggagua gaggcag                                               27

<210> SEQ ID NO 1106
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1106
```
uguccucccc uggggcaaag aggucca                                27

<210> SEQ ID NO 1107
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1107
aaugaugucc uccccugggg caaagag                                27

<210> SEQ ID NO 1108
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1108
caaugauguc cuccccuggg gcaaaga                                27

<210> SEQ ID NO 1109
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1109
ccaauaaugu ccucccugg ggcaaag                                 27

<210> SEQ ID NO 1110
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1110
accaaugaug uccuccccug gggcaaa                                27

<210> SEQ ID NO 1111
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1111
caccaaugau guccuccccu ggggcaa                                27

<210> SEQ ID NO 1112
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1112
gggcgacggc uguggccauc cguguag                                27

<210> SEQ ID NO 1113
<211> LENGTH: 27
<212> TYPE: DNA
<213> ORGANISM: Artificial Sequence

```
<220> FEATURE:
<223> OTHER INFORMATION: Synthetic Nucleic Acid

<400> SEQUENCE: 1113
gccccaccgc uucccacucc uggagaa                                              27

<210> SEQ ID NO 1114
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1114
cgcccagccg cuucccacuc cuggaga                                              27

<210> SEQ ID NO 1115
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1115
ucgccacgcc gcuucccacu ccuggag                                              27

<210> SEQ ID NO 1116
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1116
cucgcaccgc cgcuucccac uccugga                                              27

<210> SEQ ID NO 1117
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1117
gcucgacccg ccgcuuccca cuccugg                                              27

<210> SEQ ID NO 1118
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1118
cgcucacccc gccgcuuccc acuccug                                              27

<210> SEQ ID NO 1119
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1119
gcgcuagccc cgccgcuucc cacuccu                                              27
```

<210> SEQ ID NO 1120
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1120
ugcgcucgcc ccgccgcuuc ccacucc                                27

<210> SEQ ID NO 1121
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1121
cuccaugcgc ucgccccgcc gcuuccc                                27

<210> SEQ ID NO 1122
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1122
ccuccaugcg cucgccccgc cgcuucc                                27

<210> SEQ ID NO 1123
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1123
gccucaaugc gcucgccccg ccgcuuc                                27

<210> SEQ ID NO 1124
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1124
uuggcauggg guagcaggca gcaccug                                27

<210> SEQ ID NO 1125
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1125
guuggacugg gguagcaggc agcaccu                                27

<210> SEQ ID NO 1126
<211> LENGTH: 27
<212> TYPE: DNA
<213> ORGANISM: Artificial Sequence
<220> FEATURE:
<223> OTHER INFORMATION: Synthetic Nucleic Acid

```
<400> SEQUENCE: 1126
aguugaccug ggguagcagg cagcacc                                             27

<210> SEQ ID NO 1127
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1127
gcugcagccu gugaggacgu ggcccug                                             27

<210> SEQ ID NO 1128
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1128
agcugaagcc ugugaggacg uggccu                                              27

<210> SEQ ID NO 1129
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1129
gagcuacagc cugugaggac guggccc                                             27

<210> SEQ ID NO 1130
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1130
ccaccuccca gugggagcug cagccug                                             27

<210> SEQ ID NO 1131
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1131
uccacauccc agugggagcu gcagccu                                             27

<210> SEQ ID NO 1132
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1132
cuccaacucc cagugggagc ugcagcc                                             27

<210> SEQ ID NO 1133
```

```
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1133
ccuccaccuc ccagugggag cugcagc                                              27

<210> SEQ ID NO 1134
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1134
uccucaaccu cccaguggga gcugcag                                              27

<210> SEQ ID NO 1135
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1135
guccuacacc ucccaguggg agcugca                                              27

<210> SEQ ID NO 1136
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1136
gguccuccac cucccagugg gagcugc                                              27

<210> SEQ ID NO 1137
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1137
aggucaucca ccucccagug ggagcug                                              27

<210> SEQ ID NO 1138
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1138
aagguacucc accucccagu gggagcu                                              27

<210> SEQ ID NO 1139
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1139
```
caagguccuc caccucccag ugggagc                                              27

<210> SEQ ID NO 1140
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1140
cagcaaaggc ggcuuguggg ugccaag                                              27

<210> SEQ ID NO 1141
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1141
ucagcacagg cggcuugugg gugccaa                                              27

<210> SEQ ID NO 1142
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1142
ccucguggcc ucagcacagg cggcuug                                              27

<210> SEQ ID NO 1143
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1143
accucauggc cucagcacag gcggcuu                                              27

<210> SEQ ID NO 1144
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1144
gaccuagugg cccucagcaca ggcggcu                                             27

<210> SEQ ID NO 1145
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1145
guggaugcug gccucccugu ggcccac                                              27

<210> SEQ ID NO 1146
<211> LENGTH: 27
<212> TYPE: DNA

```
<213> ORGANISM: Artificial Sequence
<220> FEATURE:
<223> OTHER INFORMATION: Synthetic Nucleic Acid

<400> SEQUENCE: 1146
cguggaugcu ggccucccug uggccca                                              27

<210> SEQ ID NO 1147
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1147
gcgugaaugc uggccucccu guggccc                                              27

<210> SEQ ID NO 1148
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1148
acgguaaccu gcuccugagg ggccggg                                              27

<210> SEQ ID NO 1149
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1149
gcgccaggug ccggcuccgg cagcaga                                              27

<210> SEQ ID NO 1150
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1150
cagccacgug ggcagcagcc ugugaug                                              27

<210> SEQ ID NO 1151
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1151
ccagcaacgu gggcagcagc cugugau                                              27

<210> SEQ ID NO 1152
<211> LENGTH: 27
<212> TYPE: DNA
<213> ORGANISM: Artificial Sequence
<220> FEATURE:
<223> OTHER INFORMATION: Synthetic Nucleic Acid

<400> SEQUENCE: 1152
gaccuagggc auggcagcag gaagcgu                                              27
```

<210> SEQ ID NO 1153
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1153
aacuucagcu ccugcacagu gcagccgaaa ggcugc                                    36

<210> SEQ ID NO 1154
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1154
uggcccucau gggcaccguu gcagccgaaa ggcugc                                    36

<210> SEQ ID NO 1155
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1155
aggaggagac ccaccucucu gcagccgaaa ggcugc                                    36

<210> SEQ ID NO 1156
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1156
ugcuggagcu ggccuugaau gcagccgaaa ggcugc                                    36

<210> SEQ ID NO 1157
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1157
ucugucuuug cccagagcau gcagccgaaa ggcugc                                    36

<210> SEQ ID NO 1158
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1158
cugucuuugc ccagagcauu gcagccgaaa ggcugc                                    36

<210> SEQ ID NO 1159
<211> LENGTH: 36
<212> TYPE: DNA
<213> ORGANISM: Artificial Sequence
<220> FEATURE:

<223> OTHER INFORMATION: Synthetic Nucleic Acid

<400> SEQUENCE: 1159
cuugccugga acucacucau gcagccgaaa ggcugc                                    36

<210> SEQ ID NO 1160
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1160
uugccuggaa cucacucacu gcagccgaaa ggcugc                                    36

<210> SEQ ID NO 1161
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1161
agaaugacuu uuauugagcu gcagccgaaa ggcugc                                    36

<210> SEQ ID NO 1162
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1162
gaaugacuuu uauugagcuu gcagccgaaa ggcugc                                    36

<210> SEQ ID NO 1163
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1163
augacuuuua uugagcucuu gcagccgaaa ggcugc                                    36

<210> SEQ ID NO 1164
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1164
ugacuuuuau ugagcucuuu gcagccgaaa ggcugc                                    36

<210> SEQ ID NO 1165
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1165
cuuguuccgu gccaggcauu gcagccgaaa ggcugc                                    36

```
<210> SEQ ID NO 1166
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1166
ugugaaaggu gcugauggcu gcagccgaaa ggcugc                                  36

<210> SEQ ID NO 1167
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1167
auggaggcuu agcuuucugu gcagccgaaa ggcugc                                  36

<210> SEQ ID NO 1168
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1168
gaggcuuagc uuucuggauu gcagccgaaa ggcugc                                  36

<210> SEQ ID NO 1169
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1169
aggcuuagcu uucuggaugu gcagccgaaa ggcugc                                  36

<210> SEQ ID NO 1170
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1170
gcuuagcuuu cuggauggca gcagccgaaa ggcugc                                  36

<210> SEQ ID NO 1171
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1171
ccaggcugug cuagcaacau gcagccgaaa ggcugc                                  36

<210> SEQ ID NO 1172
<211> LENGTH: 36
<212> TYPE: DNA
<213> ORGANISM: Artificial Sequence
<220> FEATURE:
<223> OTHER INFORMATION: Synthetic Nucleic Acid
```

-continued

<400> SEQUENCE: 1172
ugcggggagc caucaccuau gcagccgaaa ggcugc                               36

<210> SEQ ID NO 1173
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1173
cggcagugug caguggugca gcagccgaaa ggcugc                               36

<210> SEQ ID NO 1174
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1174
acagaggaag aaaccuggaa gcagccgaaa ggcugc                               36

<210> SEQ ID NO 1175
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1175
cagaggaaga aaccuggaau gcagccgaaa ggcugc                               36

<210> SEQ ID NO 1176
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1176
agaggaagaa accuggaacu gcagccgaaa ggcugc                               36

<210> SEQ ID NO 1177
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1177
uggcggagau gcuucuaagu gcagccgaaa ggcugc                               36

<210> SEQ ID NO 1178
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1178
uuacagccaa cuuuucuaga gcagccgaaa ggcugc                               36

<210> SEQ ID NO 1179
<211> LENGTH: 36

```
<212> TYPE: DNA
<213> ORGANISM: Artificial Sequence
<220> FEATURE:
<223> OTHER INFORMATION: Synthetic Nucleic Acid

<400> SEQUENCE: 1179 cguuuugcu uuguaacuu gcagccgaaa ggcugc                              36

<210> SEQ ID NO 1180
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1180
uguuuugcuu uuguaacuuu gcagccgaaa ggcugc                            36

<210> SEQ ID NO 1181
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1181
uuugcuuuug uaacuugaau gcagccgaaa ggcugc                            36

<210> SEQ ID NO 1182
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1182
uuuguagcau uuuuauuaau gcagccgaaa ggcugc                            36

<210> SEQ ID NO 1183
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1183
uguagcauuu uuauuaauau gcagccgaaa ggcugc                            36

<210> SEQ ID NO 1184
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1184
guagcauuuu uauuaauauu gcagccgaaa ggcugc                            36

<210> SEQ ID NO 1185
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1185
```
auuaauaugg ugacuuuuua gcagccgaaa ggcugc    36

<210> SEQ ID NO 1186
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1186
uuaauauggu gacuuuuuaa gcagccgaaa ggcugc    36

<210> SEQ ID NO 1187
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1187
aauaugguga cuuuuaaaa gcagccgaaa ggcugc    36

<210> SEQ ID NO 1188
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1188
auauggugac uuuuuaaaau gcagccgaaa ggcugc    36

<210> SEQ ID NO 1189
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1189
uauggugacu uuuaaaaua gcagccgaaa ggcugc    36

<210> SEQ ID NO 1190
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1190
auggugacuu uuaaaauaa gcagccgaaa ggcugc    36

<210> SEQ ID NO 1191
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1191
uggugacuuu uuaaaauaaa gcagccgaaa ggcugc    36

<210> SEQ ID NO 1192
<211> LENGTH: 36
<212> TYPE: DNA
<213> ORGANISM: Artificial Sequence

```
<220> FEATURE:
<223> OTHER INFORMATION: Synthetic Nucleic Acid

<400> SEQUENCE: 1192
gugacuuuuu aaaauaaaaa gcagccgaaa ggcugc                              36

<210> SEQ ID NO 1193
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1193
acugugcagg agcugaaguu ca                                             22

<210> SEQ ID NO 1194
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1194
aacggugccc augagggcca gg                                             22

<210> SEQ ID NO 1195
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1195
agagaggugg gucuccuccu uc                                             22

<210> SEQ ID NO 1196
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1196
auucaaggcc agcuccagca gg                                             22

<210> SEQ ID NO 1197
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1197
augcucuggg caaagacaga gg                                             22

<210> SEQ ID NO 1198
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1198
aaugcucugg gcaaagacag ag                                             22
```

<210> SEQ ID NO 1199
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1199
augagugagu uccaggcaag ga                                              22

<210> SEQ ID NO 1200
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1200
agugagugag uuccaggcaa gg                                              22

<210> SEQ ID NO 1201
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1201
agcucaauaa aagucauucu gc                                              22

<210> SEQ ID NO 1202
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1202
aagcucaaua aaagucauuc ug                                              22

<210> SEQ ID NO 1203
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1203
aagagcucaa uaaaagucau uc                                              22

<210> SEQ ID NO 1204
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1204
aaagagcuca auaaaaguca uu                                              22

<210> SEQ ID NO 1205
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1205
aaugccuggc acggaacaag ag                                                    22

<210> SEQ ID NO 1206
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1206
agccaucagc accuuucaca cu                                                    22

<210> SEQ ID NO 1207
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1207
acagaaagcu aagccuccau ua                                                    22

<210> SEQ ID NO 1208
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1208
aauccagaaa gcuaagccuc ca                                                    22

<210> SEQ ID NO 1209
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1209
acauccagaa agcuaagccu cc                                                    22

<210> SEQ ID NO 1210
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1210
ugccauccag aaagcuaagc cu                                                    22

<210> SEQ ID NO 1211
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1211
auguugcuag cacagccugg ca                                                    22

<210> SEQ ID NO 1212

```
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1212
auaggugaug gcuccccgca gg                                              22

<210> SEQ ID NO 1213
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1213
ugcaccacug cacacugccg ag                                              22

<210> SEQ ID NO 1214
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1214
uuccagguuu cuuccucugu ga                                              22

<210> SEQ ID NO 1215
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1215
auuccagguu ucuuccucug ug                                              22

<210> SEQ ID NO 1216
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1216
aguuccaggu uucuuccucu gu                                              22

<210> SEQ ID NO 1217
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1217
acuuagaagc aucuccgcca gg                                              22

<210> SEQ ID NO 1218
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1218
```
ucuagaaaag uuggcuguaa aa                                                22

<210> SEQ ID NO 1219
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1219
aaguuacaaa agcaaaacag gu                                                22

<210> SEQ ID NO 1220
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1220
aaaguuacaa agcaaaaca gg                                                 22

<210> SEQ ID NO 1221
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1221
auucaaguua caaaagcaaa ac                                                22

<210> SEQ ID NO 1222
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1222
auuaauaaaa augcuacaaa ac                                                22

<210> SEQ ID NO 1223
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1223
auauuaauaa aaaugcuaca aa                                                22

<210> SEQ ID NO 1224
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1224
aauauuaaua aaaugcuac aa                                                 22

<210> SEQ ID NO 1225
<211> LENGTH: 22
<212> TYPE: DNA

```
<213> ORGANISM: Artificial Sequence
<220> FEATURE:
<223> OTHER INFORMATION: Synthetic Nucleic Acid

<400> SEQUENCE: 1225
uaaaaaguca ccauauuaau aa                                               22

<210> SEQ ID NO 1226
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1226
uuaaaaaguc accauauuaa ua                                               22

<210> SEQ ID NO 1227
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1227
uuuuaaaaag ucaccauauu aa                                               22

<210> SEQ ID NO 1228
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1228
auuuuaaaaa gucaccauau ua                                               22

<210> SEQ ID NO 1229
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1229
uauuuuaaaa agucaccaua uu                                               22

<210> SEQ ID NO 1230
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1230
uuauuuuaaa aagucaccau au                                               22

<210> SEQ ID NO 1231
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1231
uuuauuuuaa aaagucacca ua                                               22
```

<210> SEQ ID NO 1232
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1232
uuuuuauuuu aaaaagucac ca        22

<210> SEQ ID NO 1233
<211> LENGTH: 38
<212> TYPE: DNA
<213> ORGANISM: Artificial Sequence
<220> FEATURE:
<223> OTHER INFORMATION: Synthetic Nucleic Acid

<400> SEQUENCE: 1233
cgacctgctg gagctggcct tgaagttgcc ccatgtcg        38

<210> SEQ ID NO 1234
<211> LENGTH: 38
<212> TYPE: DNA
<213> ORGANISM: Artificial Sequence
<220> FEATURE:
<223> OTHER INFORMATION: Synthetic Nucleic Acid

<400> SEQUENCE: 1234
agcctccttg cctggaactc actcactctg ggtgcctc        38

<210> SEQ ID NO 1235
<211> LENGTH: 56
<212> TYPE: DNA
<213> ORGANISM: Artificial Sequence
<220> FEATURE:
<223> OTHER INFORMATION: Synthetic Nucleic Acid

<400> SEQUENCE: 1235
caatgtgccg atgtccgtgg gcagaatgac ttttattgag ctcttgttcc gtgcca        56

<210> SEQ ID NO 1236
<211> LENGTH: 44
<212> TYPE: DNA
<213> ORGANISM: Artificial Sequence
<220> FEATURE:
<223> OTHER INFORMATION: Synthetic Nucleic Acid

<400> SEQUENCE: 1236
cgttgggggg tgagtgtgaa aggtgctgat ggccctcatc tcca        44

<210> SEQ ID NO 1237
<211> LENGTH: 41
<212> TYPE: DNA
<213> ORGANISM: Artificial Sequence
<220> FEATURE:
<223> OTHER INFORMATION: Synthetic Nucleic Acid

<400> SEQUENCE: 1237
gattaatgga ggcttagctt tctggatggc atctagccag a        41

<210> SEQ ID NO 1238
<211> LENGTH: 61
<212> TYPE: DNA
<213> ORGANISM: Artificial Sequence
<220> FEATURE:

<223> OTHER INFORMATION: Synthetic Nucleic Acid

<400> SEQUENCE: 1238 cctggtggt cacaggctgt gccttggttt cctgagccac ctttactctg ctctatgcca    60
g    61

<210> SEQ ID NO 1239
<211> LENGTH: 80
<212> TYPE: DNA
<213> ORGANISM: Artificial Sequence
<220> FEATURE:
<223> OTHER INFORMATION: Synthetic Nucleic Acid

<400> SEQUENCE: 1239
tggcctgcgg ggagccatca cctaggactg actcggcagt gtgcagtggt gcatgcactg    60
tctcagccaa cccgctccac    80

<210> SEQ ID NO 1240
<211> LENGTH: 55
<212> TYPE: DNA
<213> ORGANISM: Artificial Sequence
<220> FEATURE:
<223> OTHER INFORMATION: Synthetic Nucleic Acid

<400> SEQUENCE: 1240
gtacacattc gcaccctac ttcacagagg aagaaacctg aaccagagg gggcg    55

<210> SEQ ID NO 1241
<211> LENGTH: 63
<212> TYPE: DNA
<213> ORGANISM: Artificial Sequence
<220> FEATURE:
<223> OTHER INFORMATION: Synthetic Nucleic Acid

<400> SEQUENCE: 1241
gctctgaagc caagcctctt cttacttcac ccggctgggc tcctcatttt tacgggtaac    60
agt    63

<210> SEQ ID NO 1242
<211> LENGTH: 46
<212> TYPE: DNA
<213> ORGANISM: Artificial Sequence
<220> FEATURE:
<223> OTHER INFORMATION: Synthetic Nucleic Acid

<400> SEQUENCE: 1242
aacgatgcct gcaggcatgg aacttttcc gttatcaccc aggcct    46

<210> SEQ ID NO 1243
<211> LENGTH: 43
<212> TYPE: DNA
<213> ORGANISM: Artificial Sequence
<220> FEATURE:
<223> OTHER INFORMATION: Synthetic Nucleic Acid

<400> SEQUENCE: 1243
ttcactggcc tggcggagat gcttctaagg catggtcggg gga    43

<210> SEQ ID NO 1244
<211> LENGTH: 184
<212> TYPE: DNA
<213> ORGANISM: Artificial Sequence
<220> FEATURE:
<223> OTHER INFORMATION: Synthetic Nucleic Acid

<400> SEQUENCE: 1244

```
gccccaccca agcaagcaga catttatctt ttgggtctgt cctctctgtt gccttttttac    60
agccaacttt tctagacctg ttttgctttt gtaacttgaa gatatttatt ctgggttttg   120
tagcattttt attaatatgg tgactttttta aaataaaaac aaacaaacgt tgtcctaaca   180
aaaa                                                                184
```

<210> SEQ ID NO 1245
<211> LENGTH: 3731
<212> TYPE: DNA
<213> ORGANISM: Homo Sapiens

<400> SEQUENCE: 1245

```
gtccgatggg gctctggtgg cgtgatctgc gcgcccagg cgtcaagcac ccacacccta     60
gaaggtttcc gcagcgacgt cgaggcgctc atggttgcag gcgggcgccg ccgttcagtt   120
cagggtctga gcctggagga gtgagccagg cagtgagact ggctcgggcg ggccgggacg   180
cgtcgttgca gcagcggctc ccagctccca gccaggattc cgcgcgcccc ttcacgcgcc   240
ctgctcctga acttcagctc ctgcacagtc ctccccaccg caaggctcaa ggcgccgccg   300
gcgtggaccg cgcacggcct ctaggtctcc tcgccaggac agcaacctct ccctggccc    360
tcatgggcac cgtcagctcc aggcggtcct ggtggccgct gccactgctg ctgctgctgc   420
tgctgctcct gggtcccgcg gcgcccgtg cgcaggagga cgaggacggc gactacgagg    480
agctggtgct agccttgcgt tccgaggagg acggcctggc cgaagcaccc gagcacggaa   540
ccacagccac cttccaccgc tgcgccaagg atccgtggag gttgcctggc acctacgtgg   600
tggtgctgaa ggaggagacc cacctctcgc agtcagagcg cactgcccgc cgcctgcagg   660
cccaggctgc ccgccgggga tacctcacca agatcctgca tgtcttccat ggccttcttc   720
ctggcttcct ggtgaagatg agtggcgacc tgctggagct ggccttgaag ttgccccatg   780
tcgactacat cgaggaggac tcctctgtct ttgcccagag catcccgtgg aacctggagc   840
ggattacccc tccacggtac cgggcggatg aataccagcc cccgacgga ggcagcctgg    900
tggaggtgta tctcctagac accagcatac agagtgacca ccgggaaatc gagggcaggg   960
tcatggtcac cgacttcgag aatgtgcccg aggaggacgg gacccgcttc cacagacagg  1020
ccagcaagtg tgacagtcat ggcacccacc tggcagggt ggtcagcggc cgggatgccg   1080
gcgtggccaa gggtgccagc atgcgcagcc tgcgcgtgct caactgccaa gggaagggca  1140
cggttagcgg caccctcata ggcctggagt ttattcggaa aagccagctg gtccagcctg  1200
tggggccact ggtggtgctg ctgccctgg cgggtgggta cagccgcgtc ctcaacgccg   1260
cctgccagcg cctggcgagg gctggggtcg tgctggtcac cgctgccggc aacttccggg  1320
acgatgcctg cctctactcc ccagcctcag ctcccgaggt catcacagtt ggggccacca  1380
atgcccaaga ccagccggtg acctgggga ctttggggac caactttggc cgctgtgtgg   1440
acctctttgc cccaggggag gacatcattg gtgcctccag cgactgcagc acctgctttg  1500
tgtcacagag tgggacatca caggctgctg cccacgtggc tggcattgca gccatgatgc  1560
tgtctgccga gccggagctc acctggccg agttgaggca gagactgatc cacttctctg   1620
ccaaagatgt catcaatgag gcctggttcc ctgaggacca gcgggtactg accccccaacc  1680
tggtggccgc cctgcccccc agcacccatg gggcaggttg gcagctgttt tgcaggactg  1740
tatggtcagc acactcgggg cctacacgga tggccacagc cgtcgcccgc tgcgcccag   1800
```

```
atgaggagct gctgagctgc tccagtttct ccaggagtgg gaagcggcgg ggcgagcgca    1860
tggaggccca aggggcaag ctggtctgcc gggcccacaa cgcttttggg ggtgagggtg    1920
tctacgccat tgccaggtgc tgcctgctac cccaggccaa ctgcagcgtc acacagctc    1980
caccagctga ggccagcatg ggacccgtg tccactgcca ccaacagggc cacgtcctca    2040
caggctgcag ctcccactgg gaggtggagg accttggcac ccacaagccg cctgtgctga    2100
ggccacgagg tcagcccaac cagtgcgtgg ccacaggga ggccagcatc cacgcttcct    2160
gctgccatgc cccaggtctg aatgcaaag tcaaggagca tggaatcccg ccccctcagg    2220
agcaggtgac cgtggcctgc gaggagggct ggaccctgac tggctgcagt gccctccctg    2280
ggacctccca cgtcctgggg gcctacgccg tagacaacac gtgtgtagtc aggagccggg    2340
acgtcagcac tacaggcagc accagcgaag gggccgtgac agccgttgcc atctgctgcc    2400
ggagccggca cctggcgcag gcctcccagg agctccagtg acagccccat cccaggatgg    2460
gtgtctgggg agggtcaagg gctggggctg agctttaaaa tggttccgac ttgtccctct    2520
ctcagccctc catggcctgg cacgaggga tggggatgct tccgcctttc cggggctgct    2580
ggcctggccc ttgagtgggg cagcctcctt gcctggaact cactcactct gggtgcctcc    2640
tccccaggtg gaggtgccag gaagctccct ccctcactgt ggggcatttc accattcaaa    2700
caggtcgagc tgtgctcggg tgctgccagc tgctcccaat gtgccgatgt ccgtgggcag    2760
aatgactttt attgagctct tgttccgtgc caggcattca atcctcaggt ctccaccaag    2820
gaggcaggat tcttcccatg datagggag ggggcggtag gggctgcagg gacaaacatc    2880
gttgggggt gagtgtgaaa ggtgctgatg gccctcatct ccagctaact gtggagaagc    2940
ccctgggggc tccctgatta atggaggctt agctttctgg atggcatcta gccagaggct    3000
ggagacaggt gcgcccctgg tggtcacagg ctgtgccttg gtttcctgag ccacctttac    3060
tctgctctat gccaggctgt gctagcaaca cccaaaggtg gcctgcgggg agccatcacc    3120
taggactgac tcggcagtgt gcagtggtgc atgcactgtc tcagccaacc cgctccacta    3180
cccggcaggg tacacattcg cacccctact tcacagagga agaaacctgg aaccagaggg    3240
ggcgtgcctg ccaagctcac acagcaggaa ctgagccaga acgcagatt gggctggctc    3300
tgaagccaag cctcttctta cttcacccgg ctgggctcct cattttacg ggtaacagtg    3360
aggctgggaa ggggaacaca gaccaggaag ctcggtgagt gatggcagaa cgatgcctgc    3420
aggcatggaa cttttccgt tatcacccag gcctgattca ctggcctggc ggagatgctt    3480
ctaaggcatg gtcggggag agggccaaca actgtccctc cttgagcacc agccccaccc    3540
aagcaagcag acatttatct tttgggtctg tcctctctgt tgccttttta cagccaactt    3600
ttctagacct gttttgcttt tgtaacttga agatatttat tctgggtttt gtagcatttt    3660
tattaatatg gtgactttt aaaataaaaa caaacaaacg ttgtcctaac aaaaaaaaaa    3720
aaaaaaaaaa a                                                          3731

<210> SEQ ID NO 1246
<211> LENGTH: 2079
<212> TYPE: DNA
<213> ORGANISM: Macaca mulatta

<400> SEQUENCE: 1246
atgggtaccg tcagctccag gcggtcctgg tggcctctgc cgctgccact gctgctgctc      60
ctgctcctgg gtcccgctgg cgccgtgcg caggaggacg aggacggcga ctacgaggag     120
ctggtgctag ccttgcgttc cgaggaggac ggcctggccg acgcacccga gcacggagcc     180
```

```
acagccacct tccaccgctg cgccaaggat ccgtggaggc tgcccggcac ctacgtggtg    240
gtgctgaagg aggagaccca ccgctcgcag tcagagcgca ctgcccgccg cctgcaggcc    300
caagctgccc gccggggata cctcaccaag atcctgcatg tcttccatca ccttcttcct    360
ggcttcctgg tgaagatgag tggcgacctg ctggagctgg ccctgaagtt gccccatgtc    420
gactacatcg aggaggactc ctctgtcttt gcccagagca tcccatggaa cctggagcga    480
attactcctg cacggtaccg ggcggatgaa taccagcccc ccaaaggagg cagcctggtg    540
gaggtgtatc tcctagacac cagcatacag agtgaccacc gggaaatcga gggcagggtc    600
atggtcaccg acttcgagag tgtgcccgag aggacgggaa cccgcttcca cagacaggcc    660
agcaagtgtg acagccatgg cacccacctg gcaggggtgg tcagcggccg ggatgccggc    720
gtggccaagg gtgccggcct gcgtagcctg cgcgtgctca actgccaagg gaagggcacg    780
gtcagcggca ccctcatagg tctggagttt attcggaaaa gccagctggt ccagcccgtg    840
gggccactgg ttgtgctgct gcccctggcg ggtgggtaca gccgggtctt caacgccgcc    900
tgccagcgcc tggcgagggc tggggtcgtg ctggtcaccg ctgccggcaa cttccgggac    960
gatgcctgcc tctactcccc agcctcggct cccgaggtca tcacagttgg ggccaccaat   1020
gcccaggacc agccggtgac cctggggact ttggggacca actttggccg ctgtgtggac   1080
ctctttgccc caggggagga catcattggt gcctccagcg actgcagcac ctgctttgtg   1140
tcacggagtg ggacatcgca ggctgctgcc cacgtggctg gcattgcagc catgatgctg   1200
tctgccgagc cggagctcac tctggccgag ttgaggcaga gactgatcca cttctctgcc   1260
aaagatgtca tcaatgaggc ctggttccct gaggaccagc gggtactgac ccccaacctg   1320
gtggccgccc tgccccccag cacccacagg gcaggttggc agctgttttg caggactgtg   1380
tggtcagcac actcggggcc tacacggatg gccacagccg tagcccgctg cgcccaggat   1440
gaggagctgc tgagctgctc cagtttctcc aggagtggga gcggcgggg cgagcgcatc   1500 gaggcccaag ggggcaagcg ggtctgccgg gcccacaacg cttttggggg tgagggtgtc   1560
tacgccattg ccaggtgctg cctgctaccc caggtcaact gcagcgtcca cacagctcca   1620
ccagctgggg ccagcatggg gacccgtgtc cactgccatc agcagggcca cgtcctcaca   1680
ggctgcagct cccactggga ggtggaggac cttggcaccc acaagccgcc tgtgctgagg   1740
ccacgaggtc agcccaacca gtgtgtgggc acagggagg ccagcatcca cgcttcctgc   1800
tgccatgccc caggtctgga atgcaaagtc aaggagcatg gaatcccggc ccctcaggag   1860
caggttatcg tggcctgtga ggacggctgg accctgaccg gctgcagtcc cctccctggg   1920
acctcccatg tcctggggc ctacgctgta gacaacacgt gtgtggtcag gagccgggac   1980
gtcagcacca caggcagcac cagcaaagaa gccgtggcag ccgttgccat ctgctgccgg   2040
agccggcacc tggtgcaggc ctcccaagag ctccagtga                          2079
```

<210> SEQ ID NO 1247
<211> LENGTH: 3512
<212> TYPE: DNA
<213> ORGANISM: Mus musculus

<400> SEQUENCE: 1247

```
tggggattaa gagggggaa tgtaacaggt cccgtttgca gcccaattag gatttggggt     60
tttgtcctca ctctgagcgt catttgacgc tgtctgggga gggcgaggcc gaaacctgat   120
cctttagtac cggggcccgt taatgtttaa tcagagagga tcttccgatg gggctcgggg   180
```

```
tggcgtgatc tcccggcccc caggcgtcca gtacccacac cccagaaggc ttccaccttc        240
acgtggacgc gcaggctgcc ggtgggctcc cgttctctct ctctttctga ggctagagga        300
ctgagccagt ccttggctcc ccagagacat cacggcccgc agccccggag ccaagtgccc        360
cgagtcccag gcgtccatgt ccttcccgag gccgcgcgca cctctcctcg ccccgatggg        420
cacccactgc tctgcgtggc tgcggtggcc gctgttgccg ctgttgccgc cgctgctgct        480
gctgttgctg ctactgtgcc ccaccggcgc tggtgcccag gacgaggatg gagattatga        540
agagctgatg ctcgccctcc cgtcccagga ggatggcctg gctgatgagg ccgcacatgt        600
ggccaccgcc accttccgcc gttgctccaa ggaggcctgg aggctgccag gaacctacat        660
tgtggtgctg atggaggaga cccagaggct acagattgaa caaactgccc accgctgca         720 gacccgggct gccgccgggg ctatgtcat caaggttcta catatctttt atgacctctt         780
ccctggcttc ttggtgaaga tgagcagtga cctgttgggc ctggccctga gttgcccca         840 tgtggagtac attgaggaag actcctttgt cttcgcccag agcatcccat ggaacctgga        900
gcgaattatc ccagcatggc accagacaga ggaagaccgc tcccctgatg gaagcagcca       960
ggtggaggtg tatctcttag ataccagcat ccagggtgcc catcgggaga ttgagggcag       1020
ggtcaccatc accgacttca cagcgtgcc ggaggaggat gggacacgct ccacagaca        1080 ggcgagcaag tgtgacagcc acggcaccca cctggcaggt gtggtcagcg gccgggatgc       1140
tggtgtggcc aagggcacca gcctgcacag cctgcgtgtg ctcaactgtc aagggaaggg       1200
cacagtcagc ggcaccctca taggcctgga gtttattcgg aagagtcagc taatccagcc       1260
ctcggggcca ctcgtggttc tgctgcccct ggccggtggg tatagccgca tcctcaacgc       1320
tgcctgccgg cacctggcga ggactggggt ggtgctggtt gcagcagctg gaacttccg        1380 ggacgacgcc tgcctctact ccccagcttc tgctccagag gtcatcacag tcggggccac       1440
gaatgcccag gaccagccag ttaccttggg gactttgggg actaattttg gacgctgtgt       1500
ggatctcttt gccccggga aggacatcat cggagcgtcc agtgactgca gcacatgctt       1560
catgtcacag agtgggacct cacaggctgc tgcccacgtg gccggcattg tggctcggat       1620
gctgagccgg gagcccacac ttaccctggc cgagctgcgg cagaggctga tccacttctc       1680
taccaaagac gtcatcaaca tggcctggtt ccctgaggac cagcaggtgc tgaccccaa        1740 cctggtggcc acactgcccc ccagcaccca tgagacaggc gggcagctgc tctgtaggac       1800
ggtgtggtcg gcacactcgg ggcccactcg aacagctaca gctacagccc gctgtgcccc       1860
agaagaggag ctgctgagct gctccagctt ctccaggagc gggaggcgtc gtggtgattg       1920
gattgaggcc ataggaggcc agcaggtctg caaggccctc aatgcatttg ggggtgaggg       1980
tgtctatgcc gtcgcgagat gctgcctggt tcccgtgcc aactgcagca tccacaacac        2040
ccctgcagcc agagctggcc tggagaccca tgtccactgc caccagaagg accatgttct       2100
cacaggctgc agcttccatt gggaagtgga agaccttagt gtccggaggc agcctgcgct       2160
gaggtccaga cgtcagcctg gccagtgcgt tggccaccag gcggccagtg tctatgcttc       2220
ctgctgccat gccccagggc tggaatgcaa aatcaaggag catgggatct caggtccttc       2280
agagcaggtc actgtggcct gcgaagcagg atggaccctg actggatgca atgtgctccc       2340 tgggcatcc ctcactctgg gagcctacag cgtggacaac ctgtgtgtgg caagagtcca        2400
tgacactgcc agagcagaca ggaccagtgg agaagccaca gtagctgctg ccatctgctg       2460
ccggagccgg ccttcagcaa aggcctcctg ggttcagtga cagcctcagg cagggatggt       2520
gcttgaggct gggtgcagag atatgcctgc atggctctct tgtagccaaa ggtggggaga       2580
```

```
ttctgcgtgg gagaacttgg tgtctcaccc tgggtaccca ttcctggtgt atggaagcac    2640
ctccttcacg gtcagggggc ctgtgcttgg ctttctgcca tcagacatta agctgtagct    2700
ggctctggcc agctgctcca gtgtaccaga acctgaggat gctcgctgca aggcctcagt    2760
tctcaggcct tagggtgtat ttgtctttca ggaagatcat aatggacaga gatccttgga    2820
ggttcaaaga ccaagtacca gactggaaaa ttgagtctga aagccacaag gacagtcaac    2880
tcacagccag ctcacattgc agacaccatt ttgggctccc tgattaaatg cagatcagtt    2940
ctgcacacct ccaggggtgg atccagctgt aaggccatac ctatatcttc cagatgtcct    3000
catctgctgc agggctttgg ccctgctcag gataatgtgc tatgagccct catctgactc    3060
tcagtttgta ctggagaacc atacaggact taccgcacct taccccatcc actaccatgt    3120
gcactgactg gcctcatttt atgaaggaag agacaggacc agagaggcga tgtcacacag    3180
ccagtgatgt caggacataa attcagagtg ctggccctg aataatgcca ggctgggcag     3240
cgagaggaca ggctatggct tgctcctgga cctatactcc cttagcccca gtcccacaga    3300
tcaggtggag actggagtga cagagggcga ctgtaccaag gccacaccag ctgaccagca    3360
cacctctatc cttttgagct cttctgtctt tttatagtaa gcttcctcca cctgtgttgc    3420
ttttgtaact tgatatttat gcagggtttt gtagttttta ttatgtagtg acttttcaga    3480
ataaaagcag ctgatgtgac tgactgcatc cg                                  3512
```

<210> SEQ ID NO 1248
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1248
gcugggcucc ucauuuuuau gcagccgaaa ggcugc    36

<210> SEQ ID NO 1249
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1249
gcuggcggag augcuucuaa gcagccgaaa ggcugc    36

<210> SEQ ID NO 1250
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1250
uuuacagcca acuuuucuau gcagccgaaa ggcugc    36

<210> SEQ ID NO 1251
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1251
ggcugggcuc ucauuuuua gcagccgaaa ggcugc        36

<210> SEQ ID NO 1252
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1252
agcacggaac cacagccacu gcagccgaaa ggcugc        36

<210> SEQ ID NO 1253
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1253
aaugacuuuu auugagcucu gcagccgaaa ggcugc        36

<210> SEQ ID NO 1254
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1254
uuuuguagca uuuuauuaa gcagccgaaa ggcugc         36

<210> SEQ ID NO 1255
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1255
gcuugccugg aacucacuca gcagccgaaa ggcugc        36

<210> SEQ ID NO 1256
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1256
uggaggcuua gcuuucugga gcagccgaaa ggcugc        36

<210> SEQ ID NO 1257
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1257
auaaaaauga ggagcccagc gg                       22

<210> SEQ ID NO 1258
<211> LENGTH: 22
<212> TYPE: DNA
<213> ORGANISM: Artificial Sequence

```
<220> FEATURE:
<223> OTHER INFORMATION: Synthetic Nucleic Acid

<400> SEQUENCE: 1258
uuagaagcau cuccgccagc gg                                    22

<210> SEQ ID NO 1259
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1259
auagaaaagu uggcuguaaa gg                                    22

<210> SEQ ID NO 1260
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1260
uaaaaaugag gagcccagcc gg                                    22

<210> SEQ ID NO 1261
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1261
aguggcugug guuccgugcu gg                                    22

<210> SEQ ID NO 1262
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1262
agagcucaau aaaagucauu gg                                    22

<210> SEQ ID NO 1263
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1263
uuaauaaaaa ugcuacaaaa gg                                    22

<210> SEQ ID NO 1264
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1264
ugagugaguu ccaggcaagc gg                                    22
```

<210> SEQ ID NO 1265
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1265
uccagaaagc uaagccucca gg                                              22

<210> SEQ ID NO 1266
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1266
uguuuugcuu uuguaacuuw gcagccgaaa ggcugc                               36

<210> SEQ ID NO 1267
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1267
uuuuguaacu ugaagauaua gcagccgaaa ggcugc                               36

<210> SEQ ID NO 1268
<211> LENGTH: 36
<212> TYPE: DNA
<213> ORGANISM: Artificial Sequence
<220> FEATURE:
<223> OTHER INFORMATION: Synthetic Nucleic Acid

<400> SEQUENCE: 1268
cuggguuuug uagcauuuua gcagccgaaa ggcugc                               36

<210> SEQ ID NO 1269
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1269
waaguuacaa aagcaaaaca gg                                              22

<210> SEQ ID NO 1270
<211> LENGTH: 22
<212> TYPE: DNA
<213> ORGANISM: Artificial Sequence
<220> FEATURE:
<223> OTHER INFORMATION: Synthetic Nucleic Acid

<400> SEQUENCE: 1270
uauaucuuca aguuacaaaa gg                                              22

<210> SEQ ID NO 1271
<211> LENGTH: 22
<212> TYPE: DNA
<213> ORGANISM: Artificial Sequence
<220> FEATURE:
<223> OTHER INFORMATION: Synthetic Nucleic Acid

```
<400> SEQUENCE: 1271
uaaaaugcua caaaacccag gg                                              22
```